United States Patent
Heron et al.

(10) Patent No.: US 10,808,231 B2
(45) Date of Patent: Oct. 20, 2020

(54) MODIFIED HELICASES

(71) Applicant: Oxford Nanopore Technologies Limited, Oxford (GB)

(72) Inventors: Andrew Heron, Oxford (GB); James Clarke, Oxford (GB); Ruth Moysey, Oxford (GB); Elizabeth Jayne Wallace, Oxford (GB); Mark Bruce, Oxford (GB); Lakmal Jayasinghe, Oxford (GB); Domenico Caprotti, Oxford (GB); Szabolcs Soeroes, Oxford (GB); Luke McNeill, Oxford (GB); David Alves, Oxford (GB); Rebecca Bowen, Oxford (GB); John Milton, Oxford (GB)

(73) Assignee: Oxford Nanopore Technologies Limited, Oxford (GB)

(*) Notice: Subject to any disclaimer, the term of this patent is extended or adjusted under 35 U.S.C. 154(b) by 415 days.

(21) Appl. No.: 14/415,453

(22) PCT Filed: Jul. 18, 2013

(86) PCT No.: PCT/GB2013/051925
§ 371 (c)(1),
(2) Date: Jan. 16, 2015

(87) PCT Pub. No.: WO2014/013260
PCT Pub. Date: Jan. 23, 2014

(65) Prior Publication Data
US 2015/0191709 A1    Jul. 9, 2015

Related U.S. Application Data

(60) Provisional application No. 61/774,862, filed on Mar. 8, 2013, provisional application No. 61/673,452, filed on Jul. 19, 2012.

(51) Int. Cl.
*C12N 9/14* (2006.01)
*C12N 9/90* (2006.01)
*C12Q 1/6827* (2018.01)

(52) U.S. Cl.
CPC ............... *C12N 9/14* (2013.01); *C12N 9/90* (2013.01); *C12Q 1/6827* (2013.01); *C12Y 306/04012* (2013.01); *C12Y 599/01002* (2013.01); *C12Y 599/01003* (2013.01); *C07K 2319/80* (2013.01)

(58) Field of Classification Search
None
See application file for complete search history.

(56) References Cited

U.S. PATENT DOCUMENTS

| | | | |
|---|---|---|---|
| 7,338,807 B2 | 3/2008 | Harris et al. | |
| 7,625,706 B2 | 12/2009 | Akeson et al. | |
| 7,745,116 B2 | 6/2010 | Williams | |
| 7,851,203 B2 | 12/2010 | Letant et al. | |
| 7,947,454 B2 | 5/2011 | Akeson et al. | |
| 8,105,846 B2 | 1/2012 | Bayley et al. | |
| 8,785,211 B2 | 7/2014 | Bayley et al. | |
| 8,828,208 B2 | 9/2014 | Canas et al. | |
| 9,617,591 B2 | 4/2017 | Moysey et al. | |
| 9,758,823 B2 | 9/2017 | Moysey et al. | |
| 9,797,009 B2 | 10/2017 | Heron et al. | |
| 10,221,450 B2 | 3/2019 | Heron et al. | |
| 10,322,150 B2 | 6/2019 | Honda et al. | |
| 10,385,382 B2 | 8/2019 | Heron et al. | |
| 10,392,658 B2 | 8/2019 | Heron et al. | |
| 2003/0010638 A1 | 1/2003 | Hansford et al. | |
| 2004/0058378 A1 | 3/2004 | Kong et al. | |
| 2004/0248114 A1 | 12/2004 | Taira et al. | |
| 2006/0063171 A1 | 3/2006 | Akeson et al. | |
| 2008/0293045 A1 | 11/2008 | Piepenburg et al. | |
| 2009/0256116 A1 | 10/2009 | Shumaker-Parry et al. | |
| 2010/0035260 A1 | 2/2010 | Olasagasti et al. | |
| 2010/0092960 A1 | 4/2010 | Fehr | |
| 2010/0120098 A1 | 5/2010 | Grunenwald et al. | |
| 2010/0221212 A1 | 9/2010 | Stagliano et al. | |
| 2011/0177498 A1 | 7/2011 | Clarke et al. | |
| 2011/0229877 A1 | 9/2011 | Jayasinghe et al. | |
| 2011/0311965 A1 | 12/2011 | Maglia et al. | |
| 2012/0058468 A1 | 3/2012 | Mckeown | |
| 2012/0107802 A1 | 5/2012 | Stoddart et al. | |
| 2013/0048499 A1 | 2/2013 | Mayer et al. | |
| 2013/0149769 A1 | 6/2013 | Kizaki et al. | |
| 2013/0225421 A1 | 8/2013 | Li et al. | |
| 2014/0051069 A1 | 2/2014 | Jayasinghe et al. | |
| 2014/0186823 A1 | 7/2014 | Clarke et al. | |
| 2014/0255921 A1 | 9/2014 | Moysey et al. | |
| 2014/0262784 A1 | 9/2014 | Clarke et al. | |
| 2014/0335512 A1 | 11/2014 | Moysey et al. | |
| 2015/0008126 A1 | 1/2015 | Maglia et al. | |
| 2015/0031020 A1 | 1/2015 | Jayasinghe et al. | |
| 2015/0065354 A1 | 3/2015 | Moysey et al. | |
| 2015/0152492 A1 | 6/2015 | Brown et al. | |

(Continued)

FOREIGN PATENT DOCUMENTS

CA    2927728    4/2015
CA    2937411    7/2015
(Continued)

OTHER PUBLICATIONS

Zhang et al. (Nature Structural & Molecular Biology vol. 16 No. 7 Jul. 2009, pp. 731-740).*

(Continued)

*Primary Examiner* — Suzanne M Noakes
*Assistant Examiner* — Jae W Lee
(74) *Attorney, Agent, or Firm* — Wolf, Greenfield & Sacks, P.C.

(57) ABSTRACT

The invention relates to modified helicases with reduced unbinding from polynucleotides. The helicases can be used to control the movement of polynucleotides and are particularly useful for sequencing polynucleotides.

12 Claims, 23 Drawing Sheets
Specification includes a Sequence Listing.

(56) References Cited

U.S. PATENT DOCUMENTS

| | | |
|---|---|---|
| 2015/0197796 A1 | 7/2015 | White et al. |
| 2015/0218629 A1 | 8/2015 | Heron et al. |
| 2016/0257942 A1 | 9/2016 | Bruce et al. |
| 2017/0002406 A1 | 1/2017 | Bowen et al. |
| 2018/0030530 A1 | 2/2018 | Moysey et al. |
| 2018/0037874 A9 | 2/2018 | Bruce et al. |
| 2018/0179500 A1 | 6/2018 | Heron et al. |
| 2018/0230526 A1 | 8/2018 | Heron et al. |
| 2019/0203288 A1 | 7/2019 | Gutierrez et al. |
| 2019/0345550 A1 | 11/2019 | Bowen et al. |

FOREIGN PATENT DOCUMENTS

| | | |
|---|---|---|
| JP | 2006-500028 A | 1/2006 |
| WO | 00/028312 A1 | 5/2000 |
| WO | WO 2002/092821 | 11/2002 |
| WO | WO 2004/027025 A2 | 4/2004 |
| WO | 2005/124888 A1 | 12/2005 |
| WO | WO 2006/028508 | 3/2006 |
| WO | 2006/100484 A2 | 9/2006 |
| WO | 2007/057668 A1 | 5/2007 |
| WO | 2008102120 A1 | 8/2008 |
| WO | 2008102121 A1 | 8/2008 |
| WO | WO 2008/124107 A1 | 10/2008 |
| WO | 2009/035647 A1 | 3/2009 |
| WO | 2009/044170 A1 | 4/2009 |
| WO | 2009/077734 A2 | 6/2009 |
| WO | 2010/004265 A1 | 1/2010 |
| WO | 2010/004273 A1 | 1/2010 |
| WO | WO 2010/034018 | 3/2010 |
| WO | 2010/086602 A1 | 8/2010 |
| WO | 2010/086603 A1 | 8/2010 |
| WO | WO 2010/086622 | 8/2010 |
| WO | 2010/109197 A2 | 9/2010 |
| WO | 10/122293 A1 | 10/2010 |
| WO | WO 2010/117470 A2 | 10/2010 |
| WO | 2011/067559 A1 | 6/2011 |
| WO | WO 2012/033524 A2 | 3/2012 |
| WO | 2012/098561 A2 | 7/2012 |
| WO | 2012/098562 A2 | 7/2012 |
| WO | WO 2012/164270 A1 | 12/2012 |
| WO | WO 2013/014451 A1 | 1/2013 |
| WO | WO 2013/041878 | 3/2013 |
| WO | 2013/057495 A2 | 4/2013 |
| WO | 2013/098561 A1 | 7/2013 |
| WO | 2013/098562 A2 | 7/2013 |
| WO | WO 2013/153359 | 10/2013 |
| WO | WO 2013/185137 A1 | 12/2013 |
| WO | 2014/013259 A1 | 1/2014 |
| WO | WO 2014/013260 A1 | 1/2014 |
| WO | WO 2014/013262 A1 | 1/2014 |
| WO | WO 2014/064443 A2 | 5/2014 |
| WO | WO 2014/064444 A1 | 5/2014 |
| WO | WO 2014/135838 A1 | 9/2014 |
| WO | WO 2014/158665 A1 | 10/2014 |
| WO | WO 2015/022544 A1 | 2/2015 |
| WO | WO 2015/055981 A2 | 4/2015 |
| WO | WO 2015/110777 A1 | 7/2015 |
| WO | WO 2015/124935 A1 | 8/2015 |
| WO | WO 2015/150786 A1 | 10/2015 |
| WO | WO 2016/034591 A2 | 3/2016 |
| WO | WO 2016/055777 A2 | 4/2016 |
| WO | WO 2016/059363 A1 | 4/2016 |

OTHER PUBLICATIONS

Byrd et al. (Superfamily 2 helicases, Front Biosci (Landmark Ed). Jun. 1, 2012; 17: 2070-2088).*

Jia et al. (Rotations of the 2B Sub-domain of *E. coli* UvrD Helicase/Translocase Coupled to Nucleotide and DNA Binding, J. Mol. Biol. (2011) 411, 633-648).*

[No Author Listed] Antibodies bind specific molecules through their hypervariable loops. 33.3 Antibody Binding. 6th edition. 2007;953-954.

Blast® NCBI. Sequence ID No. 10; ZSYBNHWV114. Sep. 18, 2015.

Blast® NCBI. Sequence ID No. 52; ZT1133A811N. Sep. 18, 2015.

Genbank Submission. NCBI; Accession No. AM778123. Richards et al.; Sep. 18, 2008.

Sequence ID No. 2 Search Results. US-14-351-038-2. Sep. 16, 2015. 69 pages.

UniProt Database accession No. D0KN27. Dec. 15, 2009.

UniProt Database accession No. I7J3V8 sequence. Oct. 3, 2012.

UniProt Database accession No. k7nri8 sequence. Feb. 6, 2013.

UniProt Database accession No. Q7Y5C3 sequence. Oct. 1, 2003.

Allen et al., The genome sequence of the psychrophilic archaeon, Methanococcoides burtonii: the role of genome evolution in cold adaptation. ISME J. Sep. 2009;3(9):1012-35. doi: 10.1038/ismej.2009.45.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

Buttner et al., Structural basis for DNA duplex separation by a superfamily-2 helicase. Nat Struct Mol Biol. Jul. 2007;14(7):647-52.

Byrd et al., A parallel quadruplex DNA is bound tightly but unfolded slowly by pif1 helicase. J Biol Chem. Mar. 6, 2015;290(10):6482-94. doi:10.1074/jbc.M114.630749. Epub Jan. 14, 2015.

Colas et al., Microscopical investigations of nisin-loaded nanoliposomes prepared by Mozafari method and their bacterial targeting. Micron. 2007;38(8):841-7.

Comer et al., Microscopic mechanics of hairpin DNA translocation through synthetic nanopores. Biophys J. Jan. 2009;96(2):593-608. doi: 10.1016/j.bpj.2008.09.023.

Deamer, Nanopore analysis of nucleic acids bound to exonucleases and polymerases. Annu Rev Biophys. 2010;39:79-90. doi:10.1146/annurev.biophys.093008.131250.

Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.

Dostál et al., Tracking F plasmid TraI relaxase processing reactions provides insight into F plasmid transfer. Nucleic Acids Res. Apr. 2011;39(7):2658-70. doi: 10.1093/nar/gkq1137. Epub Nov. 24, 2010.

Dou et al., The DNA binding properties of the *Escherichia coli* RecQ helicase. J Biol Chem. Feb. 20, 2004;279(8):6354-63. Epub Dec. 9, 2003.

Eliseev et al., Molecular Recognition of Nucleotides, Nucleosides, and Sugars by Aminocyclodextrins. J. Am. Chem. Soc., vol. 116:6081-6088 (1994).

Garalde et al., Highly parallel direct RNA sequencing on an array of nanopores. bioRxiv. 2016. doi: http://dx.doi.org/10.1101/068809.

Graham et al., Sequence-specific assembly of FtsK hexamers establishes directional translocation on DNA. Proc Natl Acad Sci U S A. Nov. 23, 2010;107(47):20263-8. doi: 10.1073/pnas.1007518107. Epub Nov. 3, 2010.

He et al, The T4 phage SF1B helicase Dda is structurally optimized to perform DNA strand separation. Structure. Jul. 3, 2012;20(7):1189-200. doi:10.1016/j.str.2012.04.013. Epub May 31, 2012.

Hopfner et al., Mechanisms of nucleic acid translocases: lessons from structural biology and single-molecule biophysics. Curr Opin Struct Biol. Feb. 2007;17(1):87-95. Epub Dec. 6, 2006.

Hornblower et al., Single-molecule analysis of DNA-protein complexes using nanopores. Nat Methods. Apr. 2007;4(4):315-7. Epub Mar. 4, 2007.

Howorka et al., Nanopore analytics: sensing of single molecules. Chem Soc Rev. Aug. 2009;38(8):2360-84. doi: 10.1039/b813796j. Epub Jun. 15, 2009.

(56) References Cited

OTHER PUBLICATIONS

James, Aptamers. Encyclopedia of Analytical Chemistry. R.A. Meyers (Ed.). 4848-4871. John Wiley & Sons Ltd, Chichester, 2000.
Jezewska et al., Interactions of *Escherichia coli* replicative helicase PriA protein with single-stranded DNA. Biochemistry. Aug. 29, 2000;39(34):10454-67.
Kafri et al., Dynamics of molecular motors and polymer translocation with sequence heterogeneity. Biophys J. Jun. 2004;86(6):3373-91.
Kar et al., Defining the structure-function relationships of bluetongue virus helicase protein VP6. J Virol. Nov. 2003;77(21):11347-56.
Keyser, Controlling molecular transport through nanopores. J R Soc Interface. Oct. 7, 2011;8(63):1369-78. doi: 10.1098/rsif.2011.0222. Epub Jun. 29, 2011.
Khafizov, Single Molecule Force Spectroscopy of Single Stranded Dna Binding Protein and Rep Helicase. University of Illinois at Urbana-Champaign Dissertation. 2012.
Korolev et al., Major domain swiveling revealed by the crystal structures of complexes of *E. coli* Rep helicase bound to single-stranded DNA and ADP. Cell. Aug. 22, 1997;90(4):635-47.
Kuper et al., Functional and structural studies of the nucleotide excision repair helicase XPD suggest a polarity for DNA translocation. EMBO J. Jan. 18, 2012;31(2):494-502. doi: 10.1038/emboj.2011.374.
Langecker et al., Synthetic lipid membrane channels formed by designed DNA nanostructures. Science. Nov. 16, 2012;338(6109):932-6. doi: 10.1126/science.1225624.
Lee et al., Direct imaging of single UvrD helicase dynamics on long single-stranded DNA. Nat Commun. 2013;4:1878. doi:10.1038/ncomms2882.
Lohman et al., Mechanisms of helicase-catalyzed DNA unwinding. Annu Rev Biochem. 1996;65:169-214.
Maddox et al., Elevated serum levels in human pregnancy of a molecule immunochemically similar to eosinophil granule major basic protein. J Exp Med. Oct. 1, 1983;158(4):1211-26.
Marini et al., A human DNA helicase homologous to the DNA cross-link sensitivity protein Mus308. J Biol Chem. Mar. 8, 2002;277(10):8716-23. Epub Dec. 18, 2001.
Morris et al., Evidence for a functional monomeric form of the bacteriophage T4 Dda helicase. Dda does not form stable oligomeric structures. J Biol Chem. Jun. 8, 2001;276(23): 19691-8. Epub Feb. 27, 2001.
Pinero-Fernandez et al., Indole transport across *Escherichia coli* membranes. J Bacteriol. Apr. 2011;193(8):1793-8. doi:10.1128/JB.01477-10. Epub Feb. 4, 2011.
Portakal et al., Construction of recB-recD genetic fusion and functional analysis of RecBDC fusion enzyme in *Escherichia coli*. BMC Biochem. Oct. 10, 2008;9:27. doi: 10.1186/1471-2091-9-27.
Raney et al., Structure and Mechanisms of SF1 DNA Helicases. Adv Exp Med Biol. 2013;767:17-46. doi: 10.1007/978-1-4614-5037-5_2.
Richards et al., Structure of the DNA repair helicase hel308 reveals DNA binding and autoinhibitory domains. J Biol Chem. Feb. 22, 2008;283(8):5118-26. Epub Dec. 4, 2007.
Rudolf et al., The DNA repair helicases XPD and FancJ have essential iron-sulfur domains. Mol Cell. Sep. 15, 2006;23(6):801-8.
Rudolf et al., The helicase XPD unwinds bubble structures and is not stalled by DNA lesions removed by the nucleotide excision repair pathway. Nucleic Acids Res. Jan. 2010;38(3):931-41. doi:10.1093/nar/gkp1058.
Saariaho et al., Characteristics of MuA transposase-catalyzed processing of model transposon end DNA hairpin substrates. Nucleic Acids Res. Jun. 6, 2006;34(10):3139-49. Print 2006.
Sathiyamoorthy et al., The crystal structure of *Escherichia coli* group 4 capsule protein GfcC reveals a domain organization resembling that of Wza. Biochemistry. Jun. 21, 2011;50(24):5465-76. doi: 10.1021/bi101869h.
Singleton et al., Structure and mechanism of helicases and nucleic acid translocases. Annu Rev Biochem. 2007;76:23-50.
Venkatesan et al., Nanopore sensors for nucleic acid analysis. Nat Nanotechnol. Sep. 18, 2011;6(10):615-24. doi: 10.1038/nnano.2011.129.
Wang et al., DNA helicase activity of the RecD protein from Deinococcus radiodurans. J Biol Chem. Dec. 10, 2004;279(50):52024-32.
White, Structure, function and evolution of the XPD family of iron-sulfur-containing 5'→3' DNA helicases. Biochem Soc Trans. 2009;37:547-551.
Woodman et al., Molecular biology of Hel308 helicase in archaea. Biochem Soc Trans. Feb. 2009;37(Pt 1):74-8. doi: 10.1042/BST0370074.
Woodman et al., Winged helix domains with unknown function in Hel308 and related helicases. Biochem Soc Trans. Jan. 2011;39(1):140-4. doi:10.1042/BST0390140.
Activating signal cointegrator 1 complex subunit 3-like [Strongylocentrotus purpuratus]Database accession No. XP_003728286 abstract.
Altschul S. F. (1993) J Mol Evol 36:290-300.
Altschul, S.F et al (1990) J Mol Biol 215:403-10.
Braha, et al., Chem Biol. Jul. 1997; 4(7):497-505.
Cheng, Y. et al., J Biol Chem.Apr. 8, 2001, 286(14): 12670-12682. Epub Feb. 2, 2011.
G123225 Database accession No. B4KAC8 sequence.
DEAD/DEAH box helicase Database accession No. I3D0E7 sequence.
Devereux et al (1984) Nucleic Acids Research 12, p. 387-395.
Fairman-Williams et al, Current Opinion in Structural Biology, 2010, vol. 20, 313-324.
Garcillaán-Barcia MP, et al., FEMS Microbiol Rev. May 2009; 33(3): 657-687.
Gonzalez-Perez et al., Langmuir, 2009, 25, 10447-10450.
Grant, G. P. et al., (2007), Nucleic Acids Res 35(10): e77.
Green et al., Protein Science 2001, vol. 10, 1293-1304.
Hammerstein et al. J Biol Chem. Apr. 22, 2001, 286(16): 14324-14334.
Holden et al., J Am Chem Soc. Jul. 11, 2007;129(27):8650-8655.
International Preliminary Report on Patentability,PCT/GB2013/051925, dated Jan. 20, 2015, pp. 1-13.
International Search Report and Written Opinion,PCT/GB2013/051925, dated Oct. 18, 2013, pp. 1-19.
Ivanov AP et al., Nano Lett. Jan. 12, 2011;11(1):279-85.
Kumar, A. et al. (1988). Anal Biochem; 169(2): 376-82.
Lieberman KR et al, J Am Chem Soc. 2010;132(50):17961-72.
Liu C. C. et al., Annu. Rev. Biochem., 2010, 79, 413-444.
Liu H, et al., Cell, May 30, 2008, 133(5):801-812.
Lohman et al., Nature Reviews Molecular Cell Biology, 2008, 9, 391-401.
M.A. Holden, H. Bayley. J. Am. Chem. Soc. 2005, 127, 6502-6503.
Montal and Mueller (Proc. Natl. Acad. Sci. USA., 1972; 69: 3561-3566).
Nikolov, V., R. Lipowsky, et al. (2007). "Behavior of giant vesicles with anchored DNA molecules." Biophys J 92(12): 4356-68.
O'Shea et al., Science 254 (5031): 539-544.
Pfeiffer, I. and F. Hook (2004). "Bivalent cholesterol-based coupling of oligonucletides to lipid membrane assemblies." J Am Chem Soc 126(33): 10224-5.
Predicted protein Database accession No. A4S1E1 sequence.
Press release: Oxford Nanopore introduces DNA 'strand sequencing' on the high-throughput GridION platform and presents MinION, a sequencer the size of a USB; memory stick, Feb. 2012.
Putative ski2-type helicase; EC=3.6.4.—Database accession No. E1QUS6 sequence.
Putative ski2-type helicase; EC=3.6.4.—Database accession No. K0IM99 sequence.
Remaut and Waksman Trends Biochem. Sci. (2006) 31 436-444.
Richards et al, J BioChem 2008, vol. 283, 5118-5128.
Satapathy AK, et al., FEBS J.; Apr. 2008; 275(8): 1835-1851. Epub Mar. 9, 2008.
Schneider et al, Nature Biotech 2012, vol. 30, 326-328.
Soni GV et al., Rev Sci Instrum. Jan. 2010;81(1):014301.
Stoddart et al., PNAS, 2009; 106(19): 7702-7707.
Troutt, A. B., et al. (1992). Proc Natl Acad Sci U S A 89(20): 9823-9825.

(56) References Cited

OTHER PUBLICATIONS

Tuteja and Tuteja, Eur. J. Biochem. 271, 1849-1863 (2004).
Van Heel M, et al., Q Rev Biophys.(2000) 33: 307-369.
Van Lengerich, B., R. J. Rawle, et al. "Covalent attachment of lipid vesicles to a fluid-supported bilayer allows observation of DNA-mediated vesicle interactions." Langmuir 26(11): 8666-72.
Vinson, Science, 2009: 324(5924): 197.
Woodman et al. J. Mol. Biol. (2007)374, 1139-1144.
Xiang Ma, et al., Chem. Soc. Rev., 2010,39, 70-80.
Yoshina-Ishii, C. and S. G. Boxer (2003). "Arrays of mobile tethered vesicles on supported lipid bilayers." J Am Chem Soc 125(13): 3696-7.
U.S. Appl. No. 14/415,459, filed Jan. 16, 2015, James White.
U.S. Appl. No. 14/415,533, filed Jan. 16, 2015, Andrew Heron.
U.S. Appl. No. 14/369,024, filed Jun. 26, 2014, Ruth Moysey.
U.S. Appl. No. 14/369,072, filed Jun. 26, 2014, Ruth Moysey.
U.S. Appl. No. 14/351,038, filed Apr. 10, 2014, Ruth Moysey.
U.S. Appl. No. 13/260,178, filed Jan. 17, 2012, David Stoddart.
U.S. Appl. No. 13/147,159, filed Nov. 15, 2011, Brian Mckeown.
U.S. Appl. No. 14/234,698, filed Apr. 25, 2014, Clive Gavin Brown.
U.S. Appl. No. 14/122,573, filed Apr. 16, 2014, James Clarke.
U.S. Appl. No. 14/334,285, filed Jul. 17, 2014, Giovanni Maglia.
U.S. Appl. No. 13/984,628, filed Feb. 27, 2014, James Clarke.
U.S. Appl. No. 13/002,717, filed Mar. 30, 2011, James Clarke.
U.S. Appl. No. 14/455,394, filed Aug. 8, 2014, Lakmal Jayasinghe.
U.S. Appl. No. 13/968,778, filed Aug. 16, 2013, Lakmal Jayasinghe.
U.S. Appl. No. 12/093,610, filed Jul. 28, 2008, Hagan Bayley.
U.S. Appl. No. 14/773,164, filed Sep. 4, 2015, Andrew John Heron.
U.S. Appl. No. 14/858,138, filed Sep. 18, 2015, Lakmal Jayasinghe.
U.S. Appl. No. 15/517,592, filed Apr. 7, 2017, Heron et al.
U.S. Appl. No. 15/674,653, filed Aug. 11, 2017, Moysey et al.
U.S. Appl. No. 15/704,395, filed Sep. 14, 2017, Heron et al.
Genbank accession No. AEA72977.1 sequence. Apr. 6, 2011.
UniProt Database accession No. D7RM26 sequence. Aug. 10, 2010.
UniProt Database accession No. I6ZR75 sequence. Oct. 3, 2012.
UniProt Database accession No. Q12WZ6 sequence. Apr. 12, 2017.
Arslan et al., Protein structure. Engineering of a superhelicase through conformational control. Science. Apr. 17, 2015;348(6232):344-7. doi: 10.1126/science.aaa0445.
Data sheet SEQ ID No. 2 search results from STIC, printed on Oct. 29, 2018, pp. 1-24 (Year: 2018).
Data sheet SEQ ID No. 10 search results from STIC, printed on Oct. 29, 2018, pp. 1-38 (Year: 2018).
Balci et al., Single-molecule nanopositioning: structural transitions of a helicase-DNA complex during ATP hydrolysis. Biophys J. Aug. 17, 2011;101(4):976-84. doi: 10.1016/j.bpj.2011.07.010.
Bennett et al., Association of yeast DNA topoisomerase III and Sgs1 DNA helicase: studies of fusion proteins. Proc Natl Acad Sci U S A. Sep. 25, 2001;98(20):11108-13. Epub Sep. 11, 2001.
Bessler et al., The amino terminus of the Saccharomyces cerevisiae DNA helicase Rrm3p modulates protein function ltering replication and checkpoint activity. Genetics. Nov. 2004;168(3):1205-18.
Durrieu et al., Interactions between neuronal fusion proteins explored by molecular dynamics. Biophys J. May 1, 2008;94(9):3436-46. doi:10.1529/biophysj.107.123117. Epub Jan. 22, 2008.
Guo et al., The linker region between the helicase and primase domains of the bacteriophage T7 gene 4 protein is critical for hexamer formation. J Biol Chem. Oct. 15, 1999;274(42):30303-9.
Kalli et al., Conformational changes in talin on binding to anionic phospholipid membranes facilitate signaling by integrin transmembrane helices. PLoS Comput Biol. Oct. 2013;9(10):e1003316. doi:10.1371/journal.pcbi.1003316. Epub Oct. 31, 2013.
Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.
Marsault et al., Macrocycles are great cycles: applications, opportunities, and challenges of synthetic macrocycles in drug discovery. J Med Chem. Apr. 14, 2011;54(7):1961-2004. doi: 10.1021/jm1012374. Epub Mar. 7, 2011.
Mechanic et al., *Escherichia coli* DNA helicase II is active as a monomer. J Biol Chem. Apr. 30, 1999;274(18):12488-98.
Miles et al., Properties of Bacillus cereus hemolysin II: a heptameric transmembrane pore. Protein Sci. Jul. 2002;11(7):1813-24.
Farah et al., The RecBCD enzyme initiation complex for DNA unwinding: enzyme positioning and DNA opening. J Mol Biol. Oct. 10, 1997;272(5):699-715.
Jankowsky, RNA helicases at work: binding and rearranging. Trends Biochem Sci. Jan. 2011;36(1):19-29. doi: 10.1016/j.tibs.2010.07.008.
Ngo et al., Computational complexity, protein structure prediction, and the Levinthal paradox. 14. The protein folding problem tertiary structure prediction. Ed(s):Merz et al. Birkhauser, Boston, Ma. 1994. 433, 492-5.
Balakrishnan et al., Dna2 exhibits a unique strand end-dependent helicase function. J Biol Chem Dec. 10, 2010;285(50):38861-8. doi: 10.1074/jbc.M110.165191. Epub Oct. 6, 2010.
Berger, SnapShot: nucleic acid helicases and translocases. Cell. Sep. 5, 2008;134(5):888-888.e1. doi: 10.1016/j.cell.2008.08.027.
Chandler et al., A new microparticle size calibration standard for use in measuring smaller microparticles using a new flow cytometer. J Thromb Haemost. Jun. 2011;9(6):1216-24. doi: 10.1111/j.1538-7836.2011.04283.x.
Eoff et al., The Kinetic Mechanism for DNA Unwinding by Multiple Molecules of Dda Helicase Aligned on DNA. Biochemistry. Jun. 1, 2010; 49(21): 4543-4553. doi: 10.1021/bi100061v. Author Manuscript.
Heron et al., Simultaneous measurement of ionic current and fluorescence from single protein pores. J Am Chem Soc. Feb. 11, 2009;131(5):1652-3. doi: 10.1021/ja808128s.
Japrung et al., Urea facilitates the translocation of single-stranded DNA and RNA through the alpha-hemolysin nanopore. Biophys J. May 19, 2010;98(9):1856-63. doi: 10.1016/j.bpj.2009.12.4333.
Kankia et al., Folding of the thrombin aptamer into a G-quadruplex with Sr(2+): stability, heat, and hydration. J Am Chem Soc. Nov. 7, 2001;123(44):10799-804.
Kutyavin et al., Oligonucleotides containing 2-aminoadenine and 2-thiothymine act as selectively binding complementary agents. Biochemistry. Aug. 27, 1996;35(34):11170-6.
Lee et al., Cooperative translocation enhances the unwinding of duplex DNA by SARS coronavirus helicase nsP13. Nucleic Acids Res. Nov. 2010;38(21):7626-36. doi: 10.1093/nar/gkq647. Epub Jul. 29, 2010.
Levin et al., Helicase from hepatitis C virus, energetics of DNA binding. J Biol Chem. Aug. 16, 2002;277(33):29377-85. Epub May 28, 2002.
Marathias et al., Structures of the potassium-saturated, 2:1, and intermediate, 1:1, forms of a quadruplex DNA. Nucleic Acids Res. May 1, 20001;28(9):1969-77.
Marušič et al., Solution-state structure of an intramolecular G-quadruplex with propeller, diagonal and edgewise loops. Nucleic Acids Res. Aug. 2012;40(14):6946-56. doi: 10.1093/nar/gks329. Epub Apr. 24, 2012.
Nishikiori et al., Crystal structure of the superfamily 1 helicase from Tomato mosaic virus. J Virol. Jul. 2012;86(14):7565-76. doi: 10.1128/JVI.00118-12. Epub May 9, 2012.
Stelter et al., Structural and mechanistic insight into DNA unwinding by Deinococcus radiodurans UvrD. PLoS One. Oct. 15, 2013;8(10):e77364. doi: 10.1371/journal.pone.0077364.
Yusko et al., Controlling the translocation of proteins through nanopores with bioinspired fluid walls. Nat Nanotechnol. Nat Nanotechnol. Apr. 2011; 6(4): 253-260. EPub Feb. 20, 2011. doi: 10.1038/nnano.2011.12 Author manuscript; available in PMC Oct. 1, 2011.

\* cited by examiner

SEQUENCE LISTING

```
<160> NUMBER OF SEQ ID NOS: 156

<210> SEQ ID NO 1
<211> LENGTH: 558
<212> TYPE: DNA
<213> ORGANISM: Artificial sequence
<220> FEATURE:
<223> OTHER INFORMATION: Mycobacterium smegmatis porin A mutant
      (D90N/D91N/D93N/D118R/D134R/E139K)

<400> SEQUENCE: 1
atgggtctgg ataatgaact gagcctggtg gacggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc aacaatggta acattaccgc accgccgttt     300
```

-continued

```
ggcctgaaca gcgtgattac gccgaacctg tttccgggtg ttagcatctc tgcccgtctg    360
ggcaatggtc cgggcattca agaagtggca acctttagtg tgcgcgtttc cggcgctaaa    420
ggcggtgtcg cggtgtctaa cgcccacggt accgttacgg gcgcggccgg cggtgtcctg    480
ctgcgtccgt tcgcgcgcct gattgcctct accggcgaca cgttacgac ctatggcgaa     540 ccgtggaata tgaactaa                                                   558
```

<210> SEQ ID NO 2
<211> LENGTH: 184
<212> TYPE: PRT
<213> ORGANISM: Artificial sequence
<220> FEATURE:
<223> OTHER INFORMATION: Mycobacterium smegmatis porin A mutant
  (D90N/D91N/D93N/D118R/D134R/E139K)

<400> SEQUENCE: 2

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 3
<211> LENGTH: 885
<212> TYPE: DNA
<213> ORGANISM: Artificial sequence
<220> FEATURE:
<223> OTHER INFORMATION: alpha-hemolysin mutant E111N/K147N

<400> SEQUENCE: 3

```
atggcagatt ctgatattaa tattaaaacc ggtactacag atattggaag caatactaca    60
gtaaaaacag gtgatttagt cacttatgat aaagaaatg gcatgcacaa aaagtatttt    120
tatagtttta tcgatgataa aaatcacaat aaaaaactgc tagttattag aacaaaaggt    180
accattgctg gtcaatatag agtttatagc gaagaaggtg ctaacaaaag tggtttagcc    240
tggccttcag cctttaaggt acagttgcaa ctacctgata tgaagtagc tcaaatatct    300 gattactatc caagaaattc gattgataca aaaaactata tgagtacttt aacttatgga    360
```

-continued

```
ttcaacggta atgttactgg tgatgataca ggaaaaattg gcggccttat tggtgcaaat    420
gtttcgattg gtcatacact gaactatgtt caacctgatt tcaaaacaat tttagagagc    480
ccaactgata aaaaagtagg ctggaaagtg atatttaaca atatggtgaa tcaaaattgg    540
ggaccatacg atcgagattc ttggaacccg gtatatggca atcaactttt catgaaaact    600
agaaatggtt ctatgaaagc agcagataac ttccttgatc ctaacaaagc aagttctcta    660
ttatcttcag ggttttcacc agacttcgct acagttatta ctatggatag aaaagcatcc    720
aaacaacaaa caaatataga tgtaatatac gaacgagttc gtgatgatta ccaattgcat    780
tggacttcaa caaattggaa aggtaccaat actaaagata aatggacaga tcgttcttca    840
gaaagatata aaatcgattg ggaaaaagaa gaaatgacaa attaa                    885

<210> SEQ ID NO 4
<211> LENGTH: 293
<212> TYPE: PRT
<213> ORGANISM: Artificial sequence
<220> FEATURE:
<223> OTHER INFORMATION: alpha-hemolysin mutant E111N/K147N

<400> SEQUENCE: 4

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270
```

Lys Trp Thr Asp Arg Ser Ser Glu Arg Tyr Lys Ile Asp Trp Glu Lys
            275                 280                 285

Glu Glu Met Thr Asn
        290

<210> SEQ ID NO 5
<211> LENGTH: 184
<212> TYPE: PRT
<213> ORGANISM: Mycobacterium smegmatis

<400> SEQUENCE: 5

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Val Ala Val
    130                 135                 140

Ser Asn Ala His Gly Thr Val Thr Gly Ala Ala Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 6
<211> LENGTH: 184
<212> TYPE: PRT
<213> ORGANISM: Mycobacterium smegmatis

<400> SEQUENCE: 6

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
            100                 105                 110

```
Val Ser Ile Ser Ala Asp Leu Gly Asn Gly Pro Gly Ile Gln Glu Val
            115                 120                 125

Ala Thr Phe Ser Val Asp Val Ser Gly Pro Ala Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 7
<211> LENGTH: 183
<212> TYPE: PRT
<213> ORGANISM: Mycobacterium smegmatis

<400> SEQUENCE: 7

```
Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
            20                  25                  30

Asn Arg Leu Thr Arg Glu Trp Phe His Ser Gly Arg Ala Thr Tyr His
        35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Gly Asp Ile Thr Gln Pro
                85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
        115                 120                 125

Thr Phe Ser Val Asp Val Lys Gly Ala Lys Gly Ala Val Ala Val Ser
    130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180
```

<210> SEQ ID NO 8
<211> LENGTH: 8
<212> TYPE: PRT
<213> ORGANISM: Artificial sequence
<220> FEATURE:
<223> OTHER INFORMATION: Amino acid sequence of the Hel308 motif
<220> FEATURE:
<221> NAME/KEY: MISC_FEATURE
<222> LOCATION: (2)..(2)
<223> OTHER INFORMATION: Xaa = C, M or L
<220> FEATURE:
<221> NAME/KEY: MISC_FEATURE
<222> LOCATION: (3)..(3)
<223> OTHER INFORMATION: Xaa = any amino acid

<400> SEQUENCE: 8

```
Gln Xaa Xaa Gly Arg Ala Gly Arg
1               5
```

-continued

```
<210> SEQ ID NO 9
<211> LENGTH: 9
<212> TYPE: PRT
<213> ORGANISM: Artificial sequence
<220> FEATURE:
<223> OTHER INFORMATION: Amino acid sequence of the extended Hel308
      motif
<220> FEATURE:
<221> NAME/KEY: MISC_FEATURE
<222> LOCATION: (2)..(2)
<223> OTHER INFORMATION: Xaa = C, M or L
<220> FEATURE:
<221> NAME/KEY: MISC_FEATURE
<222> LOCATION: (3)..(3)
<223> OTHER INFORMATION: Xaa = any amino acid

<400> SEQUENCE: 9

Gln Xaa Xaa Gly Arg Ala Gly Arg Pro
1               5

<210> SEQ ID NO 10
<211> LENGTH: 760
<212> TYPE: PRT
<213> ORGANISM: Methanococcoides burtonii

<400> SEQUENCE: 10

Met Met Ile Arg Glu Leu Asp Ile Pro Arg Asp Ile Ile Gly Phe Tyr
1               5                   10                  15

Glu Asp Ser Gly Ile Lys Glu Leu Tyr Pro Pro Gln Ala Glu Ala Ile
                20                  25                  30

Glu Met Gly Leu Leu Glu Lys Lys Asn Leu Leu Ala Ala Ile Pro Thr
            35                  40                  45

Ala Ser Gly Lys Thr Leu Leu Ala Glu Leu Ala Met Ile Lys Ala Ile
        50                  55                  60

Arg Glu Gly Gly Lys Ala Leu Tyr Ile Val Pro Leu Arg Ala Leu Ala
65                  70                  75                  80

Ser Glu Lys Phe Glu Arg Phe Lys Glu Leu Ala Pro Phe Gly Ile Lys
                85                  90                  95

Val Gly Ile Ser Thr Gly Asp Leu Asp Ser Arg Ala Asp Trp Leu Gly
                100                 105                 110

Val Asn Asp Ile Ile Val Ala Thr Ser Glu Lys Thr Asp Ser Leu Leu
            115                 120                 125

Arg Asn Gly Thr Ser Trp Met Asp Glu Ile Thr Thr Val Val Val Asp
        130                 135                 140

Glu Ile His Leu Leu Asp Ser Lys Asn Arg Gly Pro Thr Leu Glu Val
145                 150                 155                 160

Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
                180                 185                 190

Ala Ala Leu Val Leu Ser Glu Trp Arg Pro Thr Asp Leu His Glu Gly
            195                 200                 205

Val Leu Phe Gly Asp Ala Ile Asn Phe Pro Gly Ser Gln Lys Lys Ile
        210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255
```

-continued

```
Ala Gly Phe Ala Lys Thr Ala Ser Ser Lys Val Ala Lys Ile Leu Asp
            260                 265                 270

Asn Asp Ile Met Ile Lys Leu Ala Gly Ile Ala Glu Glu Val Glu Ser
        275                 280                 285

Thr Gly Glu Thr Asp Thr Ala Ile Val Leu Ala Asn Cys Ile Arg Lys
    290                 295                 300

Gly Val Ala Phe His His Ala Gly Leu Asn Ser Asn His Arg Lys Leu
305                 310                 315                 320

Val Glu Asn Gly Phe Arg Gln Asn Leu Ile Lys Val Ile Ser Ser Thr
                325                 330                 335

Pro Thr Leu Ala Ala Gly Leu Asn Leu Pro Ala Arg Arg Val Ile Ile
            340                 345                 350

Arg Ser Tyr Arg Arg Phe Asp Ser Asn Phe Gly Met Gln Pro Ile Pro
        355                 360                 365

Val Leu Glu Tyr Lys Gln Met Ala Gly Arg Ala Gly Arg Pro His Leu
    370                 375                 380

Asp Pro Tyr Gly Glu Ser Val Leu Leu Ala Lys Thr Tyr Asp Glu Phe
385                 390                 395                 400

Ala Gln Leu Met Glu Asn Tyr Val Glu Ala Asp Ala Glu Asp Ile Trp
                405                 410                 415

Ser Lys Leu Gly Thr Glu Asn Ala Leu Arg Thr His Val Leu Ser Thr
            420                 425                 430

Ile Val Asn Gly Phe Ala Ser Thr Arg Gln Glu Leu Phe Asp Phe Phe
        435                 440                 445

Gly Ala Thr Phe Phe Ala Tyr Gln Gln Asp Lys Trp Met Leu Glu Glu
    450                 455                 460

Val Ile Asn Asp Cys Leu Glu Phe Leu Ile Asp Lys Ala Met Val Ser
465                 470                 475                 480

Glu Thr Glu Asp Ile Glu Asp Ala Ser Lys Leu Phe Leu Arg Gly Thr
                485                 490                 495

Arg Leu Gly Ser Leu Val Ser Met Leu Tyr Ile Asp Pro Leu Ser Gly
            500                 505                 510

Ser Lys Ile Val Asp Gly Phe Lys Asp Ile Gly Lys Ser Thr Gly Gly
        515                 520                 525

Asn Met Gly Ser Leu Glu Asp Asp Lys Gly Asp Asp Ile Thr Val Thr
    530                 535                 540

Asp Met Thr Leu Leu His Leu Val Cys Ser Thr Pro Asp Met Arg Gln
545                 550                 555                 560

Leu Tyr Leu Arg Asn Thr Asp Tyr Thr Ile Val Asn Glu Tyr Ile Val
                565                 570                 575

Ala His Ser Asp Glu Phe His Glu Ile Pro Asp Lys Leu Lys Glu Thr
            580                 585                 590

Asp Tyr Glu Trp Phe Met Gly Glu Val Lys Thr Ala Met Leu Leu Glu
        595                 600                 605

Glu Trp Val Thr Glu Val Ser Ala Glu Asp Ile Thr Arg His Phe Asn
    610                 615                 620

Val Gly Glu Gly Asp Ile His Ala Leu Ala Asp Thr Ser Glu Trp Leu
625                 630                 635                 640

Met His Ala Ala Ala Lys Leu Ala Glu Leu Leu Gly Val Glu Tyr Ser
                645                 650                 655

Ser His Ala Tyr Ser Leu Glu Lys Arg Ile Arg Tyr Gly Ser Gly Leu
            660                 665                 670

Asp Leu Met Glu Leu Val Gly Ile Arg Gly Val Gly Arg Val Arg Ala
```

```
              675                 680                 685
Arg Lys Leu Tyr Asn Ala Gly Phe Val Ser Val Ala Lys Leu Lys Gly
        690                 695                 700

Ala Asp Ile Ser Val Leu Ser Lys Leu Val Gly Pro Lys Val Ala Tyr
705                 710                 715                 720

Asn Ile Leu Ser Gly Ile Gly Val Arg Val Asn Asp Lys His Phe Asn
                725                 730                 735

Ser Ala Pro Ile Ser Ser Asn Thr Leu Asp Thr Leu Leu Asp Lys Asn
            740                 745                 750

Gln Lys Thr Phe Asn Asp Phe Gln
        755                 760

<210> SEQ ID NO 11
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 11

Gln Met Ala Gly Arg Ala Gly Arg
1               5

<210> SEQ ID NO 12
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 12

Gln Met Ala Gly Arg Ala Gly Arg Pro
1               5

<210> SEQ ID NO 13
<211> LENGTH: 720
<212> TYPE: PRT
<213> ORGANISM: Pyrococcus furiosus

<400> SEQUENCE: 13

Met Arg Val Asp Glu Leu Arg Val Asp Glu Arg Ile Lys Ser Thr Leu
1               5                   10                  15

Lys Glu Arg Gly Ile Glu Ser Phe Tyr Pro Pro Gln Ala Glu Ala Leu
            20                  25                  30

Lys Ser Gly Ile Leu Glu Gly Lys Asn Ala Leu Ile Ser Ile Pro Thr
        35                  40                  45

Ala Ser Gly Lys Thr Leu Ile Ala Glu Ile Ala Met Val His Arg Ile
    50                  55                  60

Leu Thr Gln Gly Gly Lys Ala Val Tyr Ile Val Pro Leu Lys Ala Leu
65                  70                  75                  80

Ala Glu Glu Lys Phe Gln Glu Phe Gln Asp Trp Glu Lys Ile Gly Leu
                85                  90                  95

Arg Val Ala Met Ala Thr Gly Asp Tyr Asp Ser Lys Asp Glu Trp Leu
            100                 105                 110

Gly Lys Tyr Asp Ile Ile Ile Ala Thr Ala Glu Lys Phe Asp Ser Leu
        115                 120                 125

Leu Arg His Gly Ser Ser Trp Ile Lys Asp Val Lys Ile Leu Val Ala
    130                 135                 140

Asp Glu Ile His Leu Ile Gly Ser Arg Asp Arg Gly Ala Thr Leu Glu
```

```
            145                 150                 155                 160
        Val Ile Leu Ala His Met Leu Gly Lys Ala Gln Ile Ile Gly Leu Ser
                        165                 170                 175
        Ala Thr Ile Gly Asn Pro Glu Glu Leu Ala Glu Trp Leu Asn Ala Glu
                        180                 185                 190
        Leu Ile Val Ser Asp Trp Arg Pro Val Lys Leu Arg Arg Gly Val Phe
                        195                 200                 205
        Tyr Gln Gly Phe Val Thr Trp Glu Asp Gly Ser Ile Asp Arg Phe Ser
                        210                 215                 220
        Ser Trp Glu Glu Leu Val Tyr Asp Ala Ile Arg Lys Lys Gly Ala
        225                 230                 235                 240
        Leu Ile Phe Val Asn Met Arg Arg Lys Ala Glu Arg Val Ala Leu Glu
                        245                 250                 255
        Leu Ser Lys Lys Val Lys Ser Leu Leu Thr Lys Pro Glu Ile Arg Ala
                        260                 265                 270
        Leu Asn Glu Leu Ala Asp Ser Leu Glu Glu Asn Pro Thr Asn Glu Lys
                        275                 280                 285
        Leu Ala Lys Ala Ile Arg Gly Val Ala Phe His His Ala Gly Leu
                        290                 295                 300
        Gly Arg Asp Glu Arg Val Leu Val Glu Glu Asn Phe Arg Lys Gly Ile
        305                 310                 315                 320
        Ile Lys Ala Val Val Ala Thr Pro Thr Leu Ser Ala Gly Ile Asn Thr
                        325                 330                 335
        Pro Ala Phe Arg Val Ile Ile Arg Asp Ile Trp Arg Tyr Ser Asp Phe
                        340                 345                 350
        Gly Met Glu Arg Ile Pro Ile Ile Glu Val His Gln Met Leu Gly Arg
                        355                 360                 365
        Ala Gly Arg Pro Lys Tyr Asp Glu Val Gly Glu Gly Ile Ile Val Ser
                        370                 375                 380
        Thr Ser Asp Asp Pro Arg Glu Val Met Asn His Tyr Ile Phe Gly Lys
        385                 390                 395                 400
        Pro Glu Lys Leu Phe Ser Gln Leu Ser Asn Glu Ser Asn Leu Arg Ser
                        405                 410                 415
        Gln Val Leu Ala Leu Ile Ala Thr Phe Gly Tyr Ser Thr Val Glu Glu
                        420                 425                 430
        Ile Leu Lys Phe Ile Ser Asn Thr Phe Tyr Ala Tyr Gln Arg Lys Asp
                        435                 440                 445
        Thr Tyr Ser Leu Glu Glu Lys Ile Arg Asn Ile Leu Tyr Phe Leu Leu
        450                 455                 460
        Glu Asn Glu Phe Ile Glu Ile Ser Leu Glu Asp Lys Ile Arg Pro Leu
        465                 470                 475                 480
        Ser Leu Gly Ile Arg Thr Ala Lys Leu Tyr Ile Asp Pro Tyr Thr Ala
                        485                 490                 495
        Lys Met Phe Lys Asp Lys Met Glu Glu Val Val Lys Asp Pro Asn Pro
                        500                 505                 510
        Ile Gly Ile Phe His Leu Ile Ser Leu Thr Pro Asp Ile Thr Pro Phe
                        515                 520                 525
        Asn Tyr Ser Lys Arg Glu Phe Glu Arg Leu Glu Glu Tyr Tyr Glu
                        530                 535                 540
        Phe Lys Asp Arg Leu Tyr Phe Asp Asp Pro Tyr Ile Ser Gly Tyr Asp
        545                 550                 555                 560
        Pro Tyr Leu Glu Arg Lys Phe Phe Arg Ala Phe Lys Thr Ala Leu Val
                        565                 570                 575
```

-continued

```
Leu Leu Ala Trp Ile Asn Glu Val Pro Glu Gly Ile Val Glu Lys
            580                 585                 590

Tyr Ser Val Glu Pro Gly Asp Ile Tyr Arg Ile Val Glu Thr Ala Glu
        595                 600                 605

Trp Leu Val Tyr Ser Leu Lys Glu Ile Ala Lys Val Leu Gly Ala Tyr
    610                 615                 620

Glu Ile Val Asp Tyr Leu Glu Thr Leu Arg Val Arg Val Lys Tyr Gly
625                 630                 635                 640

Ile Arg Glu Glu Leu Ile Pro Leu Met Gln Leu Pro Leu Val Gly Arg
                645                 650                 655

Arg Arg Ala Arg Ala Leu Tyr Asn Ser Gly Phe Arg Ser Ile Glu Asp
            660                 665                 670

Ile Ser Gln Ala Arg Pro Glu Glu Leu Leu Lys Ile Glu Gly Ile Gly
        675                 680                 685

Val Lys Thr Val Glu Ala Ile Phe Lys Phe Leu Gly Lys Asn Val Lys
    690                 695                 700

Ile Ser Glu Lys Pro Arg Lys Ser Thr Leu Asp Tyr Phe Leu Lys Ser
705                 710                 715                 720

<210> SEQ ID NO 14
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 14

Gln Met Leu Gly Arg Ala Gly Arg
1               5

<210> SEQ ID NO 15
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 15

Gln Met Leu Gly Arg Ala Gly Arg Pro
1               5

<210> SEQ ID NO 16
<211> LENGTH: 829
<212> TYPE: PRT
<213> ORGANISM: Haloferax volcanii

<400> SEQUENCE: 16

Met Arg Thr Ala Asp Leu Thr Gly Leu Pro Thr Gly Ile Pro Glu Ala
1               5                   10                  15

Leu Arg Asp Glu Gly Ile Glu Glu Leu Tyr Pro Pro Gln Ala Glu Ala
            20                  25                  30

Val Glu Ala Gly Leu Thr Asp Gly Glu Ser Leu Val Ala Ala Val Pro
        35                  40                  45

Thr Ala Ser Gly Lys Thr Leu Ile Ala Glu Leu Ala Met Leu Ser Ser
    50                  55                  60

Val Ala Arg Gly Gly Lys Ala Leu Tyr Ile Val Pro Leu Arg Ala Leu
65                  70                  75                  80

Ala Ser Glu Lys Lys Ala Glu Phe Glu Arg Trp Glu Glu Tyr Gly Ile
                85                  90                  95
```

```
Asp Val Gly Val Ser Thr Gly Asn Tyr Glu Ser Asp Gly Glu Trp Leu
            100                 105                 110

Ser Ser Arg Asp Ile Ile Val Ala Thr Ser Glu Lys Val Asp Ser Leu
            115                 120                 125

Val Arg Asn Asn Ala Ala Trp Met Asp Gln Leu Thr Cys Val Val Ala
            130                 135                 140

Asp Glu Val His Leu Val Asp Asp Arg His Arg Gly Pro Thr Leu Glu
145                 150                 155                 160

Val Thr Leu Ala Lys Leu Arg Arg Leu Asn Thr Asn Leu Gln Val Val
                165                 170                 175

Ala Leu Ser Ala Thr Val Gly Asn Ala Gly Val Val Ser Asp Trp Leu
            180                 185                 190

Asp Ala Glu Leu Val Lys Ser Asp Trp Arg Pro Ile Asp Leu Lys Met
            195                 200                 205

Gly Val His Tyr Gly Asn Ala Val Ser Phe Ala Asp Gly Ser Gln Arg
            210                 215                 220

Glu Val Pro Val Gly Arg Gly Glu Arg Gln Thr Pro Ala Leu Val Ala
225                 230                 235                 240

Asp Ala Leu Glu Gly Asp Gly Glu Gly Asp Gln Gly Ser Ser Leu Val
                245                 250                 255

Phe Val Asn Ser Arg Arg Asn Ala Glu Ser Ala Ala Arg Arg Met Ala
            260                 265                 270

Asp Val Thr Glu Arg Tyr Val Thr Gly Asp Glu Arg Ser Asp Leu Ala
            275                 280                 285

Glu Leu Ala Ala Glu Ile Arg Asp Val Ser Asp Thr Glu Thr Ser Asp
            290                 295                 300

Asp Leu Ala Asn Ala Val Ala Lys Gly Ala Ala Phe His His Ala Gly
305                 310                 315                 320

Leu Ala Ala Glu His Arg Thr Leu Val Glu Asp Ala Phe Arg Asp Arg
                325                 330                 335

Leu Ile Lys Cys Ile Cys Ala Thr Pro Thr Leu Ala Ala Gly Val Asn
            340                 345                 350

Thr Pro Ser Arg Arg Val Val Arg Asp Trp Gln Arg Tyr Asp Gly
            355                 360                 365

Asp Tyr Gly Gly Met Lys Pro Leu Asp Val Leu Glu Val His Gln Met
            370                 375                 380

Met Gly Arg Ala Gly Arg Pro Gly Leu Asp Pro Tyr Gly Glu Ala Val
385                 390                 395                 400

Leu Leu Ala Lys Asp Ala Asp Ala Arg Asp Glu Leu Phe Glu Arg Tyr
                405                 410                 415

Ile Trp Ala Asp Ala Glu Asp Val Arg Ser Lys Leu Ala Ala Glu Pro
            420                 425                 430

Ala Leu Arg Thr His Leu Leu Ala Thr Val Ala Ser Gly Phe Ala His
            435                 440                 445

Thr Arg Glu Gly Leu Leu Glu Phe Leu Asp Gln Thr Leu Tyr Ala Thr
            450                 455                 460

Gln Thr Asp Asp Pro Glu Arg Leu Gly Gln Val Thr Asp Arg Val Leu
465                 470                 475                 480

Asp Tyr Leu Glu Val Asn Gly Phe Val Glu Phe Gly Glu Thr Ile
                485                 490                 495

Gln Ala Thr Pro Val Gly His Thr Val Ser Arg Leu Tyr Leu Asp Pro
            500                 505                 510
```

Met Ser Ala Ala Glu Ile Ile Asp Gly Leu Glu Trp Ala Ala Asp His
            515                 520                 525

Arg Thr Glu Lys Leu Arg Ala Leu Ala Gly Thr Pro Glu Lys Pro
    530                 535                 540

Thr Arg Asp Arg Ser Glu Ser Asp Glu Ser Gly Gly Phe Gln Arg Ala
545                 550                 555                 560

Ser Glu Met Val Ala Asp Asp Gly Asp Gly Gly Gly Glu Asp Gly
            565                 570                 575

Val Gly Ala Asn Gly Asp Gly Asp Ser Asp Asp Ala Asp Gly Val Glu
                580                 585                 590

Thr Asp Arg Thr Tyr Pro Thr Pro Leu Gly Leu Tyr His Leu Val Cys
            595                 600                 605

Arg Thr Pro Asp Met Tyr Gln Leu Tyr Leu Lys Ser Gly Asp Arg Glu
    610                 615                 620

Thr Tyr Thr Glu Leu Cys Tyr Glu Arg Glu Pro Glu Phe Leu Gly Arg
625                 630                 635                 640

Val Pro Ser Glu Tyr Glu Asp Val Ala Phe Glu Asp Trp Leu Ser Ala
            645                 650                 655

Leu Lys Thr Ala Lys Leu Leu Glu Asp Trp Val Gly Glu Val Asp Glu
    660                 665                 670

Asp Arg Ile Thr Glu Arg Tyr Gly Val Gly Pro Gly Asp Ile Arg Gly
    675                 680                 685

Lys Val Glu Thr Ser Glu Trp Leu Leu Gly Ala Ala Glu Arg Leu Ala
    690                 695                 700

Thr Glu Leu Asp Leu Asp Ser Val Tyr Ala Val Arg Glu Ala Lys Lys
705                 710                 715                 720

Arg Val Glu Tyr Gly Val Arg Glu Glu Leu Leu Asp Leu Ala Gly Val
            725                 730                 735

Arg Gly Val Gly Arg Lys Arg Ala Arg Arg Leu Phe Glu Ala Gly Val
            740                 745                 750

Glu Thr Arg Ala Asp Leu Arg Glu Ala Asp Lys Pro Arg Val Leu Ala
            755                 760                 765

Ala Leu Arg Gly Arg Arg Lys Thr Ala Glu Asn Ile Leu Glu Ala Ala
    770                 775                 780

Gly Arg Lys Asp Pro Ser Met Asp Ala Val Asp Glu Asp Ala Pro
785                 790                 795                 800

Asp Asp Ala Val Pro Asp Ala Gly Phe Glu Thr Ala Lys Glu Arg
                805                 810                 815

Ala Asp Gln Gln Ala Ser Leu Gly Asp Phe Glu Gly Ser
            820                 825

<210> SEQ ID NO 17
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 17

Gln Met Met Gly Arg Ala Gly Arg
1               5

<210> SEQ ID NO 18
<211> LENGTH: 9
<212> TYPE: PRT
<213> ORGANISM: Artificial sequence
<220> FEATURE:

<223> OTHER INFORMATION: Exemplary extended Hel308 motif

<400> SEQUENCE: 18

Gln Met Met Gly Arg Ala Gly Arg Pro
1               5

<210> SEQ ID NO 19
<211> LENGTH: 824
<212> TYPE: PRT
<213> ORGANISM: Halorubrum lacusprofundi

<400> SEQUENCE: 19

Met Gln Pro Ser Ser Leu Ser Gly Leu Pro Ala Gly Val Gly Glu Ala
1               5                   10                  15

Leu Glu Ala Glu Gly Val Ala Glu Leu Tyr Pro Pro Gln Glu Ala Ala
                20                  25                  30

Val Glu Ala Gly Val Ala Asp Gly Glu Ser Leu Val Ala Ala Val Pro
            35                  40                  45

Thr Ala Ser Gly Lys Thr Leu Ile Ala Glu Leu Ala Met Leu Ser Ser
    50                  55                  60

Ile Glu Arg Gly Gly Lys Ala Leu Tyr Ile Val Pro Leu Arg Ala Leu
65                  70                  75                  80

Ala Ser Glu Lys Lys Thr Glu Phe Glu Arg Trp Glu Phe Gly Val
                85                  90                  95

Thr Val Gly Val Ser Thr Gly Asn Tyr Glu Ser Asp Gly Glu Trp Leu
                100                 105                 110

Ala Thr Arg Asp Ile Ile Val Ala Thr Ser Glu Lys Val Asp Ser Leu
            115                 120                 125

Ile Arg Asn Gly Ala Pro Trp Ile Asp Asp Leu Thr Cys Val Val Ser
    130                 135                 140

Asp Glu Val His Leu Val Asp Asp Pro Asn Arg Gly Pro Thr Leu Glu
145                 150                 155                 160

Val Thr Leu Ala Lys Leu Arg Lys Val Asn Pro Gly Leu Gln Thr Val
                165                 170                 175

Ala Leu Ser Ala Thr Val Gly Asn Ala Asp Val Ile Ala Glu Trp Leu
            180                 185                 190

Asp Ala Glu Leu Val Glu Ser Asp Trp Arg Pro Ile Asp Leu Arg Met
        195                 200                 205

Gly Val His Phe Gly Asn Ala Ile Asp Phe Ala Asp Gly Ser Lys Arg
    210                 215                 220

Glu Val Pro Val Glu Arg Gly Glu Asp Gln Thr Ala Arg Leu Val Ala
225                 230                 235                 240

Asp Ala Leu Asp Thr Glu Glu Asp Gly Gln Gly Gly Ser Ser Leu Val
                245                 250                 255

Phe Val Asn Ser Arg Arg Asn Ala Glu Ser Ser Ala Arg Lys Leu Thr
            260                 265                 270

Asp Val Thr Gly Pro Arg Leu Thr Asp Glu Arg Asp Gln Leu Arg
        275                 280                 285

Glu Leu Ala Asp Glu Ile Arg Ser Gly Ser Asp Thr Asp Thr Ala Ser
    290                 295                 300

Asp Leu Ala Asp Ala Val Glu Gln Gly Ser Ala Phe His His Ala Gly
305                 310                 315                 320

Leu Arg Ser Glu Asp Arg Ala Arg Val Glu Asp Ala Phe Arg Asp Arg
                325                 330                 335

Leu Ile Lys Cys Ile Ser Ala Thr Pro Thr Leu Ala Ala Gly Val Asn

-continued

```
                340                 345                 350
Thr Pro Ala Arg Arg Val Ile Val Arg Asp Trp Arg Arg Tyr Asp Gly
            355                 360                 365
Glu Phe Gly Gly Met Lys Pro Leu Asp Val Leu Glu Val His Gln Met
        370                 375                 380
Cys Gly Arg Ala Gly Arg Pro Gly Leu Asp Pro Tyr Gly Glu Ala Val
385                 390                 395                 400
Leu Leu Ala Asn Asp Ala Asp Thr Lys Glu Glu Leu Phe Glu Arg Tyr
                405                 410                 415
Leu Trp Ala Asp Pro Glu Pro Val Arg Ser Lys Leu Ala Ala Glu Pro
            420                 425                 430
Ala Leu Arg Thr His Val Leu Ala Thr Val Ala Ser Gly Phe Ala Ser
        435                 440                 445
Thr Arg Asp Gly Leu Leu Ser Phe Leu Asp Asn Thr Leu Tyr Ala Thr
    450                 455                 460
Gln Thr Asp Asp Glu Gly Arg Leu Ala Ala Val Thr Asp Thr Val Leu
465                 470                 475                 480
Asp Tyr Leu Ala Val Asn Asp Phe Ile Glu Arg Asp Arg Asp Gly Gly
                485                 490                 495
Ser Glu Ser Leu Thr Ala Thr Gly Ile Gly His Thr Val Ser Arg Leu
            500                 505                 510
Tyr Leu Asp Pro Met Ser Ala Ala Glu Met Ile Asp Gly Leu Arg Ser
        515                 520                 525
Val Ala Arg Asp Ala Ala Asp Thr Gly Ala Ser Ala Glu Ala Asp Asn
    530                 535                 540
Gly Glu Phe Val Arg Thr Gly Asp Ala Asp Ala Ser Gly Gly Asp
545                 550                 555                 560
Glu Pro Gly Phe Gly Thr Tyr Thr Arg Ala Gly Asp Asp Glu Ser Gly
                565                 570                 575
Glu Arg Glu Thr Glu Asn Glu Glu Thr Asp Glu Glu Thr Glu Ala
            580                 585                 590
Ser Glu Val Thr Pro Leu Gly Leu Tyr His Leu Ile Ser Arg Thr Pro
        595                 600                 605
Asp Met Tyr Glu Leu Tyr Leu Lys Ser Gly Asp Arg Glu Thr Tyr Thr
    610                 615                 620
Glu Leu Cys Tyr Glu Arg Glu Thr Glu Phe Leu Gly Asp Val Pro Ser
625                 630                 635                 640
Glu Tyr Glu Asp Val Arg Phe Glu Asp Trp Leu Ala Ser Leu Lys Thr
                645                 650                 655
Ala Arg Leu Leu Glu Asp Trp Val Asn Glu Val Asp Glu Asp Arg Ile
            660                 665                 670
Thr Glu Arg Tyr Gly Val Gly Pro Gly Asp Ile Arg Gly Lys Val Asp
        675                 680                 685
Thr Ala Glu Trp Leu Leu Arg Ala Ala Glu Thr Leu Ala Arg Asp Val
    690                 695                 700
Glu Gly Val Asp Gly Asp Val Val Ala Val Arg Glu Ala Arg Lys
705                 710                 715                 720
Arg Ile Glu Tyr Gly Val Arg Glu Glu Leu Leu Asp Leu Ala Gly Val
                725                 730                 735
Arg Asn Val Gly Arg Lys Arg Ala Arg Arg Leu Phe Glu Ala Gly Ile
            740                 745                 750
Glu Thr Arg Ala Asp Leu Arg Glu Ala Asp Lys Ala Val Val Leu Gly
        755                 760                 765
```

```
Ala Leu Arg Gly Arg Glu Arg Thr Ala Glu Arg Ile Leu Glu His Ala
            770                 775                 780

Gly Arg Glu Asp Pro Ser Met Asp Asp Val Arg Pro Asp Lys Ser Ala
785                 790                 795                 800

Ser Ala Ala Ala Thr Ala Gly Ser Ala Ser Asp Glu Asp Gly Glu Gly
            805                 810                 815

Gln Ala Ser Leu Gly Asp Phe Arg
            820

<210> SEQ ID NO 20
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 20

Gln Met Cys Gly Arg Ala Gly Arg
1               5

<210> SEQ ID NO 21
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 21

Gln Met Cys Gly Arg Ala Gly Arg Pro
1               5

<210> SEQ ID NO 22
<211> LENGTH: 707
<212> TYPE: PRT
<213> ORGANISM: Cenarchaeum symbiosum

<400> SEQUENCE: 22

Met Arg Ile Ser Glu Leu Asp Ile Pro Arg Pro Ala Ile Glu Phe Leu
1               5                   10                  15

Glu Gly Glu Gly Tyr Lys Lys Leu Tyr Pro Pro Gln Ala Ala Ala Ala
            20                  25                  30

Lys Ala Gly Leu Thr Asp Gly Lys Ser Val Leu Val Ser Ala Pro Thr
        35                  40                  45

Ala Ser Gly Lys Thr Leu Ile Ala Ala Ile Ala Met Ile Ser His Leu
    50                  55                  60

Ser Arg Asn Arg Gly Lys Ala Val Tyr Leu Ser Pro Leu Arg Ala Leu
65                  70                  75                  80

Ala Ala Glu Lys Phe Ala Glu Phe Gly Lys Ile Gly Gly Ile Pro Leu
                85                  90                  95

Gly Arg Pro Val Arg Val Gly Val Ser Thr Gly Asp Phe Glu Lys Ala
            100                 105                 110

Gly Arg Ser Leu Gly Asn Asn Asp Ile Leu Val Leu Thr Asn Glu Arg
        115                 120                 125

Met Asp Ser Leu Ile Arg Arg Arg Pro Asp Trp Met Asp Glu Val Gly
    130                 135                 140

Leu Val Ile Ala Asp Glu Ile His Leu Ile Gly Asp Arg Ser Arg Gly
145                 150                 155                 160

Pro Thr Leu Glu Met Val Leu Thr Lys Leu Arg Gly Leu Arg Ser Ser
                165                 170                 175
```

```
Pro Gln Val Val Ala Leu Ser Ala Thr Ile Ser Asn Ala Asp Glu Ile
            180                 185                 190

Ala Gly Trp Leu Asp Cys Thr Leu Val His Ser Thr Trp Arg Pro Val
        195                 200                 205

Pro Leu Ser Glu Gly Val Tyr Gln Asp Gly Glu Val Ala Met Gly Asp
    210                 215                 220

Gly Ser Arg His Glu Val Ala Ala Thr Gly Gly Pro Ala Val Asp
225                 230                 235                 240

Leu Ala Ala Glu Ser Val Ala Glu Gly Gly Gln Ser Leu Ile Phe Ala
                245                 250                 255

Asp Thr Arg Ala Arg Ser Ala Ser Leu Ala Ala Lys Ala Ser Ala Val
            260                 265                 270

Ile Pro Glu Ala Lys Gly Ala Asp Ala Ala Lys Leu Ala Ala Ala Ala
        275                 280                 285

Lys Lys Ile Ile Ser Ser Gly Gly Glu Thr Lys Leu Ala Lys Thr Leu
    290                 295                 300

Ala Glu Leu Val Glu Lys Gly Ala Ala Phe His His Ala Gly Leu Asn
305                 310                 315                 320

Gln Asp Cys Arg Ser Val Val Glu Glu Phe Arg Ser Gly Arg Ile
                325                 330                 335

Arg Leu Leu Ala Ser Thr Pro Thr Leu Ala Ala Gly Val Asn Leu Pro
            340                 345                 350

Ala Arg Arg Val Val Ile Ser Ser Val Met Arg Tyr Asn Ser Ser Ser
        355                 360                 365

Gly Met Ser Glu Pro Ile Ser Ile Leu Glu Tyr Lys Gln Leu Cys Gly
    370                 375                 380

Arg Ala Gly Arg Pro Gln Tyr Asp Lys Ser Gly Glu Ala Ile Val Val
385                 390                 395                 400

Gly Gly Val Asn Ala Asp Glu Ile Phe Asp Arg Tyr Ile Gly Glu
                405                 410                 415

Pro Glu Pro Ile Arg Ser Ala Met Val Asp Asp Arg Ala Leu Arg Ile
            420                 425                 430

His Val Leu Ser Leu Val Thr Thr Ser Pro Gly Ile Lys Glu Asp Asp
        435                 440                 445

Val Thr Glu Phe Phe Leu Gly Thr Leu Gly Gly Gln Gln Ser Gly Glu
    450                 455                 460

Ser Thr Val Lys Phe Ser Val Ala Val Ala Leu Arg Phe Leu Gln Glu
465                 470                 475                 480

Glu Gly Met Leu Gly Arg Arg Gly Gly Arg Leu Ala Ala Thr Lys Met
                485                 490                 495

Gly Arg Leu Val Ser Arg Leu Tyr Met Asp Pro Met Thr Ala Val Thr
            500                 505                 510

Leu Arg Asp Ala Val Gly Glu Ala Ser Pro Gly Arg Met His Thr Leu
        515                 520                 525

Gly Phe Leu His Leu Val Ser Glu Cys Ser Glu Phe Met Pro Arg Phe
    530                 535                 540

Ala Leu Arg Gln Lys Asp His Glu Val Ala Glu Met Met Leu Glu Ala
545                 550                 555                 560

Gly Arg Gly Glu Leu Leu Arg Pro Val Tyr Ser Tyr Glu Cys Gly Arg
                565                 570                 575

Gly Leu Leu Ala Leu His Arg Trp Ile Gly Glu Ser Pro Glu Ala Lys
            580                 585                 590
```

```
Leu Ala Glu Asp Leu Lys Phe Glu Ser Gly Asp Val His Arg Met Val
            595                 600                 605

Glu Ser Ser Gly Trp Leu Leu Arg Cys Ile Trp Glu Ile Ser Lys His
        610                 615                 620

Gln Glu Arg Pro Asp Leu Leu Gly Glu Leu Asp Val Leu Arg Ser Arg
625                 630                 635                 640

Val Ala Tyr Gly Ile Lys Ala Glu Leu Val Pro Leu Val Ser Ile Lys
                645                 650                 655

Gly Ile Gly Arg Val Arg Ser Arg Leu Phe Arg Gly Gly Ile Lys
            660                 665                 670

Gly Pro Gly Asp Leu Ala Ala Val Pro Val Glu Arg Leu Ser Arg Val
            675                 680                 685

Glu Gly Ile Gly Ala Thr Leu Ala Asn Asn Ile Lys Ser Gln Leu Arg
    690                 695                 700

Lys Gly Gly
705

<210> SEQ ID NO 23
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 23

Gln Leu Cys Gly Arg Ala Gly Arg
1               5

<210> SEQ ID NO 24
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 24

Gln Leu Cys Gly Arg Ala Gly Arg Pro
1               5

<210> SEQ ID NO 25
<211> LENGTH: 715
<212> TYPE: PRT
<213> ORGANISM: Sulfolobus solfataricus

<400> SEQUENCE: 25

Met Ser Leu Glu Leu Glu Trp Met Pro Ile Glu Asp Leu Lys Leu Pro
1               5                   10                  15

Ser Asn Val Ile Glu Ile Ile Lys Lys Arg Gly Ile Lys Leu Asn
            20                  25                  30

Pro Pro Gln Thr Glu Ala Val Lys Lys Gly Leu Leu Glu Gly Asn Arg
        35                  40                  45

Leu Leu Leu Thr Ser Pro Thr Gly Ser Gly Lys Thr Leu Ile Ala Glu
    50                  55                  60

Met Gly Ile Ile Ser Phe Leu Leu Lys Asn Gly Lys Ala Ile Tyr
65                  70                  75                  80

Val Thr Pro Leu Arg Ala Leu Thr Asn Glu Lys Tyr Leu Thr Phe Lys
                85                  90                  95

Asp Trp Glu Leu Ile Gly Phe Lys Val Ala Met Thr Ser Gly Asp Tyr
            100                 105                 110
```

```
Asp Thr Asp Asp Ala Trp Leu Lys Asn Tyr Asp Ile Ile Thr Thr
            115                 120                 125

Tyr Glu Lys Leu Asp Ser Leu Trp Arg His Arg Pro Glu Trp Leu Asn
130                 135                 140

Glu Val Asn Tyr Phe Val Leu Asp Glu Leu His Tyr Leu Asn Asp Pro
145                 150                 155                 160

Glu Arg Gly Pro Val Val Glu Ser Val Thr Ile Arg Ala Lys Arg Arg
                165                 170                 175

Asn Leu Leu Ala Leu Ser Ala Thr Ile Ser Asn Tyr Lys Gln Ile Ala
            180                 185                 190

Lys Trp Leu Gly Ala Glu Pro Val Ala Thr Asn Trp Arg Pro Val Pro
        195                 200                 205

Leu Ile Glu Gly Val Ile Tyr Pro Glu Arg Lys Lys Lys Glu Tyr Asn
    210                 215                 220

Val Ile Phe Lys Asp Asn Thr Thr Lys Lys Val His Gly Asp Asp Ala
225                 230                 235                 240

Ile Ile Ala Tyr Thr Leu Asp Ser Leu Ser Lys Asn Gly Gln Val Leu
                245                 250                 255

Val Phe Arg Asn Ser Arg Lys Met Ala Glu Ser Thr Ala Leu Lys Ile
            260                 265                 270

Ala Asn Tyr Met Asn Phe Val Ser Leu Asp Glu Asn Ala Leu Ser Glu
        275                 280                 285

Ile Leu Lys Gln Leu Asp Asp Ile Glu Glu Gly Gly Ser Asp Glu Lys
    290                 295                 300

Glu Leu Leu Lys Ser Leu Ile Ser Lys Gly Val Ala Tyr His His Ala
305                 310                 315                 320

Gly Leu Ser Lys Ala Leu Arg Asp Leu Ile Glu Glu Gly Phe Arg Gln
                325                 330                 335

Arg Lys Ile Lys Val Ile Val Ala Thr Pro Thr Leu Ala Ala Gly Val
            340                 345                 350

Asn Leu Pro Ala Arg Thr Val Ile Ile Gly Asp Ile Tyr Arg Phe Asn
        355                 360                 365

Lys Lys Ile Ala Gly Tyr Tyr Asp Glu Ile Pro Ile Met Glu Tyr Lys
    370                 375                 380

Gln Met Ser Gly Arg Ala Gly Arg Pro Gly Phe Asp Gln Ile Gly Glu
385                 390                 395                 400

Ser Ile Val Val Val Arg Asp Lys Glu Asp Val Asp Arg Val Phe Lys
                405                 410                 415

Lys Tyr Val Leu Ser Asp Val Glu Pro Ile Glu Ser Lys Leu Gly Ser
            420                 425                 430

Glu Arg Ala Phe Tyr Thr Phe Leu Leu Gly Ile Leu Ser Ala Glu Gly
        435                 440                 445

Asn Leu Ser Glu Lys Gln Leu Glu Asn Phe Ala Tyr Glu Ser Leu Leu
    450                 455                 460

Ala Lys Gln Leu Val Asp Val Tyr Phe Asp Arg Ala Ile Arg Trp Leu
465                 470                 475                 480

Leu Glu His Ser Phe Ile Lys Glu Gly Asn Thr Phe Ala Leu Thr
                485                 490                 495

Asn Phe Gly Lys Arg Val Ala Asp Leu Tyr Ile Asn Pro Phe Thr Ala
            500                 505                 510

Asp Ile Ile Arg Lys Gly Leu Glu Gly His Lys Ala Ser Cys Glu Leu
        515                 520                 525

Ala Tyr Leu His Leu Leu Ala Phe Thr Pro Asp Gly Pro Leu Val Ser
```

```
                530                 535                 540
Val Gly Arg Asn Glu Glu Glu Leu Ile Glu Leu Leu Glu Asp Leu
545                 550                 555                 560

Asp Cys Glu Leu Leu Ile Glu Pro Tyr Glu Glu Asp Glu Tyr Ser
                565                 570                 575

Leu Tyr Ile Asn Ala Leu Lys Val Ala Leu Ile Met Lys Asp Trp Met
            580                 585                 590

Asp Glu Val Asp Glu Asp Thr Ile Leu Ser Lys Tyr Asn Ile Gly Ser
        595                 600                 605

Gly Asp Leu Arg Asn Met Val Glu Thr Met Asp Trp Leu Thr Tyr Ser
    610                 615                 620

Ala Tyr His Leu Ser Arg Glu Leu Lys Leu Asn Glu His Ala Asp Lys
625                 630                 635                 640

Leu Arg Ile Leu Asn Leu Arg Val Arg Asp Gly Ile Lys Glu Glu Leu
                645                 650                 655

Leu Glu Leu Val Gln Ile Ser Gly Val Gly Arg Lys Arg Ala Arg Leu
                660                 665                 670

Leu Tyr Asn Asn Gly Ile Lys Glu Leu Gly Asp Val Val Met Asn Pro
            675                 680                 685

Asp Lys Val Lys Asn Leu Leu Gly Gln Lys Leu Gly Glu Lys Val Val
        690                 695                 700

Gln Glu Ala Ala Arg Leu Leu Asn Arg Phe His
705                 710                 715

<210> SEQ ID NO 26
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 26

Gln Met Ser Gly Arg Ala Gly Arg
1               5

<210> SEQ ID NO 27
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 27

Gln Met Ser Gly Arg Ala Gly Arg Pro
1               5

<210> SEQ ID NO 28
<211> LENGTH: 685
<212> TYPE: PRT
<213> ORGANISM: Methanogenium frigidum

<400> SEQUENCE: 28

Met Asp Leu Ser Leu Pro Lys Ala Phe Ile Gln Tyr Tyr Lys Asp Lys
1               5                   10                  15

Gly Ile Glu Ser Leu Tyr Pro Pro Gln Ser Glu Cys Ile Glu Asn Gly
            20                  25                  30

Leu Leu Asp Gly Ala Asp Leu Leu Val Ala Ile Pro Thr Ala Ser Gly
        35                  40                  45

Lys Thr Leu Ile Ala Glu Met Ala Met His Ala Ala Ile Ala Arg Gly
```

```
            50                  55                  60
Gly Met Cys Leu Tyr Ile Val Pro Leu Lys Ala Leu Ala Thr Glu Lys
65                  70                  75                  80

Ala Gln Glu Phe Lys Gly Lys Gly Ala Glu Ile Gly Val Ala Thr Gly
                85                  90                  95

Asp Tyr Asp Gln Lys Glu Lys Arg Leu Gly Ser Asn Asp Ile Val Ile
            100                 105                 110

Ala Thr Ser Glu Lys Val Asp Ser Leu Leu Arg Asn Gly Val Pro Trp
        115                 120                 125

Leu Ser Gln Val Thr Cys Leu Val Val Asp Glu Val His Leu Ile Asp
130                 135                 140

Asp Glu Ser Arg Gly Pro Thr Leu Glu Met Val Ile Thr Lys Leu Arg
145                 150                 155                 160

His Ala Ser Pro Asp Met Gln Val Ile Gly Leu Ser Ala Thr Ile Gly
                165                 170                 175

Asn Pro Lys Glu Leu Ala Gly Trp Leu Gly Ala Asp Leu Ile Thr Ser
            180                 185                 190

Asp Trp Arg Pro Val Asp Leu Arg Glu Gly Ile Cys Tyr His Asn Thr
        195                 200                 205

Ile Tyr Phe Asp Asn Glu Asp Lys Glu Ile Pro Ala Pro Ala Lys Thr
    210                 215                 220

Glu Asp Ile Asn Leu Leu Leu Asp Cys Val Ala Asp Gly Gly Gln Cys
225                 230                 235                 240

Leu Val Phe Val Ser Ser Arg Arg Asn Ala Glu Gly Tyr Ala Lys Arg
                245                 250                 255

Ala Ala Thr Ala Leu Lys Cys Ser His Ala Ala Leu Asp Ser Ile Ala
            260                 265                 270

Glu Lys Leu Glu Ala Ala Ala Glu Thr Asp Met Gly Arg Val Leu Ala
        275                 280                 285

Thr Cys Val Lys Lys Gly Ala Ala Phe His His Ala Gly Met Asn Arg
290                 295                 300

Met Gln Arg Thr Leu Val Glu Gly Gly Phe Arg Asp Gly Phe Ile Lys
305                 310                 315                 320

Ser Ile Ser Ser Thr Pro Thr Leu Ala Ala Gly Leu Asn Leu Pro Ala
                325                 330                 335

Arg Arg Val Ile Ile Arg Asp Tyr Leu Arg Tyr Ser Gly Gly Glu Gly
            340                 345                 350

Met Arg Pro Ile Pro Val Arg Glu Tyr Arg Gln Met Ala Gly Arg Ala
        355                 360                 365

Gly Arg Pro His Leu Asp Pro Tyr Gly Glu Ala Ile Leu Ile Ala Lys
    370                 375                 380

Thr Glu Tyr Ala Val Asn Asp Leu His Glu Glu Tyr Val Glu Ala Pro
385                 390                 395                 400

Asp Glu Asp Val Thr Ser Arg Cys Gly Glu Lys Gly Val Leu Thr Ala
                405                 410                 415

His Ile Leu Ser Leu Ile Ala Thr Gly Tyr Ala Arg Ser Tyr Asp Glu
            420                 425                 430

Leu Met Ala Phe Leu Glu Lys Thr Leu Tyr Ala Tyr Gln His Thr Gly
        435                 440                 445

Lys Lys Ala Leu Thr Arg Thr Leu Asp Asp Ala Leu Gly Phe Leu Thr
    450                 455                 460

Glu Ala Glu Met Val Thr Asp Leu Ser Gly Met Leu His Ala Thr Glu
465                 470                 475                 480
```

```
Tyr Gly Asp Leu Thr Ser Arg Leu Tyr Ile Asp Pro His Ser Ala Glu
                485                 490                 495

Ile Ile Thr Thr Ala Leu Arg Glu Glu Gly Leu Thr Asp Leu Ala
            500                 505                 510

Leu Leu Gln Leu Leu Cys Met Thr Pro Asp Met Phe Thr Leu Tyr Val
            515                 520                 525

Lys Lys Asn Asp Leu Gly Thr Leu Glu Lys Phe Phe Glu His Glu
        530                 535                 540

Glu Glu Phe Arg Thr Glu Phe Ser Tyr Asp Glu Met Glu Asp Phe Phe
545                 550                 555                 560

Arg Ser Leu Lys Thr Ala Met Leu Leu Ser Asp Trp Thr Asp Glu Ile
                565                 570                 575

Gly Asp Asp Thr Ile Cys Thr Arg Phe Gly Val Gly Pro Gly Asp Ile
            580                 585                 590

Phe Asn Ala Val Gln Gly Ile Ser Trp Leu Leu His Ala Ser Gly Arg
595                 600                 605

Leu Ala Arg Leu Val Ala Pro Glu His Arg Asp Ala Val Glu Glu Thr
        610                 615                 620

Thr Leu Arg Val Arg His Gly Ile Arg Arg Glu Leu Ile Pro Leu Val
625                 630                 635                 640

Arg Val Lys Gly Ile Gly Arg Val Arg Ala Arg Arg Leu Phe Asn Asn
                645                 650                 655

Gly Ile Thr Gly Pro Glu Leu Leu Ala Ala Asp Pro Ser Val Val
            660                 665                 670

Gly His Ile Val Gly Gly Lys Thr Ala Glu Ser Ile Ile
        675                 680                 685

<210> SEQ ID NO 29
<211> LENGTH: 775
<212> TYPE: PRT
<213> ORGANISM: Methanothermococcus okinawensis

<400> SEQUENCE: 29

Met Leu Met Leu Met Glu Val Leu Lys Glu Asn Gly Ile Ala Glu Leu
1               5                   10                  15

Arg Pro Pro Gln Lys Lys Val Glu Gly Gly Leu Leu Asn Lys Asn
            20                  25                  30

Lys Asn Phe Leu Ile Cys Ile Pro Thr Ala Ser Gly Lys Thr Leu Ile
        35                  40                  45

Gly Glu Met Ala Phe Ile Asn His Leu Leu Asp Asn Asn Lys Thr Pro
    50                  55                  60

Thr Asn Lys Lys Gly Leu Phe Ile Val Pro Leu Lys Ala Leu Ala Asn
65                  70                  75                  80

Glu Lys Tyr Glu Glu Phe Lys Gly Lys Tyr Glu Lys Tyr Gly Leu Lys
                85                  90                  95

Ile Ala Leu Ser Ile Gly Asp Phe Asp Glu Lys Glu Asp Leu Lys Gly
            100                 105                 110

Tyr Asp Leu Ile Ile Thr Thr Ala Glu Lys Leu Asp Ser Leu Ile Arg
        115                 120                 125

His Lys Val Glu Trp Ile Lys Asp Ile Ser Val Val Ile Asp Glu
    130                 135                 140

Ile His Leu Ile Gly Asp Glu Ser Arg Gly Gly Thr Leu Glu Val Leu
145                 150                 155                 160

Leu Thr Lys Leu Lys Thr Lys Lys Thr Ile Gln Ile Ile Gly Leu Ser
```

```
            165                 170                 175
Ala Thr Ile Gly Asn Pro Glu Glu Leu Ala Lys Trp Leu Asn Ala Glu
            180                 185                 190

Leu Ile Val Asp Glu Trp Arg Pro Val Lys Leu Lys Lys Gly Ile Gly
            195                 200                 205

Tyr Gly Asn Lys Ile Met Phe Ile Asp Asp Asn Gly Asn Thr Ile Asn
            210                 215                 220

Glu Val Ile Val Asp Glu Ile Ser Lys Asn Asn Met Phe Asn Leu Val
225                 230                 235                 240

Val Asp Ser Ile Leu Lys Asp Gly Ser Cys Ile Ile Phe Cys Asn Ser
                245                 250                 255

Lys Arg Gly Ala Val Gly Glu Ala Lys Lys Leu Asn Leu Lys Lys Tyr
                260                 265                 270

Leu Ser Pro Asp Glu Ile Ser Glu Leu Arg His Leu Lys Glu Glu Val
                275                 280                 285

Leu Ser Val Leu Asp Asn Pro Thr Lys Thr Cys Lys Asp Leu Ala Glu
            290                 295                 300

Cys Ile Glu Lys Gly Val Ala Phe His His Ala Gly Leu Thr Tyr Glu
305                 310                 315                 320

Gln Arg Lys Ile Val Glu Glu Gly Phe Arg Lys Lys Leu Ile Lys Ala
                325                 330                 335

Ile Cys Cys Thr Pro Thr Leu Ser Ala Gly Ile Asn Met Pro Cys Arg
                340                 345                 350

Arg Ala Ile Ile Arg Asp Leu Lys Arg Phe Ser Ser Arg Gly Tyr Ile
            355                 360                 365

Pro Ile Pro Lys Met Glu Ile His Gln Cys Ile Gly Arg Ala Gly Arg
            370                 375                 380

Pro Asn Leu Asp Pro Tyr Gly Glu Gly Ile Ile Tyr Ile Asn Asn Thr
385                 390                 395                 400

Glu Asn Pro Glu Leu Ile Glu Asn Ala Lys Asn Tyr Leu Ile Gly Asn
                405                 410                 415

Val Glu Glu Ile Tyr Ser Lys Leu Ser Asn Gln Lys Val Leu Arg Thr
                420                 425                 430

His Met Leu Gly Leu Ile Thr Thr Gly Asp Ile Lys Asn Lys Asn Asp
            435                 440                 445

Leu Glu Glu Phe Ile Lys Asn Thr Phe Tyr Ala Tyr Gln Tyr Gln Asn
            450                 455                 460

Thr Lys Lys Ile Leu Glu Asn Ile Tyr Glu Ile Thr Asn Phe Leu Glu
465                 470                 475                 480

Lys Asn Gly Phe Ile Glu Leu Asn Tyr Arg Arg Asp Glu Asn Lys Asp
                485                 490                 495

Lys Ser Asn Asn Ser His Asn Asn Lys Lys Asn Ile Ser Asn Thr Asn
                500                 505                 510

Asn Ser Ile Lys Met Leu Val Leu Asp Asn Asn Ser Leu Thr Ile
            515                 520                 525

Lys Ser Arg His Glu Glu Asp Val Tyr Tyr Asn Ile Thr Pro Leu Gly
            530                 535                 540

Lys Lys Val Ser Glu Leu Tyr Ile Asp Pro Leu Ser Ala Glu Tyr Ile
545                 550                 555                 560

Ile Asp Gly Leu Lys Asn Leu His Lys Lys Thr Leu Ser Asn Pro Lys
                565                 570                 575

Asn Met Glu Cys Tyr Ile Leu His Ile Leu Tyr Ile Ile Ser Lys Thr
            580                 585                 590
```

```
Thr Glu Met Gln Pro Val Leu Arg Val Arg Lys Glu Glu Asn Asp
            595                 600                 605

Leu Ile Asn Asp Met Ile Lys Leu Asp Ile Asp Val Asp Val Ile
610                 615                 620

Tyr Gly Ile Ser Ser Glu Asn Leu Glu Tyr Phe Lys Asn Ala Lys Leu
625                 630                 635                 640

Phe Tyr Asp Trp Ile Asn Glu Ile Pro Glu Glu Leu Leu Gly
                645                 650                 655

Tyr Asn Ile Glu Pro Gly Ile Leu Arg Tyr Asn Val Glu Gln Ala Lys
                660                 665                 670

Trp Met Ile His Ser Ala Lys Glu Ile Phe Asn Leu Asn Ile Asp
            675                 680                 685

Asn Lys Val Ile Lys Asp Cys Leu Asn Asp Leu Glu Ile Arg Met Glu
            690                 695                 700

Tyr Gly Ala Lys Gln Asp Ile Ile Glu Leu Leu Lys Ile Lys His Ile
705                 710                 715                 720

Gly Arg Ala Arg Ala Arg Ile Leu Tyr Asn Ala Gly Ile Lys Asn Ala
                725                 730                 735

Asn Asp Ile Ile Asn Asn Gln Lys Asn Ile Ile Asn Leu Leu Gly Glu
                740                 745                 750

Lys Ile Ala Arg Lys Ile Leu Ser Glu Leu Gly Val Asp Thr Lys Phe
                755                 760                 765

Gly Gln Met Arg Leu Ser Ile
                770                 775

<210> SEQ ID NO 30
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 30

Gln Cys Ile Gly Arg Ala Gly Arg
1               5

<210> SEQ ID NO 31
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 31

Gln Cys Ile Gly Arg Ala Gly Arg Pro
1               5

<210> SEQ ID NO 32
<211> LENGTH: 699
<212> TYPE: PRT
<213> ORGANISM: Methanotorris igneus

<400> SEQUENCE: 32

Met Gln Lys Tyr Ser His Val Phe Glu Val Leu Lys Glu Asn Gly Ile
1               5                   10                  15

Lys Glu Leu Arg Pro Pro Gln Lys Val Ile Glu Lys Gly Leu Leu
                20                  25                  30

Asn Lys Glu Lys Asn Phe Leu Ile Cys Ile Pro Thr Ala Ser Gly Lys
            35                  40                  45
```

```
Thr Leu Ile Gly Glu Met Ala Leu Ile Asn His Leu Leu Asp Glu Asn
 50                  55                  60

Lys Thr Pro Thr Asn Lys Lys Gly Leu Phe Ile Val Pro Leu Lys Ala
 65                  70                  75                  80

Leu Ala Ser Glu Lys Tyr Glu Glu Phe Lys Arg Lys Tyr Glu Lys Tyr
                 85                  90                  95

Gly Leu Lys Val Ala Leu Ser Ile Gly Asp Tyr Asp Glu Lys Glu Asp
                100                 105                 110

Leu Ser Ser Tyr Asn Ile Ile Ile Thr Thr Ala Glu Lys Leu Asp Ser
                115                 120                 125

Leu Met Arg His Glu Ile Asp Trp Leu Asn Tyr Val Ser Val Ala Ile
            130                 135                 140

Val Asp Glu Ile His Met Ile Asn Asp Glu Lys Arg Gly Gly Thr Leu
145                 150                 155                 160

Glu Val Leu Leu Thr Lys Leu Lys Asn Leu Asp Val Gln Ile Ile Gly
                165                 170                 175

Leu Ser Ala Thr Ile Gly Asn Pro Glu Glu Leu Ala Glu Trp Leu Asn
                180                 185                 190

Ala Glu Leu Ile Ile Asp Asn Trp Arg Pro Val Lys Leu Arg Lys Gly
            195                 200                 205

Ile Phe Phe Gln Asn Lys Ile Met Tyr Leu Asn Gly Ala Cys Lys Glu
            210                 215                 220

Leu Pro Asn Phe Ser Asn Asn Pro Met Leu Asn Leu Val Leu Asp Cys
225                 230                 235                 240

Val Lys Glu Gly Gly Cys Cys Leu Val Phe Cys Asn Ser Lys Asn Gly
                245                 250                 255

Ala Val Ser Glu Ala Lys Lys Leu Asn Leu Lys Lys Tyr Leu Ser Asn
                260                 265                 270

Ser Glu Lys Tyr Glu Leu Gln Lys Leu Lys Glu Glu Ile Leu Ser Ile
            275                 280                 285

Leu Asp Pro Pro Thr Glu Thr Cys Lys Thr Leu Ala Glu Cys Leu Glu
290                 295                 300

Lys Gly Val Ala Phe His His Ala Gly Leu Thr Tyr Glu His Arg Lys
305                 310                 315                 320

Ile Val Glu Glu Gly Phe Arg Asn Lys Leu Ile Lys Val Ile Cys Cys
                325                 330                 335

Thr Pro Thr Leu Ser Ala Gly Ile Asn Ile Pro Cys Arg Arg Ala Ile
                340                 345                 350

Val Arg Asp Leu Met Arg Phe Ser Asn Gly Arg Met Lys Pro Ile Pro
            355                 360                 365

Ile Met Glu Ile His Gln Cys Ile Gly Arg Ala Gly Arg Pro Gly Leu
        370                 375                 380

Asp Pro Tyr Gly Glu Gly Ile Ile Phe Val Lys Asn Glu Arg Asp Leu
385                 390                 395                 400

Glu Arg Ala Glu Gln Tyr Leu Glu Gly Lys Pro Glu Tyr Ile Tyr Ser
                405                 410                 415

Lys Leu Ser Asn Gln Ala Val Leu Arg Thr Gln Leu Leu Gly Met Ile
            420                 425                 430

Ala Thr Arg Glu Ile Glu Asn Glu Phe Asp Leu Ile Ser Phe Ile Lys
            435                 440                 445

Asn Thr Phe Tyr Ala His Gln Tyr Gly Asn Leu Gly Gly Val Leu Arg
        450                 455                 460
```

```
Asn Ile Lys Glu Val Ile Asn Phe Leu Glu Asn Asp Phe Ile Ala
465                 470                 475                 480

Asp Tyr Phe Pro Thr Lys Leu Gly Lys Arg Val Ser Glu Leu Tyr Ile
                485                 490                 495

Asp Pro Leu Ser Ala Lys Ile Ile Ile Asp Gly Leu Lys Glu Met Gly
                500                 505                 510

Asn Val Asp Asn Glu Glu Leu Tyr Tyr Leu Tyr Leu Ile Ser Lys Thr
                515                 520                 525

Leu Glu Met Met Pro Leu Leu Arg Val Asn Ser Phe Glu Glu Leu Asp
                530                 535                 540

Leu Ile Leu Glu Met Glu Glu Ala Gly Ile Tyr Asp Arg Thr Tyr Asp
545                 550                 555                 560

Asp Leu Ala Ala Phe Lys Asn Ala Lys Met Leu Tyr Asp Trp Ile Asn
                565                 570                 575

Glu Val Pro Glu Asp Glu Ile Leu Lys Lys Tyr Lys Ile Glu Pro Gly
                580                 585                 590

Ile Leu Arg Tyr Lys Val Glu Gln Ala Lys Trp Met Ile Tyr Ser Thr
                595                 600                 605

Lys Glu Ile Ala Lys Leu Leu Asn Arg Asn Ile Asp Thr Leu Ser Lys
                610                 615                 620

Leu Glu Ile Arg Leu Glu Tyr Gly Ala Lys Glu Asp Ile Ile Glu Leu
625                 630                 635                 640

Leu Lys Ile Lys Tyr Val Gly Arg Ala Arg Ala Arg Lys Leu Tyr Asp
                645                 650                 655

Ala Gly Ile Arg Ser Val Glu Asp Ile Ile Asn Asn Pro Lys Lys Val
                660                 665                 670

Ala Ser Leu Leu Gly Glu Lys Ile Ala Lys Lys Ile Leu Gly Glu Leu
                675                 680                 685

Gly Met Lys Phe Gly Gln Gln Thr Leu Gln Ile
                690                 695

<210> SEQ ID NO 33
<211> LENGTH: 720
<212> TYPE: PRT
<213> ORGANISM: Thermococcus gammatolerans

<400> SEQUENCE: 33

Met Lys Val Asp Glu Leu Pro Val Asp Glu Arg Leu Lys Ala Val Leu
1               5                   10                  15

Lys Glu Arg Gly Ile Glu Glu Leu Tyr Pro Pro Gln Ala Glu Ala Leu
                20                  25                  30

Lys Ser Gly Ala Leu Glu Gly Arg Asn Leu Val Leu Ala Ile Pro Thr
            35                  40                  45

Ala Ser Gly Lys Thr Leu Val Ser Glu Ile Val Met Val Asn Lys Leu
        50                  55                  60

Ile Gln Glu Gly Gly Lys Ala Val Tyr Leu Val Pro Leu Lys Ala Leu
65                  70                  75                  80

Ala Glu Glu Lys Tyr Arg Glu Phe Lys Glu Trp Glu Lys Leu Gly Leu
                85                  90                  95

Lys Val Ala Ala Thr Thr Gly Asp Tyr Asp Ser Thr Asp Asp Trp Leu
                100                 105                 110

Gly Arg Tyr Asp Ile Ile Val Ala Thr Ala Glu Lys Phe Asp Ser Leu
            115                 120                 125

Leu Arg His Gly Ala Arg Trp Ile Asn Asp Val Lys Leu Val Val Ala
        130                 135                 140
```

```
Asp Glu Val His Leu Ile Gly Ser Tyr Asp Arg Gly Ala Thr Leu Glu
145                 150                 155                 160

Met Ile Leu Thr His Met Leu Gly Arg Ala Gln Ile Leu Ala Leu Ser
                165                 170                 175

Ala Thr Val Gly Asn Ala Glu Glu Leu Ala Glu Trp Leu Asp Ala Ser
                180                 185                 190

Leu Val Val Ser Asp Trp Arg Pro Val Gln Leu Arg Arg Gly Val Phe
            195                 200                 205

His Leu Gly Thr Leu Ile Trp Glu Asp Gly Lys Val Glu Ser Tyr Pro
        210                 215                 220

Glu Asn Trp Tyr Ser Leu Val Val Asp Ala Val Lys Arg Gly Lys Gly
225                 230                 235                 240

Ala Leu Val Phe Val Asn Thr Arg Arg Ser Ala Glu Lys Glu Ala Leu
                245                 250                 255

Ala Leu Ser Lys Leu Val Ser Ser His Leu Thr Lys Pro Glu Lys Arg
            260                 265                 270

Ala Leu Glu Ser Leu Ala Ser Gln Leu Glu Asp Asn Pro Thr Ser Glu
        275                 280                 285

Lys Leu Lys Arg Ala Leu Arg Gly Gly Val Ala Phe His His Ala Gly
290                 295                 300

Leu Ser Arg Val Glu Arg Thr Leu Ile Glu Asp Ala Phe Arg Glu Gly
305                 310                 315                 320

Leu Ile Lys Val Ile Thr Ala Thr Pro Thr Leu Ser Ala Gly Val Asn
                325                 330                 335

Leu Pro Ser Phe Arg Val Ile Arg Asp Thr Lys Arg Tyr Ala Gly
            340                 345                 350

Phe Gly Trp Thr Asp Ile Pro Val Leu Glu Ile Gln Gln Met Met Gly
        355                 360                 365

Arg Ala Gly Arg Pro Arg Tyr Asp Lys Tyr Gly Glu Ala Ile Ile Val
370                 375                 380

Ala Arg Thr Asp Glu Pro Gly Lys Leu Met Glu Arg Tyr Ile Arg Gly
385                 390                 395                 400

Lys Pro Glu Lys Leu Phe Ser Met Leu Ala Asn Glu Gln Ala Phe Arg
                405                 410                 415

Ser Gln Val Leu Ala Leu Ile Thr Asn Phe Gly Ile Arg Ser Phe Pro
            420                 425                 430

Glu Leu Val Arg Phe Leu Glu Arg Thr Phe Tyr Ala His Gln Arg Lys
        435                 440                 445

Asp Leu Ser Ser Leu Glu Tyr Lys Ala Lys Glu Val Val Tyr Phe Leu
450                 455                 460

Ile Glu Asn Glu Phe Ile Asp Leu Asp Leu Glu Asp Arg Phe Ile Pro
465                 470                 475                 480

Leu Pro Phe Gly Lys Arg Thr Ser Gln Leu Tyr Ile Asp Pro Leu Thr
                485                 490                 495

Ala Lys Lys Phe Lys Asp Ala Phe Pro Ala Ile Glu Arg Asn Pro Asn
            500                 505                 510

Pro Phe Gly Ile Phe Gln Leu Ile Ala Ser Thr Pro Asp Met Ala Thr
        515                 520                 525

Leu Thr Ala Arg Arg Glu Met Glu Asp Tyr Leu Asp Leu Ala Tyr
        530                 535                 540

Glu Leu Glu Asp Lys Leu Tyr Ala Ser Ile Pro Tyr Tyr Glu Asp Ser
545                 550                 555                 560
```

```
Arg Phe Gln Gly Phe Leu Gly Gln Val Lys Thr Ala Lys Val Leu Leu
                565                 570                 575

Asp Trp Ile Asn Glu Val Pro Glu Ala Arg Ile Tyr Glu Thr Tyr Ser
            580                 585                 590

Ile Asp Pro Gly Asp Leu Tyr Arg Leu Glu Leu Ala Asp Trp Leu
        595                 600                 605

Met Tyr Ser Leu Ile Glu Leu Tyr Lys Leu Phe Glu Pro Lys Glu Glu
    610                 615                 620

Ile Leu Asn Tyr Leu Arg Asp Leu His Leu Arg Leu Arg His Gly Val
625                 630                 635                 640

Arg Glu Glu Leu Leu Glu Leu Val Arg Leu Pro Asn Ile Gly Arg Lys
                645                 650                 655

Arg Ala Arg Ala Leu Tyr Asn Ala Gly Phe Arg Ser Val Glu Ala Ile
            660                 665                 670

Ala Asn Ala Lys Pro Ala Glu Leu Leu Ala Val Glu Gly Ile Gly Ala
        675                 680                 685

Lys Ile Leu Asp Gly Ile Tyr Arg His Leu Gly Ile Glu Lys Arg Val
690                 695                 700

Thr Glu Glu Lys Pro Lys Arg Lys Gly Thr Leu Glu Asp Phe Leu Arg
705                 710                 715                 720

<210> SEQ ID NO 34
<211> LENGTH: 755
<212> TYPE: PRT
<213> ORGANISM: Thermococcus barophilus

<400> SEQUENCE: 34

Met Leu Ser Thr Lys Pro Lys Ala Tyr Lys Arg Phe Ser Pro Ile Gly
1               5                   10                  15

Tyr Ala Met Gln Val Asp Glu Leu Ser Lys Phe Gly Val Asp Glu Arg
            20                  25                  30

Ile Ile Arg Lys Ile Lys Glu Arg Gly Ile Ser Glu Phe Tyr Pro Pro
        35                  40                  45

Gln Ala Glu Ala Leu Arg Ser Gly Val Leu Asn Gly Glu Asn Leu Leu
    50                  55                  60

Leu Ala Ile Pro Thr Ala Ser Gly Lys Thr Leu Val Ala Glu Ile Val
65                  70                  75                  80

Met Leu His Lys Leu Phe Thr Gly Gly Lys Ala Val Tyr Leu Val
                85                  90                  95

Pro Leu Lys Ala Leu Ala Glu Glu Lys Tyr Arg Glu Phe Lys Thr Trp
            100                 105                 110

Glu Asp Leu Gly Val Arg Val Ala Val Thr Thr Gly Asp Tyr Asp Ser
        115                 120                 125

Ser Glu Glu Trp Leu Gly Lys Tyr Asp Ile Ile Ala Thr Ser Glu
    130                 135                 140

Lys Phe Asp Ser Leu Leu Arg His Lys Ser Arg Trp Ile Arg Asp Val
145                 150                 155                 160

Thr Leu Ile Val Ala Asp Glu Ile His Leu Leu Gly Ser Tyr Asp Arg
                165                 170                 175

Gly Ala Thr Leu Glu Met Ile Leu Ser His Met Leu Gly Lys Ala Gln
            180                 185                 190

Ile Leu Gly Leu Ser Ala Thr Val Gly Asn Ala Glu Glu Leu Ala Glu
        195                 200                 205

Trp Leu Asn Ala Lys Leu Val Val Ser Asp Trp Arg Pro Val Lys Leu
    210                 215                 220
```

-continued

Arg Lys Gly Val Phe Ala His Gly Gln Leu Ile Trp Glu Asp Gly Lys
225                 230                 235                 240

Val Asp Lys Phe Pro Pro Gln Trp Asp Ser Leu Val Ile Asp Ala Val
            245                 250                 255

Lys Lys Gly Lys Gln Ala Leu Val Phe Val Asn Thr Arg Arg Ser Ala
        260                 265                 270

Glu Lys Glu Ala Gly Met Leu Gly Lys Lys Val Arg Arg Leu Leu Thr
    275                 280                 285

Lys Pro Glu Ala Arg Arg Leu Lys Glu Leu Ala Glu Ser Leu Glu Ser
290                 295                 300

Asn Pro Thr Asn Asp Lys Leu Lys Glu Val Leu Val Asn Gly Ala Ala
305                 310                 315                 320

Phe His His Ala Gly Leu Gly Arg Ala Glu Arg Thr Leu Ile Glu Asp
                325                 330                 335

Ala Phe Arg Glu Gly Leu Ile Lys Val Leu Thr Ala Thr Pro Thr Leu
            340                 345                 350

Ala Met Gly Val Asn Leu Pro Ser Phe Arg Val Ile Ile Arg Asp Thr
        355                 360                 365

Lys Arg Tyr Ser Thr Phe Gly Trp Ser Asp Ile Pro Val Leu Glu Ile
    370                 375                 380

Gln Gln Met Ile Gly Arg Ala Gly Arg Pro Lys Tyr Asp Lys Glu Gly
385                 390                 395                 400

Glu Ala Ile Ile Val Ala Lys Thr Glu Lys Pro Glu Glu Leu Met Glu
                405                 410                 415

Lys Tyr Ile Phe Gly Lys Pro Glu Lys Leu Phe Ser Met Leu Ser Asn
            420                 425                 430

Asp Ala Ala Phe Arg Ser Gln Val Leu Ala Leu Ile Thr Asn Phe Gly
        435                 440                 445

Val Glu Ser Phe Arg Glu Leu Ile Gly Phe Leu Glu Lys Thr Phe Tyr
    450                 455                 460

Tyr His Gln Arg Lys Asp Leu Glu Ile Leu Glu Gly Lys Ala Lys Ser
465                 470                 475                 480

Ile Val Tyr Phe Leu Leu Glu Asn Glu Phe Ile Asp Ile Asp Leu Asn
                485                 490                 495

Asp Ser Phe Ile Ala Leu Pro Phe Gly Ile Arg Thr Ser Gln Leu Tyr
            500                 505                 510

Leu Asp Pro Leu Thr Ala Lys Lys Phe Lys Asp Ala Leu Pro Gln Ile
        515                 520                 525

Glu Glu Asn Pro Asn Pro Leu Gly Ile Phe Gln Leu Leu Ala Ser Thr
    530                 535                 540

Pro Asp Met Gly Thr Leu Ser Ile Lys Arg Lys Glu Gln Glu Ser Tyr
545                 550                 555                 560

Leu Asp Tyr Ala Tyr Glu Met Glu Asp Tyr Leu Tyr Arg Ser Ile Pro
                565                 570                 575

Tyr Trp Glu Asp Tyr Glu Phe Gln Lys Phe Leu Ser Glu Val Lys Thr
            580                 585                 590

Ala Lys Leu Leu Leu Asp Trp Ile Asn Glu Val Ser Glu Ala Lys Leu
        595                 600                 605

Ile Glu Ala Tyr Gly Ile Asp Thr Gly Asp Leu Tyr Arg Ile Ile Glu
    610                 615                 620

Leu Ala Asp Trp Leu Met Tyr Ser Leu Ile Glu Leu Ala Lys Val Leu
625                 630                 635                 640

```
Asn Ala Gly Gly Glu Thr Ile Lys Tyr Leu Arg Arg Leu His Leu Arg
                645                 650                 655

Leu Lys His Gly Val Arg Glu Glu Leu Leu Glu Leu Val Glu Leu Pro
            660                 665                 670

Met Ile Gly Arg Arg Arg Ala Arg Ala Leu Tyr Asn Ala Gly Phe Lys
        675                 680                 685

Asn Val Asn Asp Ile Val Lys Ala Lys Pro Ser Glu Leu Leu Ala Val
    690                 695                 700

Glu Gly Ile Gly Val Lys Val Leu Glu Arg Ile Tyr Arg His Phe Gly
705                 710                 715                 720

Val Glu Leu Pro Leu Leu Lys Asn Ile Lys Asp Pro Asp Lys Pro Glu
                725                 730                 735

Asp Lys Pro Lys Glu Lys Pro Lys Pro Lys Lys Gly Thr Leu Asp Tyr
            740                 745                 750

Phe Leu Lys
        755

<210> SEQ ID NO 35
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 35

Gln Met Ile Gly Arg Ala Gly Arg
1               5

<210> SEQ ID NO 36
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 36

Gln Met Ile Gly Arg Ala Gly Arg Pro
1               5

<210> SEQ ID NO 37
<211> LENGTH: 744
<212> TYPE: PRT
<213> ORGANISM: Thermococcus sibiricus

<400> SEQUENCE: 37

Met Lys Leu Asn Lys Leu Lys Ser Tyr Ile Asn Ala Phe Leu Leu Gly
1               5                   10                  15

Met Val Met Ser Met Lys Val Asp Glu Leu Lys Ser Leu Gly Val Asp
            20                  25                  30

Glu Arg Ile Leu Arg Leu Leu Arg Glu Arg Gly Ile Glu Glu Leu Tyr
        35                  40                  45

Pro Pro Gln Ala Asp Ala Leu Lys Thr Glu Val Leu Lys Gly Lys Asn
    50                  55                  60

Leu Val Leu Ala Ile Pro Thr Ala Ser Gly Lys Thr Leu Val Ala Glu
65                  70                  75                  80

Ile Val Met Ile Asn Lys Ile Leu Arg Glu Gly Gly Lys Thr Val Tyr
                85                  90                  95

Leu Val Pro Leu Lys Ala Leu Ala Glu Glu Lys Tyr Lys Glu Phe Lys
                100                 105                 110
```

```
Phe Trp Glu Lys Leu Gly Ile Arg Ile Ala Met Thr Thr Gly Asp Tyr
            115                 120                 125

Asp Ser Thr Glu Glu Trp Leu Gly Lys Tyr Asp Ile Ile Ala Thr
130                 135                 140

Ser Glu Lys Phe Asp Ser Leu Leu Arg His Lys Ser Pro Trp Ile Lys
145                 150                 155                 160

Asp Ile Asn Leu Val Ile Ala Asp Glu Ile His Leu Leu Gly Ser Tyr
                165                 170                 175

Asp Arg Gly Ala Thr Leu Glu Met Ile Leu Ala His Leu Asp Asp Lys
            180                 185                 190

Ala Gln Ile Leu Gly Leu Ser Ala Thr Val Gly Asn Ala Glu Glu Val
        195                 200                 205

Ala Glu Trp Leu Asn Ala Asp Leu Val Met Ser Glu Trp Arg Pro Val
210                 215                 220

Ala Leu Arg Lys Gly Val Phe Tyr His Gly Glu Leu Phe Trp Glu Asp
225                 230                 235                 240

Gly Ser Ile Glu Arg Phe Pro Thr Gln Trp Asp Ser Leu Val Ile Asp
            245                 250                 255

Ala Leu Lys Lys Gly Lys Gln Ala Leu Val Phe Val Asn Thr Arg Arg
            260                 265                 270

Ser Ala Glu Lys Glu Ala Leu Leu Leu Ala Gly Lys Ile Gln Arg Phe
275                 280                 285

Leu Thr Lys Pro Glu Glu Arg Lys Leu Lys Gln Leu Ala Asp Gly Leu
    290                 295                 300

Asp Thr Thr Pro Thr Asn Gln Lys Leu Lys Glu Ala Leu Thr Lys Gly
305                 310                 315                 320

Val Ala Phe His His Ala Gly Leu Gly Arg Thr Glu Arg Ser Ile Ile
                325                 330                 335

Glu Asp Ala Phe Arg Glu Gly Leu Ile Lys Val Ile Ala Thr Pro
            340                 345                 350

Thr Leu Ser Ala Gly Val Asn Leu Pro Ala Tyr Arg Val Ile Ile Arg
    355                 360                 365

Asp Thr Lys Arg Tyr Ser Asn Phe Gly Trp Val Asp Ile Pro Val Leu
370                 375                 380

Glu Ile Gln Gln Met Met Gly Arg Ala Gly Arg Pro Lys Tyr Asp Ile
385                 390                 395                 400

Glu Gly Gln Ala Ile Ile Ile Ala Lys Thr Glu Lys Pro Glu Asp Leu
                405                 410                 415

Met Lys Arg Tyr Val Leu Gly Lys Pro Glu Lys Leu Phe Ser Met Leu
            420                 425                 430

Ser Asn Glu Ala Ser Phe Arg Ser Gln Val Leu Ala Leu Ile Thr Asn
        435                 440                 445

Phe Gly Val Gly Asn Phe Lys Glu Leu Val Asn Phe Leu Glu Arg Thr
450                 455                 460

Phe Tyr Tyr His Gln Arg Lys Asn Leu Glu Ala Leu Glu Gly Lys Ala
465                 470                 475                 480

Lys Ser Ile Val Tyr Phe Leu Phe Glu Asn Glu Phe Ile Asp Ile Asp
                485                 490                 495

Leu Asn Asp Gln Phe Met Pro Leu Pro Leu Gly Ile Arg Thr Ser Gln
            500                 505                 510

Leu Tyr Leu Asp Pro Val Thr Ala Lys Lys Phe Lys Asp Ala Phe Glu
        515                 520                 525

Lys Leu Glu Lys Asn Pro Asn Pro Leu Gly Ile Phe Gln Leu Leu Ala
```

```
                 530                 535                 540
Ser Thr Pro Asp Met Ser Ser Leu Arg Val Lys Arg Lys Glu Gln Glu
545                 550                 555                 560

Asp Leu Leu Asp Tyr Ala Tyr Glu Met Glu Glu Tyr Leu Tyr Gln Asn
                565                 570                 575

Ile Pro Tyr Trp Glu Asp Tyr Lys Phe Glu Lys Phe Leu Gly Glu Thr
                580                 585                 590

Lys Thr Ala Lys Leu Leu Leu Asp Trp Ile Asn Glu Val Asn Asp Val
                595                 600                 605

Lys Ile Leu Glu Thr Tyr Glu Ile Asp Thr Gly Asp Leu Tyr Arg Ile
                610                 615                 620

Leu Glu Leu Val Asp Trp Leu Met Tyr Ser Leu Ile Glu Leu Tyr Lys
625                 630                 635                 640

Leu Phe Asp Pro Lys Pro Glu Val Leu Asp Phe Leu Lys Lys Leu His
                645                 650                 655

Ile Arg Val Lys His Gly Val Arg Glu Glu Leu Leu Glu Leu Ile Thr
                660                 665                 670

Leu Pro Met Ile Gly Arg Lys Arg Ala Arg Ala Leu Tyr Asn Ala Gly
                675                 680                 685

Phe Lys Gly Ile Asp Asp Ile Val Arg Ala Lys Ala Ser Glu Leu Leu
                690                 695                 700

Lys Val Glu Gly Ile Gly Ile Gly Val Ile Glu Lys Ile Tyr Gln His
705                 710                 715                 720

Phe Gly Val Glu Leu Pro Thr Asn Glu Lys Lys Lys Val Lys Lys
                725                 730                 735

Gly Thr Leu Asp Glu Phe Phe Lys
                740

<210> SEQ ID NO 38
<211> LENGTH: 729
<212> TYPE: PRT
<213> ORGANISM: Methanosarcina barkeri fusaro

<400> SEQUENCE: 38

Met Lys Ile Glu Ser Leu Asp Leu Pro Asp Glu Val Lys Gln Phe Tyr
1               5                   10                  15

Leu Asn Ser Gly Ile Met Glu Leu Tyr Pro Pro Gln Ala Glu Ala Val
                20                  25                  30

Glu Lys Gly Leu Leu Glu Gly Arg Asn Leu Leu Ala Ala Ile Pro Thr
            35                  40                  45

Ala Ser Gly Lys Thr Leu Leu Ala Glu Leu Ala Met Leu Lys Ser Ile
        50                  55                  60

Leu Ala Gly Gly Lys Ala Leu Tyr Ile Val Pro Leu Arg Ala Leu Ala
65                  70                  75                  80

Ser Glu Lys Phe Arg Arg Phe Arg Glu Phe Ser Glu Leu Gly Ile Arg
                85                  90                  95

Val Gly Ile Ser Thr Gly Asp Tyr Asp Leu Arg Asp Glu Gly Leu Gly
                100                 105                 110

Val Asn Asp Ile Ile Val Ala Thr Ser Glu Lys Thr Asp Ser Leu Leu
                115                 120                 125

Arg Asn Glu Thr Val Trp Met Gln Glu Ile Ser Val Val Val Ala Asp
            130                 135                 140

Glu Val His Leu Ile Asp Ser Pro Asp Arg Gly Pro Thr Leu Glu Val
145                 150                 155                 160
```

```
Thr Leu Ala Lys Leu Arg Lys Met Asn Pro Ser Cys Gln Ile Leu Ala
            165                 170                 175

Leu Ser Ala Thr Val Gly Asn Ala Asp Glu Leu Ala Val Trp Leu Glu
        180                 185                 190

Ala Glu Leu Val Val Ser Glu Trp Arg Pro Thr Glu Leu Leu Glu Gly
        195                 200                 205

Val Phe Phe Asn Gly Thr Phe Tyr Cys Lys Asp Arg Glu Lys Thr Val
        210                 215                 220

Glu Gln Ser Thr Lys Asp Glu Ala Val Asn Leu Ala Leu Asp Thr Leu
225                 230                 235                 240

Lys Lys Asp Gly Gln Cys Leu Val Phe Glu Ser Ser Arg Lys Asn Cys
                245                 250                 255

Met Ala Phe Ala Lys Lys Ala Ala Ser Thr Val Lys Lys Thr Leu Ser
            260                 265                 270

Ala Glu Asp Arg Asn Ala Leu Ala Gly Ile Ala Asp Glu Ile Leu Glu
        275                 280                 285

Asn Ser Glu Thr Asp Thr Ser Thr Asn Leu Ala Val Cys Ile Arg Ser
        290                 295                 300

Gly Thr Ala Phe His His Ala Gly Leu Thr Thr Pro Leu Arg Glu Leu
305                 310                 315                 320

Val Glu Asp Gly Phe Arg Ala Gly Arg Ile Lys Leu Ile Ser Ser Thr
                325                 330                 335

Pro Thr Leu Ala Ala Gly Leu Asn Leu Pro Ala Arg Arg Val Ile Ile
            340                 345                 350

Arg Asn Tyr Arg Arg Tyr Ser Ser Glu Asp Gly Met Gln Pro Ile Pro
        355                 360                 365

Val Leu Glu Tyr Lys Gln Met Ala Gly Arg Ala Gly Arg Pro Arg Leu
        370                 375                 380

Asp Pro Tyr Gly Glu Ala Val Leu Val Ala Lys Ser Tyr Lys Glu Phe
385                 390                 395                 400

Val Phe Leu Phe Glu Asn Tyr Ile Glu Ala Asn Ala Glu Asp Ile Trp
                405                 410                 415

Ser Lys Leu Gly Thr Glu Asn Ala Leu Arg Thr His Val Leu Ser Thr
            420                 425                 430

Ile Ser Asn Gly Phe Ala Arg Thr Tyr Asp Glu Leu Met Asp Phe Leu
        435                 440                 445

Glu Ala Thr Phe Phe Ala Phe Gln Tyr Ser Asn Phe Gly Leu Ser Thr
        450                 455                 460

Val Val Asn Glu Cys Leu Asn Phe Leu Arg Gln Glu Gly Met Leu Glu
465                 470                 475                 480

Lys Asp Asp Ala Leu Ile Pro Thr Ser Phe Gly Lys Leu Val Ser Arg
                485                 490                 495

Leu Tyr Ile Asp Pro Leu Ser Ala Ala Arg Ile Ala Lys Gly Leu Lys
            500                 505                 510

Gly Ala Lys Ser Leu Ser Glu Leu Thr Leu Leu His Leu Val Cys Ser
        515                 520                 525

Thr Pro Asp Met Arg Leu Leu Tyr Met Arg Ser His Asp Tyr Gln Asp
        530                 535                 540

Ile Asn Asp Tyr Val Met Ala His Ala Ser Glu Phe Val Lys Val Pro
545                 550                 555                 560

Ser Pro Phe Asp Thr Thr Glu Tyr Glu Trp Phe Leu Gly Glu Val Lys
                565                 570                 575

Thr Ser Leu Leu Leu Leu Asp Trp Ile His Glu Lys Ser Glu Asn Glu
```

```
                580             585             590
Ile Cys Leu Lys Phe Gly Thr Gly Glu Gly Asp Ile His Ser Ile Ala
            595             600             605

Asp Ile Ala Glu Trp Ile Met His Val Thr Ser Gln Leu Ala Gly Leu
610             615             620

Leu Asp Leu Lys Gly Ala Arg Glu Ala Ala Glu Leu Glu Lys Arg Ile
625             630             635             640

His Tyr Gly Ala Ala Pro Glu Leu Ile Asp Leu Leu Asn Ile Arg Gly
            645             650             655

Ile Gly Arg Val Arg Ala Arg Lys Leu Tyr Glu Ala Gly Phe Lys Ser
            660             665             670

Ser Ala Glu Leu Ala Glu Val Asp Pro Glu Lys Val Ala Ala Leu Leu
            675             680             685

Gly Pro Lys Ile Ala Asp Arg Ile Phe Lys Gln Ile Arg Gly Arg Gly
            690             695             700

Thr Ser Ser Gly Ile Ile Ala Ser Glu Pro Pro Glu Lys Ser Pro Tyr
705             710             715             720

Ser Gly Gln Lys Thr Ile Ser Asp Tyr
            725

<210> SEQ ID NO 39
<211> LENGTH: 730
<212> TYPE: PRT
<213> ORGANISM: Methanosarcina acetivorans

<400> SEQUENCE: 39

Met Lys Ile Glu Ser Leu Asp Leu Pro Asp Glu Val Lys Arg Phe Tyr
1               5                   10                  15

Glu Asn Ser Gly Ile Pro Glu Leu Tyr Pro Pro Gln Ala Glu Ala Val
            20                  25                  30

Glu Lys Gly Leu Leu Glu Gly Lys Asn Leu Leu Ala Ala Ile Pro Thr
        35                  40                  45

Ala Ser Gly Lys Thr Leu Leu Ala Glu Leu Ala Met Leu Lys Ser Val
    50                  55                  60

Leu Ala Gly Gly Lys Ala Leu Tyr Ile Val Pro Leu Arg Ala Leu Ala
65                  70                  75                  80

Ser Glu Lys Phe Arg Arg Phe Gln Asp Phe Ser Glu Leu Gly Ile Arg
                85                  90                  95

Val Gly Ile Ser Thr Gly Asp Tyr Asp Arg Arg Asp Glu Gly Leu Gly
            100                 105                 110

Ile Asn Asp Ile Ile Val Ala Thr Ser Glu Lys Thr Asp Ser Leu Leu
        115                 120                 125

Arg Asn Glu Thr Ala Trp Met Gln Glu Ile Ser Val Val Val Val Asp
    130                 135                 140

Glu Val His Leu Ile Asp Ser Ala Asp Arg Gly Pro Thr Leu Glu Val
145                 150                 155                 160

Thr Leu Ala Lys Leu Arg Lys Met Asn Pro Phe Cys Gln Ile Leu Ala
                165                 170                 175

Leu Ser Ala Thr Val Gly Asn Ala Asp Glu Leu Ala Ala Trp Leu Asp
            180                 185                 190

Ala Glu Leu Val Leu Ser Glu Trp Arg Pro Thr Asp Leu Met Glu Gly
        195                 200                 205

Val Phe Phe Asp Gly Thr Phe Phe Cys Lys Asp Lys Glu Lys Leu Ile
    210                 215                 220
```

-continued

```
Glu Gln Pro Thr Lys Asp Glu Ala Ile Asn Leu Val Leu Asp Thr Leu
225                 230                 235                 240

Arg Glu Gly Gly Gln Cys Leu Val Phe Glu Ser Ser Arg Lys Asn Cys
            245                 250                 255

Met Gly Phe Ala Lys Lys Ala Thr Ser Ala Val Lys Lys Thr Leu Ser
        260                 265                 270

Ala Glu Asp Lys Glu Lys Leu Ala Gly Ile Ala Asp Glu Ile Leu Glu
    275                 280                 285

Asn Ser Glu Thr Asp Thr Ala Ser Val Leu Ala Ser Cys Val Arg Ala
290                 295                 300

Gly Thr Ala Phe His His Ala Gly Leu Thr Ser Pro Leu Arg Glu Leu
305                 310                 315                 320

Val Glu Thr Gly Phe Arg Glu Gly Tyr Val Lys Leu Ile Ser Ser Thr
                325                 330                 335

Pro Thr Leu Ala Ala Gly Leu Asn Leu Pro Ala Arg Arg Val Ile Ile
            340                 345                 350

Arg Ser Tyr Arg Arg Tyr Ser Ser Asp Ser Gly Met Gln Pro Ile Pro
        355                 360                 365

Val Leu Glu Tyr Lys Gln Met Ala Gly Arg Ala Gly Arg Pro Arg Leu
    370                 375                 380

Asp Pro Tyr Gly Glu Ala Val Leu Leu Ala Lys Ser Tyr Glu Glu Leu
385                 390                 395                 400

Leu Phe Leu Phe Glu Lys Tyr Ile Glu Ala Gly Ala Glu Asp Ile Trp
                405                 410                 415

Ser Lys Leu Gly Thr Glu Asn Ala Leu Arg Thr His Val Leu Ser Thr
            420                 425                 430

Ile Ser Asn Gly Phe Ala Arg Thr Lys Glu Glu Leu Met Asp Phe Leu
        435                 440                 445

Glu Ala Thr Phe Phe Ala Tyr Gln Tyr Ser Asn Phe Gly Leu Ser Val
    450                 455                 460

Val Val Asp Glu Cys Leu Asn Phe Leu Arg Gln Glu Gly Met Leu Glu
465                 470                 475                 480

Gln Asp Ser Asp Ala Leu Ile Ser Thr Met Phe Gly Lys Leu Val Ser
                485                 490                 495

Arg Leu Tyr Ile Asp Pro Leu Ser Ala Ala Leu Ile Ala Lys Gly Leu
            500                 505                 510

Arg Glu Ala Gly Thr Leu Thr Glu Leu Thr Leu Leu His Leu Val Cys
        515                 520                 525

Ser Thr Pro Asp Met Arg Leu Met Tyr Met Arg Ser Gln Asp Tyr Gln
    530                 535                 540

Asp Ile Asn Asp Phe Val Met Ala His Ala Glu Glu Phe Ser Lys Val
545                 550                 555                 560

Pro Ser Pro Phe Asn Ile Val Glu Tyr Glu Trp Phe Leu Ser Glu Val
                565                 570                 575

Lys Thr Ser Leu Leu Leu Met Asp Trp Ile His Glu Lys Pro Glu Asn
            580                 585                 590

Glu Ile Cys Leu Lys Phe Gly Thr Gly Glu Gly Asp Ile His Thr Thr
        595                 600                 605

Ala Asp Ile Ala Glu Trp Ile Met His Val Ala Thr Gln Leu Ala Arg
    610                 615                 620

Leu Leu Asp Leu Lys Gly Ala Lys Glu Ala Ala Glu Leu Glu Lys Arg
625                 630                 635                 640

Ile His Tyr Gly Ala Gly Pro Glu Leu Met Asp Leu Leu Asp Ile Arg
```

```
                    645                 650                 655
Gly Ile Gly Arg Val Arg Ala Arg Lys Leu Tyr Gly Ala Gly Phe Lys
            660                 665                 670

Ser Thr Ala Asp Leu Ala Gly Ala Thr Pro Glu Lys Val Ala Ala Leu
            675                 680                 685

Val Gly Pro Lys Ile Ala Glu Arg Ile Phe Arg Gln Ile Gly Arg Arg
            690                 695                 700

Glu Ala Val Ser Glu Ile Ser Asp Ser Glu Arg Leu Glu Lys Ser Ser
705                 710                 715                 720

Gln Asp Gly Gln Ser Thr Ile Ser Asp Phe
            725                 730

<210> SEQ ID NO 40
<211> LENGTH: 729
<212> TYPE: PRT
<213> ORGANISM: Methanohalophilus mahii

<400> SEQUENCE: 40

Met Lys Ile Glu Glu Leu Asp Leu Pro Ser Glu Ala Ile Glu Val Tyr
1               5                   10                  15

Leu Gln Ala Gly Ile Glu Glu Leu Tyr Pro Pro Gln Ala Asp Ala Val
            20                  25                  30

Glu Lys Gly Leu Leu Gln Gly Glu Asn Leu Leu Ala Ala Ile Pro Thr
        35                  40                  45

Ala Ser Gly Lys Thr Leu Leu Ala Glu Met Ala Met Leu Lys Ala Ile
    50                  55                  60

Lys Lys Gly Gly Lys Ala Leu Tyr Ile Val Pro Leu Arg Ala Leu Ala
65                  70                  75                  80

Ser Glu Lys Phe Arg Asp Phe Lys Arg Phe Glu Ser Leu Gly Ile Lys
                85                  90                  95

Thr Ala Ile Ser Thr Gly Asp Phe Asp Ser Arg Asp Glu Trp Leu Gly
            100                 105                 110

Ser Asn Asp Ile Ile Val Ala Thr Ser Glu Lys Thr Asp Ser Leu Leu
        115                 120                 125

Arg Asn Ser Thr Pro Trp Met Lys Asp Ile Thr Ala Val Ile Val Asp
    130                 135                 140

Glu Val His Leu Leu Asp Ser Ala Asn Arg Gly Pro Thr Leu Glu Val
145                 150                 155                 160

Thr Leu Ala Lys Leu Lys Arg Leu Asn Pro Gly Ala Gln Val Val Ala
                165                 170                 175

Leu Ser Ala Thr Val Gly Asn Ala Met Glu Ile Ala Gln Trp Leu Glu
            180                 185                 190

Ala Lys Leu Val Leu Ser Glu Trp Arg Pro Thr Tyr Leu His Glu Gly
        195                 200                 205

Ile Phe Tyr Gly Asp Ala Ile Asn Phe Asp Glu Asp Gln Thr Phe Ile
    210                 215                 220

Glu Arg Arg His Lys Glu Asp Ser Val Asn Leu Val Ile Asp Thr Val
225                 230                 235                 240

Ile Gln Gly Gly Gln Cys Leu Val Phe Asp Ser Ser Arg Arg Asn Cys
                245                 250                 255

Val Gly Phe Ala Lys Lys Cys Ala Pro Ala Val Gly Glu Leu Leu Asp
            260                 265                 270

Arg Gln Asn Arg Asn Glu Leu Glu Glu Val Ala Lys Glu Val Leu Glu
        275                 280                 285
```

```
Asn Gly Glu Thr Lys Leu Thr Glu Thr Leu Ala Tyr Cys Ile Lys Lys
    290                 295                 300

Gly Val Ala Phe His His Ala Gly Leu Asn Ser Ala His Arg Arg Ile
305                 310                 315                 320

Val Glu Asp Ala Phe Arg Asn Asn Leu Ile Lys Met Ile Cys Ser Thr
                325                 330                 335

Pro Thr Leu Ala Ala Gly Leu Asn Leu Pro Ala Arg Arg Val Ile Ile
            340                 345                 350

Arg Ser Tyr Lys Arg Tyr Asp Pro Asn Ala Gly Met Gln Pro Ile Pro
        355                 360                 365

Val Leu Asp Tyr Lys Gln Met Ala Gly Arg Ala Gly Arg Pro His Leu
    370                 375                 380

Asp Pro Tyr Gly Glu Ala Val Ile Val Lys Thr Tyr Glu Glu Phe
385                 390                 395                 400

Thr Asp Val Leu Glu Arg Tyr Ile Ser Ala Ser Ala Glu Asp Ile Trp
                405                 410                 415

Ser Lys Leu Gly Thr Glu Asn Ala Leu Arg Thr His Ile Leu Ser Thr
            420                 425                 430

Ile Ala Ser Gly Phe Ala Asn Cys His Arg Glu Ile Leu Thr Phe Leu
        435                 440                 445

Gly Ser Thr Phe Phe Ala His Gln Gln Gln Ser Trp Asn Phe Glu Glu
    450                 455                 460

Leu Leu Glu Asp Cys Leu Ile Phe Leu Lys Asn Glu Gly Met Leu Glu
465                 470                 475                 480

Gln Asp Asn Glu Thr Ile Arg Ala Thr Glu Leu Gly Lys Met Ile Ser
                485                 490                 495

Ser Leu Tyr Ile Asp Pro Leu Ser Ala Ser Lys Ile Ile Arg Gly Leu
            500                 505                 510

Glu Lys Thr Thr His Val Thr Asp Met Thr Leu Leu Gln Leu Ile Cys
        515                 520                 525

Ser Thr Pro Asp Met Arg Leu Leu Tyr Leu Arg Asn Arg Asp Tyr Glu
    530                 535                 540

Ile Ile Asn Asp Tyr Val Met Asn His Thr Glu Glu Phe Ile Glu Val
545                 550                 555                 560

Pro Ser Pro Phe Lys Gln Ile Glu Tyr Glu Trp Phe Leu Ser Glu Val
                565                 570                 575

Lys Thr Ala Leu Leu Leu Glu Trp Ile Asn Glu Lys Ser Leu Glu
            580                 585                 590

Lys Ile Val Glu Asn Tyr Gln Val Gly Glu Gly Asp Ile Tyr Ala Ser
        595                 600                 605

Ser Asp Ile Ala Glu Trp Leu Met His Ala Thr Gln Arg Ile Ala Ser
    610                 615                 620

Arg Ile Asn Pro Gln Leu Glu Thr Glu Cys Ala Lys Leu Glu Lys Arg
625                 630                 635                 640

Ile His Tyr Gly Ala Gly Ser Glu Leu Ile Glu Leu Val Glu Ile Pro
                645                 650                 655

Asn Val Gly Arg Ala Arg Ala Arg Lys Leu Phe Lys Lys Gly Tyr Arg
            660                 665                 670

Ser Arg Gln Lys Leu Ala Thr Ala Asp Glu Lys Gln Leu Ala Gly Ile
        675                 680                 685

Val Gly Pro Lys Ile Ala Gln Lys Ile Leu Ser Tyr Leu Gly Arg Glu
    690                 695                 700

Thr Asp Ser Asn Gly Tyr Val Glu Pro Glu Thr Leu Glu Asn Lys Lys
```

-continued

```
                705                 710                 715                 720

Gln Gln Lys Thr Phe Gln Asp Phe Ile
                725

<210> SEQ ID NO 41
<211> LENGTH: 730
<212> TYPE: PRT
<213> ORGANISM: Methanosarcina mazei

<400> SEQUENCE: 41

Met Lys Ile Glu Ser Leu Asp Leu Pro Asp Glu Ile Lys Arg Phe Tyr
1               5                   10                  15

Glu Asn Ser Gly Ile Leu Glu Leu Tyr Pro Pro Gln Ala Glu Ala Val
                20                  25                  30

Glu Lys Gly Leu Leu Glu Gly Lys Asn Leu Leu Ala Ala Ile Pro Thr
            35                  40                  45

Ala Ser Gly Lys Thr Leu Leu Ala Glu Leu Ala Met Leu Lys Ser Val
        50                  55                  60

Leu Asn Gly Gly Lys Ala Leu Tyr Ile Val Pro Leu Arg Ala Leu Ala
65                  70                  75                  80

Ser Glu Lys Phe Arg Arg Phe Gln Glu Phe Ser Val Leu Gly Met Arg
                85                  90                  95

Val Gly Ile Ser Thr Gly Asp Tyr Asp Arg Arg Asp Glu Gly Leu Gly
                100                 105                 110

Ile Asn Asp Ile Ile Val Ala Thr Ser Glu Lys Thr Asp Ser Leu Leu
            115                 120                 125

Arg Asn Glu Thr Ala Trp Met Gln Glu Ile Ser Val Val Ala Asp
        130                 135                 140

Glu Val His Leu Ile Asp Ser Pro Asp Arg Gly Pro Thr Leu Glu Ile
145                 150                 155                 160

Thr Leu Ser Lys Leu Arg Arg Met Asn Pro Ser Cys Gln Val Leu Ala
                165                 170                 175

Leu Ser Ala Thr Val Gly Asn Ala Asp Glu Leu Ala Ala Trp Leu Asp
                180                 185                 190

Ala Glu Leu Val Leu Ser Glu Trp Arg Pro Thr Asp Leu Met Glu Gly
            195                 200                 205

Val Phe Tyr Asn Gly Ile Phe Tyr Cys Lys Asp Lys Glu Lys Pro Val
        210                 215                 220

Gly Gln Pro Thr Lys Asp Glu Ala Val Asn Leu Val Leu Asp Thr Ile
225                 230                 235                 240

Lys Glu Gly Gly Gln Cys Leu Val Phe Glu Ser Ser Arg Lys Asn Cys
                245                 250                 255

Met Gly Phe Ala Lys Lys Ala Val Ser Ala Val Lys Lys Thr Leu Ser
                260                 265                 270

Asn Glu Asp Arg Glu Thr Leu Ala Gly Ile Ala Asp Glu Ile Ile Glu
            275                 280                 285

Asn Ser Glu Thr Asp Val Ser Ser Val Leu Ala Thr Cys Val Arg Ser
        290                 295                 300

Gly Thr Ala Phe His His Ala Gly Leu Thr Thr Pro Leu Arg Glu Leu
305                 310                 315                 320

Val Glu Asn Gly Phe Arg Glu Gly Arg Ile Lys Ile Ile Ser Ser Thr
                325                 330                 335

Pro Thr Leu Ala Ala Gly Leu Asn Leu Pro Ala Arg Arg Val Ile Ile
                340                 345                 350
```

Arg Ser Tyr Arg Arg Tyr Ser Ser Asp Ser Gly Met Gln Pro Ile Pro
355                 360                 365

Val Leu Glu Tyr Lys Gln Met Ala Gly Arg Ala Gly Arg Pro Arg Leu
370                 375                 380

Asp Pro Tyr Gly Glu Ala Val Leu Leu Ala Lys Ser Tyr Glu Glu Phe
385                 390                 395                 400

Val Phe Leu Phe Glu Lys Tyr Ile Glu Ala Gly Ala Glu Asp Ile Trp
            405                 410                 415

Ser Lys Leu Gly Thr Glu Asn Ala Leu Arg Thr His Ile Leu Ser Thr
            420                 425                 430

Ile Ser Asn Gly Phe Ala Arg Thr Arg Glu Glu Leu Met Asp Phe Leu
        435                 440                 445

Glu Ala Thr Phe Phe Ala Phe Gln Tyr Ser Asn Phe Gly Leu Ser Ala
    450                 455                 460

Val Val Asp Glu Cys Leu Asp Phe Leu Arg Arg Glu Gly Met Leu Glu
465                 470                 475                 480

Lys Asp Pro Asp Ala Leu Val Ser Thr Val Phe Gly Lys Leu Val Ser
            485                 490                 495

Arg Leu Tyr Ile Asp Pro Leu Ser Ala Ala Leu Ile Ala Lys Gly Leu
            500                 505                 510

Arg Glu Ala Gly Thr Leu Thr Glu Leu Thr Leu Leu His Leu Ile Cys
    515                 520                 525

Ser Thr Pro Asp Met Arg Leu Met Tyr Met Arg Ser Gln Asp Tyr Gln
    530                 535                 540

Glu Val Asn Asp Tyr Val Met Ala His Ala Gly Glu Phe Ser Lys Val
545                 550                 555                 560

Pro Asn Pro Phe Asn Ile Ala Glu Tyr Glu Trp Phe Leu Gly Glu Val
            565                 570                 575

Lys Thr Ser Leu Leu Leu Met Asp Trp Ile His Glu Lys Pro Glu Asn
            580                 585                 590

Glu Ile Cys Leu Lys Phe Gly Ile Gly Glu Gly Asp Ile His Ala Thr
    595                 600                 605

Ala Asp Ile Ala Glu Trp Ile Met His Val Thr Ala Gln Leu Ala Gly
610                 615                 620

Leu Leu Asp Leu Lys Gly Ala Lys Glu Ala Ser Glu Leu Glu Lys Arg
625                 630                 635                 640

Ile Arg Tyr Gly Ala Ala Pro Glu Leu Met Asp Leu Leu Asp Ile Arg
            645                 650                 655

Ser Val Gly Arg Val Arg Ala Arg Lys Leu Tyr Glu Ala Gly Phe Lys
            660                 665                 670

Ser Thr Ala Glu Leu Ala Ala Ser Pro Glu His Ile Ala Val Leu
    675                 680                 685

Val Gly Pro Lys Ile Thr Glu Arg Ile Phe Lys Gln Ile Gly Arg Arg
690                 695                 700

Glu Ala Val Ser Glu Phe Ser Asp Ile Glu Pro Leu Glu Lys Gly Ser
705                 710                 715                 720

Ser Asp Gly Gln Arg Thr Ile Ser Asp Tyr
            725                 730

<210> SEQ ID NO 42
<211> LENGTH: 693
<212> TYPE: PRT
<213> ORGANISM: Methanosaeta thermophila

<400> SEQUENCE: 42

```
Met Leu Thr Ile Arg Asp Leu Ile Arg Trp Leu Pro Glu Ser Val Ile
1               5                   10                  15

Glu Leu Tyr Glu Ala Leu Gly Ile Asp Glu Leu Tyr Pro Pro Gln Ala
            20                  25                  30

Glu Ala Ile Glu Arg Gly Leu Leu Asp Gly Arg Asn Met Ile Ile Ser
        35                  40                  45

Val Pro Thr Ala Ala Gly Lys Thr Leu Leu Ala Glu Leu Ala Met Leu
50                  55                  60

Arg Gly Ala Leu Ser Gly Lys Arg Ser Leu Tyr Ile Val Pro Leu Arg
65                  70                  75                  80

Ala Leu Ala Ser Glu Lys Phe Glu Ser Phe Ser Arg Phe Ser Lys Leu
            85                  90                  95

Gly Leu Arg Val Gly Ile Ser Thr Gly Asp Phe Glu Lys Arg Asp Glu
            100                 105                 110

Arg Leu Gly Arg Asn Asp Ile Ile Ala Thr Ser Glu Lys Ala Asp
        115                 120                 125

Ser Leu Ile Arg Asn Gly Ala Ser Trp Val Arg Arg Ile Gly Val Leu
    130                 135                 140

Val Val Asp Glu Ile His Leu Leu Asp Ser Ala Asn Arg Gly Pro Thr
145                 150                 155                 160

Leu Glu Met Thr Met Thr Lys Leu Met His Leu Asn Pro Glu Met Gln
            165                 170                 175

Val Ile Gly Leu Ser Ala Thr Ile Ala Asn Gly Arg Glu Ile Ala Asp
            180                 185                 190

Trp Ile Lys Gly Glu Ile Val Ser Ser Asp Trp Arg Pro Val Arg Leu
        195                 200                 205

Arg Glu Gly Val Leu Leu Glu Asp Arg Leu Val Phe Pro Asp Gly Glu
210                 215                 220

Ile Gln Leu Glu Asn Arg Asn Arg Asp Pro Val Leu Asn Leu Val Leu
225                 230                 235                 240

Asp Thr Val Asp Gln Gly Gly Gln Met Leu Ile Phe Glu Ser Thr Arg
                245                 250                 255

Arg Asn Ala Glu Ser Met Ala Lys Lys Val Ser Gly Ala Leu Gln Glu
                260                 265                 270

Ser Gly Glu Thr Ile Glu Leu Ala Glu Arg Leu Ser Gly Glu Gly Lys
    275                 280                 285

Thr Ala Lys Lys Leu Ala Met Cys Leu Arg His Gly Ala Ala Phe His
290                 295                 300

His Ala Gly Leu Leu Pro Glu Gln Arg Arg Leu Ile Glu Leu Gly Phe
305                 310                 315                 320

Arg Gln Asn Val Val Lys Val Ile Ala Cys Thr Pro Thr Leu Ala Ala
                325                 330                 335

Gly Leu Asn Leu Pro Ala Arg Arg Val Leu Ile Arg Ser Tyr Lys Arg
                340                 345                 350

Tyr Glu Ala Gly Leu Gly Thr Arg Pro Ile Pro Val Met Glu Tyr Arg
            355                 360                 365

Gln Met Ala Gly Arg Ala Gly Arg Pro Gly Leu Asp Pro Tyr Gly Glu
    370                 375                 380

Ser Leu Ile Met Ala Arg Ser Glu Ser Glu Leu Gln Lys Leu Met Asp
385                 390                 395                 400

His Tyr Val Met Gly Glu Pro Glu Asp Ile Trp Ser Lys Leu Ala Ser
            405                 410                 415
```

```
Glu Arg Ala Leu Arg Thr His Val Leu Ala Thr Ile Ala Ser Arg Phe
                420                 425                 430

Ala Asp Ser Val Asp Ser Leu Ser Arg Leu Met Ala Ser Thr Phe Tyr
            435                 440                 445

Ala Arg Gln Gln Asp Pro Ser Tyr Leu Gly Glu Thr Ile Ala Ser Val
        450                 455                 460

Leu Glu Phe Leu Val Arg Ser Asp Met Ile Asp Lys Asp Leu Thr Pro
465                 470                 475                 480

Thr Pro Leu Gly Ala Leu Val Ser Arg Leu Tyr Ile Asp Pro Leu Ser
                485                 490                 495

Ala Met Val Met Ile Gln Glu Ile Arg Gly Ile Arg Arg Pro Thr Val
            500                 505                 510

Leu Thr Leu Leu His Val Ile Thr Met Thr Pro Asp Met Glu Leu Leu
        515                 520                 525

Phe Val Gln Gln Ser Asp Asn Trp Leu Glu Asp Phe Ile Ser Glu His
                530                 535                 540

Ser Ser Glu Leu Gly Asn Glu Lys Asn Phe Asp Trp Leu Leu Arg Glu
545                 550                 555                 560

Val Lys Thr Ala Ser Met Leu Met Asp Trp Ile Asn Glu Val His Glu
                565                 570                 575

Asp Arg Ile Glu Asp Arg Tyr Ser Ile Ser Pro Gly Asp Leu Val Arg
            580                 585                 590

Ile Ala Glu Thr Ala Glu Trp Leu Met Ser Ala Leu His Arg Ile Ser
        595                 600                 605

Lys His Met Asp Leu Gly Val Thr Tyr Leu Ala Glu Arg Leu Ala Leu
                610                 615                 620

Arg Ile His Tyr Gly Ala Gly Asp Glu Leu Leu Gln Leu Leu Glu Leu
625                 630                 635                 640

Lys Gly Ile Gly Arg Val Arg Ala Arg Lys Leu Tyr Gln Ala Gly Tyr
                645                 650                 655

Arg Ser Leu Glu Asp Leu Lys Ala Ala Asp Lys Ser Thr Leu Ser Glu
            660                 665                 670

Ile Leu Gly Pro Lys Ile Ala Glu Gly Val Ile Ser Gln Leu Lys Glu
        675                 680                 685

Pro Gly Val Ser Ala
            690

<210> SEQ ID NO 43
<211> LENGTH: 739
<212> TYPE: PRT
<213> ORGANISM: Methanosalsum zhilinae

<400> SEQUENCE: 43

Met Asn Ile Asn Asn Leu Asn Leu Pro Glu Lys Val Lys Lys Tyr Tyr
1               5                   10                  15

Thr Asp Thr Gly Ile Val Asp Leu Tyr Pro Pro Gln Arg Glu Ala Val
                20                  25                  30

Asp Lys Gly Leu Leu Asp Gly Glu Asn Ile Val Ala Ala Ile Pro Thr
            35                  40                  45

Ala Ser Gly Lys Thr Leu Leu Ala Glu Leu Cys Met Leu Lys Ser Ile
        50                  55                  60

Gly Met Gly Gly Lys Cys Leu Tyr Ile Val Pro Leu Lys Ala Leu Ala
65                  70                  75                  80

Ser Glu Lys Tyr Ser Arg Phe Arg Glu Phe Glu Ser Leu Gly Ile Lys
                85                  90                  95
```

```
Val Gly Ile Ala Thr Gly Asp Leu Asp Ser Arg Glu Trp Leu Gly
            100                 105                 110

Lys Asn Asp Ile Ile Ala Thr Ser Glu Lys Val Asp Ser Leu Leu
            115                 120                 125

Arg Asn Glu Ser Ser Trp Met Lys Glu Ile Asn Thr Val Val Ala Asp
130                 135                 140

Glu Val His Leu Leu Asn Ser Val Asn Arg Gly Pro Thr Leu Glu Ile
145                 150                 155                 160

Thr Leu Ala Lys Leu Ile His Leu Asn Pro Gly Ser Gln Ile Ile Ala
                165                 170                 175

Leu Ser Ala Thr Ile Gly Asn Pro Glu Asp Ile Ala Gly Trp Leu Gly
            180                 185                 190

Ala Arg Leu Val Val Ser Glu Trp Arg Pro Thr Asp Leu Tyr Glu Gly
            195                 200                 205

Ile Leu Leu Asp Gly Leu Leu His Ile Gly Asn Ile Lys Lys Asp Ile
            210                 215                 220

Gln Asp Glu Ser Arg Asp Asp Ala Val Asn Leu Val Ile Asp Thr Val
225                 230                 235                 240

Lys Asp Lys Gly Gln Cys Leu Val Phe Glu Ser Ser Arg Arg Asn Cys
                245                 250                 255

Met Gly Phe Ala Lys Lys Ala Gly Lys Trp Val Ser Lys Ile Leu Asp
            260                 265                 270

Glu His Asp Thr Ile Gln Leu Lys Ser Leu Ser Gln Glu Ile Gly Glu
            275                 280                 285

Ala Gly Glu Thr Glu Ile Ala Asp Val Leu Ser Arg Cys Val Arg Gln
            290                 295                 300

Gly Val Ala Phe His His Ala Gly Leu Asn Ser Glu His Arg Arg Met
305                 310                 315                 320

Val Glu Glu Gly Phe Arg Lys Asn Leu Ile Lys Met Ile Ser Ser Thr
                325                 330                 335

Pro Thr Leu Ala Ala Gly Leu Asn Leu Pro Ala Arg Arg Val Ile Ile
            340                 345                 350

Arg Ser Tyr Lys Arg Tyr Asp Pro Asn Phe Gly Met Lys Pro Ile Pro
            355                 360                 365

Val Leu Glu Tyr Lys Gln Met Ala Gly Arg Ala Gly Arg Pro His Leu
            370                 375                 380

Asp Pro Tyr Gly Glu Ser Val Leu Ile Ala Arg Ser Tyr Asp Glu Phe
385                 390                 395                 400

Met Asp Ile Met Glu Asn Tyr Val Asn Ala Asp Pro Glu Asp Ile Trp
            405                 410                 415

Ser Lys Leu Gly Thr Glu Asn Ala Leu Arg Thr His Val Leu Ser Thr
            420                 425                 430

Ile Val Asn Gly Phe Ala Tyr Thr Tyr Arg Gly Leu Met Asp Phe Val
            435                 440                 445

Lys Met Thr Phe Phe Ala Tyr Gln Lys Glu Ala Ser Asp Leu His Asp
            450                 455                 460

Val Ile Glu Glu Cys Val Arg Phe Leu Ile Asp Asn Glu Met Ile Ile
465                 470                 475                 480

Ser Asp Ser Asn Asp Ile Leu Pro Glu Ser Ala Phe Arg Ser Thr Ala
                485                 490                 495

Thr Gly Lys Leu Ile Ser Met Leu Tyr Ile Asp Pro Leu Ser Gly Ser
            500                 505                 510
```

```
Leu Ile Met Asp Gly Ile Arg Lys Ala Asp Tyr Phe Glu Asp Ile Thr
            515                 520                 525
Met Met His Leu Ile Cys Ser Thr Pro Asp Met Lys Asn Leu Tyr Met
            530                 535                 540
Arg Ser Ser Asp Tyr Glu Asn Val Asn Met Tyr Val Leu Gln Asn Lys
545                 550                 555                 560
Asp Lys Phe Ile Ser Met Pro Ser Pro Phe Lys Met Ile Glu Tyr Glu
                565                 570                 575
Trp Phe Leu Gly Glu Val Lys Thr Ala Leu Leu Leu Leu Asp Trp Ile
            580                 585                 590
Asn Glu Val Pro Ala Asp Asp Ile Cys Lys Lys Tyr Gly Ile Gly Glu
            595                 600                 605
Gly Asp Ile Arg Met Phe Ser Glu Thr Ala Val Trp Leu Met His Ala
610                 615                 620
Thr Ser Arg Leu Ser Gly Leu Leu Lys Val Ser Glu Ala Ser Glu Lys
625                 630                 635                 640
Ser Lys Glu Leu Glu Lys Arg Leu Ser Tyr Gly Ile Asn Ser Glu Leu
                645                 650                 655
Val Asn Ile Val Ala Leu Lys Gly Ile Gly Arg Val Arg Ala Arg Lys
            660                 665                 670
Ile Tyr Glu Asn Gly Tyr Arg Ser Ile Asp Asp Leu Lys Lys Ala Asp
            675                 680                 685
Pro Leu Lys Leu Ser Lys Ile Val Gly Ser Lys Ile Ser Gln Lys Ile
            690                 695                 700
Leu Lys Gln Leu Asp Ile Asp Val Asp Ile Ser Glu Ile Lys Glu Lys
705                 710                 715                 720
Asp Ser Asp Thr Val Pro Glu Pro Glu Ser Ser Gln Lys Thr Ile Ser
                725                 730                 735
Asp Phe Thr

<210> SEQ ID NO 44
<211> LENGTH: 733
<212> TYPE: PRT
<213> ORGANISM: Methanohalobium evestigatum

<400> SEQUENCE: 44

Met Glu Thr Gly Lys Leu Glu Leu Pro Glu Tyr Val Ile Gln Phe Tyr
1               5                   10                  15
Leu Asp Thr Gly Ile Glu Lys Leu Tyr Pro Pro Gln Ala Glu Ala Val
            20                  25                  30
Glu Lys Gly Leu Leu Asp Asn Lys Asn Leu Leu Ala Ala Ile Pro Thr
        35                  40                  45
Ala Ser Gly Lys Thr Leu Ile Ser Glu Leu Ala Met Leu Lys Ser Ile
    50                  55                  60
Ser Asn Gly Gly Lys Cys Leu Tyr Ile Val Pro Leu Arg Ala Leu Ala
65                  70                  75                  80
Ser Glu Lys Phe Glu Arg Phe Lys Gln Phe Ser Ser Ile Gly Val Asn
                85                  90                  95
Ile Gly Ile Ser Thr Gly Asp Phe Asp Ser Thr Asp Glu Trp Leu Gly
            100                 105                 110
Ser Asn Asp Ile Ile Val Ala Thr Ser Glu Lys Ala Asp Ser Leu Leu
            115                 120                 125
Arg Asn Glu Thr Ser Trp Met Lys Asp Ile Thr Ile Val Val Asp
        130                 135                 140
```

-continued

| | | | | | | | | | | | | | | | |
|---|---|---|---|---|---|---|---|---|---|---|---|---|---|---|---|

Glu Ile His Leu Leu Asp Ser Ala Asp Arg Gly Pro Thr Leu Glu Ile
145                 150                 155                 160

Thr Ile Ala Lys Leu Leu Arg Leu Asn Pro Asn Ser Gln Ile Ile Gly
                165                 170                 175

Leu Ser Ala Thr Ile Gly Asn Ala Glu Glu Ile Ala Gly Trp Leu Asp
            180                 185                 190

Ala Glu Leu Val Gln Ser Gln Trp Arg Pro Ile Glu Leu Tyr Glu Gly
        195                 200                 205

Val Phe Leu Glu Asp Asn Ile Asn Phe Lys Gln Ser Gln Lys Pro Ile
    210                 215                 220

Lys Asn Ile Val Lys Asp Thr Ala Val Asn Leu Val Leu Asp Thr Ile
225                 230                 235                 240

Asp Glu Asn Gly Gln Cys Leu Val Phe Glu Ser Ser Arg Arg Asn Cys
                245                 250                 255

Ala Gly Phe Ala Lys Lys Ala Lys Ser Lys Val Gly Lys Ser Leu Asp
            260                 265                 270

Lys Gly Leu Leu Ala Glu Leu Asn Asn Ile Ala Glu Glu Val Leu Glu
        275                 280                 285

Thr Ser Asp Thr Glu Thr Thr Lys Glu Leu Ala Ser Cys Ile Lys Arg
    290                 295                 300

Gly Thr Ala Phe His His Ala Gly Leu Asn Ser Ala Gln Arg Lys Ile
305                 310                 315                 320

Val Glu Asp Asn Phe Arg Asn Asn Lys Ile Lys Val Ile Ser Ser Thr
                325                 330                 335

Pro Thr Leu Ala Ala Gly Leu Asn Leu Pro Ala Arg Arg Val Ile Val
            340                 345                 350

Arg Asn Tyr Lys Arg Tyr Asp Pro Asn Phe Gly Met Gln Pro Ile Pro
        355                 360                 365

Val Leu Asp Tyr Lys Gln Met Ala Gly Arg Ala Gly Arg Pro Ser Leu
    370                 375                 380

Asp Pro Tyr Gly Glu Ser Val Leu Ile Ser His Thr Tyr Asn Glu Phe
385                 390                 395                 400

Thr Asp Leu Leu Asp Arg Tyr Ile Asp Ala Glu Pro Glu Asp Ile Leu
                405                 410                 415

Ser Lys Leu Gly Thr Glu Asn Ala Leu Arg Thr His Val Leu Ser Thr
            420                 425                 430

Ile Val Asn Gly Phe Ala Thr Thr Arg Gln Gly Met Val Asp Phe Met
        435                 440                 445

Gly Ser Ser Phe Phe Ala Tyr Gln Gln Gln Lys Trp Ser Leu Ile Asp
    450                 455                 460

Val Val Asp Asp Cys Ile Glu Phe Leu Gln Asp Asn Glu Met Ile Lys
465                 470                 475                 480

Asp Asp Gly Glu Arg Leu Tyr Ala Thr Arg Leu Gly Gln Val Ile Ser
                485                 490                 495

Thr Leu Tyr Ile Asp Pro Leu Ser Gly Ala Ile Ile Asp Lys Leu
            500                 505                 510

Lys Lys Ala Asp Lys Val Thr Asp Met Thr Met Leu His Ile Ile Cys
        515                 520                 525

Ser Thr Pro Asp Met Arg Gln Leu Tyr Leu Arg Ser Lys Glu Tyr Glu
    530                 535                 540

Lys Ile Asn Glu Tyr Val Met Thr His Ser Asp Glu Phe Val Glu Val
545                 550                 555                 560

Pro Asn Pro Phe Lys Ser Ile Glu Tyr Glu Trp Phe Leu Gly Glu Val

```
                        565                 570                 575
Lys Thr Ala Leu Leu Ile Asn Glu Trp Ile Asp Glu Lys Thr Leu Asp
                    580                 585                 590

Asp Ile Thr Ala Glu Phe Gly Val Gly Glu Gly Asp Ile Asn Ala Leu
                595                 600                 605

Ser Asp Ile Ser Glu Trp Leu Met His Ser Ala Val Asn Leu Ala Asn
    610                 615                 620

Leu Thr Asp Leu Asp Ala Asp Lys Ala Gln Glu Leu Glu Lys Arg Ile
625                 630                 635                 640

His His Gly Val Asn Lys Asp Leu Ile Gln Leu Val Ser Ile Ser Asn
                645                 650                 655

Ile Gly Arg Val Arg Ala Arg Lys Leu Tyr Glu Ala Gly Ile Gln Ser
                660                 665                 670

Val Ser Asp Ile Lys Asn Thr Lys Leu His Ile Leu Ser Asn Tyr Leu
                675                 680                 685

Gly Arg Lys Thr Ala Tyr Lys Val Leu Glu Gln Leu Gly Val Glu Pro
            690                 695                 700

Glu Asp Asn Gln Gln Ile Asp Glu Glu Pro Glu Ser Ile Lys Ser Tyr
705                 710                 715                 720

Ser Gly Asn Asp Gln Gly Gln Lys Thr Phe Asn Asp Phe
                725                 730

<210> SEQ ID NO 45
<211> LENGTH: 747
<212> TYPE: PRT
<213> ORGANISM: Methanococcus maripaludis

<400> SEQUENCE: 45

Met His Val Leu Asp Leu Leu Lys Glu Asn Lys Ile Thr Glu Leu Arg
1               5                   10                  15

Pro Pro Gln Lys Lys Val Ile Asp Glu Gly Leu Phe Asp Lys Thr Lys
                20                  25                  30

Asn Phe Leu Ile Cys Ile Pro Thr Ala Ser Gly Lys Thr Leu Ile Gly
            35                  40                  45

Glu Met Ala Leu Leu Asn His Ile Leu Asp Glu Asn Lys Asn Leu Thr
        50                  55                  60

Gly Lys Lys Gly Leu Phe Ile Val Pro Leu Lys Ala Leu Ala Asn Glu
65                  70                  75                  80

Lys Phe Asp Glu Phe Arg Glu Lys Tyr Glu Lys Tyr Gly Ile Lys Val
                85                  90                  95

Gly Leu Ser Ile Gly Asp Phe Asp Thr Lys Glu Asn Leu Ser Lys Phe
            100                 105                 110

His Ile Ile Ile Thr Thr Ser Glu Lys Leu Asp Ser Leu Met Arg His
        115                 120                 125

Asn Val Glu Trp Ile Asn Asp Val Ser Leu Ala Val Ile Asp Glu Ile
    130                 135                 140

His Leu Ile Gly Asp Asn Glu Arg Gly Gly Thr Leu Glu Val Ile Leu
145                 150                 155                 160

Thr Lys Leu Lys Asn Leu Asn Ala Gln Ile Val Gly Leu Ser Ala Thr
                165                 170                 175

Ile Gly Asn Pro Glu Glu Leu Ser Asn Trp Leu Asn Ala Lys Leu Ile
            180                 185                 190

Val Asp Gly Trp Arg Pro Val Glu Leu Lys Lys Gly Ile Tyr Phe Glu
        195                 200                 205
```

-continued

```
Asn Glu Leu Glu Phe Leu Lys Asn Pro Ala Lys Lys Ile Lys Gln Val
    210                 215                 220

Ser Arg Asn Asn Leu Thr Asp Leu Ile Val Asp Ser Val Glu Lys
225                 230                 235                 240

Gly Ser Cys Leu Ile Phe Cys Asn Ser Lys Arg Asn Ala Val Gly Glu
                245                 250                 255

Ala Lys Lys His Asn Leu Ala Lys Tyr Leu Thr Arg Thr Glu Gln His
                260                 265                 270

Glu Leu Asn Lys Leu Ser Glu Ile Leu Ser Ile Leu Asp Arg Pro
                275                 280                 285

Val Glu Thr Cys Lys Ala Leu Ser Lys Cys Ile Gln Asn Gly Val Ala
    290                 295                 300

Phe His His Ala Gly Leu Thr Tyr Lys His Arg Lys Ile Val Glu Asp
305                 310                 315                 320

Gly Phe Arg Asn Arg Leu Ile Lys Val Ile Cys Cys Thr Pro Thr Leu
                325                 330                 335

Ser Ala Gly Leu Asn Leu Pro Cys Arg Arg Ala Ile Val Arg Asp Ile
                340                 345                 350

Lys Arg Tyr Ser Gln Asn Gly Leu Val Asp Ile Pro Arg Met Glu Ile
                355                 360                 365

Gln Gln Cys Ile Gly Arg Ala Gly Arg Pro Gly Leu Asp Pro Tyr Gly
    370                 375                 380

Glu Gly Ile Ile Tyr Ile Lys Asn Glu Arg Asp Ala Glu Lys Ala Tyr
385                 390                 395                 400

Glu Ile Leu Thr Gly Ser Val Glu Asn Ile Tyr Ser Lys Leu Ala Asn
                405                 410                 415

Gln Lys Val Leu Arg Ile His Ile Leu Gly Leu Ile Ser Thr Gly Glu
                420                 425                 430

Ile Lys Asp Gly Gln Asn Leu Val Asn Phe Met Lys Asn Thr Phe Tyr
                435                 440                 445

Ala His Gln Phe Gly Asn Ile Gly Ala Val Leu Leu Asn Val Ser Glu
    450                 455                 460

Val Val Glu Phe Leu Glu Lys Asn Lys Phe Leu Glu Thr Thr Ile His
465                 470                 475                 480

Lys Lys Thr Glu Asn Lys Val Arg Glu Leu Ser Phe Asp Ser Ser Asn
                485                 490                 495

Asn Leu Val Leu Asp Ser Lys Glu Thr Ser Phe Asp Leu Thr Asn Pro
                500                 505                 510

Asn Ser Asn Ile Glu Phe Arg Ser Thr Lys Leu Gly Lys Arg Ile Ser
                515                 520                 525

Glu Leu Tyr Ile Asp Pro Met Ser Ser Glu Ile Ile Ile Glu Glu Leu
    530                 535                 540

His Glu Leu Lys Lys Lys Cys Asp Gln Leu Asp Arg Ser Lys Ile Asp
545                 550                 555                 560

Gln Tyr Leu Phe Tyr Leu Ile Ser Lys Thr Asn Glu Met Arg Pro Leu
                565                 570                 575

Leu Arg Ile Arg Pro Asn Glu Glu Leu Asp Leu Ile Leu Glu Met Asp
                580                 585                 590

Lys Met Gly Leu Lys Asp Tyr Ser Ile Glu Asn Ile Glu Ala Phe Lys
                595                 600                 605

Asn Ser Lys Met Phe Cys Asp Trp Val Ser Glu Ile Pro Glu Glu Ile
    610                 615                 620

Ile Leu Glu Lys Tyr Gly Val Glu Pro Gly Ile Leu Arg Tyr Lys Val
```

```
            625                 630                 635                 640
Glu Gln Ala Lys Trp Met Ile Tyr Ser Thr Lys Glu Ile Ala Lys Leu
                    645                 650                 655

Ile His Leu Asp Asn Ser Glu Ile Tyr Lys Ser Leu Leu Lys Met Glu
                    660                 665                 670

Val Arg Ile Glu Tyr Gly Ala Lys Glu Leu Ile Glu Leu Leu Asn
                    675                 680                 685

Val Lys Asn Val Gly Arg Ile Arg Ser Arg Lys Leu Tyr Asp Ala Gly
        690                 695                 700

Ile Arg Ser Lys Ile Glu Ile Asn Lys Asn Pro Glu Lys Ile Leu Glu
705                 710                 715                 720

Leu Phe Gly Glu Lys Ile Gly Lys Lys Ile Leu Gly Glu His Gly Met
                        725                 730                 735

Lys Tyr Gly Gln Gln Thr Leu Leu Asn Phe Asn
                    740                 745

<210> SEQ ID NO 46
<211> LENGTH: 799
<212> TYPE: PRT
<213> ORGANISM: Natrialba magadii

<400> SEQUENCE: 46

Met Asn Val Glu Glu Leu Ser Gly Leu Pro Pro Gly Ala Arg Ser His
1               5                   10                  15

Phe Gln Glu Gln Gly Ile Glu Glu Leu Tyr Pro Pro Gln Ala Glu Ala
                20                  25                  30

Val Glu Ala Gly Ala Thr Gly Glu Asn Leu Val Ala Ala Val Pro
            35                  40                  45

Thr Ala Ser Gly Lys Thr Met Ile Ala Ala Leu Ser Met Leu Ser Ala
50                  55                  60

Val Gln Arg Gly Gly Lys Ala Leu Tyr Ile Val Pro Leu Arg Ala Leu
65                  70                  75                  80

Ala Ser Glu Lys Lys Ala Glu Phe Asp Ala Tyr Glu Gly Phe Gly Val
                85                  90                  95

Thr Thr Gly Val Ala Thr Gly Asn Tyr Glu Ser Thr Ser Glu Trp Leu
            100                 105                 110

Ala Thr Lys Asp Ile Ile Val Ala Thr Ser Glu Lys Val Asp Ser Leu
        115                 120                 125

Val Arg Asn Gly Ala Asp Trp Leu Ser Asp Leu Thr Cys Val Val Ser
130                 135                 140

Asp Glu Val His Leu Ile Asp Asp Arg Asn Arg Gly Pro Thr Leu Glu
145                 150                 155                 160

Val Thr Leu Ala Lys Leu Arg Arg Leu Asn Pro Gln Leu Gln Val Val
                165                 170                 175

Ala Leu Ser Ala Thr Val Gly Asn Ala Asp Glu Leu Ala Asp Trp Leu
            180                 185                 190

Asp Ala Glu Leu Val Asp Thr Asp Trp Arg Pro Ile Asp Leu Gln Met
        195                 200                 205

Gly Val His Tyr Gly Asn Ala Leu Asn Phe Asp Asp Gly Glu Thr Arg
210                 215                 220

Glu Val Pro Val Glu Ala Gly Glu Lys Gln Glu Ala Ala Leu Val Arg
225                 230                 235                 240

Asp Ile Leu Gln Glu Gly Gly Ser Ser Leu Val Phe Val Asn Ser Arg
                245                 250                 255
```

```
Arg Asn Ala Glu Ala Ala Arg Arg Leu Gly Gln Val Ser Ser Arg
            260                 265                 270

Glu Leu Thr Ala Gly Glu Gln Asn Asp Leu Ala Ala Leu Ala Thr Glu
            275                 280                 285

Ile Arg Glu Asp Ser Asp Thr Glu Thr Ser Gln Asp Leu Ala Asp Cys
            290                 295                 300

Val Glu Arg Gly Ala Ala Phe His His Ala Gly Leu Ser Ser Thr Gln
305                 310                 315                 320

Arg Ser Leu Val Glu Asp Ala Phe Arg Asp Arg Leu Leu Lys Val Ile
                325                 330                 335

Ser Ala Thr Pro Thr Leu Ala Ala Gly Val Asn Thr Pro Ala Arg Arg
            340                 345                 350

Val Ile Val Arg Asp Trp Arg Arg Phe Asp Pro Ser Ala Gly Gly Met
            355                 360                 365

Ala Pro Leu Asp Val Leu Glu Val His Gln Met Met Gly Arg Ala Gly
            370                 375                 380

Arg Pro Gly Leu Asp Pro Tyr Gly Glu Ala Val Leu Leu Ala Lys Ser
385                 390                 395                 400

His Asp Glu Ser Gln Glu Leu Phe Asp Arg Tyr Val Trp Ala Asp Pro
                405                 410                 415

Glu Pro Val Arg Ser Lys Leu Ala Ala Glu Pro Ala Leu Arg Thr His
            420                 425                 430

Val Leu Ala Thr Ile Ala Ser Gly Phe Ala Arg Thr Arg Glu Gly Leu
            435                 440                 445

Leu Glu Phe Leu Glu Ala Thr Leu Tyr Ala Ser Gln Ser Ser Glu Gly
            450                 455                 460

Gly Arg Leu Glu Arg Val Thr Asp Asp Val Leu Ser Tyr Leu Glu Arg
465                 470                 475                 480

Asn Asp Phe Ile Glu Arg Ser Gly Gly Pro Glu Asp Thr Leu Asn Ser
                485                 490                 495

Glu Ala Asp Ala Ala Ser Ala Phe Thr Ser Ala Ala Asp Leu Ala Asp
            500                 505                 510

Ser Asp Gly Gly Asp Ser Gly Gly Thr Thr Gly Gln Glu Glu Asp Leu
            515                 520                 525

Glu Ala Thr Ser Leu Gly His Thr Val Ser Arg Leu Tyr Leu Asp Pro
530                 535                 540

Met Ser Ala Ala Glu Ile Val His Gly Leu Glu Asp Ala Asp Glu Arg
545                 550                 555                 560

Pro Thr Ala Leu Gly Leu Tyr Gln Leu Val Ser Arg Thr Pro Asp Met
            565                 570                 575

Tyr Glu Leu Tyr Leu Arg Ser Gly Glu Asp Glu Lys Phe Gly Glu Leu
            580                 585                 590

Tyr Tyr Glu Arg Glu Arg Glu Leu Leu Gly Asp Ala Pro Ser Glu Phe
            595                 600                 605

Glu Glu Glu Arg Phe Glu Asp Trp Leu Ala Ala Leu Lys Thr Gly Lys
            610                 615                 620

Leu Leu Glu Asp Trp Ala Thr Glu Asp Asp Glu Glu Gln Ile Thr Glu
625                 630                 635                 640

Arg Tyr Lys Ile Gly Pro Gly Asp Leu Arg Gly Lys Val Asp Thr Ala
                645                 650                 655

Glu Trp Leu Leu Gly Ala Ala Glu Ser Leu Ala Ser Glu Ile Asp Ser
            660                 665                 670

Glu Trp Ala Val Ala Val Arg Glu Ala Arg Ala Arg Val Glu His Gly
```

-continued

```
                675                 680                 685
Val Gly Glu Leu Leu Glu Leu Val Ser Val Ser Gly Ile Gly Arg
    690                 695                 700

Lys Arg Ala Arg Leu Tyr Ala Ala Gly Ile Glu Glu Pro Ala Ala
705                 710                 715                 720

Leu Arg Ser Ala Asp Lys Gly Val Ile Leu His Val Leu Lys Gly Glu
                725                 730                 735

Lys Thr Ala Glu Asn Ile Leu Glu Asn Ala Gly Arg Glu Glu Pro Ser
                740                 745                 750

Met Asp Gly Val Glu Pro Ile Pro Val Glu Gly Gly Ser Gly Ser Gly
                755                 760                 765

Ser Ser Asn Ser Ser Gly Ser Ser Glu Pro Asn Ala Asp Ala Asn Ala
                770                 775                 780

Thr Glu Asp Asp Ala Asp Asp Asn Gln Ser Ser Leu Gly Asp Phe
785                 790                 795

<210> SEQ ID NO 47
<211> LENGTH: 723
<212> TYPE: PRT
<213> ORGANISM: Methanoregula boonei

<400> SEQUENCE: 47

Met Gln Ile Gln Asp Leu Ala Ile Pro Glu Pro Leu Arg Gln Tyr
1               5                   10                  15

Leu Gly Leu Gly Ile Arg Glu Leu Tyr Pro Pro Gln Ala Ala Cys Val
                20                  25                  30

Glu Arg Gly Leu Leu Asp Gly Lys Asn Leu Leu Val Ala Ile Pro Thr
                35                  40                  45

Ala Ser Gly Lys Thr Leu Ile Ala Glu Met Ala Met His Arg His Ile
50                  55                  60

Ala Asn Gly Gly Lys Cys Leu Tyr Ile Val Pro Leu Lys Ala Leu Ala
65                  70                  75                  80

Ser Glu Lys Tyr Glu Glu Phe Gly Asn Lys Gly Val Lys Val Gly Leu
                85                  90                  95

Ser Thr Gly Asp Leu Asp Arg Arg Asp Ala Leu Gly Lys Asn Asp
                100                 105                 110

Ile Ile Val Ala Thr Ser Glu Lys Val Asp Ser Leu Leu Arg Asn Gly
                115                 120                 125

Ala Arg Trp Ile Pro Asp Ile Thr Leu Val Val Ile Asp Glu Ile His
            130                 135                 140

Leu Ile Asp Ser Pro Asp Arg Gly Pro Thr Leu Glu Met Val Ile Ala
145                 150                 155                 160

Lys Met Arg Ser Lys Asn Pro Gly Met Gln Leu Ile Gly Leu Ser Ala
                165                 170                 175

Thr Ile Gly Asn Pro Lys Val Leu Ala Gly Trp Leu Asp Ala Glu Leu
                180                 185                 190

Val Thr Ser Ser Trp Arg Pro Val Asp Leu Arg Gln Gly Val Phe Tyr
                195                 200                 205

Asp Asn Arg Ile Gln Phe Ala Glu Arg Met Arg Pro Val Lys Gln Val
            210                 215                 220

Ser Lys Asn Tyr Asp Asp Leu Asn Leu Cys Leu Asp Thr Ile Ala Glu
225                 230                 235                 240

Gly Gly Gln Cys Leu Val Phe Val Ser Ser Arg Arg Asn Ala Glu Ala
                245                 250                 255
```

```
Phe Ala Lys Arg Ala Ala Gly Ala Ile Lys Ser Glu Asp Ala Ala Leu
                260                 265                 270

Ala Ala Cys Ala Glu Arg Leu Leu Glu Gly Thr Pro Thr Glu Met Val
            275                 280                 285

Lys Thr Leu Ala Ala Cys Val Ala Lys Gly Ala Ala Phe His His Ala
        290                 295                 300

Gly Leu Ser Arg Lys Glu Arg Ser Ile Val Glu Ala Phe Arg Lys
305                 310                 315                 320

Asn Leu Leu Lys Cys Ile Ser Ser Thr Pro Thr Leu Ala Ala Gly Leu
                325                 330                 335

Asn Leu Pro Ala Arg Arg Val Ile Ile Arg Asp Tyr Leu Arg Phe Ser
            340                 345                 350

Ala Gly Glu Gly Met Gln Pro Ile Pro Val Ser Glu Tyr Arg Gln Met
        355                 360                 365

Ala Gly Arg Ala Gly Arg Pro Arg Leu Asp Pro Tyr Gly Glu Ala Val
    370                 375                 380

Leu Ile Ala Lys Glu Ala Glu Gln Val Pro Glu Leu Phe Glu Val Tyr
385                 390                 395                 400

Ile Glu Ala Glu Ala Glu Asp Val His Ser Arg Ile Ala Glu Pro Thr
                405                 410                 415

Ala Leu Tyr Thr His Val Leu Ser Leu Val Ala Ser Gly Phe Ala Gly
            420                 425                 430

Thr Arg Gly Glu Leu Thr Glu Phe Met Asn Arg Ser Phe Tyr Val His
        435                 440                 445

Glu His Lys Gln Gly Arg Leu Ile His Arg Ala Ile Asp Glu Ala Leu
    450                 455                 460

Gln Phe Leu Ile Thr Ala Glu Met Val Val Glu Val Gly Glu His Ile
465                 470                 475                 480

Gly Ala Thr Glu Leu Gly Thr Leu Val Ser Arg Met Tyr Ile Asp Pro
                485                 490                 495

Arg Ser Ala Phe Ala Ile Val Thr Thr Leu Arg Glu Gln Glu Lys Tyr
            500                 505                 510

Ala Asp Leu Gly Leu Ile Gln Leu Ile Cys Thr Thr Pro Asp Met Pro
        515                 520                 525

Thr Leu Tyr Ala Lys Asn Ala Asp Leu Pro Ala Leu Ser Arg Met Leu
    530                 535                 540

Glu Val Arg Gly Ala Asp Ile Trp Leu Pro Pro Leu Asp Asp Asp
545                 550                 555                 560

Ala Ala Glu Thr Tyr Tyr Arg Ala Val Lys Thr Ala Met Leu Leu Ser
                565                 570                 575

Asp Trp Thr Asp Glu Leu Ser Glu Glu Lys Ile Cys Glu Arg Tyr Gly
            580                 585                 590

Val Gly Pro Gly Asp Val Phe Gly Met Val Glu Asn Ile Asn Trp Leu
        595                 600                 605

Leu His Ala Thr Ser Gln Leu Ala Arg Met Phe Val Pro Lys Phe Tyr
    610                 615                 620

Gly Gln Ile Ala Asp Cys Glu Ile Cys Met Lys Asn Gly Ile Arg Arg
625                 630                 635                 640

Glu Leu Leu Pro Leu Val Arg Leu Arg Gly Ile Arg Val Arg Ala
                645                 650                 655

Arg Arg Leu Phe Asn Asn Gly Ile Thr Ser Pro Glu Glu Leu Ser Arg
            660                 665                 670

His Lys Lys Glu Asp Leu Val Lys Ile Leu Gly Ser Gly Ile Ala Glu
```

```
                675                 680                 685
Gln Val Leu Glu Gln Leu His Pro Ser Lys Asp Thr Gly Lys Lys Glu
            690                 695                 700

Pro Pro Ser Gly Asp Lys Asn Thr Asn Pro Gly Gln Ser Thr Leu Phe
705                 710                 715                 720

His Phe Gly

<210> SEQ ID NO 48
<211> LENGTH: 681
<212> TYPE: PRT
<213> ORGANISM: Ferroplasma acidarmanus

<400> SEQUENCE: 48

Met Lys Leu Ser Glu Ile Thr Pro Ser Glu Phe Leu Lys Val Thr Asp
1               5                   10                  15

Asn Asn Asp Phe Thr Leu Tyr Glu His Gln Glu Ala Val Ala Lys
            20                  25                  30

Leu Arg Glu Asn Lys Asn Val Ile Val Ser Val Pro Thr Ala Ser Gly
        35                  40                  45

Lys Thr Leu Ile Gly Tyr Ile Ser Ile Tyr Asp Thr Tyr Leu Lys Gly
    50                  55                  60

Lys Lys Ser Met Tyr Ile Val Pro Leu Arg Ser Leu Ala Met Glu Lys
65                  70                  75                  80

Phe Ser Glu Leu Leu Ser Leu Arg Asn Leu Gly Val Lys Val Thr Met
                85                  90                  95

Ser Ile Gly Asp Tyr Asp Val Pro Pro Ser Phe Val Lys Asn Tyr Asp
            100                 105                 110

Val Ile Ile Ala Thr Ser Glu Arg Ala Asp Ser Met Leu His Arg Asp
        115                 120                 125

Pro Asp Ile Leu Asn Tyr Phe Gly Leu Val Ile Ile Asp Glu Ile His
    130                 135                 140

Met Ile Ser Asp Pro Ser Arg Gly Pro Arg Leu Glu Thr Val Ile Ser
145                 150                 155                 160

Ser Leu Leu Tyr Leu Asn Pro Glu Ile Leu Leu Gly Leu Ser Ala
                165                 170                 175

Thr Val Ser Asn Ile Gln Glu Ile Ala Glu Trp Met Asn Ala Glu Thr
            180                 185                 190

Val Val Ser Asn Phe Arg Ala Val Pro Leu Glu Thr Gly Ile Ile Phe
        195                 200                 205

Lys Gly Asn Leu Ile Thr Asp Gly Glu Lys Lys His Leu Gly Arg Asp
    210                 215                 220

Asp Glu Val Ser Leu Ile Lys Glu Ser Ile Glu Ser Gly Gly Gln Ala
225                 230                 235                 240

Leu Val Phe Arg Asn Ser Arg Arg Asn Ala Glu Lys Tyr Ala Gln Ser
                245                 250                 255

Met Val Asn Phe Phe Asp Phe Gln Asn Asp Phe Glu Lys Leu Glu Ile
            260                 265                 270

Pro Pro Asp Leu Phe Asn Glu Ala Gln Ala Asn Met Val Ala His Gly
        275                 280                 285

Val Met Phe His His Ala Gly Leu Ser Asn Asp Gln Arg Thr Met Ile
    290                 295                 300

Glu Lys Leu Phe Lys Gln Gly Tyr Ile Lys Ile Leu Thr Ala Thr Pro
305                 310                 315                 320

Thr Leu Ala Ala Gly Val Asn Leu Pro Ala Arg Thr Val Ile Ile Arg
```

```
                    325                 330                 335
Asp Ile Thr Arg Phe Ser Asp Gly Tyr Ser Lys Pro Ile Ser Gly Ile
                340                 345                 350
Glu Ile Gln Gln Met Ile Gly Arg Ala Gly Arg Pro Lys Tyr Asp Lys
            355                 360                 365
Lys Gly Tyr Gly Tyr Ile Tyr Ala Ala Ser Pro Gly Met Leu Arg Val
        370                 375                 380
Ala Glu Gly Tyr Leu Thr Gly Glu Leu Glu Pro Val Ile Ser Arg Met
385                 390                 395                 400
Asp Ser Asn Ser Leu Ile Arg Phe Asn Val Leu Ala Leu Ile Ser Ser
                405                 410                 415
Gly Ile Ala Thr Asp Leu Lys Gly Ile Gln Asp Phe Tyr Gly Lys Thr
            420                 425                 430
Leu Leu Ala Ala Gln Asn Asp Ile Asp Gly Tyr Glu Leu Ala Phe Glu
        435                 440                 445
Ser Ala Leu Tyr Phe Leu Lys Asp Asn Asp Phe Ile Thr Glu Glu Asn
    450                 455                 460
Asp Ile Tyr Ser Ala Thr Lys Phe Gly Arg Leu Thr Ser Asp Leu Tyr
465                 470                 475                 480
Ile Asp Pro Val Ser Ser Leu Ile Leu Lys Lys Cys Leu Asp Leu Glu
                485                 490                 495
Phe Ser Glu Glu Leu Tyr Leu Tyr Tyr Ile Ser Lys Thr Pro Asp Met
            500                 505                 510
Leu Thr Phe Asn Tyr Arg Ala Ser Asp Tyr Glu Tyr Leu Glu Glu Phe
        515                 520                 525
Leu Asp Arg His Asn Ile Ser Asp Phe Ser Glu Glu Ser Met Gly Ala
    530                 535                 540
Ala Lys Thr Ala Ile Ile Leu Asn Glu Trp Ile Asn Glu Val Pro Ile
545                 550                 555                 560
Asn Thr Ile Ala Glu Thr Phe Gly Ile Gly Pro Gly Asp Ile Gln Ala
                565                 570                 575
Lys Ala Ser Ser Ala Asp Trp Ile Ser Tyr Ser Leu Tyr Arg Leu Gly
            580                 585                 590
Ser Met Phe Asp Lys Glu Asn Glu Asn Asn Leu Leu His Leu Asn Ile
        595                 600                 605
Arg Ile Lys Glu Gly Val Lys Glu Glu Ile Ile Arg Ile Ile Glu Ile
    610                 615                 620
Pro Gln Val Gly Arg Val Arg Gly Arg Arg Leu Tyr Asn Asn Gly Phe
625                 630                 635                 640
Lys Ser Ile Asp Asp Ile Ala Asn Ala Arg Val Glu Asp Ile Ser Arg
                645                 650                 655
Ile Phe Gly Phe Ser Thr Lys Leu Ala Lys Asp Ile Glu Asn Ala
            660                 665                 670
Gly Lys Leu Asn Asn Arg Tyr Tyr Arg
        675                 680

<210> SEQ ID NO 49
<211> LENGTH: 696
<212> TYPE: PRT
<213> ORGANISM: Methanocaldococcus fervens

<400> SEQUENCE: 49

Met Pro Thr Asn Lys Ile Leu Glu Ile Leu Lys Asp Phe Gly Ile Glu
1               5                   10                  15
```

Glu Leu Arg Pro Pro Gln Lys Lys Ala Leu Glu Lys Gly Leu Leu Asp
              20                  25                  30

Lys Asn Lys Asn Phe Leu Ile Ser Ile Pro Thr Ala Ser Gly Lys Thr
 35                  40                  45

Leu Ile Gly Glu Met Ala Leu Ile Asn His Leu Leu Asp Glu Asn Lys
 50                  55                  60

Asn Pro Thr Asn Lys Lys Gly Ile Phe Ile Val Pro Leu Lys Ala Leu
65                   70                  75                  80

Ala Ser Glu Lys Tyr Glu Glu Phe Lys Asn Lys Tyr Glu Arg Tyr Gly
              85                  90                  95

Leu Arg Val Ala Leu Ser Ile Gly Asp Tyr Asp Glu Asp Glu Asp Leu
             100                 105                 110

Ser Arg Tyr His Leu Ile Ile Thr Thr Ala Glu Lys Leu Asp Ser Leu
             115                 120                 125

Trp Arg His Lys Ile Asp Trp Ile Asp Asp Val Ser Val Val Val Val
         130                 135                 140

Asp Glu Ile His Leu Ile Asn Asp Glu Ser Arg Gly Gly Thr Leu Glu
145                 150                 155                 160

Ile Leu Leu Thr Lys Leu Lys Lys Phe Asn Ile Gln Ile Ile Gly Leu
                 165                 170                 175

Ser Ala Thr Ile Gly Asn Pro Glu Glu Leu Ala Asn Trp Leu Asn Ala
             180                 185                 190

Glu Leu Ile Val Asp Asp Trp Arg Pro Val Glu Leu Lys Lys Gly Ile
         195                 200                 205

Tyr Lys Asn Gly Ile Ile Glu Phe Ile Asn Gly Glu Asn Arg Glu Ile
210                 215                 220

Lys Ala Ile Asn Asn Asp Ile Tyr Asn Leu Val Val Asp Cys Val
225                 230                 235                 240

Lys Asp Gly Gly Cys Cys Ile Val Phe Cys Asn Thr Lys Arg Gly Ala
             245                 250                 255

Val Asn Glu Ala Lys Lys Leu Asn Leu Lys Lys Phe Leu Thr Asn Glu
             260                 265                 270

Glu Lys Arg Lys Leu Lys Glu Val Ala Glu Glu Ile Leu Ser Ile Leu
         275                 280                 285

Glu Pro Pro Thr Glu Met Cys Lys Thr Leu Ala Glu Cys Ile Leu Asn
290                 295                 300

Gly Ser Ala Phe His His Ala Gly Leu Thr Tyr Gln His Arg Lys Ile
305                 310                 315                 320

Val Glu Asp Ala Phe Arg Asn Lys Leu Ile Lys Val Ile Cys Cys Thr
                 325                 330                 335

Pro Thr Leu Ser Val Gly Leu Asn Leu Pro Cys Arg Arg Ala Ile Val
             340                 345                 350

Lys Asp Leu Thr Arg Tyr Thr Asn Arg Gly Met Arg Tyr Ile Pro Ile
         355                 360                 365

Met Glu Ile Gln Gln Cys Ile Gly Arg Ala Gly Arg Leu Gly Leu Asp
         370                 375                 380

Pro Tyr Gly Glu Gly Ile Ile Val Ala Lys Asn Asp Arg Asp Tyr Leu
385                 390                 395                 400

Arg Ser Tyr Gln Val Leu Thr Gln Lys Pro Glu Pro Ile Tyr Ser Lys
                 405                 410                 415

Leu Ser Asn Gln Ala Val Leu Arg Thr Gln Leu Leu Gly Leu Ile Ala
             420                 425                 430

Thr Ile Glu Ile Arg Asp Glu Tyr Asp Leu Glu Trp Phe Ile Arg Asn

```
                435                 440                 445
Thr Phe Tyr Ala Tyr Gln Tyr Gly Asn Leu Arg Glu Val Ala Lys Asn
450                 455                 460

Ile Asn Glu Val Ile Arg Phe Leu Glu Glu Lys Glu Phe Met Ile Asp
465                 470                 475                 480

Phe Ile Pro Thr Glu Leu Gly Lys Arg Val Ala Glu Leu Tyr Ile Asp
                485                 490                 495

Pro Leu Ser Ala Lys Tyr Met Ile Asp Gly Leu Asn Glu Met Glu Asn
                500                 505                 510

Glu Asp Asp Ile Tyr Tyr Leu Tyr Leu Ile Ser Lys Thr Leu Glu Met
                515                 520                 525

Met Pro Asn Leu Arg Val Tyr Lys Ser Glu Glu Leu Asn Leu Ile Asp
530                 535                 540

Glu Met Glu Asn Leu Gly Ile Lys Ser Phe Glu Ile Glu Asp Leu Glu
545                 550                 555                 560

Ala Phe Lys Thr Ala Lys Met Leu Tyr Asp Trp Ile Ser Glu Val Pro
                565                 570                 575

Glu Asp Glu Ile Leu Lys Lys Tyr Lys Ile Glu Pro Gly Ile Leu Arg
                580                 585                 590

Tyr Lys Val Glu Asn Ala Val Trp Leu Met His Ala Leu Lys Glu Met
                595                 600                 605

Ala Lys Ile Ile Gly Lys Asn Ser Glu Ile Pro Glu Lys Leu Glu Ile
610                 615                 620

Arg Leu Glu Tyr Gly Ala Lys Glu Asp Ile Ile Glu Leu Leu Asn Val
625                 630                 635                 640

Lys Tyr Ile Gly Arg Val Arg Ala Arg Lys Leu Tyr Asn Ala Gly Ile
                645                 650                 655

Arg Asn Val Glu Asp Ile Asn Asn Pro Ser Lys Val Ala Ser Ile
                660                 665                 670

Ile Gly Glu Lys Ile Thr Lys Lys Ile Leu Glu Asp Leu Gly Ile Lys
                675                 680                 685

Phe Gly Gln Gln Lys Leu Ile Phe
    690                 695

<210> SEQ ID NO 50
<211> LENGTH: 729
<212> TYPE: PRT
<213> ORGANISM: Methanocaldococcus jannaschii

<400> SEQUENCE: 50

Met Asp Lys Ile Leu Glu Ile Leu Lys Asp Phe Gly Ile Val Glu Leu
1               5                   10                  15

Arg Pro Pro Gln Lys Lys Ala Leu Glu Arg Gly Leu Leu Asp Lys Asn
                20                  25                  30

Lys Asn Phe Leu Ile Ser Ile Pro Thr Ala Ser Gly Lys Thr Leu Ile
            35                  40                  45

Gly Glu Met Ala Leu Ile Asn His Leu Leu Asp Gly Asn Lys Asn Pro
        50                  55                  60

Thr Asn Lys Lys Gly Ile Phe Ile Val Pro Leu Lys Ala Leu Ala Ser
65                  70                  75                  80

Glu Lys Tyr Glu Glu Phe Lys Ser Lys Tyr Glu Arg Tyr Gly Leu Arg
                85                  90                  95

Ile Ala Leu Ser Ile Gly Asp Tyr Asp Glu Asp Glu Asp Leu Ser Lys
            100                 105                 110
```

Tyr His Leu Ile Ile Thr Thr Ala Glu Lys Leu Asp Ser Leu Trp Arg
            115                 120                 125
His Lys Ile Asp Trp Ile Asn Asp Val Ser Val Val Val Asp Glu
130                 135                 140
Ile His Leu Ile Asn Asp Glu Thr Arg Gly Thr Leu Glu Ile Leu
145                 150                 155                 160
Leu Thr Lys Leu Lys Glu Phe Asn Val Gln Ile Ile Gly Leu Ser Ala
                165                 170                 175
Thr Ile Gly Asn Pro Asp Glu Leu Ala Glu Trp Leu Asn Ala Glu Leu
                180                 185                 190
Ile Val Asp Asp Trp Arg Pro Val Glu Leu Lys Lys Gly Ile Tyr Lys
        195                 200                 205
Asn Glu Ala Ile Glu Phe Ile Asn Gly Glu Ile Arg Glu Ile Lys Ala
        210                 215                 220
Val Asp Asn Asn Asp Ile Tyr Asn Leu Val Val Asp Cys Val Lys Glu
225                 230                 235                 240
Gly Gly Cys Cys Leu Val Phe Cys Asn Thr Lys Arg Asn Ala Val Asn
                245                 250                 255
Glu Ala Lys Lys Leu Asn Leu Lys Lys Phe Leu Thr Glu Glu Glu Lys
            260                 265                 270
Ile Arg Leu Lys Glu Ile Ala Glu Glu Ile Leu Ser Ile Leu Glu Pro
        275                 280                 285
Pro Thr Glu Met Cys Lys Thr Leu Ala Glu Cys Ile Leu Asn Gly Ser
        290                 295                 300
Ala Phe His His Ala Gly Leu Thr Tyr Gln His Arg Lys Ile Val Glu
305                 310                 315                 320
Asp Ala Phe Arg Lys Arg Leu Ile Lys Val Ile Cys Cys Thr Pro Thr
                325                 330                 335
Leu Ser Ala Gly Leu Asn Leu Pro Cys Arg Arg Ala Ile Val Lys Asp
            340                 345                 350
Leu Thr Arg Phe Thr Asn Lys Gly Met Arg Tyr Ile Pro Ile Met Glu
        355                 360                 365
Ile Gln Gln Cys Ile Gly Arg Ala Gly Arg Pro Gly Leu Asp Pro Tyr
        370                 375                 380
Gly Glu Gly Ile Ile Val Ala Lys Asn Asp Arg Asp Tyr Leu Arg Ala
385                 390                 395                 400
Tyr Gln Ala Leu Thr Gln Lys Pro Glu Pro Ile Tyr Ser Lys Leu Ser
                405                 410                 415
Asn Gln Ala Val Leu Arg Thr Gln Leu Leu Gly Leu Ile Ala Thr Gly
            420                 425                 430
Glu Ile Arg Asp Glu Tyr Asp Leu Glu Trp Phe Ile Arg Asn Thr Phe
        435                 440                 445
Tyr Ala His Gln Tyr Gly Asn Leu Arg Glu Val Ala Lys Asn Ile Asn
        450                 455                 460
Glu Val Ile Arg Phe Leu Glu Glu Asn Glu Phe Ile Ile Asp Phe Met
465                 470                 475                 480
Pro Thr Glu Leu Gly Lys Arg Val Ser Glu Leu Tyr Ile Asp Pro Leu
                485                 490                 495
Ser Ala Lys Phe Ile Ile Asp Gly Leu Glu Glu Met Glu Asn Glu Glu
            500                 505                 510
Glu Ile Tyr Tyr Leu Tyr Leu Ile Ser Lys Thr Leu Glu Met Met Pro
        515                 520                 525
Asn Leu Arg Val Tyr Asn Ser Glu Glu Leu Asn Leu Ile Asp Glu Met

```
                530             535             540
Asp Ser Leu Gly Ile Lys Ser Phe Glu Ile Glu Asp Leu Glu Ala Phe
545                 550                 555                 560

Lys Thr Ala Lys Met Leu Tyr Asp Trp Ile Asn Glu Val Pro Glu Asp
                565                 570                 575

Glu Ile Leu Lys Arg Tyr Lys Ile Glu Pro Gly Ile Leu Arg Tyr Lys
                580                 585                 590

Val Glu Asn Ala Val Trp Ile Met His Ala Leu Lys Glu Ile Ala Lys
                595                 600                 605

Leu Ile Gly Lys Ser Ser Asp Ile Pro Glu Lys Leu Glu Ile Arg Leu
                610                 615                 620

Glu Tyr Gly Ala Lys Glu Asp Ile Ile Glu Leu Leu Ser Ile Lys Tyr
625                 630                 635                 640

Ile Gly Arg Val Arg Ala Arg Lys Leu Tyr Asn Ala Gly Ile Arg Ser
                645                 650                 655

Ile Glu Asp Ile Ile Asn Asn Pro Ser Lys Val Ala Ser Ile Ile Gly
                660                 665                 670

Glu Lys Ile Ala Lys Lys Ile Leu Asp Glu Leu Gly Val Lys Phe Gly
                675                 680                 685

Gln Gln Lys Leu Ser Phe Ser Gly Gly Ser Ala Trp Ser His Pro Gln
                690                 695                 700

Phe Glu Lys Gly Gly Ser Gly Gly Ser Gly Gly Ser Ala Trp
705                 710                 715                 720

Ser His Pro Gln Phe Glu Lys Lys Leu
                725

<210> SEQ ID NO 51
<211> LENGTH: 670
<212> TYPE: PRT
<213> ORGANISM: Methanocaldococcus infernus

<400> SEQUENCE: 51

Met Asp Glu Ile Leu Lys Phe Leu Gly Ile Lys Glu Leu Arg Pro Pro
1               5                   10                  15

Gln Lys Lys Ala Leu Glu Leu Gly Ile Leu Asp Lys Lys Lys Asn Phe
                20                  25                  30

Leu Ile Ser Ile Pro Thr Gly Ala Gly Lys Thr Val Ile Ala Glu Met
                35                  40                  45

Ala Leu Ile Asn His Leu Leu Leu Asp Lys Gly Lys Lys Gly Val Tyr
50                  55                  60

Ile Val Pro Leu Lys Ala Leu Ala Ser Glu Lys Tyr Glu Glu Phe Lys
65                  70                  75                  80

Lys Lys Tyr Glu Lys Phe Gly Val Arg Val Ala Leu Ser Ile Gly Asp
                85                  90                  95

Tyr Asp Glu Asp Glu Asp Leu Glu Asn Tyr Asp Leu Ile Ile Thr Thr
                100                 105                 110

Ala Glu Lys Phe Asp Ser Leu Trp Arg His Gly Ile Lys Leu Ser Asp
                115                 120                 125

Ile Ser Val Val Val Asp Glu Ile His Val Ile Gly Asp Ser Glu
                130                 135                 140

Arg Gly Gly Thr Leu Glu Val Leu Leu Thr Lys Leu Lys Glu Leu Asp
145                 150                 155                 160

Val Gln Ile Ile Gly Leu Ser Ala Thr Ile Gly Asn Pro Glu Glu Leu
                165                 170                 175
```

-continued

```
Ser Glu Trp Leu Asn Ala Glu Leu Leu Leu Asp Asn Trp Arg Pro Val
            180                 185                 190

Glu Leu Arg Lys Gly Ile Tyr Arg Gly Val Ile Glu Tyr Leu Asp
        195                 200                 205

Gly Glu Val Lys Glu Cys Gln Asp Ile Val Lys Glu Val Val Lys Asp
    210                 215                 220

Asn Gly Ser Val Ile Ile Phe Cys Pro Thr Lys Lys Ala Glu Asn
225                 230                 235                 240

Arg Ala Leu Ser Leu Asp Leu Ser Asp Leu Leu Lys Lys Ser Glu Lys
                245                 250                 255

Arg Lys Leu Glu Glu Ile Ser Glu Leu Leu Ser Leu Phe Asp Pro
        260                 265                 270

Pro Thr Glu Leu Cys Lys Lys Leu Ala Ser Cys Val Arg Lys Gly Ile
        275                 280                 285

Ala Phe His His Ser Gly Leu Thr Tyr Glu His Arg Lys Ile Ile Glu
        290                 295                 300

Lys Ala Phe Arg Glu Arg Ile Leu Lys Val Ile Cys Ser Thr Thr Thr
305                 310                 315                 320

Leu Ala Phe Gly Leu Asn Leu Pro Cys Arg Arg Val Ile Ile Ser Glu
                325                 330                 335

Leu Lys Arg Tyr Thr Arg Arg Gly Leu Thr Tyr Ile Pro Ile Met Glu
        340                 345                 350

Val Gln Gln Cys Ile Gly Arg Ala Gly Arg Pro Gly Leu Asp Glu Tyr
        355                 360                 365

Gly Glu Gly Ile Leu Val Ala Lys Asp Glu Arg Asp Tyr Leu Arg Ala
    370                 375                 380

Leu Gln Cys Leu Thr Gln Lys Pro Glu Pro Ile Tyr Ser Lys Leu Ser
385                 390                 395                 400

Asn Asp Ser Val Leu Arg Thr Gln Ile Leu Gly Leu Ile Ala Thr Arg
                405                 410                 415

Tyr Val Leu Asp Glu Tyr Asp Leu Glu Glu Phe Ile Lys Asn Thr Phe
        420                 425                 430

Tyr Ala Tyr Gln Tyr Lys Asn Leu Asp Glu Ile Lys Lys Lys Ile Lys
        435                 440                 445

Glu Ile Ile Glu Phe Leu Glu Asp Cys Asn Phe Ile Lys Asn Phe Glu
    450                 455                 460

Val Thr Pro Leu Gly Lys Lys Val Ser Asn Leu Tyr Leu Asp Pro Leu
465                 470                 475                 480

Ser Ala Lys Ile Met Ile Asp Asn Ile Glu Val Lys Asp Asp Leu His
                485                 490                 495

Leu Leu Tyr Ile Leu Cys Lys Cys Ile Glu Met Lys Pro Leu Leu Arg
        500                 505                 510

Val Tyr Arg Lys Glu Glu Glu Leu Ala Glu Glu Leu Leu Asn Tyr
        515                 520                 525

Glu Ile Phe Ile Ser Tyr Glu Asn Leu Glu Glu Phe Lys Thr Ala Lys
    530                 535                 540

Met Leu Tyr Asp Trp Ile Asn Glu Val Pro Glu Asp Glu Ile Leu Lys
545                 550                 555                 560

Thr Tyr Lys Val Glu Pro Gly Ile Leu Arg Tyr Lys Val Glu Val Ala
                565                 570                 575

Lys Trp Leu Ser Tyr Ser Leu Lys Glu Ile Ala Lys Ile Leu Asn Lys
        580                 585                 590

Glu Val Pro Asn Leu Glu Leu Arg Leu Glu Tyr Gly Ala Lys Glu Glu
```

```
                    595                 600                 605
Leu Leu Glu Leu Leu Lys Ile Lys Tyr Ile Gly Arg Val Ala Arg
    610                 615                 620
Lys Leu Tyr Ser Ala Gly Ile Arg Asn Arg Glu Asp Ile Ile Lys Asn
625                 630                 635                 640
Pro Lys Lys Val Ala Asn Ile Leu Gly Glu Lys Ile Ser Lys Lys Ile
                645                 650                 655
Phe Glu Glu Leu Gly Val Arg Tyr Gly Gln Gln Arg Leu Ile
            660                 665                 670

<210> SEQ ID NO 52
<211> LENGTH: 799
<212> TYPE: PRT
<213> ORGANISM: Methanospirillum hungatei

<400> SEQUENCE: 52

Met Glu Ile Ala Ser Leu Pro Leu Pro Asp Ser Phe Ile Arg Ala Cys
1               5                   10                  15
His Ala Lys Gly Ile Arg Ser Leu Tyr Pro Pro Gln Ala Glu Cys Ile
            20                  25                  30
Glu Lys Gly Leu Leu Gly Lys Asn Leu Leu Ile Ser Ile Pro Thr
        35                  40                  45
Ala Ser Gly Lys Thr Leu Leu Ala Glu Met Ala Met Trp Ser Arg Ile
50                  55                  60
Ala Ala Gly Gly Lys Cys Leu Tyr Ile Val Pro Leu Arg Ala Leu Ala
65                  70                  75                  80
Ser Glu Lys Tyr Asp Glu Phe Ser Lys Lys Gly Val Ile Arg Val Gly
                85                  90                  95
Ile Ala Thr Gly Asp Leu Asp Arg Thr Asp Ala Tyr Leu Gly Glu Asn
            100                 105                 110
Asp Ile Ile Val Ala Thr Ser Glu Lys Thr Asp Ser Leu Leu Arg Asn
        115                 120                 125
Arg Thr Pro Trp Leu Ser Gln Ile Thr Cys Ile Val Leu Asp Glu Val
    130                 135                 140
His Leu Ile Gly Ser Glu Asn Arg Gly Ala Thr Leu Glu Met Val Ile
145                 150                 155                 160
Thr Lys Leu Arg Tyr Thr Asn Pro Val Met Gln Ile Ile Gly Leu Ser
                165                 170                 175
Ala Thr Ile Gly Asn Pro Ala Gln Leu Ala Glu Trp Leu Asp Ala Thr
            180                 185                 190
Leu Ile Thr Ser Thr Trp Arg Pro Val Asp Leu Arg Gln Gly Val Tyr
        195                 200                 205
Tyr Asn Gly Lys Ile Arg Phe Ser Asp Ser Glu Arg Pro Ile Gln Gly
    210                 215                 220
Lys Thr Lys His Asp Asp Leu Asn Leu Cys Leu Asp Thr Ile Glu Glu
225                 230                 235                 240
Gly Gly Gln Cys Leu Val Phe Val Ser Ser Arg Arg Asn Ala Glu Gly
                245                 250                 255
Phe Ala Lys Lys Ala Ala Gly Ala Leu Lys Ala Gly Ser Pro Asp Ser
            260                 265                 270
Lys Ala Leu Ala Gln Glu Leu Arg Arg Leu Arg Asp Arg Asp Glu Gly
        275                 280                 285
Asn Val Leu Ala Asp Cys Val Glu Arg Gly Ala Ala Phe His His Ala
    290                 295                 300
```

```
Gly Leu Ile Arg Gln Glu Arg Thr Ile Ile Glu Gly Phe Arg Asn
305                 310                 315                 320

Gly Tyr Ile Glu Val Ile Ala Ala Thr Pro Thr Leu Ala Ala Gly Leu
            325                 330                 335

Asn Leu Pro Ala Arg Arg Val Ile Ile Arg Asp Tyr Asn Arg Phe Ala
                340                 345                 350

Ser Gly Leu Gly Met Val Pro Ile Pro Val Gly Glu Tyr His Gln Met
            355                 360                 365

Ala Gly Arg Ala Gly Arg Pro His Leu Asp Pro Tyr Gly Glu Ala Val
            370                 375                 380

Leu Leu Ala Lys Asp Ala Pro Ser Val Glu Arg Leu Phe Glu Thr Phe
385                 390                 395                 400

Ile Asp Ala Glu Ala Glu Arg Val Asp Ser Gln Cys Val Asp Asp Ala
                405                 410                 415

Ser Leu Cys Ala His Ile Leu Ser Leu Ile Ala Thr Gly Phe Ala His
            420                 425                 430

Asp Gln Glu Ala Leu Ser Ser Phe Met Glu Arg Thr Phe Tyr Phe Phe
            435                 440                 445

Gln His Pro Lys Thr Arg Ser Leu Pro Arg Leu Val Ala Asp Ala Ile
    450                 455                 460

Arg Phe Leu Thr Thr Ala Gly Met Val Glu Glu Arg Glu Asn Thr Leu
465                 470                 475                 480

Ser Ala Thr Arg Leu Gly Ser Leu Val Ser Arg Leu Tyr Leu Asn Pro
                485                 490                 495

Cys Thr Ala Arg Leu Ile Leu Asp Ser Leu Lys Ser Cys Lys Thr Pro
            500                 505                 510

Thr Leu Ile Gly Leu Leu His Val Ile Cys Val Ser Pro Asp Met Gln
    515                 520                 525

Arg Leu Tyr Leu Lys Ala Ala Asp Thr Gln Leu Leu Arg Thr Phe Leu
    530                 535                 540

Phe Lys His Lys Asp Asp Leu Ile Leu Pro Leu Pro Phe Glu Gln Glu
545                 550                 555                 560

Glu Glu Glu Leu Trp Leu Ser Gly Leu Lys Thr Ala Leu Val Leu Thr
                565                 570                 575

Asp Trp Ala Asp Glu Phe Ser Glu Gly Met Ile Glu Glu Arg Tyr Gly
            580                 585                 590

Ile Gly Ala Gly Asp Leu Tyr Asn Ile Val Asp Ser Gly Lys Trp Leu
            595                 600                 605

Leu His Gly Thr Glu Arg Leu Val Ser Val Glu Met Pro Glu Met Ser
    610                 615                 620

Gln Val Val Lys Thr Leu Ser Val Arg Val His His Gly Val Lys Ser
625                 630                 635                 640

Glu Leu Leu Pro Leu Val Ala Leu Arg Asn Ile Gly Arg Val Arg Ala
                645                 650                 655

Arg Thr Leu Tyr Asn Ala Gly Tyr Pro Asp Pro Glu Ala Val Ala Arg
            660                 665                 670

Ala Gly Leu Ser Thr Ile Ala Arg Ile Ile Gly Glu Gly Ile Ala Arg
            675                 680                 685

Gln Val Ile Asp Glu Ile Thr Gly Val Lys Arg Ser Gly Ile His Ser
    690                 695                 700

Ser Asp Asp Asp Tyr Gln Gln Lys Thr Pro Glu Leu Leu Thr Asp Ile
705                 710                 715                 720

Pro Gly Ile Gly Lys Lys Met Ala Glu Lys Leu Gln Asn Ala Gly Ile
```

```
                    725                 730                 735
Ile Thr Val Ser Asp Leu Leu Thr Ala Asp Glu Val Leu Leu Ser Asp
                740                 745                 750

Val Leu Gly Ala Ala Arg Ala Arg Lys Val Leu Ala Phe Leu Ser Asn
            755                 760                 765

Ser Glu Lys Glu Asn Ser Ser Ser Asp Lys Thr Glu Ile Pro Asp
770                 775                 780

Thr Gln Lys Ile Arg Gly Gln Ser Ser Trp Glu Asp Phe Gly Cys
785                 790                 795

<210> SEQ ID NO 53
<211> LENGTH: 702
<212> TYPE: PRT
<213> ORGANISM: Archaeoglobus fulgidus

<400> SEQUENCE: 53

Met Lys Val Glu Glu Leu Ala Glu Ser Ile Ser Ser Tyr Ala Val Gly
1               5                   10                  15

Ile Leu Lys Glu Gly Ile Glu Glu Leu Phe Pro Pro Gln Ala Glu
            20                  25                  30

Ala Val Glu Lys Val Phe Ser Gly Lys Asn Leu Leu Leu Ala Met Pro
            35                  40                  45

Thr Ala Ala Gly Lys Thr Leu Leu Ala Glu Met Ala Met Val Arg Glu
50                  55                  60

Ala Ile Lys Gly Gly Lys Ser Leu Tyr Val Val Pro Leu Arg Ala Leu
65                  70                  75                  80

Ala Gly Glu Lys Tyr Glu Ser Phe Lys Lys Trp Glu Lys Ile Gly Leu
                85                  90                  95

Arg Ile Gly Ile Ser Thr Gly Asp Tyr Glu Ser Arg Asp Glu His Leu
            100                 105                 110

Gly Asp Cys Asp Ile Ile Val Thr Thr Ser Glu Lys Ala Asp Ser Leu
        115                 120                 125

Ile Arg Asn Arg Ala Ser Trp Ile Lys Ala Val Ser Cys Leu Val Val
130                 135                 140

Asp Glu Ile His Leu Leu Asp Ser Glu Lys Arg Gly Ala Thr Leu Glu
145                 150                 155                 160

Ile Leu Val Thr Lys Met Arg Arg Met Asn Lys Ala Leu Arg Val Ile
                165                 170                 175

Gly Leu Ser Ala Thr Ala Pro Asn Val Thr Glu Ile Ala Glu Trp Leu
            180                 185                 190

Asp Ala Asp Tyr Tyr Val Ser Asp Trp Arg Pro Val Pro Leu Val Glu
        195                 200                 205

Gly Val Leu Cys Glu Gly Thr Leu Glu Leu Phe Asp Gly Ala Phe Ser
    210                 215                 220

Thr Ser Arg Arg Val Lys Phe Glu Glu Leu Val Glu Glu Cys Val Ala
225                 230                 235                 240

Glu Asn Gly Gly Val Leu Val Phe Glu Ser Thr Arg Arg Gly Ala Glu
                245                 250                 255

Lys Thr Ala Val Lys Leu Ser Ala Ile Thr Ala Lys Tyr Val Glu Asn
            260                 265                 270

Glu Gly Leu Glu Lys Ala Ile Leu Glu Glu Asn Glu Gly Glu Met Ser
        275                 280                 285

Arg Lys Leu Ala Glu Cys Val Arg Lys Gly Ala Ala Phe His His Ala
    290                 295                 300
```

| | | | | | | | | | | | | | | |
|---|---|---|---|---|---|---|---|---|---|---|---|---|---|---|
|Gly|Leu|Leu|Asn|Gly|Gln|Arg|Arg|Val|Val|Glu|Asp|Ala|Phe|Arg|Arg|
|305| | | | |310| | | | |315| | | | |320|

Gly Asn Ile Lys Val Val Ala Thr Pro Thr Leu Ala Ala Gly Val
            325             330             335

Asn Leu Pro Ala Arg Arg Val Ile Val Arg Ser Leu Tyr Arg Phe Asp
        340             345             350

Gly Tyr Ser Lys Arg Ile Lys Val Ser Glu Tyr Lys Gln Met Ala Gly
        355             360             365

Arg Ala Gly Arg Pro Gly Met Asp Glu Arg Gly Glu Ala Ile Ile Ile
        370             375             380

Val Gly Lys Arg Asp Arg Glu Ile Ala Val Lys Arg Tyr Ile Phe Gly
385             390             395             400

Glu Pro Glu Arg Ile Thr Ser Lys Leu Gly Val Glu Thr His Leu Arg
            405             410             415

Phe His Ser Leu Ser Ile Ile Cys Asp Gly Tyr Ala Lys Thr Leu Glu
            420             425             430

Glu Leu Glu Asp Phe Phe Ala Asp Thr Phe Phe Lys Gln Asn Glu
        435             440             445

Ile Ser Leu Ser Tyr Glu Leu Glu Arg Val Val Arg Gln Leu Glu Asn
450             455             460

Trp Gly Met Val Val Glu Asp His His Leu Ala Pro Thr Lys Leu Gly
465             470             475             480

Ser Leu Val Ser Arg Leu Tyr Ile Asp Pro Leu Thr Gly Phe Ile Phe
            485             490             495

His Asp Val Leu Ser Arg Met Glu Leu Ser Asp Ile Gly Ala Leu His
        500             505             510

Leu Ile Cys Arg Thr Pro Asp Met Glu Arg Leu Thr Val Arg Lys Thr
        515             520             525

Asp Ser Trp Val Glu Glu Ala Phe Arg Leu Arg Lys Glu Leu Ser
        530             535             540

Tyr Tyr Pro Ser Asp Phe Ser Val Glu Tyr Asp Trp Phe Leu Ser Glu
545             550             555             560

Val Lys Thr Ala Leu Cys Leu Lys Asp Trp Ile Glu Glu Lys Asp Glu
            565             570             575

Asp Glu Ile Cys Ala Lys Tyr Gly Ile Ala Pro Gly Asp Leu Arg Arg
        580             585             590

Ile Val Glu Thr Ala Glu Trp Leu Ser Asn Ala Met Asn Arg Ile Ala
        595             600             605

Glu Glu Val Gly Asn Thr Ser Val Ser Gly Leu Thr Glu Arg Ile Lys
        610             615             620

His Gly Val Lys Glu Glu Leu Leu Glu Leu Val Arg Ile Arg His Ile
625             630             635             640

Gly Arg Val Arg Ala Arg Lys Leu Tyr Asn Ala Gly Ile Arg Asn Ala
            645             650             655

Glu Asp Ile Val Arg His Arg Glu Lys Val Ala Ser Leu Ile Gly Arg
        660             665             670

Gly Ile Ala Glu Arg Val Val Glu Gly Ile Ser Val Lys Ser Leu Asn
        675             680             685

Pro Glu Ser Ala Ala Ala Leu Glu His His His His His
        690             695             700

<210> SEQ ID NO 54
<211> LENGTH: 791
<212> TYPE: PRT

<213> ORGANISM: Haloterrigena turkmenica

<400> SEQUENCE: 54

```
Met Asn Leu Glu Glu Leu Thr Gly Leu Pro Pro Gly Ala Thr Asp His
1               5                   10                  15

Phe Arg Gly Glu Gly Ile Glu Glu Leu Tyr Pro Pro Gln Ala Asp Ala
            20                  25                  30

Val Glu Ala Gly Ala Thr Asp Gly Glu Asn Leu Val Ala Ala Val Pro
        35                  40                  45

Thr Ala Ser Gly Lys Thr Met Ile Ala Ala Leu Ser Met Leu Ser Ala
    50                  55                  60

Val Gln Arg Gly Gly Lys Ala Leu Tyr Ile Val Pro Leu Arg Ala Leu
65                  70                  75                  80

Ala Ser Glu Lys Lys Glu Glu Phe Glu Ala Tyr Glu Glu Phe Gly Val
                85                  90                  95

Thr Thr Gly Val Thr Thr Gly Asn Tyr Glu Ser Thr Asp Asp Trp Leu
            100                 105                 110

Ala Thr Lys Asp Ile Ile Val Ala Thr Ser Glu Lys Val Asp Ser Leu
        115                 120                 125

Val Arg Asn Gly Ala Asp Trp Leu Ser Glu Leu Thr Cys Val Val Ser
130                 135                 140

Asp Glu Val His Leu Ile Asp Asp Arg Asn Arg Gly Pro Thr Leu Glu
145                 150                 155                 160

Val Thr Leu Ala Lys Leu Arg Arg Leu Asn Pro Gly Met Gln Val Val
                165                 170                 175

Ala Leu Ser Ala Thr Val Gly Asn Ala Asp Glu Ile Ala Asp Trp Leu
            180                 185                 190

Asp Ala Ser Leu Val Asp Thr Asp Trp Arg Pro Ile Asp Leu Gln Met
        195                 200                 205

Gly Val His Tyr Gly Asn Ala Leu Asn Phe Asp Asp Gly Ser Thr Arg
    210                 215                 220

Glu Val Pro Val Glu Gly Ser Glu Lys Gln Glu Ala Ala Leu Val Arg
225                 230                 235                 240

Asp Ile Leu Arg Glu Gly Gly Ser Ser Leu Val Phe Val Asn Ser Arg
                245                 250                 255

Arg Asn Ala Glu Gly Ala Ala Lys Arg Leu Gly Gln Val Ser Ser Arg
            260                 265                 270

Glu Ile Thr Glu Asp Glu Arg Ala Glu Leu Ala Glu Leu Ala Asp Asp
        275                 280                 285

Ile Arg Asp Asp Ser Asp Thr Glu Thr Ser Ala Asp Leu Ala Asp Cys
    290                 295                 300

Val Glu Arg Gly Ala Ala Phe His His Ala Gly Leu Ser Ser Thr Gln
305                 310                 315                 320

Arg Ser Leu Val Glu Asp Ala Phe Arg Asp Arg Leu Leu Lys Val Ile
                325                 330                 335

Ser Ala Thr Pro Thr Leu Ala Ala Gly Val Asn Thr Pro Ala Arg Arg
            340                 345                 350

Val Ile Val Arg Asp Trp Arg Arg Phe Asp Pro Ser Ala Gly Gly Met
        355                 360                 365

Ala Pro Leu Asp Val Leu Glu Val His Gln Met Met Gly Arg Ala Gly
    370                 375                 380

Arg Pro Gly Leu Asp Pro Tyr Gly Glu Ala Val Leu Leu Ala Lys Ser
385                 390                 395                 400
```

```
His Asp Glu Ser Glu Leu Phe Asp Arg Tyr Ile Trp Ala Asp Pro
            405                 410                 415
Glu Pro Val Arg Ser Lys Leu Ala Ala Glu Pro Ala Leu Arg Thr His
        420                 425                 430
Val Leu Ala Thr Ile Ala Ser Gly Phe Ala Arg Thr Arg Gly Gly Leu
            435                 440                 445
Leu Glu Phe Leu Glu Ala Thr Leu Tyr Ala Ser Gln Ser Ser Glu Ala
450                 455                 460
Gly Arg Leu Glu Ser Val Thr Asp Asp Val Leu Asp Tyr Leu Glu Arg
465                 470                 475                 480
Asn Asp Phe Ile Glu Arg Ser Arg Asp Glu Ala Glu Asp Ser Gly
                485                 490                 495
Glu Asp Asp Gly Pro Phe Thr Ser Ala Ala Asp Leu Ala Glu Gln Gln
            500                 505                 510
Ala Ala Lys Arg Glu Glu Thr Leu Glu Ala Thr Ser Leu Gly His Thr
        515                 520                 525
Val Ser Arg Leu Tyr Leu Asp Pro Met Ser Ala Ala Glu Ile Val His
    530                 535                 540
Gly Leu Glu Arg Ala Asp Glu Arg Pro Thr Ala Leu Gly Leu Tyr Gln
545                 550                 555                 560
Leu Val Ser Arg Thr Pro Asp Met Tyr Glu Leu Tyr Leu Arg Ser Gly
                565                 570                 575
Glu Asp Glu Lys Phe Gly Glu Leu Phe Tyr Glu Arg Glu Thr Glu Leu
            580                 585                 590
Leu Gly Asp Ala Pro Ser Glu Tyr Glu Glu Asp Arg Phe Glu Asp Trp
        595                 600                 605
Leu Ala Ala Leu Lys Thr Gly Lys Leu Leu Glu Asp Trp Ala Asp Glu
    610                 615                 620
Thr Asp Glu Glu Thr Ile Thr Asp Arg Tyr Lys Ile Gly Pro Gly Asp
625                 630                 635                 640
Leu Arg Gly Lys Val Asp Thr Ala Glu Trp Leu Leu Gly Ala Ala Glu
                645                 650                 655
Ser Leu Ala Ala Glu Ile Asp Ser Glu Trp Thr Val Ala Val Arg Glu
            660                 665                 670
Ala Arg Ala Arg Val Glu His Gly Val Gly Glu Glu Leu Leu Glu Leu
        675                 680                 685
Val Ser Val Gly Gly Val Gly Arg Lys Arg Ala Arg Arg Leu Tyr Asp
    690                 695                 700
Ala Gly Ile Glu Glu Pro Ala Asp Leu Arg Ser Ala Asp Lys Gly Ile
705                 710                 715                 720
Val Leu Ser Val Leu Lys Gly Glu Lys Thr Ala Glu Asn Ile Leu Glu
                725                 730                 735
Asn Ala Gly Arg Glu Asp Pro Ser Met Asp Gly Val Glu Pro Ala Asp
            740                 745                 750
Gly Gly Pro Ala Val Gly Ala Thr Asn Gly Ser Ser Gly Gly Ser
        755                 760                 765
Glu Thr Asp Glu Thr Gly Arg Ala Asp Ala Ala Glu Ser Asp Asp Ser
    770                 775                 780
Gln Ser Ser Leu Gly Asp Phe
785                 790

<210> SEQ ID NO 55
<211> LENGTH: 752
<212> TYPE: PRT
```

<213> ORGANISM: Haladaptatus paucihalophilus

<400> SEQUENCE: 55

```
Met Asn Val Ala Asp Leu Thr Gly Leu Pro Asp Gly Val Pro Glu His
1               5                   10                  15

Phe His Ala Gln Gly Ile Glu Glu Leu Tyr Pro Pro Gln Ala Glu Ala
            20                  25                  30

Val Glu Ala Gly Ile Thr Glu Gly Ser Val Val Ala Ser Ile Pro
        35                  40                  45

Thr Ala Ser Gly Lys Thr Phe Ile Ala Glu Leu Ala Met Leu Ser Ser
    50                  55                  60

Val Ala Arg Gly Gly Lys Ala Leu Tyr Ile Val Pro Leu Arg Ala Leu
65                  70                  75                  80

Ala Ser Glu Lys Lys Glu Glu Phe Glu Glu Phe Glu Gln Tyr Gly Val
                85                  90                  95

Ser Ile Gly Val Ser Thr Gly Asn Tyr Glu Ser Asp Gly Asp Trp Leu
            100                 105                 110

Ala Ser Arg Asp Ile Ile Val Ala Thr Ser Glu Lys Val Asp Ser Leu
        115                 120                 125

Val Arg Asn Gly Ala Lys Trp Ile Asp Asp Leu Ser Cys Val Val Ala
130                 135                 140

Asp Glu Val His Leu Val Asn Asp Ala His Arg Gly Pro Thr Leu Glu
145                 150                 155                 160

Val Thr Leu Ala Lys Leu Arg Arg Val Asn Pro Asp Leu Gln Thr Val
                165                 170                 175

Ala Leu Ser Ala Thr Val Gly Asn Ala Gly Met Ala Asp Trp Leu
            180                 185                 190

Asp Ala Thr Leu Val Asp Ser Thr Trp Arg Pro Ile Asp Leu Arg Lys
        195                 200                 205

Gly Val Leu Tyr Gly Gln Ala Leu His Phe Asp Asp Gly Thr Gln Gln
210                 215                 220

Glu Leu Ala Arg Gly Asn Glu Lys Glu Thr Ala Ala Leu Val Arg Asp
225                 230                 235                 240

Thr Leu Glu Asp Gly Gly Ser Ser Leu Val Phe Val Asn Ser Arg Arg
                245                 250                 255

Asn Ala Glu Ala Ala Lys Arg Leu Ala Asp Val Thr Lys Thr His
            260                 265                 270

Leu Thr Asp Asp Glu Arg Arg Asp Leu Leu Asp Ile Ala Asp Gln Ile
        275                 280                 285

Arg Asp Val Ser Asp Thr Glu Thr Ser Asp Asp Leu Ala Thr Ala Ile
290                 295                 300

Glu Lys Gly Ala Ala Phe His His Ala Gly Leu Ala Ser Asp His Arg
305                 310                 315                 320

Ser Leu Val Glu Asp Ala Phe Arg Asp Lys Leu Ile Lys Val Ile Ser
                325                 330                 335

Ala Thr Pro Thr Leu Ala Ala Gly Val Asn Thr Pro Ser Arg Arg Val
            340                 345                 350

Ile Val Arg Asp Trp Arg Arg Tyr Asp Gly Asp Ile Gly Gly Met Gln
        355                 360                 365

Pro Leu Asp Val Leu Glu Val His Gln Met Phe Gly Arg Ala Gly Arg
370                 375                 380

Pro Gly Leu Asp Pro His Gly Glu Ala Val Leu Ile Ala Lys Ser His
385                 390                 395                 400
```

```
Asp Glu Leu Gln Glu Leu Phe Asp Gln Tyr Val Trp Ala Asp Pro Glu
                405                 410                 415

Pro Val His Ser Lys Leu Ala Ala Glu Pro Ala Leu Arg Thr His Ile
            420                 425                 430

Leu Ala Thr Val Ala Ser Gly Phe Ala Gly Thr Glu Glu Leu Leu
            435                 440                 445

Asp Phe Leu Glu Arg Thr Leu Tyr Ala Thr Gln Thr Asp Glu Thr Gly
    450                 455                 460

Arg Leu Glu Thr Val Thr Gln His Val Leu Asp Tyr Leu Asp Arg Asn
465                 470                 475                 480

Gly Phe Leu Glu Arg Asp Asp Arg Leu Arg Ala Thr Gly Leu Gly His
                485                 490                 495

Arg Val Ser Gln Leu Tyr Leu Asp Pro Met Ser Ala Ala Glu Ile Ile
            500                 505                 510

Asp Gly Leu Arg Asp Ala Asp Gly Lys Pro Thr Ala Leu Gly Leu Tyr
            515                 520                 525

His Leu Val Ser Arg Thr Pro Asp Met Tyr Gln Leu Tyr Leu Arg Ser
    530                 535                 540

Gly Asp Arg Glu Arg Tyr Thr Glu Ile Ala Tyr Glu Arg Glu Pro Glu
545                 550                 555                 560

Phe Leu Gly His Met Pro Ser Glu Phe Glu Asp Asn Ala Phe Glu Asp
                565                 570                 575

Trp Leu Ser Ala Leu Lys Thr Ala Arg Leu Leu Glu Asp Trp Ala Ser
            580                 585                 590

Glu Leu Asp Glu Asp Arg Ile Thr Glu Arg Tyr Ala Ile Gly Pro Gly
    595                 600                 605

Asp Ile Arg Gly Lys Val Glu Thr Ala Gln Trp Leu Leu Asn Ala Ala
    610                 615                 620

Glu Arg Leu Ala Ala Glu Leu Gln Arg Asp Asp Ala Glu Gly Ile Pro
625                 630                 635                 640

Ser Ala Thr Thr Thr Ala Val Arg Glu Ala Arg Lys Arg Val Glu Tyr
                645                 650                 655

Gly Val Glu Glu Glu Leu Leu Asp Leu Ala Gly Val Arg Asn Val Gly
                660                 665                 670

Arg Lys Arg Ala Arg Arg Leu Tyr Glu Ala Gly Ile Glu Ser Arg Ala
            675                 680                 685

Asp Leu Arg Glu Ala Asp Lys Ser Val Val Leu Gly Ala Leu Arg Gly
    690                 695                 700

Arg Lys Lys Thr Ala Glu Asn Ile Leu Glu Asn Val Gly Arg Gln Asp
705                 710                 715                 720

Pro Ser Leu Asp Asp Val Glu Ala Asp Ala Glu Thr Ala Ala Thr Ser
            725                 730                 735

Ala Arg Ala Thr Asn Asp Gly Gly Gln Gln Ser Leu Gly Asp Phe Glu
                740                 745                 750

<210> SEQ ID NO 56
<211> LENGTH: 8
<212> TYPE: PRT
<213> ORGANISM: Artificial sequence
<220> FEATURE:
<223> OTHER INFORMATION: Exemplary Hel308 motif

<400> SEQUENCE: 56

Gln Met Phe Gly Arg Ala Gly Arg
1               5
```

```
<210> SEQ ID NO 57
<211> LENGTH: 9
<212> TYPE: PRT
<213> ORGANISM: Artificial sequence
<220> FEATURE:
<223> OTHER INFORMATION: Exemplary extended Hel308 motif

<400> SEQUENCE: 57

Gln Met Phe Gly Arg Ala Gly Arg Pro
1               5

<210> SEQ ID NO 58
<211> LENGTH: 783
<212> TYPE: PRT
<213> ORGANISM: Halobacterium sp. NRC-1

<400> SEQUENCE: 58

Met Arg Val Ala Asp Val Pro Gly Leu Pro Gly Gly Val Ala Asp His
1               5                   10                  15

Phe Glu Gly Glu Gly Val Glu Glu Leu Tyr Pro Pro Gln Ala Glu Ala
            20                  25                  30

Val Glu Arg Gly Val Thr Glu Gly Ala Asn Leu Val Ala Ser Val Pro
        35                  40                  45

Thr Ala Ser Gly Lys Thr Leu Ile Ala Gln Leu Ala Met Leu Ser Ala
    50                  55                  60

Ile Ala Glu Gly Gly Asp Ser Pro Thr Phe Ser Asp Gly Thr Ala
65                  70                  75                  80

Leu Tyr Ile Val Pro Leu Arg Ala Leu Ala Gly Glu Lys Ala Gln Glu
                85                  90                  95

Phe Glu Ala Phe Glu Arg Phe Gly Leu Ser Val Gly Val Ser Thr Gly
            100                 105                 110

Asn Tyr Glu Arg Asp Gly Ala Arg Leu Ala Asp Asn Asp Ile Val Val
        115                 120                 125

Ala Thr Ser Glu Lys Val Asp Ser Leu Val Arg Asn Gly Ala Gly Trp
    130                 135                 140

Ile Asp Asp Leu Ser Cys Val Val Ala Asp Glu Val His Leu Val Asp
145                 150                 155                 160

Asp Asp His Arg Gly Pro Thr Leu Glu Val Thr Leu Ala Lys Leu Arg
                165                 170                 175

Gln Gln Val Ala Asp Leu Gln Val Val Ala Leu Ser Ala Thr Val Gly
            180                 185                 190

Asn Ala Gly Glu Leu Ala Ala Trp Leu Asp Ala Glu Leu Val Asp Ser
        195                 200                 205

Asp Trp Arg Pro Ile Glu Leu Arg Thr Gly Val His Tyr Gly Gln Ser
    210                 215                 220

Leu His Tyr Asp Asp Gly Thr Gln Ala Glu Leu Ser Val Gly Ser Gly
225                 230                 235                 240

Ser Gln Thr Ala Ala Val Val Ala Asp Thr Leu Ala Asp Gly Ser
                245                 250                 255

Thr Leu Val Phe Val Asn Ser Arg Arg Asn Ala Glu Ala Ser Ala Arg
            260                 265                 270

Arg Leu Ala Asp Val Thr Gly Asn Ala Leu Ser Ser Ala Glu Arg Glu
        275                 280                 285

Arg Leu Ala Asp Ile Ala Ala Glu Ile Arg Gly Val Ser Asp Thr Glu
    290                 295                 300

Thr Ser Asp Glu Leu Ala Asp Ala Val Ala Ser Gly Ala Ala Phe His
```

```
            305                 310                 315                 320
        His Ala Gly Leu Ala Arg Glu His Arg Glu Leu Val Glu Glu Ala Phe
                        325                 330                 335
        Arg Asp Arg Leu Val Lys Ala Val Ser Ala Thr Pro Thr Leu Ala Ala
                        340                 345                 350
        Gly Val Asn Thr Pro Ala Arg Val Val Arg Asp Trp Gln Arg
                        355                 360                 365
        Tyr Asp Gly Thr Ala Gly Gly Met Gln Pro Leu Asp Val Leu Glu Val
                        370                 375                 380
        His Gln Met Phe Gly Arg Ala Gly Arg Pro Gly Leu Asp Pro Tyr Gly
        385                 390                 395                 400
        Glu Ala Val Leu Leu Ala Asn Ser His Asp Glu Leu Glu Glu Leu Phe
                        405                 410                 415
        Asp Arg Tyr Val Tyr Ala Asp Pro Glu Pro Val Arg Ser Lys Leu Ala
                        420                 425                 430
        Ala Glu Pro Ala Leu Arg Thr His Val Leu Ala Ala Ile Ala Thr Gly
                        435                 440                 445
        Phe Thr Thr Thr Glu Asp Gly Leu His Glu Phe Leu Gly Gly Thr Leu
        450                 455                 460
        Tyr Ala Thr Gln Thr Asp Asp Thr Gly Arg Leu Arg Ser Val Thr Gly
        465                 470                 475                 480
        Asp Val Leu Arg Tyr Leu Asp Arg Asn Gly Phe Val Glu Arg Asp Gly
                        485                 490                 495
        Ala Ala Leu Arg Ala Thr Ala Thr Gly Gln Leu Val Ser Arg Leu Tyr
                        500                 505                 510
        Val Asp Pro Met Ser Ala Ala Thr Ile Ile Asp Gly Leu Arg Asp Ala
                        515                 520                 525
        Ala Arg Asp Ala Thr Glu Thr Asp Asp Glu Gly Ala Phe Arg Pro Ala
                        530                 535                 540
        Ser Glu Leu Gly Asp Asp Ala Ala Leu Pro Ala Asp Ala Ser Val Glu
        545                 550                 555                 560
        Pro Thr Pro Leu Gly Leu Tyr His Leu Val Ser Arg Thr Pro Asp Met
                        565                 570                 575
        Tyr Glu Leu Tyr Leu Arg Ser Gly Asp Arg Glu Gln Tyr Thr Glu Val
                        580                 585                 590
        Ala Tyr Glu His Glu Asp Glu Leu Leu Gly Ala Thr Pro Arg Glu Glu
                        595                 600                 605
        Gln Ala Glu Phe Glu Asp Trp Leu Ser Ala Leu Lys Thr Ala Arg Leu
        610                 615                 620
        Met Ala Asp Trp Ala Ser Glu Leu Asp Glu Glu Arg Ile Ala Glu Arg
        625                 630                 635                 640
        Tyr Asp Val Gly Pro Gly Asp Ile Arg Gly Lys Val Glu Thr Ala Glu
                        645                 650                 655
        Trp Leu Leu Asn Ala Ala Glu Arg Leu Ala Gly Glu Leu Asp Val Glu
                        660                 665                 670
        Cys Gly Pro Ala Val Arg Glu Ala Arg Lys Arg Val Gln Tyr Gly Val
                        675                 680                 685
        Arg Glu Glu Leu Leu Gly Leu Ala Gly Val Arg Asn Val Gly Arg Lys
                        690                 695                 700
        Arg Ala Arg Arg Leu Tyr Asn Ala Gly Val Glu Ser Arg Ala Asp Leu
        705                 710                 715                 720
        Arg Asn Ala Asp Lys Gly Val Val Leu Gly Ala Val Arg Gly Arg Ala
                        725                 730                 735
```

```
Ala Thr Ala Glu Arg Ile Leu Glu Thr Val Gly His Pro Asp Pro Gly
            740                 745                 750

Met Asp Gly Val Ala Ala Asp Thr Asp Ala Ala Pro Glu Ser Gly Gly
        755                 760                 765

Glu Ala Gly Gly Asp Glu Gly Gln Ala Ser Leu Gly Asp Phe Ser
    770                 775                 780

<210> SEQ ID NO 59
<211> LENGTH: 8
<212> TYPE: PRT
<213> ORGANISM: Artificial sequence
<220> FEATURE:
<223> OTHER INFORMATION: RecD-like motif I
<220> FEATURE:
<221> NAME/KEY: MISC_FEATURE
<222> LOCATION: (1)..(1)
<223> OTHER INFORMATION: Xaa = G, S or A
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (3)..(3)
<223> OTHER INFORMATION: Xaa = P, A, S or G
<220> FEATURE:
<221> NAME/KEY: MISC_FEATURE
<222> LOCATION: (5)..(5)
<223> OTHER INFORMATION: Xaa = T, A, V, S or C
<220> FEATURE:
<221> NAME/KEY: MISC_FEATURE
<222> LOCATION: (6)..(6)
<223> OTHER INFORMATION: Xaa = G or A
<220> FEATURE:
<221> NAME/KEY: MISC_FEATURE
<222> LOCATION: (7)..(7)
<223> OTHER INFORMATION: Xaa = K or R
<220> FEATURE:
<221> NAME/KEY: MISC_FEATURE
<222> LOCATION: (8)..(8)
<223> OTHER INFORMATION: Xaa = T or S

<400> SEQUENCE: 59

Xaa Xaa Xaa Gly Xaa Xaa Xaa Xaa
1               5

<210> SEQ ID NO 60
<211> LENGTH: 25
<212> TYPE: PRT
<213> ORGANISM: Artificial sequence
<220> FEATURE:
<223> OTHER INFORMATION: Extended RecD-like motif I
<220> FEATURE:
<221> NAME/KEY: MISC_FEATURE
<222> LOCATION: (2)..(17)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = G, S or A
<220> FEATURE:
<221> NAME/KEY: MISC_FEATURE
<222> LOCATION: (19)..(19)
<223> OTHER INFORMATION: Xaa = any amino acid
<220> FEATURE:
<221> NAME/KEY: MISC_FEATURE
<222> LOCATION: (20)..(20)
<223> OTHER INFORMATION: Xaa = P, A, S or G
<220> FEATURE:
<221> NAME/KEY: MISC_FEATURE
<222> LOCATION: (22)..(22)
<223> OTHER INFORMATION: Xaa = T, A, V, S or C
<220> FEATURE:
```

```
<221> NAME/KEY: MISC_FEATURE
<222> LOCATION: (23)..(23)
<223> OTHER INFORMATION: Xaa = G or A
<220> FEATURE:
<221> NAME/KEY: MISC_FEATURE
<222> LOCATION: (24)..(24)
<223> OTHER INFORMATION: Xaa = K or R
<220> FEATURE:
<221> NAME/KEY: MISC_FEATURE
<222> LOCATION: (25)..(25)
<223> OTHER INFORMATION: Xaa = T or S

<400> SEQUENCE: 60

Gln Xaa Xaa Xaa Xaa Xaa Xaa Xaa Xaa Xaa Xaa Xaa Xaa Xaa Xaa
1               5                   10                  15

Xaa Xaa Xaa Xaa Gly Xaa Xaa Xaa Xaa
            20                  25

<210> SEQ ID NO 61
<211> LENGTH: 26
<212> TYPE: PRT
<213> ORGANISM: Artificial sequence
<220> FEATURE:
<223> OTHER INFORMATION: Extended RecD-like motif I
<220> FEATURE:
<221> NAME/KEY: MISC_FEATURE
<222> LOCATION: (2)..(18)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = G, S or A
<220> FEATURE:
<221> NAME/KEY: MISC_FEATURE
<222> LOCATION: (20)..(20)
<223> OTHER INFORMATION: Xaa = any amino acid
<220> FEATURE:
<221> NAME/KEY: MISC_FEATURE
<222> LOCATION: (21)..(21)
<223> OTHER INFORMATION: Xaa = P, A, S or G
<220> FEATURE:
<221> NAME/KEY: MISC_FEATURE
<222> LOCATION: (23)..(23)
<223> OTHER INFORMATION: Xaa = T, A, V, S or C
<220> FEATURE:
<221> NAME/KEY: MISC_FEATURE
<222> LOCATION: (24)..(24)
<223> OTHER INFORMATION: Xaa = G or A
<220> FEATURE:
<221> NAME/KEY: MISC_FEATURE
<222> LOCATION: (25)..(25)
<223> OTHER INFORMATION: Xaa = K or A
<220> FEATURE:
<221> NAME/KEY: MISC_FEATURE
<222> LOCATION: (26)..(26)
<223> OTHER INFORMATION: Xaa = T or S

<400> SEQUENCE: 61

Gln Xaa Xaa Xaa Xaa Xaa Xaa Xaa Xaa Xaa Xaa Xaa Xaa Xaa Xaa
1               5                   10                  15

Xaa Xaa Xaa Xaa Xaa Gly Xaa Xaa Xaa Xaa
            20                  25

<210> SEQ ID NO 62
<211> LENGTH: 27
<212> TYPE: PRT
<213> ORGANISM: Artificial sequence
<220> FEATURE:
<223> OTHER INFORMATION: Extended RecD-like motif I
<220> FEATURE:
<221> NAME/KEY: MISC_FEATURE
<222> LOCATION: (2)..(19)
<223> OTHER INFORMATION: Xaa = any amino acid
```

```
<220> FEATURE:
<221> NAME/KEY: MISC_FEATURE
<222> LOCATION: (20)..(20)
<223> OTHER INFORMATION: Xaa = G, S or A
<220> FEATURE:
<221> NAME/KEY: MISC_FEATURE
<222> LOCATION: (21)..(21)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = P, A, S or G
<220> FEATURE:
<221> NAME/KEY: MISC_FEATURE
<222> LOCATION: (24)..(24)
<223> OTHER INFORMATION: Xaa = T, A, V, S or C
<220> FEATURE:
<221> NAME/KEY: MISC_FEATURE
<222> LOCATION: (25)..(25)
<223> OTHER INFORMATION: Xaa = G or A
<220> FEATURE:
<221> NAME/KEY: MISC_FEATURE
<222> LOCATION: (26)..(26)
<223> OTHER INFORMATION: Xaa = K or R
<220> FEATURE:
<221> NAME/KEY: MISC_FEATURE
<222> LOCATION: (27)..(27)
<223> OTHER INFORMATION: Xaa = T or S

<400> SEQUENCE: 62

Gln Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Gly Xaa Xaa Xaa Xaa
            20                  25

<210> SEQ ID NO 63
<211> LENGTH: 8
<212> TYPE: PRT
<213> ORGANISM: Artificial sequence
<220> FEATURE:
<223> OTHER INFORMATION: RecD motif I
<220> FEATURE:
<221> NAME/KEY: MISC_FEATURE
<222> LOCATION: (5)..(5)
<223> OTHER INFORMATION: Xaa = T, V or C
<220> FEATURE:
<221> NAME/KEY: MISC_FEATURE
<222> LOCATION: (8)..(8)
<223> OTHER INFORMATION: Xaa = T or S

<400> SEQUENCE: 63

Gly Gly Pro Gly Xaa Gly Lys Xaa
1               5

<210> SEQ ID NO 64
<211> LENGTH: 8
<212> TYPE: PRT
<213> ORGANISM: Artificial sequence
<220> FEATURE:
<223> OTHER INFORMATION: Preferred RecD motif I

<400> SEQUENCE: 64

Gly Gly Pro Gly Thr Gly Lys Thr
1               5

<210> SEQ ID NO 65
<211> LENGTH: 25
<212> TYPE: PRT
<213> ORGANISM: Artificial sequence
<220> FEATURE:
<223> OTHER INFORMATION: Extended RecD motif I
<220> FEATURE:
```

```
<221> NAME/KEY: MISC_FEATURE
<222> LOCATION: (2)..(17)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = T, V or C
<220> FEATURE:
<221> NAME/KEY: MISC_FEATURE
<222> LOCATION: (25)..(25)
<223> OTHER INFORMATION: Xaa = T or S

<400> SEQUENCE: 65

Gln Xaa Xaa Xaa Xaa Xaa Xaa Xaa Xaa Xaa Xaa Xaa Xaa Xaa Xaa
1               5                   10                  15

Xaa Gly Gly Pro Gly Xaa Gly Lys Xaa
            20                  25

<210> SEQ ID NO 66
<211> LENGTH: 26
<212> TYPE: PRT
<213> ORGANISM: Artificial sequence
<220> FEATURE:
<223> OTHER INFORMATION: Extended RecD motif I
<220> FEATURE:
<221> NAME/KEY: MISC_FEATURE
<222> LOCATION: (2)..(18)
<223> OTHER INFORMATION: Xaa = any amino acid
<220> FEATURE:
<221> NAME/KEY: MISC_FEATURE
<222> LOCATION: (23)..(23)
<223> OTHER INFORMATION: Xaa = T, V or C
<220> FEATURE:
<221> NAME/KEY: MISC_FEATURE
<222> LOCATION: (26)..(26)
<223> OTHER INFORMATION: Xaa = T or S

<400> SEQUENCE: 66

Gln Xaa Xaa Xaa Xaa Xaa Xaa Xaa Xaa Xaa Xaa Xaa Xaa Xaa Xaa
1               5                   10                  15

Xaa Xaa Gly Gly Pro Gly Xaa Gly Lys Xaa
            20                  25

<210> SEQ ID NO 67
<211> LENGTH: 27
<212> TYPE: PRT
<213> ORGANISM: Artificial sequence
<220> FEATURE:
<223> OTHER INFORMATION: Extended RecD motif I
<220> FEATURE:
<221> NAME/KEY: MISC_FEATURE
<222> LOCATION: (2)..(19)
<223> OTHER INFORMATION: Xaa = any amino acid
<220> FEATURE:
<221> NAME/KEY: MISC_FEATURE
<222> LOCATION: (24)..(24)
<223> OTHER INFORMATION: Xaa = T, V or C
<220> FEATURE:
<221> NAME/KEY: MISC_FEATURE
<222> LOCATION: (27)..(27)
<223> OTHER INFORMATION: Xaa = T or S

<400> SEQUENCE: 67

Gln Xaa Xaa Xaa Xaa Xaa Xaa Xaa Xaa Xaa Xaa Xaa Xaa Xaa Xaa
1               5                   10                  15

Xaa Xaa Xaa Gly Gly Pro Gly Xaa Gly Lys Xaa
            20                  25

<210> SEQ ID NO 68
<211> LENGTH: 10
```

```
<212> TYPE: PRT
<213> ORGANISM: Artificial sequence
<220> FEATURE:
<223> OTHER INFORMATION: RecD-like motif V
<220> FEATURE:
<221> NAME/KEY: MISC_FEATURE
<222> LOCATION: (1)..(1)
<223> OTHER INFORMATION: Xaa = Y, W or F
<220> FEATURE:
<221> NAME/KEY: MISC_FEATURE
<222> LOCATION: (2)..(2)
<223> OTHER INFORMATION: Xaa = A, T, S, M, C or V
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = T, N or S
<220> FEATURE:
<221> NAME/KEY: MISC_FEATURE
<222> LOCATION: (5)..(5)
<223> OTHER INFORMATION: Xaa = A, T, G, S, V or I
<220> FEATURE:
<221> NAME/KEY: MISC_FEATURE
<222> LOCATION: (6)..(8)
<223> OTHER INFORMATION: Xaa = any amino acid
<220> FEATURE:
<221> NAME/KEY: MISC_FEATURE
<222> LOCATION: (10)..(10)
<223> OTHER INFORMATION: Xaa = G or S

<400> SEQUENCE: 68

Xaa Xaa Xaa Xaa Xaa Xaa Xaa Xaa Gln Xaa
1               5                   10

<210> SEQ ID NO 69
<211> LENGTH: 10
<212> TYPE: PRT
<213> ORGANISM: Artificial sequence
<220> FEATURE:
<223> OTHER INFORMATION: RecD motif V
<220> FEATURE:
<221> NAME/KEY: MISC_FEATURE
<222> LOCATION: (1)..(1)
<223> OTHER INFORMATION: Xaa = Y, W or F
<220> FEATURE:
<221> NAME/KEY: MISC_FEATURE
<222> LOCATION: (2)..(2)
<223> OTHER INFORMATION: Xaa = A, M, C or V
<220> FEATURE:
<221> NAME/KEY: MISC_FEATURE
<222> LOCATION: (3)..(3)
<223> OTHER INFORMATION: Xaa = I, M or L
<220> FEATURE:
<221> NAME/KEY: MISC_FEATURE
<222> LOCATION: (4)..(4)
<223> OTHER INFORMATION: Xaa = T or S
<220> FEATURE:
<221> NAME/KEY: MISC_FEATURE
<222> LOCATION: (5)..(5)
<223> OTHER INFORMATION: Xaa = V or I

<400> SEQUENCE: 69

Xaa Xaa Xaa Xaa Xaa His Lys Ser Gln Gly
1               5                   10

<210> SEQ ID NO 70
<211> LENGTH: 13
<212> TYPE: PRT
<213> ORGANISM: Artificial sequence
<220> FEATURE:
<223> OTHER INFORMATION: MobF motif III
<220> FEATURE:
```

```
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(10)
<223> OTHER INFORMATION: Xaa = any amino acid
<220> FEATURE:
<221> NAME/KEY: MISC_FEATURE
<222> LOCATION: (12)..(12)
<223> OTHER INFORMATION: Xaa = any amino acid except D, E, R and K

<400> SEQUENCE: 70

His Xaa Xaa Xaa Arg Xaa Xaa Xaa Xaa Xaa His Xaa His
1               5                   10

<210> SEQ ID NO 71
<211> LENGTH: 14
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(11)
<223> OTHER INFORMATION: Xaa = any amino acid
<220> FEATURE:
<221> NAME/KEY: MISC_FEATURE
<222> LOCATION: (13)..(13)
<223> OTHER INFORMATION: Xaa = any amino acid except D, E, R and K

<400> SEQUENCE: 71

His Xaa Xaa Xaa Arg Xaa Xaa Xaa Xaa Xaa Xaa His Xaa His
1               5                   10

<210> SEQ ID NO 72
<211> LENGTH: 15
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(12)
<223> OTHER INFORMATION: Xaa = any amino acid
<220> FEATURE:
<221> NAME/KEY: MISC_FEATURE
<222> LOCATION: (14)..(14)
<223> OTHER INFORMATION: Xaa = any amino acid except D, E, R and K

<400> SEQUENCE: 72

His Xaa Xaa Xaa Arg Xaa Xaa Xaa Xaa Xaa Xaa Xaa His Xaa His
1               5                   10                  15
```

```
<210> SEQ ID NO 73
<211> LENGTH: 16
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(13)
<223> OTHER INFORMATION: Xaa = any amino acid
<220> FEATURE:
<221> NAME/KEY: MISC_FEATURE
<222> LOCATION: (15)..(15)
<223> OTHER INFORMATION: Xaa = any amino acid except D, E, R and K

<400> SEQUENCE: 73

His Xaa Xaa Xaa Arg Xaa Xaa Xaa Xaa Xaa Xaa Xaa Xaa His Xaa His
1               5                   10                  15

<210> SEQ ID NO 74
<211> LENGTH: 17
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(14)
<223> OTHER INFORMATION: Xaa = any amino acid
<220> FEATURE:
<221> NAME/KEY: MISC_FEATURE
<222> LOCATION: (16)..(16)
<223> OTHER INFORMATION: Xaa = any amino acid except D, E, R and K

<400> SEQUENCE: 74

His Xaa Xaa Xaa Arg Xaa Xaa Xaa Xaa Xaa Xaa Xaa Xaa Xaa His Xaa
1               5                   10                  15

His

<210> SEQ ID NO 75
<211> LENGTH: 18
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(15)
<223> OTHER INFORMATION: Xaa = any amino acid
```

-continued

```
<220> FEATURE:
<221> NAME/KEY: MISC_FEATURE
<222> LOCATION: (17)..(17)
<223> OTHER INFORMATION: Xaa = any amino acid except D, E, R and K

<400> SEQUENCE: 75

His Xaa Xaa Xaa Arg Xaa Xaa Xaa Xaa Xaa Xaa Xaa Xaa Xaa Xaa His
1               5                   10                  15

Xaa His

<210> SEQ ID NO 76
<211> LENGTH: 19
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(16)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = any amino acid except D, E, R and K

<400> SEQUENCE: 76

His Xaa Xaa Xaa Arg Xaa Xaa Xaa Xaa Xaa Xaa Xaa Xaa Xaa Xaa Xaa
1               5                   10                  15

His Xaa His

<210> SEQ ID NO 77
<211> LENGTH: 20
<212> TYPE: PRT
<213> ORGANISM: Artificial sequence
<220> FEATURE:
<223> OTHER INFORMATION: MobF motif III
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except D, E, R and K
<220> FEATURE:
<221> NAME/KEY: MISC_FEATURE
<222> LOCATION: (6)..(17)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = any amino acid

<400> SEQUENCE: 77

His Xaa Xaa Xaa Arg Xaa Xaa Xaa Xaa Xaa Xaa Xaa Xaa Xaa Xaa Xaa
1               5                   10                  15

Xaa His Xaa His
            20

<210> SEQ ID NO 78
<211> LENGTH: 17
<212> TYPE: PRT
```

-continued

```
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(15)
<223> OTHER INFORMATION: Xaa = any amino acid
<220> FEATURE:
<221> NAME/KEY: MISC_FEATURE
<222> LOCATION: (17)..(17)
<223> OTHER INFORMATION: Xaa = any amino acid except D, E, K and R

<400> SEQUENCE: 78

Gly Xaa Xaa Xaa Xaa Xaa Xaa Xaa His Xaa Xaa Xaa Xaa Xaa Xaa His
1               5                   10                  15

Xaa

<210> SEQ ID NO 79
<211> LENGTH: 18
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(16)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = any amino acid except D, E, K and R

<400> SEQUENCE: 79

Gly Xaa Xaa Xaa Xaa Xaa Xaa Xaa His Xaa Xaa Xaa Xaa Xaa Xaa Xaa
1               5                   10                  15

His Xaa

<210> SEQ ID NO 80
<211> LENGTH: 19
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
```

```
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(17)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = any amino acid except D, E, K and R

<400> SEQUENCE: 80

Gly Xaa Xaa Xaa Xaa Xaa Xaa Xaa His Xaa Xaa Xaa Xaa Xaa Xaa Xaa
 1               5                  10                  15

Xaa His Xaa

<210> SEQ ID NO 81
<211> LENGTH: 20
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(18)
<223> OTHER INFORMATION: Xaa = any amino acid
<220> FEATURE:
<221> NAME/KEY: MISC_FEATURE
<222> LOCATION: (20)..(20)
<223> OTHER INFORMATION: Xaa = any amino acid except D, E, K and R

<400> SEQUENCE: 81

Gly Xaa Xaa Xaa Xaa Xaa Xaa Xaa His Xaa Xaa Xaa Xaa Xaa Xaa Xaa
 1               5                  10                  15

Xaa Xaa His Xaa
            20

<210> SEQ ID NO 82
<211> LENGTH: 21
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
```

```
<222> LOCATION: (10)..(19)
<223> OTHER INFORMATION: Xaa = any amino acid
<220> FEATURE:
<221> NAME/KEY: MISC_FEATURE
<222> LOCATION: (21)..(21)
<223> OTHER INFORMATION: Xaa = any amino acid

<400> SEQUENCE: 82

Gly Xaa Xaa Xaa Xaa Xaa Xaa Xaa His Xaa Xaa Xaa Xaa Xaa Xaa Xaa
1               5                   10                  15

Xaa Xaa Xaa His Xaa
            20

<210> SEQ ID NO 83
<211> LENGTH: 22
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(20)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = any amino acid except D, E, K and R

<400> SEQUENCE: 83

Gly Xaa Xaa Xaa Xaa Xaa Xaa Xaa His Xaa Xaa Xaa Xaa Xaa Xaa Xaa
1               5                   10                  15

Xaa Xaa Xaa Xaa His Xaa
            20

<210> SEQ ID NO 84
<211> LENGTH: 23
<212> TYPE: PRT
<213> ORGANISM: Artificial sequence
<220> FEATURE:
<223> OTHER INFORMATION: MobQ motif III
<220> FEATURE:
<221> NAME/KEY: MISC_FEATURE
<222> LOCATION: (2)..(4)
<223> OTHER INFORMATION: Xaa = any amino acid except D, E, K and R
<220> FEATURE:
<221> NAME/KEY: MISC_FEATURE
<222> LOCATION: (5)..(5)
<223> OTHER INFORMATION: Xaa = D or E
<220> FEATURE:
<221> NAME/KEY: MISC_FEATURE
<222> LOCATION: (6)..(8)
<223> OTHER INFORMATION: Xaa = any amino acid except D, E, K and R
<220> FEATURE:
<221> NAME/KEY: MISC_FEATURE
<222> LOCATION: (10)..(21)
<223> OTHER INFORMATION: Xaa = any amino acid
<220> FEATURE:
<221> NAME/KEY: MISC_FEATURE
<222> LOCATION: (23)..(23)
<223> OTHER INFORMATION: Xaa = any amino acid except D, E, K and R
```

```
<400> SEQUENCE: 84

Gly Xaa Xaa Xaa Xaa Xaa His Xaa Xaa Xaa Xaa Xaa Xaa
1               5                   10                  15

Xaa Xaa Xaa Xaa Xaa His Xaa
            20

<210> SEQ ID NO 85
<211> LENGTH: 1756
<212> TYPE: PRT
<213> ORGANISM: Escherichia coli

<400> SEQUENCE: 85

Met Met Ser Ile Ala Gln Val Arg Ser Ala Gly Ser Ala Gly Asn Tyr
1               5                   10                  15

Tyr Thr Asp Lys Asp Asn Tyr Tyr Val Leu Gly Ser Met Gly Glu Arg
            20                  25                  30

Trp Ala Gly Lys Gly Ala Glu Gln Leu Gly Leu Gln Gly Ser Val Asp
        35                  40                  45

Lys Asp Val Phe Thr Arg Leu Leu Glu Gly Arg Leu Pro Asp Gly Ala
    50                  55                  60

Asp Leu Ser Arg Met Gln Asp Gly Ser Asn Lys His Arg Pro Gly Tyr
65                  70                  75                  80

Asp Leu Thr Phe Ser Ala Pro Lys Ser Val Ser Met Met Ala Met Leu
                85                  90                  95

Gly Gly Asp Lys Arg Leu Ile Asp Ala His Asn Gln Ala Val Asp Phe
            100                 105                 110

Ala Val Arg Gln Val Glu Ala Leu Ala Ser Thr Arg Val Met Thr Asp
        115                 120                 125

Gly Gln Ser Glu Thr Val Leu Thr Gly Asn Leu Val Met Ala Leu Phe
    130                 135                 140

Asn His Asp Thr Ser Arg Asp Gln Glu Pro Gln Leu His Thr His Ala
145                 150                 155                 160

Val Val Ala Asn Val Thr Gln His Asn Gly Glu Trp Lys Thr Leu Ser
                165                 170                 175

Ser Asp Lys Val Gly Lys Thr Gly Phe Ile Glu Asn Val Tyr Ala Asn
            180                 185                 190

Gln Ile Ala Phe Gly Arg Leu Tyr Arg Glu Lys Leu Lys Glu Gln Val
        195                 200                 205

Glu Ala Leu Gly Tyr Glu Thr Glu Val Val Gly Lys His Gly Met Trp
    210                 215                 220

Glu Met Pro Gly Val Pro Val Glu Ala Phe Ser Gly Arg Ser Gln Ala
225                 230                 235                 240

Ile Arg Glu Ala Val Gly Glu Asp Ala Ser Leu Lys Ser Arg Asp Val
                245                 250                 255

Ala Ala Leu Asp Thr Arg Lys Ser Lys Gln His Val Asp Pro Glu Ile
            260                 265                 270

Arg Met Ala Glu Trp Met Gln Thr Leu Lys Glu Thr Gly Phe Asp Ile
        275                 280                 285

Arg Ala Tyr Arg Asp Ala Ala Asp Gln Arg Thr Glu Ile Arg Thr Gln
    290                 295                 300

Ala Pro Gly Pro Ala Ser Gln Asp Gly Pro Asp Val Gln Gln Ala Val
305                 310                 315                 320

Thr Gln Ala Ile Ala Gly Leu Ser Glu Arg Lys Val Gln Phe Thr Tyr
                325                 330                 335
```

```
Thr Asp Val Leu Ala Arg Thr Val Gly Ile Leu Pro Pro Glu Asn Gly
                340                 345                 350

Val Ile Glu Arg Ala Arg Ala Gly Ile Asp Glu Ala Ile Ser Arg Glu
            355                 360                 365

Gln Leu Ile Pro Leu Asp Arg Glu Lys Gly Leu Phe Thr Ser Gly Ile
        370                 375                 380

His Val Leu Asp Glu Leu Ser Val Arg Ala Leu Ser Arg Asp Ile Met
385                 390                 395                 400

Lys Gln Asn Arg Val Thr Val His Pro Glu Lys Ser Val Pro Arg Thr
                405                 410                 415

Ala Gly Tyr Ser Asp Ala Val Ser Val Leu Ala Gln Asp Arg Pro Ser
            420                 425                 430

Leu Ala Ile Val Ser Gly Gln Gly Gly Ala Ala Gly Gln Arg Glu Arg
        435                 440                 445

Val Ala Glu Leu Val Met Met Ala Arg Glu Gln Gly Arg Glu Val Gln
    450                 455                 460

Ile Ile Ala Ala Asp Arg Arg Ser Gln Met Asn Leu Lys Gln Asp Glu
465                 470                 475                 480

Arg Leu Ser Gly Glu Leu Ile Thr Gly Arg Arg Gln Leu Leu Glu Gly
                485                 490                 495

Met Ala Phe Thr Pro Gly Ser Thr Val Ile Val Asp Gln Gly Glu Lys
            500                 505                 510

Leu Ser Leu Lys Glu Thr Leu Thr Leu Leu Asp Gly Ala Ala Arg His
        515                 520                 525

Asn Val Gln Val Leu Ile Thr Asp Ser Gly Gln Arg Thr Gly Thr Gly
    530                 535                 540

Ser Ala Leu Met Ala Met Lys Asp Ala Gly Val Asn Thr Tyr Arg Trp
545                 550                 555                 560

Gln Gly Gly Glu Gln Arg Pro Ala Thr Ile Ile Ser Glu Pro Asp Arg
                565                 570                 575

Asn Val Arg Tyr Ala Arg Leu Ala Gly Asp Phe Ala Ala Ser Val Lys
            580                 585                 590

Ala Gly Glu Glu Ser Val Ala Gln Val Ser Gly Val Arg Glu Gln Ala
        595                 600                 605

Ile Leu Thr Gln Ala Ile Arg Ser Glu Leu Lys Thr Gln Gly Val Leu
    610                 615                 620

Gly His Pro Glu Val Thr Met Thr Ala Leu Ser Pro Val Trp Leu Asp
625                 630                 635                 640

Ser Arg Ser Arg Tyr Leu Arg Asp Met Tyr Arg Pro Gly Met Val Met
                645                 650                 655

Glu Gln Trp Asn Pro Glu Thr Arg Ser His Asp Arg Tyr Val Ile Asp
            660                 665                 670

Arg Val Thr Ala Gln Ser His Ser Leu Thr Leu Arg Asp Ala Gln Gly
        675                 680                 685

Glu Thr Gln Val Val Arg Ile Ser Ser Leu Asp Ser Ser Trp Ser Leu
    690                 695                 700

Phe Arg Pro Glu Lys Met Pro Val Ala Asp Gly Glu Arg Leu Arg Val
705                 710                 715                 720

Thr Gly Lys Ile Pro Gly Leu Arg Val Ser Gly Asp Arg Leu Gln
                725                 730                 735

Val Ala Ser Val Ser Glu Asp Ala Met Thr Val Val Pro Gly Arg
            740                 745                 750

Ala Glu Pro Ala Ser Leu Pro Val Ser Asp Ser Pro Phe Thr Ala Leu
```

```
                755                 760                 765
Lys Leu Glu Asn Gly Trp Val Glu Thr Pro Gly His Ser Val Ser Asp
    770                 775                 780

Ser Ala Thr Val Phe Ala Ser Val Thr Gln Met Ala Met Asp Asn Ala
785                 790                 795                 800

Thr Leu Asn Gly Leu Ala Arg Ser Gly Arg Asp Val Arg Leu Tyr Ser
                805                 810                 815

Ser Leu Asp Glu Thr Arg Thr Ala Glu Lys Leu Ala Arg His Pro Ser
            820                 825                 830

Phe Thr Val Val Ser Glu Gln Ile Lys Ala Arg Ala Gly Glu Thr Leu
        835                 840                 845

Leu Glu Thr Ala Ile Ser Leu Gln Lys Ala Gly Leu His Thr Pro Ala
    850                 855                 860

Gln Gln Ala Ile His Leu Ala Leu Pro Val Leu Glu Ser Lys Asn Leu
865                 870                 875                 880

Ala Phe Ser Met Val Asp Leu Leu Thr Glu Ala Lys Ser Phe Ala Ala
                885                 890                 895

Glu Gly Thr Gly Phe Thr Glu Leu Gly Gly Glu Ile Asn Ala Gln Ile
            900                 905                 910

Lys Arg Gly Asp Leu Leu Tyr Val Asp Val Ala Lys Gly Tyr Gly Thr
        915                 920                 925

Gly Leu Leu Val Ser Arg Ala Ser Tyr Glu Ala Glu Lys Ser Ile Leu
    930                 935                 940

Arg His Ile Leu Glu Gly Lys Glu Ala Val Thr Pro Leu Met Glu Arg
945                 950                 955                 960

Val Pro Gly Glu Leu Met Glu Thr Leu Thr Ser Gly Gln Arg Ala Ala
                965                 970                 975

Thr Arg Met Ile Leu Glu Thr Ser Asp Arg Phe Thr Val Gln Gly
            980                 985                 990

Tyr Ala Gly Val Gly Lys Thr Thr  Gln Phe Arg Ala Val  Met Ser Ala
        995                  1000                 1005

Val Asn  Met Leu Pro Ala Ser  Glu Arg Pro Arg Val  Val Gly Leu
    1010                 1015                 1020

Gly Pro  Thr His Arg Ala Val  Gly Glu Met Arg Ser  Ala Gly Val
    1025                 1030                 1035

Asp Ala  Gln Thr Leu Ala Ser  Phe Leu His Asp Thr  Gln Leu Gln
    1040                 1045                 1050

Gln Arg  Ser Gly Glu Thr Pro  Asp Phe Ser Asn Thr  Leu Phe Leu
    1055                 1060                 1065

Leu Asp  Glu Ser Ser Met Val  Gly Asn Thr Glu Met  Ala Arg Ala
    1070                 1075                 1080

Tyr Ala  Leu Ile Ala Ala Gly  Gly Gly Arg Ala Val  Ala Ser Gly
    1085                 1090                 1095

Asp Thr  Asp Gln Leu Gln Ala  Ile Ala Pro Gly Gln  Ser Phe Arg
    1100                 1105                 1110

Leu Gln  Gln Thr Arg Ser Ala  Ala Asp Val Val Ile  Met Lys Glu
    1115                 1120                 1125

Ile Val  Arg Gln Thr Pro Glu  Leu Arg Glu Ala Val  Tyr Ser Leu
    1130                 1135                 1140

Ile Asn  Arg Asp Val Glu Arg  Ala Leu Ser Gly Leu  Glu Ser Val
    1145                 1150                 1155

Lys Pro  Ser Gln Val Pro Arg  Leu Glu Gly Ala Trp  Ala Pro Glu
    1160                 1165                 1170
```

```
His Ser Val Thr Glu Phe Ser His Ser Gln Glu Ala Lys Leu Ala
    1175            1180            1185

Glu Ala Gln Gln Lys Ala Met Leu Lys Gly Glu Ala Phe Pro Asp
    1190            1195            1200

Ile Pro Met Thr Leu Tyr Glu Ala Ile Val Arg Asp Tyr Thr Gly
    1205            1210            1215

Arg Thr Pro Glu Ala Arg Glu Gln Thr Leu Ile Val Thr His Leu
    1220            1225            1230

Asn Glu Asp Arg Arg Val Leu Asn Ser Met Ile His Asp Ala Arg
    1235            1240            1245

Glu Lys Ala Gly Glu Leu Gly Lys Glu Gln Val Met Val Pro Val
    1250            1255            1260

Leu Asn Thr Ala Asn Ile Arg Asp Gly Glu Leu Arg Arg Leu Ser
    1265            1270            1275

Thr Trp Glu Lys Asn Pro Asp Ala Leu Ala Leu Val Asp Asn Val
    1280            1285            1290

Tyr His Arg Ile Ala Gly Ile Ser Lys Asp Asp Gly Leu Ile Thr
    1295            1300            1305

Leu Gln Asp Ala Glu Gly Asn Thr Arg Leu Ile Ser Pro Arg Glu
    1310            1315            1320

Ala Val Ala Glu Gly Val Thr Leu Tyr Thr Pro Asp Lys Ile Arg
    1325            1330            1335

Val Gly Thr Gly Asp Arg Met Arg Phe Thr Lys Ser Asp Arg Glu
    1340            1345            1350

Arg Gly Tyr Val Ala Asn Ser Val Trp Thr Val Thr Ala Val Ser
    1355            1360            1365

Gly Asp Ser Val Thr Leu Ser Asp Gly Gln Gln Thr Arg Val Ile
    1370            1375            1380

Arg Pro Gly Gln Glu Arg Ala Glu Gln His Ile Asp Leu Ala Tyr
    1385            1390            1395

Ala Ile Thr Ala His Gly Ala Gln Gly Ala Ser Glu Thr Phe Ala
    1400            1405            1410

Ile Ala Leu Glu Gly Thr Glu Gly Asn Arg Lys Leu Met Ala Gly
    1415            1420            1425

Phe Glu Ser Ala Tyr Val Ala Leu Ser Arg Met Lys Gln His Val
    1430            1435            1440

Gln Val Tyr Thr Asp Asn Arg Gln Gly Trp Thr Asp Ala Ile Asn
    1445            1450            1455

Asn Ala Val Gln Lys Gly Thr Ala His Asp Val Leu Glu Pro Lys
    1460            1465            1470

Pro Asp Arg Glu Val Met Asn Ala Gln Arg Leu Phe Ser Thr Ala
    1475            1480            1485

Arg Glu Leu Arg Asp Val Ala Ala Gly Arg Ala Val Leu Arg Gln
    1490            1495            1500

Ala Gly Leu Ala Gly Gly Asp Ser Pro Ala Arg Phe Ile Ala Pro
    1505            1510            1515

Gly Arg Lys Tyr Pro Gln Pro Tyr Val Ala Leu Pro Ala Phe Asp
    1520            1525            1530

Arg Asn Gly Lys Ser Ala Gly Ile Trp Leu Asn Pro Leu Thr Thr
    1535            1540            1545

Asp Asp Gly Asn Gly Leu Arg Gly Phe Ser Gly Glu Gly Arg Val
    1550            1555            1560
```

```
Lys Gly Ser Gly Asp Ala Gln Phe Val Ala Leu Gln Gly Ser Arg
    1565                1570                1575

Asn Gly Glu Ser Leu Leu Ala Asp Asn Met Gln Asp Gly Val Arg
    1580                1585                1590

Ile Ala Arg Asp Asn Pro Asp Ser Gly Val Val Arg Ile Ala
    1595                1600                1605

Gly Glu Gly Arg Pro Trp Asn Pro Gly Ala Ile Thr Gly Gly Arg
    1610                1615                1620

Val Trp Gly Asp Ile Pro Asp Asn Ser Val Gln Pro Gly Ala Gly
    1625                1630                1635

Asn Gly Glu Pro Val Thr Ala Glu Val Leu Ala Gln Arg Gln Ala
    1640                1645                1650

Glu Glu Ala Ile Arg Arg Glu Thr Glu Arg Arg Ala Asp Glu Ile
    1655                1660                1665

Val Arg Lys Met Ala Glu Asn Lys Pro Asp Leu Pro Asp Gly Lys
    1670                1675                1680

Thr Glu Leu Ala Val Arg Asp Ile Ala Gly Gln Glu Arg Asp Arg
    1685                1690                1695

Ser Ala Ile Ser Glu Arg Glu Thr Ala Leu Pro Glu Ser Val Leu
    1700                1705                1710

Arg Glu Ser Gln Arg Glu Arg Glu Ala Val Arg Glu Val Ala Arg
    1715                1720                1725

Glu Asn Leu Leu Gln Glu Arg Leu Gln Gln Met Glu Arg Asp Met
    1730                1735                1740

Val Arg Asp Leu Gln Lys Glu Lys Thr Leu Gly Gly Asp
    1745                1750                1755

<210> SEQ ID NO 86
<211> LENGTH: 8
<212> TYPE: PRT
<213> ORGANISM: Artificial sequence
<220> FEATURE:
<223> OTHER INFORMATION: RecD-like motif I of TraI Eco

<400> SEQUENCE: 86

Gly Tyr Ala Gly Val Gly Lys Thr
1               5

<210> SEQ ID NO 87
<211> LENGTH: 10
<212> TYPE: PRT
<213> ORGANISM: Artificial sequence
<220> FEATURE:
<223> OTHER INFORMATION: RecD-like motif V of TraI Eco

<400> SEQUENCE: 87

Tyr Ala Ile Thr Ala His Gly Ala Gln Gly
1               5                   10

<210> SEQ ID NO 88
<211> LENGTH: 14
<212> TYPE: PRT
<213> ORGANISM: Artificial sequence
<220> FEATURE:
<223> OTHER INFORMATION: MobF  motif III of TraI Eco

<400> SEQUENCE: 88

His Asp Thr Ser Arg Asp Gln Glu Pro Gln Leu His Thr His
1               5                   10
```

-continued

```
<210> SEQ ID NO 89
<211> LENGTH: 9
<212> TYPE: PRT
<213> ORGANISM: Artificial Sequence
<220> FEATURE:
<223> OTHER INFORMATION: XPD motif V
<220> FEATURE:
<221> NAME/KEY: MISC_FEATURE
<222> LOCATION: (1)..(1)
<223> OTHER INFORMATION: Any amino acid except D, E, K or R.  Preferably
      not charged or H. More preferably V, L, I, S or Y.
<220> FEATURE:
<221> NAME/KEY: MISC_FEATURE
<222> LOCATION: (2)..(2)
<223> OTHER INFORMATION: Any amino acid except D, E, K or R.  Preferably
      not charged or H.
<220> FEATURE:
<221> NAME/KEY: MISC_FEATURE
<222> LOCATION: (3)..(3)
<223> OTHER INFORMATION: Any amino acid.
<220> FEATURE:
<221> NAME/KEY: MISC_FEATURE
<222> LOCATION: (5)..(5)
<223> OTHER INFORMATION: Any amino acid.  Preferably K, R or T.
<220> FEATURE:
<221> NAME/KEY: MISC_FEATURE
<222> LOCATION: (6)..(6)
<223> OTHER INFORMATION: Any amino acid except D, E, K or R.  Preferably
      not charged or H. More preferably V, L, I, N or F.
<220> FEATURE:
<221> NAME/KEY: MISC_FEATURE
<222> LOCATION: (7)..(7)
<223> OTHER INFORMATION: Any amino acid except D, E, K or R.  Preferably
      not charged or H. More preferably S or A.

<400> SEQUENCE: 89

Xaa Xaa Xaa Gly Xaa Xaa Xaa Glu Gly
1               5

<210> SEQ ID NO 90
<211> LENGTH: 22
<212> TYPE: PRT
<213> ORGANISM: Artificial Sequence
<220> FEATURE:
<223> OTHER INFORMATION: XPD motif VI
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (3)..(3)
<223> OTHER INFORMATION: Any amino acid except D, E, K, R.  Typically G,
      P, A, V, L, I, M, C, F, Y, W, H, Q, N, S or T.  Preferably not
      charged.  Preferably not H.  More preferably V, A, L, I or M.
<220> FEATURE:
<221> NAME/KEY: MISC_FEATURE
<222> LOCATION: (6)..(6)
<223> OTHER INFORMATION: Any amino acid except D, E, K, R.  Typically G,
      P, A, V, L, I, M, C, F, Y, W, H, Q, N, S or T.  Preferably not
      charged.  Preferably not H.  More preferably V, A, L, I, M or C.
<220> FEATURE:
<221> NAME/KEY: MISC_FEATURE
<222> LOCATION: (7)..(7)
<223> OTHER INFORMATION: Any amino acid except D, E, K, R.  Typically G,
      P, A, V, L, I, M, C, F, Y, W, H, Q, N, S or T.  Preferably not
      charged.  Preferably not H.  More preferably I, H, L, F, M or V.
<220> FEATURE:
<221> NAME/KEY: MISC_FEATURE
<222> LOCATION: (9)..(11)
<223> OTHER INFORMATION: Any amino acid.
<220> FEATURE:
<221> NAME/KEY: MISC_FEATURE
<222> LOCATION: (12)..(12)
<223> OTHER INFORMATION: D or E
<220> FEATURE:
<221> NAME/KEY: MISC_FEATURE
```

```
<222> LOCATION: (13)..(13)
<223> OTHER INFORMATION: Any amino acid.
<220> FEATURE:
<221> NAME/KEY: MISC_FEATURE
<222> LOCATION: (14)..(14)
<223> OTHER INFORMATION: Any amino acid.  Preferably G, A, S or C
<220> FEATURE:
<221> NAME/KEY: MISC_FEATURE
<222> LOCATION: (15)..(16)
<223> OTHER INFORMATION: Any amino acid.
<220> FEATURE:
<221> NAME/KEY: MISC_FEATURE
<222> LOCATION: (17)..(17)
<223> OTHER INFORMATION: Any amino acid. Preferably F, V, L, I, M, A, W
      or Y
<220> FEATURE:
<221> NAME/KEY: MISC_FEATURE
<222> LOCATION: (18)..(18)
<223> OTHER INFORMATION: Any amino acid. Preferably L, F, Y, M, I or V.
<220> FEATURE:
<221> NAME/KEY: MISC_FEATURE
<222> LOCATION: (19)..(19)
<223> OTHER INFORMATION: Any amino acid. Preferably A, C, V, L, I, M or
      S.

<400> SEQUENCE: 90

Gln Xaa Xaa Gly Arg Xaa Xaa Arg Xaa Xaa Xaa Xaa Xaa Xaa Xaa
1               5                   10                  15

Xaa Xaa Xaa Asp Asn Arg
            20

<210> SEQ ID NO 91
<211> LENGTH: 726
<212> TYPE: PRT
<213> ORGANISM: Methanococcoides burtonii

<400> SEQUENCE: 91

Met Ser Asp Lys Pro Ala Phe Met Lys Tyr Phe Thr Gln Ser Ser Cys
1               5                   10                  15

Tyr Pro Asn Gln Gln Glu Ala Met Asp Arg Ile His Ser Ala Leu Met
                20                  25                  30

Gln Gln Gln Leu Val Leu Phe Glu Gly Ala Cys Gly Thr Gly Lys Thr
            35                  40                  45

Leu Ser Ala Leu Val Pro Ala Leu His Val Gly Lys Met Leu Gly Lys
        50                  55                  60

Thr Val Ile Ile Ala Thr Asn Val His Gln Gln Met Val Gln Phe Ile
65                  70                  75                  80

Asn Glu Ala Arg Asp Ile Lys Lys Val Gln Asp Val Lys Val Ala Val
                85                  90                  95

Ile Lys Gly Lys Thr Ala Met Cys Pro Gln Glu Ala Asp Tyr Glu Glu
            100                 105                 110

Cys Ser Val Lys Arg Glu Asn Thr Phe Glu Leu Met Glu Thr Glu Arg
        115                 120                 125

Glu Ile Tyr Leu Lys Arg Gln Glu Leu Asn Ser Ala Arg Asp Ser Tyr
130                 135                 140

Lys Lys Ser His Asp Pro Ala Phe Val Thr Leu Arg Asp Glu Leu Ser
145                 150                 155                 160

Lys Glu Ile Asp Ala Val Glu Glu Lys Ala Arg Gly Leu Arg Asp Arg
                165                 170                 175

Ala Cys Asn Asp Leu Tyr Glu Val Leu Arg Ser Asp Ser Glu Lys Phe
            180                 185                 190

Arg Glu Trp Leu Tyr Lys Glu Val Arg Ser Pro Glu Glu Ile Asn Asp
        195                 200                 205
```

```
His Ala Ile Lys Asp Gly Met Cys Gly Tyr Glu Leu Val Lys Arg Glu
            210                 215                 220

Leu Lys His Ala Asp Leu Ile Cys Asn Tyr His His Val Leu Asn
225                 230                 235                 240

Pro Asp Ile Phe Ser Thr Val Leu Gly Trp Ile Glu Lys Glu Pro Gln
                245                 250                 255

Glu Thr Ile Val Ile Phe Asp Glu Ala His Asn Leu Glu Ser Ala Ala
            260                 265                 270

Arg Ser His Ser Ser Leu Ser Leu Thr Glu His Ser Ile Glu Lys Ala
            275                 280                 285

Ile Thr Glu Leu Glu Ala Asn Leu Asp Leu Leu Ala Asp Asp Asn Ile
290                 295                 300

His Asn Leu Phe Asn Ile Phe Leu Glu Val Ile Ser Asp Thr Tyr Asn
305                 310                 315                 320

Ser Arg Phe Lys Phe Gly Glu Arg Glu Arg Val Arg Lys Asn Trp Tyr
                325                 330                 335

Asp Ile Arg Ile Ser Asp Pro Tyr Glu Arg Asn Asp Ile Val Arg Gly
            340                 345                 350

Lys Phe Leu Arg Gln Ala Lys Gly Asp Phe Gly Glu Lys Asp Asp Ile
            355                 360                 365

Gln Ile Leu Leu Ser Glu Ala Ser Glu Leu Gly Ala Lys Leu Asp Glu
370                 375                 380

Thr Tyr Arg Asp Gln Tyr Lys Lys Gly Leu Ser Ser Val Met Lys Arg
385                 390                 395                 400

Ser His Ile Arg Tyr Val Ala Asp Phe Met Ser Ala Tyr Ile Glu Leu
                405                 410                 415

Ser His Asn Leu Asn Tyr Tyr Pro Ile Leu Asn Val Arg Arg Asp Met
            420                 425                 430

Asn Asp Glu Ile Tyr Gly Arg Val Glu Leu Phe Thr Cys Ile Pro Lys
            435                 440                 445

Asn Val Thr Glu Pro Leu Phe Asn Ser Leu Phe Ser Val Ile Leu Met
450                 455                 460

Ser Ala Thr Leu His Pro Phe Glu Met Val Lys Lys Thr Leu Gly Ile
465                 470                 475                 480

Thr Arg Asp Thr Cys Glu Met Ser Tyr Gly Thr Ser Phe Pro Glu Glu
                485                 490                 495

Lys Arg Leu Ser Ile Ala Val Ser Ile Pro Pro Leu Phe Ala Lys Asn
            500                 505                 510

Arg Asp Asp Arg His Val Thr Glu Leu Leu Glu Gln Val Leu Leu Asp
            515                 520                 525

Ser Ile Glu Asn Ser Lys Gly Asn Val Ile Leu Phe Phe Gln Ser Ala
530                 535                 540

Phe Glu Ala Lys Arg Tyr Tyr Ser Lys Ile Glu Pro Leu Val Asn Val
545                 550                 555                 560

Pro Val Phe Leu Asp Glu Val Gly Ile Ser Ser Gln Asp Val Arg Glu
                565                 570                 575

Glu Phe Phe Ser Ile Gly Glu Glu Asn Gly Lys Ala Val Leu Leu Ser
            580                 585                 590

Tyr Leu Trp Gly Thr Leu Ser Glu Gly Ile Asp Tyr Arg Asp Gly Arg
            595                 600                 605

Gly Arg Thr Val Ile Ile Ile Gly Val Gly Tyr Pro Ala Leu Asn Asp
610                 615                 620
```

```
Arg Met Asn Ala Val Glu Ser Ala Tyr Asp His Val Phe Gly Tyr Gly
625                 630                 635                 640

Ala Gly Trp Glu Phe Ala Ile Gln Val Pro Thr Ile Arg Lys Ile Arg
            645                 650                 655

Gln Ala Met Gly Arg Val Val Arg Ser Pro Thr Asp Tyr Gly Ala Arg
            660                 665                 670

Ile Leu Leu Asp Gly Arg Phe Leu Thr Asp Ser Lys Lys Arg Phe Gly
            675                 680                 685

Lys Phe Ser Val Phe Glu Val Phe Pro Pro Ala Glu Arg Ser Glu Phe
            690                 695                 700

Val Asp Val Asp Pro Glu Lys Val Lys Tyr Ser Leu Met Asn Phe Phe
705                 710                 715                 720

Met Asp Asn Asp Glu Gln
            725

<210> SEQ ID NO 92
<211> LENGTH: 9
<212> TYPE: PRT
<213> ORGANISM: Artificial Sequence
<220> FEATURE:
<223> OTHER INFORMATION: Motif V

<400> SEQUENCE: 92

Tyr Leu Trp Gly Thr Leu Ser Glu Gly
1               5

<210> SEQ ID NO 93
<211> LENGTH: 22
<212> TYPE: PRT
<213> ORGANISM: Artificial Sequence
<220> FEATURE:
<223> OTHER INFORMATION: Motif VI

<400> SEQUENCE: 93

Gln Ala Met Gly Arg Val Val Arg Ser Pro Thr Asp Tyr Gly Ala Arg
1               5                   10                  15

Ile Leu Leu Asp Gly Arg
            20

<210> SEQ ID NO 94
<211> LENGTH: 65
<212> TYPE: PRT
<213> ORGANISM: Artificial sequence
<220> FEATURE:
<223> OTHER INFORMATION: HhH domain

<400> SEQUENCE: 94

Gly Thr Gly Ser Gly Ala Trp Lys Glu Trp Leu Glu Arg Lys Val Gly
1               5                   10                  15

Glu Gly Arg Ala Arg Arg Leu Ile Glu Tyr Phe Gly Ser Ala Gly Glu
            20                  25                  30

Val Gly Lys Leu Val Glu Asn Ala Glu Val Ser Lys Leu Leu Glu Val
            35                  40                  45

Pro Gly Ile Gly Asp Glu Ala Val Ala Arg Leu Val Pro Gly Gly Ser
    50                  55                  60

Ser
65

<210> SEQ ID NO 95
<211> LENGTH: 299
<212> TYPE: PRT
```

<213> ORGANISM: Bacteriophage RB69

<400> SEQUENCE: 95

```
Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
        35                  40                  45

Pro Ala Lys Thr Asp Asp Ala Leu Pro Phe Ala Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asn Lys Thr Glu Tyr Ser Gln Leu Lys Arg Lys
            100                 105                 110

Thr Ser Tyr Trp Ala Asn Ile Leu Val Val Lys Asp Pro Gln Ala Pro
        115                 120                 125

Asp Asn Glu Gly Lys Val Phe Lys Tyr Arg Phe Gly Lys Lys Ile Trp
    130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
        195                 200                 205

Leu Phe Glu Gln Met Val Asp Leu Ser Glu Met Thr Ser Lys Asp Lys
    210                 215                 220

Phe Lys Ser Phe Glu Glu Leu Asn Thr Lys Phe Asn Gln Val Leu Gly
225                 230                 235                 240

Thr Ala Ala Leu Gly Gly Ala Ala Ala Ala Ala Ser Val Ala Asp
                245                 250                 255

Lys Val Ala Ser Asp Leu Asp Asp Phe Asp Lys Asp Met Glu Ala Phe
            260                 265                 270

Ser Ser Ala Lys Thr Glu Asp Asp Phe Met Ser Ser Ser Ser Asp
        275                 280                 285

Asp Gly Asp Leu Asp Asp Leu Leu Ala Gly Leu
    290                 295
```

<210> SEQ ID NO 96
<211> LENGTH: 232
<212> TYPE: PRT
<213> ORGANISM: Bacteriophage T7

<400> SEQUENCE: 96

```
Met Ala Lys Lys Ile Phe Thr Ser Ala Leu Gly Thr Ala Glu Pro Tyr
1               5                   10                  15

Ala Tyr Ile Ala Lys Pro Asp Tyr Gly Asn Glu Glu Arg Gly Phe Gly
            20                  25                  30

Asn Pro Arg Gly Val Tyr Lys Val Asp Leu Thr Ile Pro Asn Lys Asp
        35                  40                  45

Pro Arg Cys Gln Arg Met Val Asp Glu Ile Val Lys Cys His Glu Glu
```

```
                50                  55                  60
Ala Tyr Ala Ala Val Glu Glu Tyr Glu Ala Asn Pro Pro Ala Val
 65                  70                  75                  80

Ala Arg Gly Lys Lys Pro Leu Lys Pro Tyr Glu Gly Asp Met Pro Phe
                 85                  90                  95

Phe Asp Asn Gly Asp Gly Thr Thr Thr Phe Lys Phe Lys Cys Tyr Ala
                100                 105                 110

Ser Phe Gln Asp Lys Lys Thr Lys Glu Thr Lys His Ile Asn Leu Val
                115                 120                 125

Val Val Asp Ser Lys Gly Lys Lys Met Glu Asp Val Pro Ile Ile Gly
                130                 135                 140

Gly Gly Ser Lys Leu Lys Val Lys Tyr Ser Leu Val Pro Tyr Lys Trp
145                 150                 155                 160

Asn Thr Ala Val Gly Ala Ser Val Lys Leu Gln Leu Glu Ser Val Met
                165                 170                 175

Leu Val Glu Leu Ala Thr Phe Gly Gly Gly Glu Asp Asp Trp Ala Asp
                180                 185                 190

Glu Val Glu Glu Asn Gly Tyr Val Ala Ser Gly Ser Ala Lys Ala Ser
                195                 200                 205

Lys Pro Arg Asp Glu Glu Ser Trp Asp Glu Asp Glu Glu Ser Glu
                210                 215                 220

Glu Ala Asp Glu Asp Gly Asp Phe
225                 230

<210> SEQ ID NO 97
<211> LENGTH: 324
<212> TYPE: PRT
<213> ORGANISM: Herpes simplex virus 1

<400> SEQUENCE: 97

Met Asp Ser Pro Gly Gly Val Ala Pro Ala Ser Pro Val Glu Asp Ala
  1               5                  10                  15

Ser Asp Ala Ser Leu Gly Gln Pro Glu Glu Gly Ala Pro Cys Gln Val
                 20                  25                  30

Val Leu Gln Gly Ala Glu Leu Asn Gly Ile Leu Gln Ala Phe Ala Pro
                 35                  40                  45

Leu Arg Thr Ser Leu Leu Asp Ser Leu Leu Val Met Gly Asp Arg Gly
 50                  55                  60

Ile Leu Ile His Asn Thr Ile Phe Gly Glu Gln Val Phe Leu Pro Leu
 65                  70                  75                  80

Glu His Ser Gln Phe Ser Arg Tyr Arg Trp Arg Gly Pro Thr Ala Ala
                 85                  90                  95

Phe Leu Ser Leu Val Asp Gln Lys Arg Ser Leu Leu Ser Val Phe Arg
                100                 105                 110

Ala Asn Gln Tyr Pro Asp Leu Arg Arg Val Glu Leu Ala Ile Thr Gly
                115                 120                 125

Gln Ala Pro Phe Arg Thr Leu Val Gln Arg Ile Trp Thr Thr Thr Ser
                130                 135                 140

Asp Gly Glu Ala Val Glu Leu Ala Ser Glu Thr Leu Met Lys Arg Glu
145                 150                 155                 160

Leu Thr Ser Phe Val Val Leu Val Pro Gln Gly Thr Pro Asp Val Gln
                165                 170                 175

Leu Arg Leu Thr Arg Pro Gln Leu Thr Lys Val Leu Asn Ala Thr Gly
                180                 185                 190
```

```
Ala Asp Ser Ala Thr Pro Thr Thr Phe Glu Leu Gly Val Asn Gly Lys
            195                 200                 205

Phe Ser Val Phe Thr Thr Ser Thr Cys Val Thr Phe Ala Ala Arg Glu
    210                 215                 220

Glu Gly Val Ser Ser Thr Ser Thr Gln Val Gln Ile Leu Ser Asn
225                 230                 235                 240

Ala Leu Thr Lys Ala Gly Gln Ala Ala Asn Ala Lys Thr Val Tyr
            245                 250                 255

Gly Glu Asn Thr His Arg Thr Phe Ser Val Val Asp Asp Cys Ser
            260                 265                 270

Met Arg Ala Val Leu Arg Arg Leu Gln Val Gly Gly Thr Leu Lys
            275                 280                 285

Phe Phe Leu Thr Thr Pro Val Pro Ser Leu Cys Val Thr Ala Thr Gly
    290                 295                 300

Pro Asn Ala Val Ser Ala Val Phe Leu Leu Lys Pro Gln Lys His His
305                 310                 315                 320

His His His His
```

<210> SEQ ID NO 98
<211> LENGTH: 251
<212> TYPE: PRT
<213> ORGANISM: Artificial sequence
<220> FEATURE:
<223> OTHER INFORMATION: PCNA subunit 1

<400> SEQUENCE: 98

```
Met Phe Lys Ile Val Tyr Pro Asn Ala Lys Asp Phe Phe Ser Phe Ile
1               5                   10                  15

Asn Ser Ile Thr Asn Val Thr Asp Ser Ile Ile Leu Asn Phe Thr Glu
            20                  25                  30

Asp Gly Ile Phe Ser Arg His Leu Thr Glu Asp Lys Val Leu Met Ala
        35                  40                  45

Ile Met Arg Ile Pro Lys Asp Val Leu Ser Glu Tyr Ser Ile Asp Ser
    50                  55                  60

Pro Thr Ser Val Lys Leu Asp Val Ser Ser Val Lys Lys Ile Leu Ser
65                  70                  75                  80

Lys Ala Ser Ser Lys Lys Ala Thr Ile Glu Leu Thr Glu Thr Asp Ser
                85                  90                  95

Gly Leu Lys Ile Ile Arg Asp Glu Lys Ser Gly Ala Lys Ser Thr
            100                 105                 110

Ile Tyr Ile Lys Ala Glu Lys Gly Gln Val Glu Gln Leu Thr Glu Pro
        115                 120                 125

Lys Val Asn Leu Ala Val Asn Phe Thr Thr Asp Glu Ser Val Leu Asn
    130                 135                 140

Val Ile Ala Ala Asp Val Thr Leu Val Gly Glu Glu Met Arg Ile Ser
145                 150                 155                 160

Thr Glu Glu Asp Lys Ile Lys Ile Glu Ala Gly Glu Glu Gly Lys Arg
                165                 170                 175

Tyr Val Ala Phe Leu Met Lys Asp Lys Pro Leu Lys Glu Leu Ser Ile
            180                 185                 190

Asp Thr Ser Ala Ser Ser Ser Tyr Ser Ala Glu Met Phe Lys Asp Ala
        195                 200                 205

Val Lys Gly Leu Arg Gly Phe Ser Ala Pro Thr Met Val Ser Phe Gly
    210                 215                 220

Glu Asn Leu Pro Met Lys Ile Asp Val Glu Ala Val Ser Gly Gly His
```

```
                    225                 230                 235                 240
Met Ile Phe Trp Ile Ala Pro Arg Leu Leu Glu
                245                 250

<210> SEQ ID NO 99
<211> LENGTH: 245
<212> TYPE: PRT
<213> ORGANISM: Artificial sequence
<220> FEATURE:
<223> OTHER INFORMATION: PCNA subunit 2

<400> SEQUENCE: 99

Met Lys Ala Lys Val Ile Asp Ala Val Ser Phe Ser Tyr Ile Leu Arg
1               5                   10                  15

Thr Val Gly Asp Phe Leu Ser Glu Ala Asn Phe Ile Val Thr Lys Glu
            20                  25                  30

Gly Ile Arg Val Ser Gly Ile Asp Pro Ser Arg Val Val Phe Leu Asp
        35                  40                  45

Ile Phe Leu Pro Ser Ser Tyr Phe Glu Gly Phe Glu Val Ser Gln Glu
    50                  55                  60

Lys Glu Ile Ile Gly Phe Lys Leu Glu Asp Val Asn Asp Ile Leu Lys
65                  70                  75                  80

Arg Val Leu Lys Asp Asp Thr Leu Ile Leu Ser Ser Asn Glu Ser Lys
                85                  90                  95

Leu Thr Leu Thr Phe Asp Gly Glu Phe Thr Arg Ser Phe Glu Leu Pro
            100                 105                 110

Leu Ile Gln Val Glu Ser Thr Gln Pro Pro Ser Val Asn Leu Glu Phe
        115                 120                 125

Pro Phe Lys Ala Gln Leu Leu Thr Ile Thr Phe Ala Asp Ile Ile Asp
    130                 135                 140

Glu Leu Ser Asp Leu Gly Glu Val Leu Asn Ile His Ser Lys Glu Asn
145                 150                 155                 160

Lys Leu Tyr Phe Glu Val Ile Gly Asp Leu Ser Thr Ala Lys Val Glu
                165                 170                 175

Leu Ser Thr Asp Asn Gly Thr Leu Leu Glu Ala Ser Gly Ala Asp Val
            180                 185                 190

Ser Ser Ser Tyr Gly Met Glu Tyr Val Ala Asn Thr Thr Lys Met Arg
        195                 200                 205

Arg Ala Ser Asp Ser Met Glu Leu Tyr Phe Gly Ser Gln Ile Pro Leu
    210                 215                 220

Lys Leu Arg Phe Lys Leu Pro Gln Glu Gly Tyr Gly Asp Phe Tyr Ile
225                 230                 235                 240

Ala Pro Arg Ala Asp
                245

<210> SEQ ID NO 100
<211> LENGTH: 246
<212> TYPE: PRT
<213> ORGANISM: Artificial sequence
<220> FEATURE:
<223> OTHER INFORMATION: PCNA subunit 3

<400> SEQUENCE: 100

Met Lys Val Val Tyr Asp Asp Val Arg Val Leu Lys Asp Ile Ile Gln
1               5                   10                  15

Ala Leu Ala Arg Leu Val Asp Glu Ala Val Leu Lys Phe Lys Gln Asp
            20                  25                  30
```

Ser Val Glu Leu Val Ala Leu Asp Arg Ala His Ile Ser Leu Ile Ser
    35                  40                  45

Val Asn Leu Pro Arg Glu Met Phe Lys Glu Tyr Asp Val Asn Asp Glu
 50                  55                  60

Phe Lys Phe Gly Phe Asn Thr Gln Tyr Leu Met Lys Ile Leu Lys Val
 65                  70                  75                  80

Ala Lys Arg Lys Glu Ala Ile Glu Ile Ala Ser Glu Ser Pro Asp Ser
                 85                  90                  95

Val Ile Ile Asn Ile Ile Gly Ser Thr Asn Arg Glu Phe Asn Val Arg
                100                 105                 110

Asn Leu Glu Val Ser Glu Gln Glu Ile Pro Glu Ile Asn Leu Gln Phe
            115                 120                 125

Asp Ile Ser Ala Thr Ile Ser Ser Asp Gly Phe Lys Ser Ala Ile Ser
130                 135                 140

Glu Val Ser Thr Val Thr Asp Asn Val Val Val Gly His Glu Asp
145                 150                 155                 160

Arg Ile Leu Ile Lys Ala Glu Gly Glu Ser Val Glu Val Glu Phe
                165                 170                 175

Ser Lys Asp Thr Gly Gly Leu Gln Asp Leu Glu Phe Ser Lys Glu Ser
            180                 185                 190

Lys Asn Ser Tyr Ser Ala Glu Tyr Leu Asp Asp Val Leu Ser Leu Thr
            195                 200                 205

Lys Leu Ser Asp Tyr Val Lys Ile Ser Phe Gly Asn Gln Lys Pro Leu
        210                 215                 220

Gln Leu Phe Phe Asn Met Glu Gly Gly Lys Val Thr Tyr Leu Leu
225                 230                 235                 240

Ala Pro Lys Val Leu Glu
            245

<210> SEQ ID NO 101
<211> LENGTH: 608
<212> TYPE: PRT
<213> ORGANISM: Bacteriophage phi-29

<400> SEQUENCE: 101

Met Lys His Met Pro Arg Lys Met Tyr Ser Cys Ala Phe Glu Thr Thr
 1               5                  10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Val Leu Lys Val Gln Ala Asp Leu Tyr Phe His Asn Leu Lys
 50                  55                  60

Phe Asp Gly Ala Phe Ile Ile Asn Trp Leu Glu Arg Asn Gly Phe Lys
 65                  70                  75                  80

Trp Ser Ala Asp Gly Leu Pro Asn Thr Tyr Asn Thr Ile Ile Ser Arg
                 85                  90                  95

Met Gly Gln Trp Tyr Met Ile Asp Ile Cys Leu Gly Tyr Lys Gly Lys
                100                 105                 110

Arg Lys Ile His Thr Val Ile Tyr Asp Ser Leu Lys Lys Leu Pro Phe
            115                 120                 125

Pro Val Lys Lys Ile Ala Lys Asp Phe Lys Leu Thr Val Leu Lys Gly
130                 135                 140

Asp Ile Asp Tyr His Lys Glu Arg Pro Val Gly Tyr Lys Ile Thr Pro
145                 150                 155                 160

```
Glu Glu Tyr Ala Tyr Ile Lys Asn Asp Ile Gln Ile Ala Glu Ala
            165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
            195                 200                 205

Lys Val Phe Pro Thr Leu Ser Leu Gly Leu Asp Lys Glu Val Arg Tyr
210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
            245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
            290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
            325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
            355                 360                 365

Tyr Ile Lys Thr Thr Ser Glu Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
            485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
            515                 520                 525

Lys Cys Ala Gly Met Thr Asp Lys Ile Lys Glu Val Thr Phe Glu
            530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Ser
            565                 570                 575
```

```
Gly Gly Ser Ala Trp Ser His Pro Gln Phe Glu Lys Gly Gly Ser
            580                 585                 590
Gly Gly Gly Ser Gly Gly Ser Ala Trp Ser His Pro Gln Phe Glu Lys
        595                 600                 605
```

<210> SEQ ID NO 102
<211> LENGTH: 318
<212> TYPE: PRT
<213> ORGANISM: Herpes simplex virus 1

<400> SEQUENCE: 102

```
Thr Asp Ser Pro Gly Gly Val Ala Pro Ala Ser Pro Val Glu Asp Ala
1               5                   10                  15
Ser Asp Ala Ser Leu Gly Gln Pro Glu Glu Gly Ala Pro Cys Gln Val
                20                  25                  30
Val Leu Gln Gly Ala Glu Leu Asn Gly Ile Leu Gln Ala Phe Ala Pro
            35                  40                  45
Leu Arg Thr Ser Leu Leu Asp Ser Leu Leu Val Met Gly Asp Arg Gly
        50                  55                  60
Ile Leu Ile His Asn Thr Ile Phe Gly Glu Gln Val Phe Leu Pro Leu
65                  70                  75                  80
Glu His Ser Gln Phe Ser Arg Tyr Arg Trp Arg Gly Pro Thr Ala Ala
                85                  90                  95
Phe Leu Ser Leu Val Asp Gln Lys Arg Ser Leu Leu Ser Val Phe Arg
            100                 105                 110
Ala Asn Gln Tyr Pro Asp Leu Arg Arg Val Glu Leu Ala Ile Thr Gly
        115                 120                 125
Gln Ala Pro Phe Arg Thr Leu Val Gln Arg Ile Trp Thr Thr Thr Ser
130                 135                 140
Asp Gly Glu Ala Val Glu Leu Ala Ser Glu Thr Leu Met Lys Arg Glu
145                 150                 155                 160
Leu Thr Ser Phe Val Val Leu Val Pro Gln Gly Thr Pro Asp Val Gln
                165                 170                 175
Leu Arg Leu Thr Arg Pro Gln Leu Thr Lys Val Leu Asn Ala Thr Gly
            180                 185                 190
Ala Asp Ser Ala Thr Pro Thr Thr Phe Glu Leu Gly Val Asn Gly Lys
        195                 200                 205
Phe Ser Val Phe Thr Thr Ser Thr Cys Val Thr Phe Ala Ala Arg Glu
    210                 215                 220
Glu Gly Val Ser Ser Ser Thr Ser Thr Gln Val Gln Ile Leu Ser Asn
225                 230                 235                 240
Ala Leu Thr Lys Ala Gly Gln Ala Ala Ala Asn Ala Lys Thr Val Tyr
                245                 250                 255
Gly Glu Asn Thr His Arg Thr Phe Ser Val Val Val Asp Asp Cys Ser
            260                 265                 270
Met Arg Ala Val Leu Arg Arg Leu Gln Val Gly Gly Gly Thr Leu Lys
        275                 280                 285
Phe Phe Leu Thr Thr Pro Val Pro Ser Leu Cys Val Thr Ala Thr Gly
    290                 295                 300
Pro Asn Ala Val Ser Ala Val Phe Leu Leu Lys Pro Gln Lys
305                 310                 315
```

<210> SEQ ID NO 103
<211> LENGTH: 233
<212> TYPE: PRT
<213> ORGANISM: Bacteriophage RB69

<400> SEQUENCE: 103

```
Lys Gly Phe Ser Ser Glu Asp Lys Gly Glu Trp Lys Leu Lys Leu Asp
1               5                   10                  15

Ala Ser Gly Asn Gly Gln Ala Val Ile Arg Phe Leu Pro Ala Lys Thr
            20                  25                  30

Asp Asp Ala Leu Pro Phe Ala Ile Leu Val Asn His Gly Phe Lys Lys
        35                  40                  45

Asn Gly Lys Trp Tyr Ile Glu Thr Cys Ser Ser Thr His Gly Asp Tyr
    50                  55                  60

Asp Ser Cys Pro Val Cys Gln Tyr Ile Ser Lys Asn Asp Leu Tyr Asn
65                  70                  75                  80

Thr Asn Lys Thr Glu Tyr Ser Gln Leu Lys Arg Lys Thr Ser Tyr Trp
                85                  90                  95

Ala Asn Ile Leu Val Val Lys Asp Pro Gln Ala Pro Asp Asn Glu Gly
            100                 105                 110

Lys Val Phe Lys Tyr Arg Phe Gly Lys Lys Ile Trp Asp Lys Ile Asn
        115                 120                 125

Ala Met Ile Ala Val Asp Thr Glu Met Gly Glu Thr Pro Val Asp Val
    130                 135                 140

Thr Cys Pro Trp Glu Gly Ala Asn Phe Val Leu Lys Val Lys Gln Val
145                 150                 155                 160

Ser Gly Phe Ser Asn Tyr Asp Glu Ser Lys Phe Leu Asn Gln Ser Ala
                165                 170                 175

Ile Pro Asn Ile Asp Asp Glu Ser Phe Gln Lys Glu Leu Phe Glu Gln
            180                 185                 190

Met Val Asp Leu Ser Glu Met Thr Ser Lys Asp Lys Phe Lys Ser Phe
        195                 200                 205

Glu Glu Leu Asn Thr Lys Phe Asn Gln Val Leu Gly Thr Ala Ala Leu
    210                 215                 220

Gly Gly Ala Ala Ala Ala Ala Ser
225                 230
```

<210> SEQ ID NO 104
<211> LENGTH: 210
<212> TYPE: PRT
<213> ORGANISM: Bacteriophage T7

<400> SEQUENCE: 104

```
Ala Lys Lys Ile Phe Thr Ser Ala Leu Gly Thr Ala Glu Pro Tyr Ala
1               5                   10                  15

Tyr Ile Ala Lys Pro Asp Tyr Gly Asn Glu Glu Arg Gly Phe Gly Asn
            20                  25                  30

Pro Arg Gly Val Tyr Lys Val Asp Leu Thr Ile Pro Asn Lys Asp Pro
        35                  40                  45

Arg Cys Gln Arg Met Val Asp Glu Ile Val Lys Cys His Glu Glu Ala
    50                  55                  60

Tyr Ala Ala Val Glu Glu Tyr Glu Ala Asn Pro Pro Ala Val Ala
65                  70                  75                  80

Arg Gly Lys Lys Pro Leu Lys Pro Tyr Glu Gly Asp Met Pro Phe Phe
                85                  90                  95

Asp Asn Gly Asp Gly Thr Thr Thr Phe Lys Phe Lys Cys Tyr Ala Ser
            100                 105                 110

Phe Gln Asp Lys Lys Thr Lys Glu Thr Lys His Ile Asn Leu Val Val
        115                 120                 125
```

```
Val Asp Ser Lys Gly Lys Lys Met Glu Asp Val Pro Ile Ile Gly Gly
        130                 135                 140

Gly Ser Lys Leu Lys Val Lys Tyr Ser Leu Val Pro Tyr Lys Trp Asn
145                 150                 155                 160

Thr Ala Val Gly Ala Ser Val Lys Leu Gln Leu Glu Ser Val Met Leu
                165                 170                 175

Val Glu Leu Ala Thr Phe Gly Gly Glu Asp Asp Trp Ala Asp Glu
            180                 185                 190

Val Glu Glu Asn Gly Tyr Val Ala Ser Gly Ser Ala Lys Ala Ser Lys
            195                 200                 205

Pro Arg
    210

<210> SEQ ID NO 105
<211> LENGTH: 99
<212> TYPE: PRT
<213> ORGANISM: Halorubrum lacusprofundi

<400> SEQUENCE: 105

Ser Gly Glu Glu Leu Leu Asp Leu Ala Gly Val Arg Asn Val Gly Arg
1               5                   10                  15

Lys Arg Ala Arg Arg Leu Phe Glu Ala Gly Ile Glu Thr Arg Ala Asp
            20                  25                  30

Leu Arg Glu Ala Asp Lys Ala Val Leu Gly Ala Leu Arg Gly Arg
        35                  40                  45

Glu Arg Thr Ala Glu Arg Ile Leu Glu His Ala Gly Arg Glu Asp Pro
50                  55                  60

Ser Met Asp Asp Val Arg Pro Asp Lys Ser Ala Ser Ala Ala Ala Thr
65                  70                  75                  80

Ala Gly Ser Ala Ser Asp Glu Asp Gly Glu Gly Gln Ala Ser Leu Gly
                85                  90                  95

Asp Phe Arg

<210> SEQ ID NO 106
<211> LENGTH: 102
<212> TYPE: PRT
<213> ORGANISM: Haloferax volcanii

<400> SEQUENCE: 106

Ser Gly Glu Glu Leu Leu Asp Leu Ala Gly Val Arg Gly Val Gly Arg
1               5                   10                  15

Lys Arg Ala Arg Arg Leu Phe Glu Ala Gly Val Glu Thr Arg Ala Asp
            20                  25                  30

Leu Arg Glu Ala Asp Lys Pro Arg Val Leu Ala Ala Leu Arg Gly Arg
        35                  40                  45

Arg Lys Thr Ala Glu Asn Ile Leu Glu Ala Ala Gly Arg Lys Asp Pro
50                  55                  60

Ser Met Asp Ala Val Asp Glu Asp Ala Asp Asp Ala Val Pro
65                  70                  75                  80

Asp Asp Ala Gly Phe Glu Thr Ala Lys Glu Arg Ala Asp Gln Gln Ala
                85                  90                  95

Ser Leu Gly Asp Phe Glu
            100

<210> SEQ ID NO 107
<211> LENGTH: 55
```

```
<212> TYPE: PRT
<213> ORGANISM: Artificial sequence
<220> FEATURE:
<223> OTHER INFORMATION: (HhH)2 domain

<400> SEQUENCE: 107

Trp Lys Glu Trp Leu Glu Arg Lys Val Gly Glu Gly Arg Ala Arg Arg
1               5                   10                  15

Leu Ile Glu Tyr Phe Gly Ser Ala Gly Glu Val Gly Lys Leu Val Glu
            20                  25                  30

Asn Ala Glu Val Ser Lys Leu Leu Glu Val Pro Gly Ile Gly Asp Glu
        35                  40                  45

Ala Val Ala Arg Leu Val Pro
    50                  55

<210> SEQ ID NO 108
<211> LENGTH: 107
<212> TYPE: PRT
<213> ORGANISM: Artificial sequence
<220> FEATURE:
<223> OTHER INFORMATION: (HhH)2-(HhH)2 domain

<400> SEQUENCE: 108

Trp Lys Glu Trp Leu Glu Arg Lys Val Gly Glu Gly Arg Ala Arg Arg
1               5                   10                  15

Leu Ile Glu Tyr Phe Gly Ser Ala Gly Glu Val Gly Lys Leu Val Glu
            20                  25                  30

Asn Ala Glu Val Ser Lys Leu Leu Glu Val Pro Gly Ile Gly Asp Glu
        35                  40                  45

Ala Val Ala Arg Leu Val Pro Gly Tyr Lys Thr Leu Arg Asp Ala Gly
    50                  55                  60

Leu Thr Pro Ala Glu Ala Glu Arg Val Leu Lys Arg Tyr Gly Ser Val
65                  70                  75                  80

Ser Lys Val Gln Glu Gly Ala Thr Pro Asp Glu Leu Arg Glu Leu Gly
                85                  90                  95

Leu Gly Asp Ala Lys Ile Ala Arg Ile Leu Gly
            100                 105

<210> SEQ ID NO 109
<211> LENGTH: 7
<212> TYPE: PRT
<213> ORGANISM: Artificial sequence
<220> FEATURE:
<223> OTHER INFORMATION: Peptide linker used in the Examples

<400> SEQUENCE: 109

Ser Arg Asp Phe Trp Arg Ser
1               5

<210> SEQ ID NO 110
<211> LENGTH: 117
<212> TYPE: DNA
<213> ORGANISM: Artificial sequence
<220> FEATURE:
<223> OTHER INFORMATION: Polynucleotide used in the Examples

<400> SEQUENCE: 110
tcgctgctcc acaggtctca gcttgagcag cgaaaataag aacattatga tcagtaggag      60
cactacgacc tttgttctgg tgctcgtccg ggcgcccaaa gtggagcgag tgccccc        117

<210> SEQ ID NO 111
```

```
<211> LENGTH: 80
<212> TYPE: DNA
<213> ORGANISM: Artificial sequence
<220> FEATURE:
<223> OTHER INFORMATION: Polynucleotide used in the Examples

<400> SEQUENCE: 111
gcactcgctc cactttgggc gcccggacga gcaccagaac aaaggtcgta gtgctcctac      60
tgatcataat gttcttattt                                                 80

<210> SEQ ID NO 112
<211> LENGTH: 33
<212> TYPE: DNA
<213> ORGANISM: Artificial sequence
<220> FEATURE:
<223> OTHER INFORMATION: Polynucleotide used in the Examples

<400> SEQUENCE: 112
tcgctgctca agctgagacc tgtggagcag cga                                  33

<210> SEQ ID NO 113
<211> LENGTH: 113
<212> TYPE: DNA
<213> ORGANISM: Artificial sequence
<220> FEATURE:
<223> OTHER INFORMATION: Polynucleotide used in the Examples

<400> SEQUENCE: 113
tcgctgctcc acaggtctca gcttgagcag cgaaaataag aacattatga tcagtaggag     60
cactacgacc tttgttctgg tgctcgtccg ggcgcccaaa gtggagcgag tgc            113

<210> SEQ ID NO 114
<211> LENGTH: 28
<212> TYPE: DNA
<213> ORGANISM: Artificial sequence
<220> FEATURE:
<223> OTHER INFORMATION: Polynucleotide used in the Examples

<400> SEQUENCE: 114
tcgctgctcc acaggtctca gcttcccc                                        28

<210> SEQ ID NO 115
<211> LENGTH: 974
<212> TYPE: DNA
<213> ORGANISM: Artificial sequence
<220> FEATURE:
<223> OTHER INFORMATION: Polynucleotide used in the Examples

<400> SEQUENCE: 115
tttttttttt tttttttttt tttttttttt tttttttttt tttttttttt ggttgtttct     60
gttggtgctg atattgctgt gttctatgtc ttattctgtg tatgtatctt gtctgttagc    120
cccgattgtt accggataat tcgagctcgg tacccacccc ggttgataat cagaaaagcc    180
ccaaaaacag gaagattgta taagcaaata tttaaattgt aaacgttaat attttgttaa    240
aattcgcgtt aaattttgt taaatcagct cattttttaa ccataggcc gaaatcggca      300 aaatccctta taaatcaaaa gaatagaccg atagggtt gagtgttgtt ccagtttgga      360
acaagagtcc agtattaaag aacgtggact ccaacgtcaa agggcgaaaa accgtctatc    420
agggcgatgg cccactacgt gaaccatcac cctaatcaag ttttttgggg tcgaggtgcc    480
gtaaagcact aaatcggaac cctaaaggga tgccccgatt tagagcttga cggggaaagc    540
cggcgaacgt ggcgagaaag gaagggaaga aagcgaaagg agcgggcgct agggcgctgg    600
```

```
caagtgtagc ggtcacgctg cgcgtaacca ccacacccgc cgcgcttaat gcgccgctac      660
agggcgcgtg gggatcctct agagtcgacc tgcaggcatg caagctatcc cgcaagaggc      720
ccggcagtac cggcataacc aagcctatgc ctacagcatc cagggtgacg gtgccgagga      780
tgacgatgag cgcattgtta gatttcatac acggtgcctg actgcgttag caatttaact      840
gtgataaact accgcattaa agctagctta tcgatgataa gctgtcaaac atgagaattc      900
ttgaagacga aagggcctcg tgatacgcct atttttatag gttaatgtca tgataataat      960
ggtttcttag acgt                                                        974
```

<210> SEQ ID NO 116
<211> LENGTH: 893
<212> TYPE: DNA
<213> ORGANISM: Artificial sequence
<220> FEATURE:
<223> OTHER INFORMATION: Polynucleotide used in the Examples

<400> SEQUENCE: 116

```
ctaagaaacc attattatca tgacattaac ctataaaaat aggcgtatca cgaggccctt       60
tcgtcttcaa gaattctcat gtttgacagc ttatcatcga taagctagct ttaatgcggt      120
agtttatcac agttaaattg ctaacgcagt caggcaccgt gtatgaaatc taacaatgcg      180
ctcatcgtca tcctcggcac cgtcaccctg gatgctgtag cataggctt ggttatgccg       240 gtactgccgg gcctcttgcg ggatagcttg catgcctgca ggtcgactct agaggatccc      300
cacgcgccct gtagcggcgc attaagcgcg gcgggtgtgg tggttacgcg cagcgtgacc      360
gctacacttg ccagcgccct agcgcccgct cctttcgctt tcttcccttc ctttctcgcc      420
acgttcgccg gctttccccg tcaagctcta aatcggggca tccctttagg gttccgattt      480
agtgctttac ggcacctcga ccccaaaaaa cttgattagg gtgatggttc acgtagtggg      540
ccatcgccct gatagacggt ttttcgccct ttgacgttgg agtccacgtt ctttaatact      600
ggactcttgt tccaaactgg aacaacactc aaccctatct cggtctattc ttttgattta      660
taagggattt tgccgatttc ggcctattgg ttaaaaaatg agctgattta acaaaaattt      720
aacgcgaatt ttaacaaaat attaacgttt acaatttaaa tatttgctta tacaatcttc      780
ctgttttggg gcttttctg attatcaacc ggggtgggta ccgagctcga attatccggt       840
aacaatcggg gctaacagac aagatacata cacagaataa gacatagaac aca             893
```

<210> SEQ ID NO 117
<211> LENGTH: 28
<212> TYPE: DNA
<213> ORGANISM: Artificial sequence
<220> FEATURE:
<223> OTHER INFORMATION: Polynucleotide used in the Examples

<400> SEQUENCE: 117

```
gcaatatcag caccaacaga aacaacct                                          28
```

<210> SEQ ID NO 118
<211> LENGTH: 132
<212> TYPE: PRT
<213> ORGANISM: Homo sapiens

<400> SEQUENCE: 118

Glu Ser Glu Thr Thr Thr Ser Leu Val Leu Glu Arg Ser Leu Asn Arg
1               5                   10                  15

Val His Leu Leu Gly Arg Val Gly Gln Asp Pro Val Leu Arg Gln Val

```
                    20                  25                  30
Glu Gly Lys Asn Pro Val Thr Ile Phe Ser Leu Ala Thr Asn Glu Met
                35                  40                  45

Trp Arg Ser Gly Asp Ser Glu Val Tyr Gln Leu Gly Asp Val Ser Gln
 50                  55                  60

Lys Thr Thr Trp His Arg Ile Ser Val Phe Arg Pro Gly Leu Arg Asp
 65                  70                  75                  80

Val Ala Tyr Gln Tyr Val Lys Lys Gly Ser Arg Ile Tyr Leu Glu Gly
                 85                  90                  95

Lys Ile Asp Tyr Gly Glu Tyr Met Asp Lys Asn Asn Val Arg Arg Gln
                100                 105                 110

Ala Thr Thr Ile Ile Ala Asp Asn Ile Ile Phe Leu Ser Asp Gln Thr
                115                 120                 125

Lys Glu Lys Glu
                130

<210> SEQ ID NO 119
<211> LENGTH: 123
<212> TYPE: PRT
<213> ORGANISM: Bacteriophage phi-29

<400> SEQUENCE: 119

Glu Asn Thr Asn Ile Val Lys Ala Thr Phe Asp Thr Glu Thr Leu Glu
 1               5                  10                  15

Gly Gln Ile Lys Ile Phe Asn Ala Gln Thr Gly Gly Gln Ser Phe
                 20                  25                  30

Lys Asn Leu Pro Asp Gly Thr Ile Glu Ala Asn Ala Ile Ala Gln
                 35                  40                  45

Tyr Lys Gln Val Ser Asp Thr Tyr Gly Asp Ala Lys Glu Glu Thr Val
 50                  55                  60

Thr Thr Ile Phe Ala Ala Asp Gly Ser Leu Tyr Ser Ala Ile Ser Lys
 65                  70                  75                  80

Thr Val Ala Glu Ala Ala Ser Asp Leu Ile Asp Leu Val Thr Arg His
                 85                  90                  95

Lys Leu Glu Thr Phe Lys Val Lys Val Val Gln Gly Thr Ser Ser Lys
                100                 105                 110

Gly Asn Val Phe Phe Ser Leu Gln Leu Ser Leu
                115                 120

<210> SEQ ID NO 120
<211> LENGTH: 177
<212> TYPE: PRT
<213> ORGANISM: Escherichia coli

<400> SEQUENCE: 120

Ala Ser Arg Gly Val Asn Lys Val Ile Leu Val Gly Asn Leu Gly Gln
 1               5                  10                  15

Asp Pro Glu Val Arg Tyr Met Pro Asn Gly Gly Ala Val Ala Asn Ile
                 20                  25                  30

Thr Leu Ala Thr Ser Glu Ser Trp Arg Asp Lys Ala Thr Gly Glu Met
                 35                  40                  45

Lys Glu Gln Thr Glu Trp His Arg Val Val Leu Phe Gly Lys Leu Ala
                 50                  55                  60

Glu Val Ala Ser Glu Tyr Leu Arg Lys Gly Ser Gln Val Tyr Ile Glu
 65                  70                  75                  80

Gly Gln Leu Arg Thr Arg Lys Trp Thr Asp Gln Ser Gly Gln Asp Arg
```

|  |  |  | 85 |  |  |  | 90 |  |  |  | 95 |  |  |
|--|--|--|--|--|--|--|--|--|--|--|--|--|--|

Tyr Thr Thr Glu Val Val Asn Val Gly Gly Thr Met Gln Met Leu
            100                 105                110

Gly Gly Arg Gln Gly Gly Gly Ala Pro Ala Gly Gly Asn Ile Gly Gly
       115                  120                 125

Gly Gln Pro Gln Gly Gly Trp Gly Gln Pro Gln Gln Pro Gln Gly Gly
130                   135                 140

Asn Gln Phe Ser Gly Gly Ala Gln Ser Arg Pro Gln Gln Ser Ala Pro
145                   150              155              160

Ala Ala Pro Ser Asn Glu Pro Pro Met Asp Phe Asp Asp Ile Pro
            165                170               175

Phe

<210> SEQ ID NO 121
<211> LENGTH: 301
<212> TYPE: PRT
<213> ORGANISM: Bacteriophage T4

<400> SEQUENCE: 121

Met Phe Lys Arg Lys Ser Thr Ala Glu Leu Ala Ala Gln Met Ala Lys
1             5                  10                15

Leu Asn Gly Asn Lys Gly Phe Ser Ser Glu Asp Lys Gly Glu Trp Lys
            20                 25                30

Leu Lys Leu Asp Asn Ala Gly Asn Gly Gln Ala Val Ile Arg Phe Leu
       35                  40                 45

Pro Ser Lys Asn Asp Glu Gln Ala Pro Phe Ala Ile Leu Val Asn His
50                  55                 60

Gly Phe Lys Lys Asn Gly Lys Trp Tyr Ile Glu Thr Cys Ser Ser Thr
65                 70                 75              80

His Gly Asp Tyr Asp Ser Cys Pro Val Cys Gln Tyr Ile Ser Lys Asn
               85                90               95

Asp Leu Tyr Asn Thr Asp Asn Lys Glu Tyr Ser Leu Val Lys Arg Lys
          100                105                110

Thr Ser Tyr Trp Ala Asn Ile Leu Val Val Lys Asp Pro Ala Ala Pro
       115                  120                 125

Glu Asn Glu Gly Lys Val Phe Lys Tyr Arg Phe Gly Lys Lys Ile Trp
130                   135              140

Asp Lys Ile Asn Ala Met Ile Ala Val Asp Val Glu Met Gly Glu Thr
145                   150              155              160

Pro Val Asp Val Thr Cys Pro Trp Glu Gly Ala Asn Phe Val Leu Lys
              165                170               175

Val Lys Gln Val Ser Gly Phe Ser Asn Tyr Asp Glu Ser Lys Phe Leu
          180                185                190

Asn Gln Ser Ala Ile Pro Asn Ile Asp Asp Glu Ser Phe Gln Lys Glu
       195                  200                 205

Leu Phe Glu Gln Met Val Asp Leu Ser Glu Met Thr Ser Lys Asp Lys
210                   215              220

Phe Lys Ser Phe Glu Glu Leu Asn Thr Lys Phe Gly Gln Val Met Gly
225                   230              235              240

Thr Ala Val Met Gly Gly Ala Ala Thr Ala Lys Lys Ala Asp
              245                250               255

Lys Val Ala Asp Asp Leu Asp Ala Phe Asn Val Asp Asp Phe Asn Thr
          260                265                270

Lys Thr Glu Asp Asp Phe Met Ser Ser Ser Ser Gly Ser Ser Ser Ser

```
                275                 280                 285
Ala Asp Asp Thr Asp Leu Asp Asp Leu Leu Asn Asp Leu
        290                 295                 300

<210> SEQ ID NO 122
<211> LENGTH: 177
<212> TYPE: PRT
<213> ORGANISM: Artificial sequence
<220> FEATURE:
<223> OTHER INFORMATION: EcoSSB-CterAla

<400> SEQUENCE: 122

Ala Ser Arg Gly Val Asn Lys Val Ile Leu Val Gly Asn Leu Gly Gln
1               5                   10                  15

Asp Pro Glu Val Arg Tyr Met Pro Asn Gly Gly Ala Val Ala Asn Ile
            20                  25                  30

Thr Leu Ala Thr Ser Glu Ser Trp Arg Asp Lys Ala Thr Gly Glu Met
        35                  40                  45

Lys Glu Gln Thr Glu Trp His Arg Val Val Leu Phe Gly Lys Leu Ala
    50                  55                  60

Glu Val Ala Ser Glu Tyr Leu Arg Lys Gly Ser Gln Val Tyr Ile Glu
65                  70                  75                  80

Gly Gln Leu Arg Thr Arg Lys Trp Thr Asp Gln Ser Gly Gln Asp Arg
                85                  90                  95

Tyr Thr Thr Glu Val Val Val Asn Val Gly Gly Thr Met Gln Met Leu
            100                 105                 110

Gly Gly Arg Gln Gly Gly Gly Ala Pro Ala Gly Asn Ile Gly Gly
        115                 120                 125

Gly Gln Pro Gln Gly Gly Trp Gly Gln Pro Gln Pro Gln Gly Gly
    130                 135                 140

Asn Gln Phe Ser Gly Gly Ala Gln Ser Arg Pro Gln Gln Ser Ala Pro
145                 150                 155                 160

Ala Ala Pro Ser Asn Glu Pro Pro Met Ala Phe Ala Ala Ala Ile Pro
                165                 170                 175

Phe

<210> SEQ ID NO 123
<211> LENGTH: 177
<212> TYPE: PRT
<213> ORGANISM: Artificial sequence
<220> FEATURE:
<223> OTHER INFORMATION: EcoSSB-CterNGGN

<400> SEQUENCE: 123

Ala Ser Arg Gly Val Asn Lys Val Ile Leu Val Gly Asn Leu Gly Gln
1               5                   10                  15

Asp Pro Glu Val Arg Tyr Met Pro Asn Gly Gly Ala Val Ala Asn Ile
            20                  25                  30

Thr Leu Ala Thr Ser Glu Ser Trp Arg Asp Lys Ala Thr Gly Glu Met
        35                  40                  45

Lys Glu Gln Thr Glu Trp His Arg Val Val Leu Phe Gly Lys Leu Ala
    50                  55                  60

Glu Val Ala Ser Glu Tyr Leu Arg Lys Gly Ser Gln Val Tyr Ile Glu
65                  70                  75                  80

Gly Gln Leu Arg Thr Arg Lys Trp Thr Asp Gln Ser Gly Gln Asp Arg
                85                  90                  95

Tyr Thr Thr Glu Val Val Val Asn Val Gly Gly Thr Met Gln Met Leu
```

```
                100                 105                 110
Gly Gly Arg Gln Gly Gly Gly Ala Pro Ala Gly Gly Asn Ile Gly Gly
            115                 120                 125
Gly Gln Pro Gln Gly Gly Trp Gly Gln Pro Gln Pro Gln Gly Gly
            130                 135                 140
Asn Gln Phe Ser Gly Gly Ala Gln Ser Arg Pro Gln Ser Ala Pro
145                 150                 155                 160
Ala Ala Pro Ser Asn Glu Pro Pro Met Asn Phe Gly Gly Asn Ile Pro
                165                 170                 175
Phe
```

<210> SEQ ID NO 124
<211> LENGTH: 152
<212> TYPE: PRT
<213> ORGANISM: Artificial sequence
<220> FEATURE:
<223> OTHER INFORMATION: EcoSSB-Q152del

<400> SEQUENCE: 124

```
Ala Ser Arg Gly Val Asn Lys Val Ile Leu Val Gly Asn Leu Gly Gln
1               5                   10                  15
Asp Pro Glu Val Arg Tyr Met Pro Asn Gly Gly Ala Val Ala Asn Ile
                20                  25                  30
Thr Leu Ala Thr Ser Glu Ser Trp Arg Asp Lys Ala Thr Gly Glu Met
            35                  40                  45
Lys Glu Gln Thr Glu Trp His Arg Val Val Leu Phe Gly Lys Leu Ala
    50                  55                  60
Glu Val Ala Ser Glu Tyr Leu Arg Lys Gly Ser Gln Val Tyr Ile Glu
65                  70                  75                  80
Gly Gln Leu Arg Thr Arg Lys Trp Thr Asp Gln Ser Gly Gln Asp Arg
                85                  90                  95
Tyr Thr Thr Glu Val Val Val Asn Val Gly Gly Thr Met Gln Met Leu
                100                 105                 110
Gly Gly Arg Gln Gly Gly Gly Ala Pro Ala Gly Gly Asn Ile Gly Gly
            115                 120                 125
Gly Gln Pro Gln Gly Gly Trp Gly Gln Pro Gln Gln Pro Gln Gly Gly
            130                 135                 140
Asn Gln Phe Ser Gly Gly Ala Gln
145                 150
```

<210> SEQ ID NO 125
<211> LENGTH: 117
<212> TYPE: PRT
<213> ORGANISM: Artificial sequence
<220> FEATURE:
<223> OTHER INFORMATION: EcoSSB-G117del

<400> SEQUENCE: 125

```
Ala Ser Arg Gly Val Asn Lys Val Ile Leu Val Gly Asn Leu Gly Gln
1               5                   10                  15
Asp Pro Glu Val Arg Tyr Met Pro Asn Gly Gly Ala Val Ala Asn Ile
                20                  25                  30
Thr Leu Ala Thr Ser Glu Ser Trp Arg Asp Lys Ala Thr Gly Glu Met
            35                  40                  45
Lys Glu Gln Thr Glu Trp His Arg Val Val Leu Phe Gly Lys Leu Ala
    50                  55                  60
Glu Val Ala Ser Glu Tyr Leu Arg Lys Gly Ser Gln Val Tyr Ile Glu
```

```
                65                  70                  75                  80
Gly Gln Leu Arg Thr Arg Lys Trp Thr Asp Gln Ser Gly Gln Asp Arg
                    85                  90                  95
Tyr Thr Thr Glu Val Val Asn Val Gly Gly Thr Met Gln Met Leu
                100                 105                 110
Gly Gly Arg Gln Gly
        115

<210> SEQ ID NO 126
<211> LENGTH: 970
<212> TYPE: PRT
<213> ORGANISM: Citromicrobium bathyomarinum JL354

<400> SEQUENCE: 126

Met Leu Ser Val Ala Asn Val Arg Ser Pro Ser Ala Ala Ala Ser Tyr
1               5                   10                  15

Phe Ala Ser Asp Asn Tyr Tyr Ala Ser Ala Asp Ala Asp Arg Ser Gly
                20                  25                  30

Gln Trp Ile Gly Asp Gly Ala Lys Arg Leu Gly Leu Glu Gly Lys Val
            35                  40                  45

Glu Ala Arg Ala Phe Asp Ala Leu Leu Arg Gly Glu Leu Pro Asp Gly
        50                  55                  60

Ser Ser Val Gly Asn Pro Gly Gln Ala His Arg Pro Gly Thr Asp Leu
65                  70                  75                  80

Thr Phe Ser Val Pro Lys Ser Trp Ser Leu Leu Ala Leu Val Gly Lys
                85                  90                  95

Asp Glu Arg Ile Ile Ala Ala Tyr Arg Glu Ala Val Val Glu Ala Leu
                100                 105                 110

His Trp Ala Glu Lys Asn Ala Ala Glu Thr Arg Val Val Glu Lys Gly
            115                 120                 125

Met Val Val Thr Gln Ala Thr Gly Asn Leu Ala Ile Gly Leu Phe Gln
        130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
                180                 185                 190

Ala Arg Phe Arg Val Ala Val Glu Lys Leu Gly Tyr Glu Pro Gly Pro
            195                 200                 205

Val Leu Lys His Gly Asn Phe Glu Ala Arg Gly Ile Ser Arg Glu Gln
        210                 215                 220

Val Met Ala Phe Ser Thr Arg Arg Lys Glu Val Leu Glu Ala Arg Arg
225                 230                 235                 240

Gly Pro Gly Leu Asp Ala Gly Arg Ile Ala Ala Leu Asp Thr Arg Ala
                245                 250                 255

Ser Lys Glu Gly Ile Glu Asp Arg Ala Thr Leu Ser Lys Gln Trp Ser
                260                 265                 270

Glu Ala Ala Gln Ser Ile Gly Leu Asp Leu Lys Pro Leu Val Asp Arg
            275                 280                 285

Ala Arg Thr Lys Ala Leu Gly Gln Gly Met Glu Ala Thr Arg Ile Gly
        290                 295                 300

Ser Leu Val Glu Arg Gly Arg Ala Trp Leu Ser Arg Phe Ala Ala His
305                 310                 315                 320
```

```
Val Arg Gly Asp Pro Ala Asp Pro Leu Val Pro Pro Ser Val Leu Lys
            325                 330                 335

Gln Asp Arg Gln Thr Ile Ala Ala Ala Gln Ala Val Ala Ser Ala Val
        340                 345                 350

Arg His Leu Ser Gln Arg Glu Ala Ala Phe Glu Arg Thr Ala Leu Tyr
            355                 360                 365

Lys Ala Ala Leu Asp Phe Gly Leu Pro Thr Thr Ile Ala Asp Val Glu
    370                 375                 380

Lys Arg Thr Arg Ala Leu Val Arg Ser Gly Asp Leu Ile Ala Gly Lys
385                 390                 395                 400

Gly Glu His Lys Gly Trp Leu Ala Ser Arg Asp Ala Val Val Thr Glu
                405                 410                 415

Gln Arg Ile Leu Ser Glu Val Ala Ala Gly Lys Gly Asp Ser Ser Pro
            420                 425                 430

Ala Ile Thr Pro Gln Lys Ala Ala Ser Val Gln Ala Ala Ala Ala Leu
        435                 440                 445

Thr Gly Gln Gly Phe Arg Leu Asn Glu Gly Gln Leu Ala Ala Ala Arg
    450                 455                 460

Leu Ile Leu Ile Ser Lys Asp Arg Thr Ile Ala Val Gln Gly Ile Ala
465                 470                 475                 480

Gly Ala Gly Lys Ser Ser Val Leu Lys Pro Val Ala Glu Val Leu Arg
                485                 490                 495

Asp Glu Gly His Pro Val Ile Gly Leu Ala Ile Gln Asn Thr Leu Val
            500                 505                 510

Gln Met Leu Glu Arg Asp Thr Gly Ile Gly Ser Gln Thr Leu Ala Arg
        515                 520                 525

Phe Leu Gly Gly Trp Asn Lys Leu Leu Asp Asp Pro Gly Asn Val Ala
    530                 535                 540

Leu Arg Ala Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
                565                 570                 575

Leu Ala Asn Leu Ala Gly Val His Arg Leu Val Leu Ile Gly Asp Arg
            580                 585                 590

Lys Gln Leu Gly Ala Val Asp Ala Gly Lys Pro Phe Ala Leu Leu Gln
        595                 600                 605

Arg Ala Gly Ile Ala Arg Ala Glu Met Ala Thr Asn Leu Arg Ala Arg
    610                 615                 620

Asp Pro Val Val Arg Glu Ala Gln Ala Ala Gln Ala Gly Asp Val
625                 630                 635                 640

Arg Lys Ala Leu Arg His Leu Lys Ser His Thr Val Glu Ala Arg Gly
                645                 650                 655

Asp Gly Ala Gln Val Ala Ala Glu Thr Trp Leu Ala Leu Asp Lys Glu
            660                 665                 670

Thr Arg Ala Arg Thr Ser Ile Tyr Ala Ser Gly Arg Ala Ile Arg Ser
        675                 680                 685

Ala Val Asn Ala Ala Val Gln Gln Gly Leu Leu Ala Ser Arg Glu Ile
    690                 695                 700

Gly Pro Ala Lys Met Lys Leu Glu Val Leu Asp Arg Val Asn Thr Thr
705                 710                 715                 720

Arg Glu Glu Leu Arg His Leu Pro Ala Tyr Arg Ala Gly Arg Val Leu
                725                 730                 735

Glu Val Ser Arg Lys Gln Gln Ala Leu Gly Leu Phe Ile Gly Glu Tyr
```

```
                740                 745                 750
Arg Val Ile Gly Gln Asp Arg Lys Gly Lys Leu Val Glu Val Glu Asp
            755                 760                 765

Lys Arg Gly Lys Arg Phe Arg Phe Asp Pro Ala Arg Ile Arg Ala Gly
        770                 775                 780

Lys Gly Asp Asp Asn Leu Thr Leu Leu Glu Pro Arg Lys Leu Glu Ile
785                 790                 795                 800

His Glu Gly Asp Arg Ile Arg Trp Thr Arg Asn Asp His Arg Arg Gly
                805                 810                 815

Leu Phe Asn Ala Asp Gln Ala Arg Val Val Glu Ile Ala Asn Gly Lys
            820                 825                 830

Val Thr Phe Glu Thr Ser Lys Gly Asp Leu Val Glu Leu Lys Lys Asp
        835                 840                 845

Asp Pro Met Leu Lys Arg Ile Asp Leu Ala Tyr Ala Leu Asn Val His
    850                 855                 860

Met Ala Gln Gly Leu Thr Ser Asp Arg Gly Ile Ala Val Met Asp Ser
865                 870                 875                 880

Arg Glu Arg Asn Leu Ser Asn Gln Lys Thr Phe Leu Val Thr Val Thr
                885                 890                 895

Arg Leu Arg Asp His Leu Thr Leu Val Val Asp Ser Ala Asp Lys Leu
            900                 905                 910

Gly Ala Ala Val Ala Arg Asn Lys Gly Glu Lys Ala Ser Ala Ile Glu
        915                 920                 925

Val Thr Gly Ser Val Lys Pro Thr Ala Thr Lys Gly Ser Gly Val Asp
    930                 935                 940

Gln Pro Lys Ser Val Glu Ala Asn Lys Ala Glu Lys Glu Leu Thr Arg
945                 950                 955                 960

Ser Lys Ser Lys Thr Leu Asp Phe Gly Ile
                965                 970

<210> SEQ ID NO 127
<211> LENGTH: 73
<212> TYPE: DNA
<213> ORGANISM: Artificial sequence
<220> FEATURE:
<223> OTHER INFORMATION: Polynucleotide used in the Examples

<400> SEQUENCE: 127
tttttttttt tttttttttt tttttttttt tttttttttt tttttggtt gtttctgttg    60 gtgctgatat tgc                                                      73

<210> SEQ ID NO 128
<211> LENGTH: 3523
<212> TYPE: DNA
<213> ORGANISM: Artificial sequence
<220> FEATURE:
<223> OTHER INFORMATION: Polynucleotide used in the Examples

<400> SEQUENCE: 128
gccatcagat tgtgtttgtt agtcgctttt ttttttttgga attttttttt tggaatttt    60 tttttgcgct aacaacctcc tgccgttttg cccgtgcata tcggtcacga acaaatctga   120
ttactaaaca cagtagcctg gatttgttct atcagtaatc gaccttattc ctaattaaat   180
agagcaaatc cccttattgg gggtaagaca tgaagatgcc agaaaaacat gacctgttgg   240
ccgccattct cgcggcaaag gaacaaggca tcggggcaat ccttgcgttt gcaatggcgt   300
accttcgcgg cagatataat ggcggtgcgt ttacaaaaac agtaatcgac gcaacgatgt   360
```

-continued

```
gcgccattat cgcctagttc attcgtgacc ttctcgactt cgccggacta agtagcaatc      420
tcgcttatat aacgagcgtg tttatcggct acatcggtac tgactcgatt ggttcgctta      480
tcaaacgctt cgctgctaaa aaagccggag tagaagatgg tagaaatcaa taatcaacgt      540
aaggcgttcc tcgatatgct ggcgtggtcg gagggaactg ataacggacg tcagaaaacc      600
agaaatcatg gttatgacgt cattgtaggc ggagagctat ttactgatta ctccgatcac      660
cctcgcaaac ttgtcacgct aaacccaaaa ctcaaatcaa caggcgccgg acgctaccag      720
cttctttccc gttggtggga tgcctaccgc aagcagcttg cctgaaaga cttctctccg       780
aaaagtcagg acgctgtggc attgcagcag attaaggagc gtggcgcttt acctatgatt      840
gatcgtggtg atatccgtca ggcaatcgac cgttgcagca atatctgggc ttcactgccg      900
ggcgctggtt atggtcagtt cgagcataag gctgacagcc tgattgcaaa attcaaagaa      960
gcgggcggaa cggtcagaga gattgatgta tgagcagagt caccgcgatt atctccgctc     1020
tggttatctg catcatcgtc tgcctgtcat gggctgttaa tcattaccgt gataacgcca     1080
ttacctacaa agcccagcgc gacaaaaatg ccagagaact gaagctggcg aacgcggcaa     1140
ttactgacat gcagatgcgt cagcgtgatg ttgctgcgct cgatgcaaaa tacacgaagg     1200
agttagctga tgctaaagct gaaaatgatg ctctgcgtga tgatgttgcc gctggtcgtc     1260
gtcggttgca catcaaagca gtctgtcagt cagtgcgtga agccaccacc gcctccggcg     1320
tggataatgc agcctccccc cgactggcag acaccgctga acgggattat ttcaccctca     1380
gagagaggct gatcactatg caaaacaac tggaaggaac ccagaagtat attaatgagc      1440
agtgcagata gagttgccca tatcgatggg caactcatgc aattattgtg agcaatacac     1500
acgcgcttcc agcggagtat aaatgcctaa agtaataaaa ccgagcaatc catttacgaa     1560
tgtttgctgg gtttctgttt taacaacatt ttctgcgccg ccacaaattt tggctgcatc     1620
gacagttttc ttctgcccaa ttccagaaac gaagaaatga tgggtgatgg tttcctttgg     1680
tgctactgct gccggtttgt tttgaacagt aaacgtctgt tgagcacatc ctgtaataag     1740
cagggccagc gcagtagcga gtagcatttt tttcatggtg ttattcccga tgcttttga     1800
agttcgcaga atcgtatgtg tagaaaatta acaaaccct aaacaatgag ttgaaatttc      1860
atattgttaa tatttattaa tgtatgtcag gtgcgatgaa tcgtcattgt attcccggat     1920
taactatgtc cacagccctg acggggaact tctctgcggg agtgtccggg aataattaaa     1980
acgatgcaca cagggtttag cgcgtacacg tattgcatta tgccaacgcc ccggtgctga     2040
cacgaagaa accggacgtt atgatttagc gtggaaagat ttgtgtagtg ttctgaatgc      2100
tctcagtaaa tagtaatgaa ttatcaaagg tatagtaata tcttttatgt tcatggatat     2160
ttgtaaccca tcggaaaact cctgctttag caagattttc cctgtattgc tgaaatgtga     2220
tttctcttga tttcaaccta tcataggacg tttctataag atgcgtgttt cttgagaatt     2280
taacatttac aacctttta agtccttta ttaacacggt gttatcgttt ctaacacga       2340
tgtgaatata tctgtggcta gatagtaaat ataatgtgag acgttgtgac gttttagttc     2400
agaataaaac aattcacagt ctaaatcttt tcgcacttga tcgaatattt ctttaaaaat     2460
ggcaacctga gccattggta aaaccttcca tgtgatacga gggcgcgtag tttgcattat     2520
cgttttatc gtttcaatct ggtctgacct ccttgtgttt tgttgatgat ttatgtcaaa      2580
tattaggaat gttttcactt aatagtattg gttgcgtaac aaagtgcggt cctgctggca     2640
ttctggaggg aaatacaacc gacagatgta tgtaaggcca acgtgctcaa atcttcatac     2700
```

-continued

```
agaaagattt gaagtaatat tttaaccgct agatgaagag caagcgcatg gagcgacaaa    2760
atgaataaag aacaatctgc tgatgatccc tccgtggatc tgattcgtgt aaaaaatatg    2820
cttaatagca ccatttctat gagttaccct gatgttgtaa ttgcatgtat agaacataag    2880
gtgtctctgg aagcattcag agcaattgag gcagcgttgg tgaagcacga taataatatg    2940
aaggattatt ccctggtggt tgactgatca ccataactgc taatcattca aactatttag    3000
tctgtgacag agccaacacg cagtctgtca ctgtcaggaa agtggtaaaa ctgcaactca    3060
attactgcaa tgccctcgta attaagtgaa tttacaatat cgtcctgttc ggagggaaga    3120
acgcgggatg ttcattcttc atcacttttta attgatgtat atgctctctt ttctgacgtt    3180
agtctccgac ggcaggcttc aatgacccag gctgagaaat tcccggaccc tttttgctca    3240
agagcgatgt taatttgttc aatcatttgg ttaggaaagc ggatgttgcg ggttgttgtt    3300
ctgcgggttc tgttcttcgt tgacatgagg ttgccccgta ttcagtgtcg ctgatttgta    3360
ttgtctgaag ttgttttttac gttaagttga tgcagatcaa ttaatacgat acctgcgtca    3420
taattgatta tttgacgtgg tttgatggcc tccacgcacg ttgtgatatg tagatgataa    3480
tcattatcac tttacgggtc ctttccggtg aaaaaaaagg tac                      3523
```

<210> SEQ ID NO 129
<211> LENGTH: 984
<212> TYPE: PRT
<213> ORGANISM: Methanopyrus kandleri

<400> SEQUENCE: 129

```
Met Ala Leu Val Tyr Asp Ala Glu Phe Val Gly Ser Glu Arg Glu Phe
1               5                   10                  15

Glu Glu Glu Arg Glu Thr Phe Leu Lys Gly Val Lys Ala Tyr Asp Gly
            20                  25                  30

Val Leu Ala Thr Arg Tyr Leu Met Glu Arg Ser Ser Ala Lys Asn
        35                  40                  45

Asp Glu Glu Leu Leu Glu Leu His Gln Asn Phe Ile Leu Leu Thr Gly
    50                  55                  60

Ser Tyr Ala Cys Ser Ile Asp Pro Thr Glu Asp Arg Tyr Gln Asn Val
65                  70                  75                  80

Ile Val Arg Gly Val Asn Phe Asp Glu Arg Val Gln Arg Leu Ser Thr
                85                  90                  95

Gly Gly Ser Pro Ala Arg Tyr Ala Ile Val Tyr Arg Arg Gly Trp Arg
            100                 105                 110

Ala Ile Ala Lys Ala Leu Asp Ile Asp Glu Glu Asp Val Pro Ala Ile
        115                 120                 125

Glu Val Arg Ala Val Lys Arg Asn Pro Leu Gln Pro Ala Leu Tyr Arg
    130                 135                 140

Ile Leu Val Arg Tyr Gly Arg Val Asp Leu Met Pro Val Thr Val Asp
145                 150                 155                 160

Glu Val Pro Pro Glu Met Ala Gly Glu Phe Arg Leu Ile Glu Arg
                165                 170                 175

Tyr Asp Val Pro Ile Asp Glu Lys Glu Glu Arg Ile Leu Glu Ile Leu
            180                 185                 190

Arg Glu Asn Pro Trp Thr Pro His Asp Glu Ile Ala Arg Arg Leu Gly
        195                 200                 205

Leu Ser Val Ser Glu Val Glu Gly Glu Lys Asp Pro Glu Ser Ser Gly
    210                 215                 220

Ile Tyr Ser Leu Trp Ser Arg Val Val Val Asn Ile Glu Tyr Asp Glu
```

```
                225                 230                 235                 240
Arg Thr Ala Lys Arg His Val Lys Arg Arg Asp Arg Leu Leu Glu Glu
                    245                 250                 255

Leu Tyr Glu His Leu Glu Glu Leu Ser Glu Arg Tyr Leu Arg His Pro
                260                 265                 270

Leu Thr Arg Arg Trp Ile Val Glu His Lys Arg Asp Ile Met Arg Arg
                275                 280                 285

Tyr Leu Glu Gln Arg Ile Val Glu Cys Ala Leu Lys Leu Gln Asp Arg
                290                 295                 300

Tyr Gly Ile Arg Glu Asp Val Ala Leu Cys Leu Ala Arg Ala Phe Asp
305                 310                 315                 320

Gly Ser Ile Ser Met Ile Ala Thr Thr Pro Tyr Arg Thr Leu Lys Asp
                    325                 330                 335

Val Cys Pro Asp Leu Thr Leu Glu Glu Ala Lys Ser Val Asn Arg Thr
                    340                 345                 350

Leu Ala Thr Leu Ile Asp Glu His Gly Leu Ser Pro Asp Ala Ala Asp
                355                 360                 365

Glu Leu Ile Glu His Phe Glu Ser Ile Ala Gly Ile Leu Ala Thr Asp
                370                 375                 380

Leu Glu Glu Ile Glu Arg Met Tyr Glu Glu Gly Arg Leu Ser Glu Glu
385                 390                 395                 400

Ala Tyr Arg Ala Ala Val Glu Ile Gln Leu Ala Glu Leu Thr Lys Lys
                    405                 410                 415

Glu Gly Val Gly Arg Lys Thr Ala Glu Arg Leu Leu Arg Ala Phe Gly
                    420                 425                 430

Asn Pro Glu Arg Val Lys Gln Leu Ala Arg Glu Phe Glu Ile Glu Lys
                435                 440                 445

Leu Ala Ser Val Glu Gly Val Gly Glu Arg Val Leu Arg Ser Leu Val
                450                 455                 460

Pro Gly Tyr Ala Ser Leu Ile Ser Ile Arg Gly Ile Asp Arg Glu Arg
465                 470                 475                 480

Ala Glu Arg Leu Leu Lys Lys Tyr Gly Gly Tyr Ser Lys Val Arg Glu
                    485                 490                 495

Ala Gly Val Glu Glu Leu Arg Glu Asp Gly Leu Thr Asp Ala Gln Ile
                    500                 505                 510

Arg Glu Leu Lys Gly Leu Lys Thr Leu Glu Ser Ile Val Gly Asp Leu
                515                 520                 525

Glu Lys Ala Asp Glu Leu Lys Arg Lys Tyr Gly Ser Ala Ser Ala Val
                530                 535                 540

Arg Arg Leu Pro Val Glu Glu Leu Arg Glu Leu Gly Phe Ser Asp Asp
545                 550                 555                 560

Glu Ile Ala Glu Ile Lys Gly Ile Pro Lys Lys Leu Arg Glu Ala Phe
                    565                 570                 575

Asp Leu Glu Thr Ala Ala Glu Leu Tyr Glu Arg Tyr Gly Ser Leu Lys
                580                 585                 590

Glu Ile Gly Arg Arg Leu Ser Tyr Asp Asp Leu Leu Glu Leu Gly Ala
                595                 600                 605

Thr Pro Lys Ala Ala Glu Ile Lys Gly Pro Glu Phe Lys Phe Leu
                610                 615                 620

Leu Asn Ile Glu Gly Val Gly Pro Lys Leu Ala Glu Arg Ile Leu Glu
625                 630                 635                 640

Ala Val Asp Tyr Asp Leu Glu Arg Leu Ala Ser Leu Asn Pro Glu Glu
                    645                 650                 655
```

Leu Ala Glu Lys Val Glu Gly Leu Gly Glu Leu Ala Glu Arg Val
            660                 665                 670

Val Tyr Ala Ala Arg Glu Arg Val Glu Ser Arg Arg Lys Ser Gly Arg
        675                 680                 685

Gln Glu Arg Ser Glu Glu Trp Lys Glu Trp Leu Glu Arg Lys Val
    690                 695                 700

Gly Glu Gly Arg Ala Arg Arg Leu Ile Glu Tyr Phe Gly Ser Ala Gly
705                 710                 715                 720

Glu Val Gly Lys Leu Val Glu Asn Ala Glu Val Ser Lys Leu Leu Glu
                725                 730                 735

Val Pro Gly Ile Gly Asp Glu Ala Ala Arg Leu Val Pro Gly Tyr
            740                 745                 750

Lys Thr Leu Arg Asp Ala Gly Leu Thr Pro Glu Ala Glu Arg Val
        755                 760                 765

Leu Lys Arg Tyr Gly Ser Val Ser Lys Val Gln Glu Gly Ala Thr Pro
    770                 775                 780

Asp Glu Leu Arg Glu Leu Gly Leu Gly Asp Ala Lys Ile Ala Arg Ile
785                 790                 795                 800

Leu Gly Leu Arg Ser Leu Val Asn Lys Arg Leu Asp Val Asp Thr Ala
                805                 810                 815

Tyr Glu Leu Lys Arg Arg Tyr Gly Ser Val Ser Ala Val Arg Lys Ala
            820                 825                 830

Pro Val Lys Glu Leu Arg Glu Leu Gly Leu Ser Asp Arg Lys Ile Ala
        835                 840                 845

Arg Ile Lys Gly Ile Pro Glu Thr Met Leu Gln Val Arg Gly Met Ser
    850                 855                 860

Val Glu Lys Ala Glu Arg Leu Leu Glu Arg Phe Asp Thr Trp Thr Lys
865                 870                 875                 880

Val Lys Glu Ala Pro Val Ser Glu Leu Val Arg Val Pro Gly Val Gly
                885                 890                 895

Leu Ser Leu Val Lys Glu Ile Lys Ala Gln Val Asp Pro Ala Trp Lys
            900                 905                 910

Ala Leu Leu Asp Val Lys Gly Val Ser Pro Glu Leu Ala Asp Arg Leu
        915                 920                 925

Val Glu Glu Leu Gly Ser Pro Tyr Arg Val Leu Thr Ala Lys Lys Ser
    930                 935                 940

Asp Leu Met Arg Val Glu Arg Val Gly Pro Lys Leu Ala Glu Arg Ile
945                 950                 955                 960

Arg Ala Ala Gly Lys Arg Tyr Val Glu Arg Arg Ser Arg Arg Glu
                965                 970                 975

Arg Ile Arg Arg Lys Leu Arg Gly
            980

<210> SEQ ID NO 130
<211> LENGTH: 299
<212> TYPE: PRT
<213> ORGANISM: Methanopyrus kandleri

<400> SEQUENCE: 130

Ser Gly Arg Gln Glu Arg Ser Glu Glu Trp Lys Glu Trp Leu Glu
1               5                   10                  15

Arg Lys Val Gly Glu Gly Arg Ala Arg Arg Leu Ile Glu Tyr Phe Gly
                20                  25                  30

Ser Ala Gly Glu Val Gly Lys Leu Val Glu Asn Ala Glu Val Ser Lys

```
                35                  40                  45
Leu Leu Glu Val Pro Gly Ile Gly Asp Glu Ala Val Ala Arg Leu Val
 50                  55                  60

Pro Gly Tyr Lys Thr Leu Arg Asp Ala Gly Leu Thr Pro Ala Glu Ala
 65                  70                  75                  80

Glu Arg Val Leu Lys Arg Tyr Gly Ser Val Ser Lys Val Gln Glu Gly
                 85                  90                  95

Ala Thr Pro Asp Glu Leu Arg Glu Leu Gly Leu Gly Asp Ala Lys Ile
            100                 105                 110

Ala Arg Ile Leu Gly Leu Arg Ser Leu Val Asn Lys Arg Leu Asp Val
        115                 120                 125

Asp Thr Ala Tyr Glu Leu Lys Arg Arg Tyr Gly Ser Val Ser Ala Val
    130                 135                 140

Arg Lys Ala Pro Val Lys Glu Leu Arg Glu Leu Gly Leu Ser Asp Arg
145                 150                 155                 160

Lys Ile Ala Arg Ile Lys Gly Ile Pro Glu Thr Met Leu Gln Val Arg
                165                 170                 175

Gly Met Ser Val Glu Lys Ala Glu Arg Leu Leu Glu Arg Phe Asp Thr
            180                 185                 190

Trp Thr Lys Val Lys Glu Ala Pro Val Ser Glu Leu Val Arg Val Pro
        195                 200                 205

Gly Val Gly Leu Ser Leu Val Lys Glu Ile Lys Ala Gln Val Asp Pro
    210                 215                 220

Ala Trp Lys Ala Leu Leu Asp Val Lys Gly Val Ser Pro Glu Leu Ala
225                 230                 235                 240

Asp Arg Leu Val Glu Glu Leu Gly Ser Pro Tyr Arg Val Leu Thr Ala
                245                 250                 255

Lys Lys Ser Asp Leu Met Arg Val Glu Arg Val Gly Pro Lys Leu Ala
            260                 265                 270

Glu Arg Ile Arg Ala Ala Gly Lys Arg Tyr Val Glu Glu Arg Arg Ser
        275                 280                 285

Arg Arg Glu Arg Ile Arg Arg Lys Leu Arg Gly
    290                 295

<210> SEQ ID NO 131
<211> LENGTH: 8
<212> TYPE: PRT
<213> ORGANISM: Artificial sequence
<220> FEATURE:
<223> OTHER INFORMATION: RecD-like motif I of TrwC Cba

<400> SEQUENCE: 131

Gly Ile Ala Gly Ala Gly Lys Ser
1               5

<210> SEQ ID NO 132
<211> LENGTH: 10
<212> TYPE: PRT
<213> ORGANISM: Artificial sequence
<220> FEATURE:
<223> OTHER INFORMATION: RecD-like motif V of TrwC Cba

<400> SEQUENCE: 132

Tyr Ala Leu Asn Val His Met Ala Gln Gly
1               5                  10

<210> SEQ ID NO 133
<211> LENGTH: 14
```

```
<212> TYPE: PRT
<213> ORGANISM: Artificial sequence
<220> FEATURE:
<223> OTHER INFORMATION: MobF motif III of TrwC Cba

<400> SEQUENCE: 133

His Asp Thr Asn Arg Asn Gln Glu Pro Asn Leu His Phe His
1               5                   10

<210> SEQ ID NO 134
<211> LENGTH: 943
<212> TYPE: PRT
<213> ORGANISM: Halothiobacillus neapolitanus c2

<400> SEQUENCE: 134

Met Leu Arg Ile Lys Asn Leu Lys Gly Asp Pro Ser Ala Ile Ile Asp
1               5                   10                  15

Tyr Ala Glu Asn Lys Lys Asn His Pro Asp Gln Lys Ser Gly Tyr Tyr
                20                  25                  30

Asp Ala Lys Gly Ala Pro Ser Ala Trp Gly Gly Ala Leu Ala Ala Asp
            35                  40                  45

Leu Gly Leu Ser Gly Ser Val Gln Ala Ala Asp Leu Lys Lys Leu Leu
        50                  55                  60

Ser Gly Glu Leu Ser Asp Gly Thr Arg Phe Ala Lys Glu Asp Pro Asp
65                  70                  75                  80

Arg Arg Leu Gly Ile Asp Met Ser Phe Ser Ala Pro Lys Ser Val Ser
                85                  90                  95

Leu Ala Ala Leu Val Gly Gly Asp Glu Arg Ile Ile Gln Ala His Asp
            100                 105                 110

Ala Ala Val Arg Thr Ala Met Ser Met Ile Glu Gln Glu Tyr Ala Thr
        115                 120                 125

Ala Arg Phe Gly His Ala Gly Arg Asn Val Val Cys Ser Gly Lys Leu
    130                 135                 140

Val Tyr Ala Ala Tyr Arg His Glu Asp Ala Arg Thr Val Asp Asp Ile
145                 150                 155                 160

Ala Asp Pro Gln Leu His Thr His Cys Ile Val Ser Asn Ile Thr Ile
                165                 170                 175

Asp Pro Glu Thr Gly Lys Pro Arg Ser Ile Asp Phe Ala Trp Gly Gln
            180                 185                 190

Asp Gly Ile Lys Leu Ala Gly Ala Met Tyr Arg Ala Glu Leu Ala Arg
        195                 200                 205

Arg Leu Lys Glu Met Gly Tyr Glu Leu Arg Lys Ser Glu Glu Gly Phe
    210                 215                 220

Glu Leu Ala Gln Ile Ser Asp Glu Gln Val Glu Thr Phe Ser Arg Arg
225                 230                 235                 240

Arg Val Gln Val Asp Gln Ala Leu Glu Gln Gln Gly Thr Asp Arg Glu
                245                 250                 255

His Ala Ser Ser Glu Leu Lys Thr Ala Val Thr Leu Ala Thr Arg Gln
            260                 265                 270

Gly Lys Ala Gln Leu Ser Ala Glu Asp Gln Tyr Glu Glu Trp Gln Gln
        275                 280                 285

Arg Ala Ala Glu Ala Glu Leu Asp Leu Ser Gln Pro Val Gly Pro Arg
    290                 295                 300

Val Ser Val Thr Pro Pro Glu Ile Asp Leu Asp His Thr Phe Glu His
305                 310                 315                 320

Leu Ser Glu Arg Ala Ser Val Ile Asn Lys Asp Ala Val Arg Leu Asp
```

-continued

```
                325                 330                 335
Ala Leu Ile Asn His Met Ser Glu Gly Ala Thr Leu Ser Thr Val Asp
                340                 345                 350

Lys Ala Ile Gln Gly Ala Ala Val Thr Gly Asp Val Phe Glu Ile Glu
                355                 360                 365

Asp Gly Ile Lys Arg Lys Ile Ile Thr Arg Glu Thr Leu Lys Arg Glu
                370                 375                 380

Gln Gln Ile Leu Leu Ala Gln Gln Gly Arg Gly Val Asn Ser Val
385                 390                 395                 400

Leu Ile Gly Val Gly Asp Thr Lys His Leu Ile Glu Asp Ala Glu Gln
                405                 410                 415

Ala Gln Gly Phe Arg Phe Ser Glu Gly Gln Arg Arg Ala Ile Asn Leu
                420                 425                 430

Thr Ala Thr Thr Thr Asp Gln Val Ser Gly Ile Val Gly Ala Ala Gly
                435                 440                 445

Ala Gly Lys Thr Thr Ala Met Lys Thr Val Ala Asp Leu Ala Lys Ser
                450                 455                 460

Gln Gly Leu Thr Val Val Gly Ile Ala Pro Ser Ala Ala Ala Asp
465                 470                 475                 480

Glu Leu Lys Ser Ala Gly Ala Asp Asp Thr Met Thr Leu Ala Thr Phe
                485                 490                 495

Asn Leu Lys Gly Glu Ala Ala Gly Pro Arg Leu Leu Ile Leu Asp Glu
                500                 505                 510

Ala Gly Met Val Ser Ala Arg Asp Gly Glu Ala Leu Leu Lys Lys Leu
                515                 520                 525

Gly Lys Glu Asp Arg Leu Ile Phe Val Gly Asp Pro Lys Gln Leu Ala
                530                 535                 540

Ala Val Glu Ala Gly Ser Pro Phe Ala Gln Leu Met Arg Ser Gly Ala
545                 550                 555                 560

Ile Gln Tyr Ala Glu Ile Thr Glu Ile Asn Arg Gln Lys Asp Gln Lys
                565                 570                 575

Leu Leu Asp Ile Ala Gln His Phe Ala Lys Gly Lys Ala Glu Glu Ala
                580                 585                 590

Val Ala Leu Ala Thr Lys Tyr Val Thr Glu Val Pro Val Thr Leu Pro
                595                 600                 605

Asp Lys Pro Glu His Lys Ile Thr Arg Gln Ala Lys Thr Glu Ala Arg
                610                 615                 620

Arg Leu Ala Ile Ala Ser Ala Thr Ala Lys Arg Tyr Leu Glu Leu Ser
625                 630                 635                 640

Gln Glu Glu Arg Ala Thr Thr Leu Val Leu Ser Gly Thr Asn Ala Val
                645                 650                 655

Arg Lys Gln Val Asn Glu Gln Val Arg Lys Gly Leu Ile Asp Lys Gly
                660                 665                 670

Glu Ile Asn Gly Glu Ser Phe Thr Val Ser Thr Leu Asp Lys Ala Asp
                675                 680                 685

Met Thr Arg Ala Lys Met Arg Lys Ala Gly Asn Tyr Lys Pro Gly Gln
                690                 695                 700

Val Ile Lys Thr Ala Gly Lys Gln Ala Glu Gln Ser Glu Val Val Ala
705                 710                 715                 720

Val Asn Leu Asp Gln Asn Leu Ile Gln Val Lys Leu Ser Asp Gly Thr
                725                 730                 735

Leu Lys Ser Ile Asp Ala Ser Arg Phe Asp Val Lys Lys Thr Gln Val
                740                 745                 750
```

```
Phe Asn Pro Arg Gln Ile Asp Ile Ala Ala Gly Asp Lys Ile Ile Phe
        755                 760                 765

Thr Asn Asn Asp Gln Ala Thr Glu Thr Lys Asn Asn Gln Ile Gly Leu
        770                 775                 780

Ile Glu Glu Ile Lys Asp Gly Lys Ala Ile Ile Asn Ser Asn Gly Ala
785                 790                 795                 800

Lys Val Glu Ile Asp Ile Gln Arg Lys Leu His Ile Asp His Ala Tyr
                805                 810                 815

Cys Ile Thr Ile His Arg Ser Gln Gly Gln Thr Val Asp Ser Val Ile
                820                 825                 830

Val Ala Gly Glu Ala Ser Arg Thr Thr Thr Ala Glu Ala Ala Tyr Val
                835                 840                 845

Ala Cys Thr Arg Glu Arg Tyr Lys Leu Glu Ile Ile Thr Asp Asn Thr
        850                 855                 860

Glu Arg Leu Ser Lys Asn Trp Val Arg Tyr Ala Asp Arg Gln Thr Ala
865                 870                 875                 880

Ala Glu Ala Leu Lys Ser Ser Glu Lys Tyr Pro His Leu Asp Glu
                885                 890                 895

Ile Arg Glu Glu Leu Arg Arg Glu Leu Gln Gln Glu Leu Glu Arg Gln
                900                 905                 910

Glu Pro Thr Asn Ile Thr Pro Glu Leu Glu Ile Glu Met Glu Arg Ser
        915                 920                 925

Met Phe Asp Gln Tyr Thr Leu His Ser Arg Gln Pro Arg Ser Tyr
        930                 935                 940

<210> SEQ ID NO 135
<211> LENGTH: 8
<212> TYPE: PRT
<213> ORGANISM: Artificial sequence
<220> FEATURE:
<223> OTHER INFORMATION: RecD-like motif I of TrwC Hne

<400> SEQUENCE: 135

Gly Ala Ala Gly Ala Gly Lys Thr
1               5

<210> SEQ ID NO 136
<211> LENGTH: 10
<212> TYPE: PRT
<213> ORGANISM: Artificial sequence
<220> FEATURE:
<223> OTHER INFORMATION: RecD-like motif V of TrwC Hne

<400> SEQUENCE: 136

Tyr Cys Ile Thr Ile His Arg Ser Gln Gly
1               5                   10

<210> SEQ ID NO 137
<211> LENGTH: 18
<212> TYPE: PRT
<213> ORGANISM: Artificial sequence
<220> FEATURE:
<223> OTHER INFORMATION: MobF motif III of TrwC Hne

<400> SEQUENCE: 137

His Glu Asp Ala Arg Thr Val Asp Asp Ile Ala Asp Pro Gln Leu His
1               5                   10                  15

Thr His
```

```
<210> SEQ ID NO 138
<211> LENGTH: 960
<212> TYPE: PRT
<213> ORGANISM: Erythrobacter litoralis HTCC2594

<400> SEQUENCE: 138
```

| | | | | | | | | | | | | | | | |
|---|---|---|---|---|---|---|---|---|---|---|---|---|---|---|---|
| Met | Leu | Ser | Val | Ala | Asn | Val | Arg | Ser | Pro | Thr | Ala | Ala | Ser | Tyr | |
| 1 | | | | 5 | | | | | 10 | | | | | 15 | |
| Phe | Ala | Ser | Asp | Asn | Tyr | Tyr | Ala | Ser | Ala | Asp | Ala | Asp | Arg | Ser | Gly |
| | | | 20 | | | | | 25 | | | | | 30 | | |
| Gln | Trp | Ile | Gly | Gly | Gly | Ala | Lys | Arg | Leu | Gly | Leu | Glu | Gly | Lys | Val |
| | | | 35 | | | | | 40 | | | | | 45 | | |
| Glu | Ala | Lys | Ala | Phe | Asp | Ala | Leu | Leu | Arg | Gly | Glu | Leu | Pro | Asp | Gly |
| | 50 | | | | | 55 | | | | | 60 | | | | |
| Ser | Ser | Val | Gly | Asn | Pro | Gly | Gln | Ala | His | Arg | Pro | Gly | Thr | Asp | Leu |
| 65 | | | | | 70 | | | | | 75 | | | | | 80 |
| Ser | Phe | Ser | Val | Pro | Lys | Ser | Trp | Ser | Leu | Leu | Ala | Leu | Val | Gly | Lys |
| | | | | 85 | | | | | 90 | | | | | 95 | |
| Asp | Glu | Arg | Ile | Ile | Ala | Ala | Tyr | Arg | Glu | Ala | Val | Val | Glu | Ala | Leu |
| | | | 100 | | | | | 105 | | | | | 110 | | |
| Gln | Trp | Ala | Glu | Lys | Asn | Ala | Ala | Glu | Thr | Arg | Ile | Val | Glu | Lys | Gly |
| | | | 115 | | | | | 120 | | | | | 125 | | |
| Lys | Met | Val | Thr | Gln | Ala | Thr | Gly | Asn | Leu | Ala | Val | Gly | Leu | Phe | Gln |
| | 130 | | | | | 135 | | | | | 140 | | | | |
| His | Asp | Thr | Asn | Arg | Asn | Gln | Glu | Pro | Asn | Leu | His | Phe | His | Ala | Val |
| 145 | | | | | 150 | | | | | 155 | | | | | 160 |
| Ile | Ala | Asn | Val | Thr | Gln | Gly | Lys | Asp | Gly | Lys | Trp | Arg | Thr | Leu | Lys |
| | | | | 165 | | | | | 170 | | | | | 175 | |
| Asn | Asp | Arg | Leu | Trp | Gln | Leu | Asn | Thr | Thr | Leu | Asn | Ser | Ile | Ala | Met |
| | | | 180 | | | | | 185 | | | | | 190 | | |
| Ala | Arg | Phe | Arg | Val | Ala | Val | Glu | Lys | Leu | Gly | Tyr | Glu | Pro | Gly | Pro |
| | | | 195 | | | | | 200 | | | | | 205 | | |
| Val | Leu | Lys | His | Gly | Asn | Phe | Glu | Ala | Arg | Gly | Ile | Ser | Arg | Glu | Gln |
| | 210 | | | | | 215 | | | | | 220 | | | | |
| Ile | Met | Ala | Phe | Ser | Thr | Arg | Arg | Lys | Glu | Val | Leu | Glu | Ala | Arg | Arg |
| 225 | | | | | 230 | | | | | 235 | | | | | 240 |
| Gly | Pro | Gly | Leu | Glu | Ala | Gly | Arg | Ile | Ala | Ala | Leu | Asp | Thr | Arg | Ala |
| | | | | 245 | | | | | 250 | | | | | 255 | |
| Ser | Lys | Glu | Glu | Ile | Glu | Asp | Arg | Ala | Thr | Leu | Gly | Lys | Gln | Trp | Ser |
| | | | 260 | | | | | 265 | | | | | 270 | | |
| Glu | Thr | Ala | Gln | Ser | Ile | Gly | Leu | Asp | Leu | Thr | Pro | Leu | Val | Asp | Arg |
| | | | 275 | | | | | 280 | | | | | 285 | | |
| Ala | Arg | Thr | Asn | Ala | Leu | Gly | Gln | Ser | Met | Glu | Ala | Thr | Arg | Ile | Gly |
| | 290 | | | | | 295 | | | | | 300 | | | | |
| Ser | Leu | Val | Glu | Arg | Gly | Arg | Ala | Trp | Leu | Ser | Arg | Phe | Ala | Ala | His |
| 305 | | | | | 310 | | | | | 315 | | | | | 320 |
| Val | Arg | Gly | Asp | Pro | Ala | Asp | Pro | Leu | Val | Pro | Ser | Val | Leu | Lys | |
| | | | | 325 | | | | | 330 | | | | | 335 | |
| Gln | Asp | Arg | Gln | Thr | Ile | Ala | Ala | Gln | Ala | Val | Ala | Ser | Ala | Ile | |
| | | | 340 | | | | | 345 | | | | | 350 | | |
| Arg | His | Leu | Ser | Gln | Arg | Glu | Ala | Ala | Phe | Glu | Arg | Thr | Ala | Leu | Tyr |
| | | | 355 | | | | | 360 | | | | | 365 | | |
| Lys | Ala | Ala | Leu | Asp | Phe | Gly | Leu | Pro | Ala | Thr | Ile | Ala | Asp | Val | Glu |
| | 370 | | | | | 375 | | | | | 380 | | | | |

-continued

Lys Arg Thr Arg Ala Leu Val Arg Ser Gly Asp Leu Ile Ser Gly Lys
385                 390                 395                 400

Gly Glu His Lys Gly Trp Leu Ala Ser Arg Glu Ala Val Val Thr Glu
            405                 410                 415

Gln Arg Ile Leu Ser Glu Val Ala Ala Gly Lys Gly Asn Ser Ser Pro
        420                 425                 430

Ala Ile Glu Pro Gln Lys Ala Ala Ala Ser Val Gln Ala Ala Ala Ala
        435                 440                 445

Thr Gly Gln Gly Phe Arg Leu Asn Glu Gly Gln Leu Ala Ala Ala Glu
    450                 455                 460

Leu Ile Leu Thr Ser Lys Asp Arg Thr Ile Ala Ile Gln Gly Ile Ala
465                 470                 475                 480

Gly Ala Gly Lys Ser Ser Val Leu Lys Pro Val Ala Glu Val Leu Arg
                485                 490                 495

Asp Glu Gly His Pro Val Ile Gly Leu Ala Ile Gln Asn Thr Leu Val
            500                 505                 510

Gln Met Leu Glu Arg Glu Thr Gly Ile Gly Ser Gln Thr Leu Ala Arg
        515                 520                 525

Phe Leu Arg Gly Trp Thr Lys Leu Leu Gly Asp Pro Gly Asn Val Ala
    530                 535                 540

Leu Arg Thr Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
                565                 570                 575

Leu Ala Asn Leu Ala Gly Val His Arg Leu Val Leu Ile Gly Asp Arg
            580                 585                 590

Lys Gln Leu Gly Ala Val Asp Ala Gly Lys Pro Phe Ala Leu Leu Gln
        595                 600                 605

Arg Ala Gly Ile Ala Arg Ala Glu Met Ala Thr Asn Leu Arg Ala Arg
    610                 615                 620

Asp Pro Val Val Arg Glu Ala Gln Ala Ser Ala Gln Ala Gly Asp Val
625                 630                 635                 640

Arg Asn Ala Leu Arg His Leu Lys Ser His Thr Val Glu Ala Lys Gly
                645                 650                 655

Asp Gly Ala Gln Val Ala Ala Glu Thr Trp Leu Ala Leu Asp Lys Glu
            660                 665                 670

Thr Arg Ala Arg Thr Ser Ile Tyr Ala Ser Gly Arg Ala Ile Arg Ser
        675                 680                 685

Ala Val Asn Ala Ala Val Gln Gln Gly Leu Leu Ala Asn Arg Glu Ile
    690                 695                 700

Gly Pro Gly Met Met Lys Leu Asp Val Leu Asp Arg Val Asn Ala Thr
705                 710                 715                 720

Arg Glu Glu Leu Arg His Leu Pro Ala Tyr Arg Ala Gly Gln Val Leu
                725                 730                 735

Glu Ile Ser Arg Lys Gln Gln Ala Leu Gly Leu Ser Val Gly Glu Tyr
            740                 745                 750

Arg Val Leu Gly Gln Asp Arg Lys Gly Arg Leu Val Glu Val Glu Asp
        755                 760                 765

Lys Arg Gly Lys Arg Phe Arg Phe Asp Pro Ala Arg Ile Lys Ala Gly
    770                 775                 780

Lys Gly Asp Glu Asn Leu Thr Leu Leu Glu Pro Arg Lys Leu Glu Ile
785                 790                 795                 800

His Glu Gly Asp Arg Ile Arg Trp Thr Arg Asn Asp His Arg Arg Gly

```
                805                 810                 815
Leu Phe Asn Ala Asp Gln Ala Arg Val Val Ala Ile Ala Gly Gly Lys
                820                 825                 830

Ile Thr Phe Glu Thr Ser Gln Gly Asp Gln Val Glu Leu Lys Arg Asp
                835                 840                 845

Asp Pro Met Leu Lys Arg Ile Asp Leu Ala Tyr Ala Leu Asn Ala His
            850                 855                 860

Met Ala Gln Gly Leu Thr Ser Asp Arg Gly Ile Ala Val Met Thr Ser
865                 870                 875                 880

Ser Glu Arg Asn Leu Ser Asn Gln Lys Thr Phe Met Val Thr Val Thr
                885                 890                 895

Arg Leu Arg Asp His Leu Thr Leu Val Val Asp Asn Ala Glu Lys Leu
                900                 905                 910

Gly Ala Ala Val Ala Arg Asn Lys Gly Glu Lys Ala Ser Ala Leu Glu
                915                 920                 925

Val Thr Gly Ser Val Lys Ser Thr Ala Ala Lys Gly Ser Gly Val Asp
                930                 935                 940

Gln Leu Lys Pro Glu Glu Ala Asn Lys Ala Glu Lys Glu Leu Thr Arg
945                 950                 955                 960

<210> SEQ ID NO 139
<211> LENGTH: 10
<212> TYPE: PRT
<213> ORGANISM: Artificial sequence
<220> FEATURE:
<223> OTHER INFORMATION: RecD-like motif V of TrwC Eli

<400> SEQUENCE: 139

Tyr Ala Leu Asn Ala His Met Ala Gln Gly
1               5                   10

<210> SEQ ID NO 140
<211> LENGTH: 853
<212> TYPE: PRT
<213> ORGANISM: Escherichia coli

<400> SEQUENCE: 140

Met Ser Ala Ile Glu Asn Phe Asp Ala His Thr Pro Met Met Gln Gln
1               5                   10                  15

Tyr Leu Arg Leu Lys Ala Gln His Pro Glu Ile Leu Leu Phe Tyr Arg
                20                  25                  30

Met Gly Asp Phe Tyr Glu Leu Phe Tyr Asp Ala Lys Arg Ala Ser
            35                  40                  45

Gln Leu Leu Asp Ile Ser Leu Thr Lys Arg Gly Ala Ser Ala Gly Glu
        50                  55                  60

Pro Ile Pro Met Ala Gly Ile Pro Tyr His Ala Val Glu Asn Tyr Leu
65                  70                  75                  80

Ala Lys Leu Val Asn Gln Gly Glu Ser Val Ala Ile Cys Glu Gln Ile
                85                  90                  95

Gly Asp Pro Ala Thr Ser Lys Gly Pro Val Glu Arg Lys Val Val Arg
                100                 105                 110

Ile Val Thr Pro Gly Thr Ile Ser Asp Glu Ala Leu Leu Gln Glu Arg
            115                 120                 125

Gln Asp Asn Leu Leu Ala Ala Ile Trp Gln Asp Ser Lys Gly Phe Gly
        130                 135                 140

Tyr Ala Thr Leu Asp Ile Ser Ser Gly Arg Phe Arg Leu Ser Glu Pro
145                 150                 155                 160
```

```
Ala Asp Arg Glu Thr Met Ala Ala Glu Leu Gln Arg Thr Asn Pro Ala
                165                 170                 175
Glu Leu Leu Tyr Ala Glu Asp Phe Ala Glu Met Ser Leu Ile Glu Gly
            180                 185                 190
Arg Arg Gly Leu Arg Arg Pro Leu Trp Glu Phe Glu Ile Asp Thr
        195                 200                 205
Ala Arg Gln Gln Leu Asn Leu Gln Phe Gly Thr Arg Asp Leu Val Gly
        210                 215                 220
Phe Gly Val Glu Asn Ala Pro Arg Gly Leu Cys Ala Ala Gly Cys Leu
225                 230                 235                 240
Leu Gln Tyr Ala Lys Asp Thr Gln Arg Thr Thr Leu Pro His Ile Arg
                245                 250                 255
Ser Ile Thr Met Glu Arg Glu Gln Asp Ser Ile Ile Met Asp Ala Ala
                260                 265                 270
Thr Arg Arg Asn Leu Glu Ile Thr Gln Asn Leu Ala Gly Gly Ala Glu
        275                 280                 285
Asn Thr Leu Ala Ser Val Leu Asp Cys Thr Val Thr Pro Met Gly Ser
        290                 295                 300
Arg Met Leu Lys Arg Trp Leu His Met Pro Val Arg Asp Thr Arg Val
305                 310                 315                 320
Leu Leu Glu Arg Gln Gln Thr Ile Gly Ala Leu Gln Asp Phe Thr Ala
                325                 330                 335
Gly Leu Gln Pro Val Leu Arg Gln Val Gly Asp Leu Glu Arg Ile Leu
                340                 345                 350
Ala Arg Leu Ala Leu Arg Thr Ala Arg Pro Arg Asp Leu Ala Arg Met
                355                 360                 365
Arg His Ala Phe Gln Gln Leu Pro Glu Leu Arg Ala Gln Leu Glu Thr
        370                 375                 380
Val Asp Ser Ala Pro Val Gln Ala Leu Arg Glu Lys Met Gly Glu Phe
385                 390                 395                 400
Ala Glu Leu Arg Asp Leu Leu Glu Arg Ala Ile Ile Asp Thr Pro Pro
                405                 410                 415
Val Leu Val Arg Asp Gly Gly Val Ile Ala Ser Gly Tyr Asn Glu Glu
                420                 425                 430
Leu Asp Glu Trp Arg Ala Leu Ala Asp Gly Ala Thr Asp Tyr Leu Glu
        435                 440                 445
Arg Leu Glu Val Arg Glu Arg Glu Arg Thr Gly Leu Asp Thr Leu Lys
        450                 455                 460
Val Gly Phe Asn Ala Val His Gly Tyr Tyr Ile Gln Ile Ser Arg Gly
465                 470                 475                 480
Gln Ser His Leu Ala Pro Ile Asn Tyr Met Arg Arg Gln Thr Leu Lys
                485                 490                 495
Asn Ala Glu Arg Tyr Ile Ile Pro Glu Leu Lys Glu Tyr Glu Asp Lys
                500                 505                 510
Val Leu Thr Ser Lys Gly Lys Ala Leu Ala Leu Glu Lys Gln Leu Tyr
        515                 520                 525
Glu Glu Leu Phe Asp Leu Leu Leu Pro His Leu Glu Ala Leu Gln Gln
        530                 535                 540
Ser Ala Ser Ala Leu Ala Glu Leu Asp Val Leu Val Asn Leu Ala Glu
545                 550                 555                 560
Arg Ala Tyr Thr Leu Asn Tyr Thr Cys Pro Thr Phe Ile Asp Lys Pro
                565                 570                 575
```

Gly Ile Arg Ile Thr Glu Gly Arg His Pro Val Val Glu Gln Val Leu
            580                 585                 590

Asn Glu Pro Phe Ile Ala Asn Pro Leu Asn Leu Ser Pro Gln Arg Arg
        595                 600                 605

Met Leu Ile Ile Thr Gly Pro Asn Met Gly Gly Lys Ser Thr Tyr Met
    610                 615                 620

Arg Gln Thr Ala Leu Ile Ala Leu Met Ala Tyr Ile Gly Ser Tyr Val
625                 630                 635                 640

Pro Ala Gln Lys Val Glu Ile Gly Pro Ile Asp Arg Ile Phe Thr Arg
                645                 650                 655

Val Gly Ala Ala Asp Asp Leu Ala Ser Gly Arg Ser Thr Phe Met Val
            660                 665                 670

Glu Met Thr Glu Thr Ala Asn Ile Leu His Asn Ala Thr Glu Tyr Ser
        675                 680                 685

Leu Val Leu Met Asp Glu Ile Gly Arg Gly Thr Ser Thr Tyr Asp Gly
    690                 695                 700

Leu Ser Leu Ala Trp Ala Cys Ala Glu Asn Leu Ala Asn Lys Ile Lys
705                 710                 715                 720

Ala Leu Thr Leu Phe Ala Thr His Tyr Phe Glu Leu Thr Gln Leu Pro
                725                 730                 735

Glu Lys Met Glu Gly Val Ala Asn Val His Leu Asp Ala Leu Glu His
            740                 745                 750

Gly Asp Thr Ile Ala Phe Met His Ser Val Gln Asp Gly Ala Ala Ser
        755                 760                 765

Lys Ser Tyr Gly Leu Ala Val Ala Ala Leu Ala Gly Val Pro Lys Glu
    770                 775                 780

Val Ile Lys Arg Ala Arg Gln Lys Leu Arg Glu Leu Glu Ser Ile Ser
785                 790                 795                 800

Pro Asn Ala Ala Ala Thr Gln Val Asp Gly Thr Gln Met Ser Leu Leu
                805                 810                 815

Ser Val Pro Glu Glu Thr Ser Pro Ala Val Glu Ala Leu Glu Asn Leu
            820                 825                 830

Asp Pro Asp Ser Leu Thr Pro Arg Gln Ala Leu Glu Trp Ile Tyr Arg
        835                 840                 845

Leu Lys Ser Leu Val
    850

<210> SEQ ID NO 141
<211> LENGTH: 64
<212> TYPE: PRT
<213> ORGANISM: Sulfolobus solfataricus

<400> SEQUENCE: 141

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Lys Met Ile Ser Phe
                20                  25                  30

Thr Tyr Asp Glu Gly Gly Gly Lys Thr Gly Arg Gly Ala Val Ser Glu
            35                  40                  45

Lys Asp Ala Pro Lys Glu Leu Leu Gln Met Leu Glu Lys Gln Lys Lys
        50                  55                  60

<210> SEQ ID NO 142
<211> LENGTH: 99
<212> TYPE: PRT
<213> ORGANISM: Sulfolobus solfataricus

<400> SEQUENCE: 142

```
Glu Lys Met Ser Ser Gly Thr Pro Thr Pro Ser Asn Val Val Leu Ile
1               5                   10                  15

Gly Lys Lys Pro Val Met Asn Tyr Val Leu Ala Ala Leu Thr Leu Leu
            20                  25                  30

Asn Gln Gly Val Ser Glu Ile Val Lys Ala Arg Gly Arg Ala Ile
        35                  40                  45

Ser Lys Ala Val Asp Thr Val Glu Ile Val Arg Asn Arg Phe Leu Pro
50                  55                  60

Asp Lys Ile Glu Ile Lys Glu Ile Arg Val Gly Ser Gln Val Val Thr
65                  70                  75                  80

Ser Gln Asp Gly Arg Gln Ser Arg Val Ser Thr Ile Glu Ile Ala Ile
                85                  90                  95

Arg Lys Lys
```

<210> SEQ ID NO 143
<211> LENGTH: 88
<212> TYPE: PRT
<213> ORGANISM: Sulfolobus solfataricus

<400> SEQUENCE: 143

```
Thr Glu Lys Leu Asn Glu Ile Val Val Arg Lys Thr Lys Asn Val Glu
1               5                   10                  15

Asp His Val Leu Asp Val Ile Val Leu Phe Asn Gln Gly Ile Asp Glu
            20                  25                  30

Val Ile Leu Lys Gly Thr Gly Arg Glu Ile Ser Lys Ala Val Asp Val
        35                  40                  45

Tyr Asn Ser Leu Lys Asp Arg Leu Gly Asp Gly Val Gln Leu Val Asn
50                  55                  60

Val Gln Thr Gly Ser Glu Val Arg Asp Arg Arg Ile Ser Tyr Ile
65                  70                  75                  80

Leu Leu Arg Leu Lys Arg Val Tyr
                85
```

<210> SEQ ID NO 144
<211> LENGTH: 107
<212> TYPE: PRT
<213> ORGANISM: Escherichia coli

<400> SEQUENCE: 144

```
Ala Gln Gln Ser Pro Tyr Ser Ala Ala Met Ala Glu Gln Arg His Gln
1               5                   10                  15

Glu Trp Leu Arg Phe Val Asp Leu Leu Lys Asn Ala Tyr Gln Asn Asp
            20                  25                  30

Leu His Leu Pro Leu Leu Asn Leu Met Leu Thr Pro Asp Glu Arg Glu
        35                  40                  45

Ala Leu Gly Thr Arg Val Arg Ile Val Glu Glu Leu Leu Arg Gly Glu
50                  55                  60

Met Ser Gln Arg Glu Leu Lys Asn Glu Leu Gly Ala Gly Ile Ala Thr
65                  70                  75                  80

Ile Thr Arg Gly Ser Asn Ser Leu Lys Ala Ala Pro Val Glu Leu Arg
                85                  90                  95

Gln Trp Leu Glu Glu Val Leu Leu Lys Ser Asp
            100                 105
```

<210> SEQ ID NO 145
<211> LENGTH: 237
<212> TYPE: PRT
<213> ORGANISM: Bacteriophage lambda

<400> SEQUENCE: 145

Met Ser Thr Lys Lys Pro Leu Thr Gln Glu Gln Leu Glu Asp Ala
1               5                   10                  15

Arg Arg Leu Lys Ala Ile Tyr Glu Lys Lys Asn Glu Leu Gly Leu
                20                  25                  30

Ser Gln Glu Ser Val Ala Asp Lys Met Gly Met Gly Gln Ser Gly
                35                  40                  45

Gly Ala Leu Phe Asn Gly Ile Asn Ala Leu Asn Ala Tyr Asn Ala Ala
        50                  55                  60

Leu Leu Ala Lys Ile Leu Lys Val Ser Val Glu Glu Phe Ser Pro Ser
65                  70                  75                  80

Ile Ala Arg Glu Ile Tyr Glu Met Tyr Glu Ala Val Ser Met Gln Pro
                85                  90                  95

Ser Leu Arg Ser Glu Tyr Glu Tyr Pro Val Phe Ser His Val Gln Ala
                100                 105                 110

Gly Met Phe Ser Pro Glu Leu Arg Thr Phe Thr Lys Gly Asp Ala Glu
                115                 120                 125

Arg Trp Val Ser Thr Thr Lys Lys Ala Ser Asp Ser Ala Phe Trp Leu
    130                 135                 140

Glu Val Glu Gly Asn Ser Met Thr Ala Pro Thr Gly Ser Lys Pro Ser
145                 150                 155                 160

Phe Pro Asp Gly Met Leu Ile Leu Val Asp Pro Glu Gln Ala Val Glu
                165                 170                 175

Pro Gly Asp Phe Cys Ile Ala Arg Leu Gly Gly Asp Glu Phe Thr Phe
                180                 185                 190

Lys Lys Leu Ile Arg Asp Ser Gly Gln Val Phe Leu Gln Pro Leu Asn
                195                 200                 205

Pro Gln Tyr Pro Met Ile Pro Cys Asn Glu Ser Cys Ser Val Val Gly
    210                 215                 220

Lys Val Ile Ala Ser Gln Trp Pro Glu Glu Thr Phe Gly
225                 230                 235

<210> SEQ ID NO 146
<211> LENGTH: 60
<212> TYPE: PRT
<213> ORGANISM: Crenarchaea

<400> SEQUENCE: 146

Met Ser Ser Gly Lys Lys Pro Val Lys Val Lys Thr Pro Ala Gly Lys
1               5                   10                  15

Glu Ala Glu Leu Val Pro Glu Lys Val Trp Ala Leu Ala Pro Lys Gly
                20                  25                  30

Arg Lys Gly Val Lys Ile Gly Leu Phe Lys Asp Pro Gly Thr Gly Lys
                35                  40                  45

Tyr Phe Arg His Lys Leu Pro Asp Asp Tyr Pro Ile
    50                  55                  60

<210> SEQ ID NO 147
<211> LENGTH: 136
<212> TYPE: PRT
<213> ORGANISM: Homo sapiens

<400> SEQUENCE: 147

-continued

```
Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
        130                 135

<210> SEQ ID NO 148
<211> LENGTH: 89
<212> TYPE: PRT
<213> ORGANISM: Bacteriophage T4

<400> SEQUENCE: 148

Met Ala Lys Lys Glu Met Val Glu Phe Asp Glu Ala Ile His Gly Glu
1               5                   10                  15

Asp Leu Ala Lys Phe Ile Lys Glu Ala Ser Asp His Lys Leu Lys Ile
            20                  25                  30

Ser Gly Tyr Asn Glu Leu Ile Lys Asp Ile Arg Ile Arg Ala Lys Asp
        35                  40                  45

Glu Leu Gly Val Asp Gly Lys Met Phe Asn Arg Leu Leu Ala Leu Tyr
    50                  55                  60

His Lys Asp Asn Arg Asp Val Phe Glu Ala Glu Thr Glu Glu Val Val
65                  70                  75                  80

Glu Leu Tyr Asp Thr Val Phe Ser Lys
                85

<210> SEQ ID NO 149
<211> LENGTH: 339
<212> TYPE: PRT
<213> ORGANISM: Homo sapiens

<400> SEQUENCE: 149

Met Ala Met Gln Met Gln Leu Glu Ala Asn Ala Asp Thr Ser Val Glu
1               5                   10                  15

Glu Glu Ser Phe Gly Pro Gln Pro Ile Ser Arg Leu Glu Gln Cys Gly
            20                  25                  30

Ile Asn Ala Asn Asp Val Lys Lys Leu Glu Glu Ala Gly Phe His Thr
        35                  40                  45

Val Glu Ala Val Ala Tyr Ala Pro Lys Lys Glu Leu Ile Asn Ile Lys
    50                  55                  60

Gly Ile Ser Glu Ala Lys Ala Asp Lys Ile Leu Ala Glu Ala Ala Lys
65                  70                  75                  80

Leu Val Pro Met Gly Phe Thr Thr Ala Thr Glu Phe His Gln Arg Arg
                85                  90                  95
```

```
Ser Glu Ile Ile Gln Ile Thr Thr Gly Ser Lys Glu Leu Asp Lys Leu
                100                 105                 110

Leu Gln Gly Gly Ile Glu Thr Gly Ser Ile Thr Glu Met Phe Gly Glu
            115                 120                 125

Phe Arg Thr Gly Lys Thr Gln Ile Cys His Thr Leu Ala Val Thr Cys
130                 135                 140

Gln Leu Pro Ile Asp Arg Gly Gly Glu Gly Lys Ala Met Tyr Ile
145                 150                 155                 160

Asp Thr Glu Gly Thr Phe Arg Pro Glu Arg Leu Leu Ala Val Ala Glu
                165                 170                 175

Arg Tyr Gly Leu Ser Gly Ser Asp Val Leu Asp Asn Val Ala Tyr Ala
            180                 185                 190

Arg Ala Phe Asn Thr Asp His Gln Thr Gln Leu Leu Tyr Gln Ala Ser
        195                 200                 205

Ala Met Met Val Glu Ser Arg Tyr Ala Leu Leu Ile Val Asp Ser Ala
    210                 215                 220

Thr Ala Leu Tyr Arg Thr Asp Tyr Ser Gly Arg Gly Glu Leu Ser Ala
225                 230                 235                 240

Arg Gln Met His Leu Ala Arg Phe Leu Arg Met Leu Leu Arg Leu Ala
                245                 250                 255

Asp Glu Phe Gly Val Ala Val Val Ile Thr Asn Gln Val Val Ala Gln
            260                 265                 270

Val Asp Gly Ala Ala Met Phe Ala Ala Asp Pro Lys Lys Pro Ile Gly
        275                 280                 285

Gly Asn Ile Ile Ala His Ala Ser Thr Thr Arg Leu Tyr Leu Arg Lys
    290                 295                 300

Gly Arg Gly Glu Thr Arg Ile Cys Lys Ile Tyr Asp Ser Pro Cys Leu
305                 310                 315                 320

Pro Glu Ala Glu Ala Met Phe Ala Ile Asn Ala Asp Gly Val Gly Asp
                325                 330                 335

Ala Lys Asp

<210> SEQ ID NO 150
<211> LENGTH: 375
<212> TYPE: PRT
<213> ORGANISM: Citromicrobium bathyomarinum JL354

<400> SEQUENCE: 150

Met Lys Ala Thr Ile Glu Arg Ala Thr Leu Leu Arg Cys Leu Ser His
1               5                   10                  15

Val Gln Ser Val Val Glu Arg Arg Asn Thr Ile Pro Ile Leu Ser Asn
            20                  25                  30

Val Leu Ile Asp Ala Asp Ala Gly Gly Val Lys Val Met Ala Thr
        35                  40                  45

Asp Leu Asp Leu Gln Val Val Glu Thr Met Thr Ala Ala Ser Val Glu
    50                  55                  60

Ser Ala Gly Ala Ile Thr Val Ser Ala His Leu Leu Phe Asp Ile Ala
65                  70                  75                  80

Arg Lys Leu Pro Asp Gly Ser Gln Val Ser Leu Glu Thr Ala Asp Asn
                85                  90                  95

Arg Met Val Val Lys Ala Gly Arg Ser Arg Phe Gln Leu Pro Thr Leu
            100                 105                 110

Pro Arg Asp Asp Phe Pro Val Ile Val Glu Gly Glu Leu Pro Thr Ser
        115                 120                 125
```

```
Phe Glu Leu Pro Ala Arg Glu Leu Ala Glu Met Ile Asp Arg Thr Arg
    130                 135                 140
Phe Ala Ile Ser Thr Glu Thr Arg Tyr Tyr Leu Asn Gly Ile Phe
145                 150                 155                 160
Leu His Val Ser Asp Glu Ala Arg Pro Val Leu Lys Ala Ala Thr
                165                 170                 175
Asp Gly His Arg Leu Ala Arg Tyr Thr Leu Asp Arg Pro Glu Gly Ala
                180                 185                 190
Glu Gly Met Pro Asp Val Ile Val Pro Arg Lys Ala Val Gly Glu Leu
                195                 200                 205
Arg Lys Leu Leu Glu Glu Ala Leu Asp Ser Asn Val Gln Ile Asp Leu
    210                 215                 220
Ser Ala Ser Lys Ile Arg Phe Ala Leu Gly Gly Glu Gly Gly Val Val
225                 230                 235                 240
Leu Thr Ser Lys Leu Ile Asp Gly Thr Phe Pro Asp Tyr Ser Arg Val
                245                 250                 255
Ile Pro Thr Gly Asn Asp Lys Leu Leu Arg Leu Asp Pro Lys Ala Phe
                260                 265                 270
Phe Gln Gly Val Asp Arg Val Ala Thr Ile Ala Thr Glu Lys Thr Arg
    275                 280                 285
Ala Val Lys Met Gly Leu Asp Glu Asp Lys Val Thr Leu Ser Val Thr
290                 295                 300
Ser Pro Asp Asn Gly Thr Ala Ala Glu Glu Ile Ala Ala Glu Tyr Lys
305                 310                 315                 320
Ala Glu Gly Phe Glu Ile Gly Phe Asn Ala Asn Tyr Leu Lys Asp Ile
                325                 330                 335
Leu Gly Gln Ile Asp Ser Asp Thr Val Glu Leu His Leu Ala Asp Ala
                340                 345                 350
Gly Ala Pro Thr Leu Ile Arg Arg Asp Glu Asn Ser Pro Ala Leu Tyr
                355                 360                 365
Val Leu Met Pro Met Arg Val
    370                 375

<210> SEQ ID NO 151
<211> LENGTH: 88
<212> TYPE: DNA
<213> ORGANISM: Artificial sequence
<220> FEATURE:
<223> OTHER INFORMATION: Polynucleotide used in the Examples

<400> SEQUENCE: 151
cgtggtcacg aggagctcgt cctcacctcg acgtctgcac gagctttttt tttttttttt      60
tttttttttt tttttttttt tttttttt                                        88

<210> SEQ ID NO 152
<211> LENGTH: 88
<212> TYPE: DNA
<213> ORGANISM: Artificial sequence
<220> FEATURE:
<223> OTHER INFORMATION: Polynucleotide used in the Examples

<400> SEQUENCE: 152
tttttttttt tttttttttt tttttttttt tttttttttt ttttgctcgt gcagacgtcg      60
aggtgaggac gagctcctcg tgaccacg                                        88

<210> SEQ ID NO 153
```

```
<211> LENGTH: 44
<212> TYPE: DNA
<213> ORGANISM: Artificial sequence
<220> FEATURE:
<223> OTHER INFORMATION: Polynucleotide used in the Examples

<400> SEQUENCE: 153
cgtggtcacg aggagctcgt cctcacctcg acgtctgcac gagc            44

<210> SEQ ID NO 154
<211> LENGTH: 3560
<212> TYPE: DNA
<213> ORGANISM: Artificial sequence
<220> FEATURE:
<223> OTHER INFORMATION: Polynucleotide used in the Examples

<400> SEQUENCE: 154
gccatcagat tgtgtttgtt agtcgctttt ttttttggaa ttttttttt tggaattttt     60 ttttgcgct aacaacctcc tgccgttttg cccgtgcata tcggtcacga acaaatctga    120
ttactaaaca cagtagcctg gatttgttct atcagtaatc gaccttattc ctaattaaat   180
agagcaaatc cccttattgg gggtaagaca tgaagatgcc agaaaaacat gacctgttgg   240
ccgccattct cgcggcaaag gaacaaggca tcggggcaat ccttgcgttt gcaatggcgt   300
accttcgcgg cagatataat ggcggtgcgt ttacaaaaac agtaatcgac gcaacgatgt   360
gcgccattat cgcctagttc attcgtgacc ttctcgactt cgccggacta agtagcaatc   420
tcgcttatat aacgagcgtg tttatcggct acatcggtac tgactcgatt ggttcgctta   480
tcaaacgctt cgctgctaaa aagccggag tagaagatgg tagaaatcaa taatcaacgt    540
aaggcgttcc tcgatatgct ggcgtggtcg gagggaactg ataacggacg tcagaaaacc   600
agaaatcatg gttatgacgt cattgtaggc ggagagctat ttactgatta ctccgatcac   660
cctcgcaaac ttgtcacgct aaacccaaaa ctcaaatcaa caggcgccgg acgctaccag   720 cttcttttccc gttggtggga tgcctaccgc aagcagcttg gcctgaaaga cttctctccg   780
aaaagtcagg acgctgtggc attgcagcag attaaggagc gtggcgcttt acctatgatt   840
gatcgtggtg atatccgtca ggcaatcgac cgttgcagca atatctgggc ttcactgccg   900
ggcgctggtt atggtcagtt cgagcataag gctgacagcc tgattgcaaa attcaaagaa   960
gcgggcggaa cggtcagaga gattgatgta tgagcagagt caccgcgatt atctccgctc  1020
tggttatctg catcatcgtc tgcctgtcat gggctgttaa tcattaccgt gataacgcca  1080
ttacctacaa agcccagcgc gacaaaaatg ccagagaact gaagctggcg aacgcggcaa  1140
ttactgacat gcagatgcgt cagcgtgatg ttgctgcgct cgatgcaaaa tacacgaagg  1200
agttagctga tgctaaagct gaaaatgatg ctctgcgtga tgatgttgcc gctggtcgtc  1260
gtcggttgca catcaaagca gtctgtcagt cagtgcgtga agccaccacc gcctccggcg  1320
tggataatgc agcctccccc cgactggcag acaccgctga acgggattat ttcaccctca  1380
gagagaggct gatcactatg caaaacaac tggaaggaac ccagaagtat attaatgagc    1440
agtgcagata gagttgccca tatcgatggg caactcatgc aattattgtg agcaatacac  1500
acgcgcttcc agcggagtat aaatgcctaa agtaataaaa ccgagcaatc catttacgaa  1560
tgtttgctgg gtttctgttt taacaacatt ttctgcgccg ccacaaattt tggctgcatc  1620
gacagttttc ttctgcccaa ttccagaaac gaagaaatga tgggtgatgg tttcctttgg  1680
tgctactgct gccggtttgt tttgaacagt aaacgtctgt tgagcacatc ctgtaataag  1740
cagggccagc gcagtagcga gtagcatttt tttcatggtg ttattcccga tgcttttga   1800
```

```
agttcgcaga atcgtatgtg tagaaaatta acaaaccct aaacaatgag ttgaaatttc    1860
atattgttaa tatttattaa tgtatgtcag gtgcgatgaa tcgtcattgt attcccggat    1920
taactatgtc cacagccctg acggggaact tctctgcggg agtgtccggg aataattaaa    1980
acgatgcaca cagggtttag cgcgtacacg tattgcatta tgccaacgcc ccggtgctga    2040
cacggaagaa accggacgtt atgatttagc gtggaaagat tgtgtagtg ttctgaatgc    2100 tctcagtaaa tagtaatgaa ttatcaaagg tatagtaata tcttttatgt tcatggatat    2160
ttgtaaccca tcggaaaact cctgctttag caagattttc cctgtattgc tgaaatgtga    2220
tttctcttga tttcaaccta tcataggacg tttctataag atgcgtgttt cttgagaatt    2280
taacatttac aaccttttta agtccttta ttaacacggt gttatcgttt ctaacacga    2340 tgtgaatatt atctgtggct agatagtaaa tataatgtga gacgttgtga cgttttagtt    2400
cagaataaaa caattcacag tctaaatctt ttcgcacttg atcgaatatt tcttaaaaa    2460 tggcaacctg agccattggt aaaaccttcc atgtgatacg agggcgcgta gtttgcatta    2520
tcgtttttat cgtttcaatc tggtctgacc tccttgtgtt ttgttgatga tttatgtcaa    2580
atattaggaa tgttttcact taatagtatt ggttgcgtaa caaagtgcgg tcctgctggc    2640
attctggagg gaaatacaac cgacagatgt atgtaaggcc aacgtgctca aatcttcata    2700
cagaaagatt tgaagtaata ttttaaccgc tagatgaaga gcaagcgcat ggagcgacaa    2760
aatgaataaa gaacaatctg ctgatgatcc ctccgtggat ctgattcgtg taaaaaatat    2820
gcttaatagc accatttcta tgagttaccc tgatgttgta attgcatgta tagaacataa    2880
ggtgtctctg gaagcattca gagcaattga ggcagcgttg gtgaagcacg ataataatat    2940
gaaggattat tccctggtgg ttgactgatc accataactg ctaatcattc aaactattta    3000
gtctgtgaca gagccaacac gcagtctgtc actgtcagga aagtggtaaa actgcaactc    3060
aattactgca atgccctcgt aattaagtga atttacaata tcgtcctgtt cggagggaag    3120
aacgcgggat gttcattctt catcactttt aattgatgta tatgctctct tttctgacgt    3180
tagtctccga cggcaggctt caatgaccca ggctgagaaa ttcccggacc cttttttgctc    3240 aagagcgatg ttaatttgtt caatcatttg gttaggaaag cggatgttgc gggttgttgt    3300
tctgcgggtt ctgttcttcg ttgacatgag gttgccccgt attcagtgtc gctgatttgt    3360
attgtctgaa gttgttttta cgttaagttg atgcagatca attaatacga tacctgcgtc    3420
ataattgatt atttgacgtg gtttgatggc ctccacgcac gttgtgatat gtagatgata    3480
atcattatca ctttacgggt cctttccggt gaaaaaaag gtaccaaaaa aaacatcgtc    3540
gtgagtagtg aaccgtaagc                                               3560

<210> SEQ ID NO 155
<211> LENGTH: 52
<212> TYPE: DNA
<213> ORGANISM: Artificial sequence
<220> FEATURE:
<223> OTHER INFORMATION: Polynucleotide used in the Examples

<400> SEQUENCE: 155 ttttttttt tttttttttt ttttggttg tttctgttgg tgctgatatt gc             52

<210> SEQ ID NO 156
<211> LENGTH: 3556
<212> TYPE: DNA
<213> ORGANISM: Artificial sequence
<220> FEATURE:
```

<223> OTHER INFORMATION: Polynucleotide used in the Examples

<400> SEQUENCE: 156

```
acggttcact actcacgacg atgttttttt tggtaccttt ttttcaccg gaaaggaccc        60
gtaaagtgat aatgattatc atctacatat cacaacgtgc gtggaggcca tcaaaccacg      120
tcaaataatc aattatgacg caggtatcgt attaattgat ctgcatcaac ttaacgtaaa      180
aacaacttca gacaatacaa atcagcgaca ctgaatacgg ggcaacctca tgtcaacgaa      240
gaacagaacc cgcagaacaa caacccgcaa catccgcttt cctaaccaaa tgattgaaca      300
aattaacatc gctcttgagc aaaaagggtc cgggaatttc tcagcctggg tcattgaagc      360
ctgccgtcgg agactaacgt cagaaaagag agcatataca tcaattaaaa gtgatgaaga      420
atgaacatcc cgcgttcttc cctccgaaca ggacgatatt gtaaattcac ttaattacga      480
gggcattgca gtaattgagt tgcagtttta ccactttcct gacagtgaca gactgcgtgt      540
tggctctgtc acagactaaa tagtttgaat gattagcagt tatggtgatc agtcaaccac      600
cagggaataa tccttcatat tattatcgtg cttcaccaac gctgcctcaa ttgctctgaa      660
tgcttccaga gacaccttat gttctataca tgcaattaca acatcagggt aactcataga      720
aatggtgcta ttaagcatat tttttacacg aatcagatcc acggagggat catcagcaga      780
ttgttcttta ttcattttgt cgctccatgc gcttgctctt catctagcgg ttaaaatatt      840
acttcaaatc tttctgtatg aagatttgag cacgttggcc ttacatacat ctgtcggttg      900
tatttccctc cagaatgcca gcaggaccgc actttgttac gcaaccaata ctattaagtg      960
aaaacattcc taatatttga cataaatcat caacaaaaca caaggaggtc agaccagatt     1020
gaaacgataa aaacgataat gcaaactacg cgccctcgta tcacatggaa ggttttacca     1080
atggctcagg ttgccatttt taagaaaata ttcgatcaag tgcgaaaaga tttagactgt     1140
gaattgtttt attctgaact aaaacgtcac aacgtctcac attatattta ctatctagcc     1200
acagataata ttcacatcgt gttagaaaac gataacaccg tgttaataaa aggacttaaa     1260
aaggttgtaa atgttaaatt ctcaagaaac acgcatctta tagaaacgtc ctatgatagg     1320
ttgaaatcaa gagaaatcac atttcagcaa tacagggaaa atcttgctaa agcaggagtt     1380
ttccgatggg ttacaaatat ccatgaacat aaaagatatt actatacctt tgataattca     1440
ttactattta ctgagagcat tcagaacact acacaaatct ttccacgcta aatcataacg     1500
tccggtttct tccgtgtcag caccggggcg ttggcataat gcaatacgtg tacgcgctaa     1560
accctgtgtg catcgtttta attattcccg gacactcccg cagagaagtt ccccgtcagg     1620
gctgtggaca tagttaatcc gggaatacaa tgacgattca tcgcacctga catacattaa     1680
taaatattaa caatatgaaa tttcaactca ttgtttaggg tttgtttaat tttctacaca     1740
tacgattctg cgaacttcaa aaagcatcgg gaataacacc atgaaaaaaa tgctactcgc     1800
tactgcgctg gccctgctta ttacaggatg tgctcaacag acgtttactg ttcaaaacaa     1860
accggcagca gtagcaccaa aggaaaccat cacccatcat ttcttcgttt ctggaattgg     1920
gcagaagaaa actgtcgatg cagccaaaat ttgtggcggc gcagaaaatg ttgttaaaac     1980
agaaacccag caaacattcg taaatggatt gctcggtttt attactttag gcatttatac     2040
tccgctggaa gcgcgtgtgt attgctcaca ataattgcat gagttgccca tcgatatggg     2100
caactctatc tgcactgctc attaatatac ttctgggttc cttccagttg ttttgcata      2160
gtgatcagcc tctctctgag ggtgaaataa tcccgttcag cggtgtctgc cagtcggggg     2220
gaggctgcat tatccacgcc ggaggcggtg gtggcttcac gcactgactg acagactgct     2280
```

```
ttgatgtgca accgacgacg accagcggca acatcatcac gcagagcatc attttcagct    2340
ttagcatcag ctaactcctt cgtgtatttt gcatcgagcg cagcaacatc acgctgacgc    2400
atctgcatgt cagtaattgc cgcgttcgcc agcttcagtt ctctggcatt tttgtcgcgc    2460
tgggctttgt aggtaatggc gttatcacgg taatgattaa cagcccatga caggcagacg    2520
atgatgcaga taaccagagc ggagataatc gcggtgactc tgctcataca tcaatctctc    2580
tgaccgttcc gcccgcttct ttgaattttg caatcaggct gtcagcctta tgctcgaact    2640
gaccataacc agcgcccggc agtgaagccc agatattgct gcaacggtcg attgcctgac    2700
ggatatcacc acgatcaatc ataggtaaag cgccacgctc cttaatctgc tgcaatgcca    2760
cagcgtcctg acttttcgga gagaagtctt tcaggccaag ctgcttgcgg taggcatccc    2820
accaacggga aagaagctgg tagcgtccgg cgcctgttga tttgagtttt gggtttagcg    2880
tgacaagttt gcgagggtga tcggagtaat cagtaaatag ctctccgcct acaatgacgt    2940
cataaccatg atttctggtt ttctgacgtc cgttatcagt tccctccgac cacgccagca    3000
tatcgaggaa cgccttacgt tgattattga tttctaccat cttctactcc ggcttttta    3060 gcagcgaagc gtttgataag cgaaccaatc gagtcagtac cgatgtagcc gataaacacg    3120
ctcgttatat aagcgagatt gctacttagt ccggcgaagt cgagaaggtc acgaatgaac    3180
taggcgataa tggcgcacat cgttgcgtcg attactgttt ttgtaaacgc accgccatta    3240
tatctgccgc gaaggtacgc cattgcaaac gcaaggattg ccccgatgcc ttgttcchtt    3300
gccgcgagaa tggcggccaa caggtcatgt ttttctggca tcttcatgtc ttacccccaa    3360
taaggggatt tgctctattt aattaggaat aaggtcgatt actgatagaa caaatccagg    3420
ctactgtgtt tagtaatcag atttgttcgt gaccgatatg cacgggcaaa acggcaggag    3480
gttgttagcg caaaaaaaaa attccaaaaa aaaattcca aaaaaaaaaa gcgactaaca    3540
aacacaatct gatggc                                                    3556
```

MODIFIED HELICASES

RELATED APPLICATIONS

This application is a 35 U.S.C. 371 national stage filing of International Application PCT/GB2013/051925, filed Jul. 18, 2013, which claims priority to U.S. Patent Application Nos. 61/774,862 and 61/673,452, filed on Mar. 8, 2013 and Jul. 19, 2012, respectively. The contents of the aforementioned applications are hereby incorporated by reference.

FIELD OF THE INVENTION

The invention relates to modified helicases with reduced unbinding from polynucleotides. The helicases can be used to control the movement of polynucleotides and are particularly useful for sequencing polynucleotides.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the strand sequencing" method, a single polynucleotide strand is passed through the pore and the identity of the nucleotides are derived. Strand sequencing can involve the use of a nucleotide handling protein, such as a helicase, to control the movement of the polynucleotide through the pore.

SUMMARY OF THE INVENTION

Helicases are enzymes that are capable of binding to and controlling the movement of polynucleotides. Several helicases, including Hel308 helicases, have a polynucleotide binding domain which in at least one conformational state has an opening through which the polynucleotide can bind or unbind from the helicase. This allows the helicase to disengage from a polynucleotide, even if the helicase is not positioned at an end of the polynucleotide.

The inventors have surprisingly demonstrated that the ability of a helicase to control the movement of a polynucleotide can be improved by reducing the size of the opening through which the polynucleotide unbinds. In particular, the helicase's ability to control the movement of a polynucleotide can be improved by closing the opening. In accordance with the invention, the size of the opening is reduced or the opening is closed by connecting at least two parts of the helicase.

This result is surprising because a reduction in the size of the opening or a closing of the opening does not prevent the helicase from binding to a polynucleotide. Once a helicase modified in accordance with the invention has bound to a polynucleotide, it is capable of controlling the movement of most of, if not all of, the polynucleotide without unbinding or disengaging. In particular, the inventors have surprisingly demonstrated that helicases modified in accordance with the invention will strongly bind to a long polynucleotide, such as a polynucleotide comprising 400 nucleotides or more, and will control the movement of most of, if not all of, the polynucleotide. This allows the effective control of the movement of the polynucleotide, especially during Strand Sequencing.

The inventors have surprisingly demonstrated that the ability of a Hel308 helicase to control the movement of a polynucleotide can be improved by introducing one or more cysteine residues and/or one or more non-natural amino acids at specific positions. Irrespective of whether or not the introduced residues are connected, the modified Hel308 helicase is capable of controlling the movement of most of, if not all of, a polynucleotide without unbinding or disengaging.

Accordingly, the invention provides a helicase formed from one or more monomers and comprising a polynucleotide binding domain which comprises in at least one conformational state an opening through which a polynucleotide can unbind from the helicase, wherein the helicase is modified such that two or more parts on the same monomer of the helicase are connected to reduce the size of the opening and wherein the helicase retains its ability to control the movement of the polynucleotide.

The invention also provides:

a Hel308 helicase in which one or more cysteine residues and/or one or more non-natural amino acids have been introduced at one or more of the positions which correspond to D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724 in Hel308 Mbu (SEQ ID NO: 10), wherein the helicase retains its ability to control the movement of a polynucleotide;

a construct comprising a helicase of the invention and an additional polynucleotide binding moiety, wherein the helicase is attached to the polynucleotide binding moiety and the construct has the ability to control the movement of a polynucleotide;

a method of controlling the movement of a polynucleotide, comprising contacting the polynucleotide with a helicase of the invention or a construct of the invention and thereby controlling the movement of the polynucleotide;

method of characterising a target polynucleotide, comprising (a) contacting the target polynucleotide with a transmembrane pore and a helicase of the invention or a construct of the invention such that the helicase or the construct controls the movement of the target polynucleotide through the pore and (b) taking one or more measurements as the polynucleotide moves with respect to the pore wherein the measurements are indicative of one or more characteristics of the target polynucleotide and thereby characterising the target polynucleotide;

a method of forming a sensor for characterising a target polynucleotide, comprising forming a complex between (a) a pore and (b) a helicase of the invention or a construct of the invention and thereby forming a sensor for characterising the target polynucleotide;

a sensor for characterising a target polynucleotide, comprising a complex between (a) a pore and (b) a helicase of the invention or a construct of the invention;

use of a helicase of the invention or a construct of the invention to control the movement of a target polynucleotide through a pore;

a kit for characterising a target polynucleotide comprising (a) a pore and (b) a helicase of the invention or a construct of the invention;

an apparatus for characterising target polynucleotides in a sample, comprising (a) a plurality of pores and (b) a plurality of helicases of the invention or a plurality of constructs of the invention;

a method of producing a helicase of the invention, comprising (a) providing a helicase formed from one or more monomers and comprising a polynucleotide binding domain which comprises an opening through which a polynucleotide can unbind from the helicase and (b) modifying the helicase such that two or more parts on the same monomer of the helicase are connected to reduce the size of the opening and thereby producing a helicase of the invention;

a method of producing a modified Hel308 helicase of the invention, comprising (a) providing a Hel308 helicase and (b) introducing one or more cysteine residues and/or one or more non-natural amino acids at one or more of the positions which correspond to D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724 in Hel308 Mbu (SEQ ID NO: 10) and thereby producing a modified Hel308 helicase of the invention; and a method of producing a construct of the invention, comprising attaching a helicase of the invention to an additional polynucleotide binding moiety and thereby producing a construct of the invention.

DESCRIPTION OF THE SEQUENCE LISTING

Figure 1:
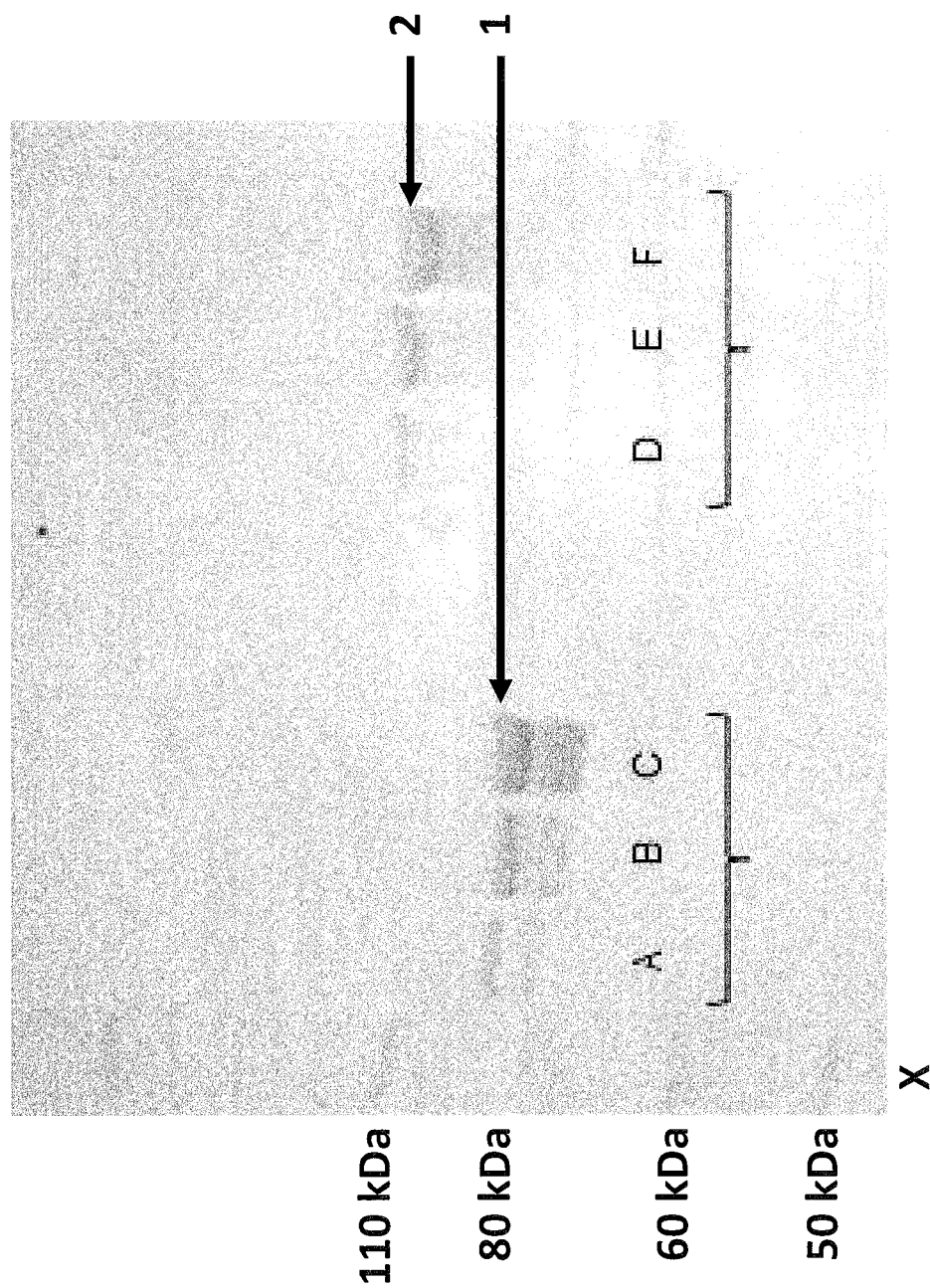
FIG. 1 shows a coomassie stained, 7.5% Tris-HCl gel (loaded with Laemmli loading buffer) of the Hel308 Mbu (E284C/S615C)-bismaleimidePEG3 reaction mixture (SEQ ID NO: 10 with mutations E284C/S615C connected by a bismaleimidePEG3 linker). Lane X shows an appropriate protein ladder (the mass unit markers are shown on the left of the gel). Lanes a-c contain 2 µL, 5 µL or 10 µL of approximately 2.5 µM Hel308 Mbu(E284C/S615C) monomer (SEQ ID NO: 10 with mutations E284C/S615C). Lanes d-f contain 2 µL, 5 µL or 10 µL of approximately 2.5 µM Hel308 Mbu(E284C/S615C)-bismaleimidePEG3 (SEQ ID NO: 10 with mutations E284C/S615C connected by a bismaleimidePEG3 linker, i.e. a helicase in which the opening has been closed), it was clear from the gel that the reaction to attach the bismaleimidePEG3 linker went to nearly 100% yield. Arrow 1 corresponds to Hel308 Mbu (E284C/S615C) monomer (SEQ ID NO: 10 with mutations E284C/S615C) and arrow 2 corresponds to Hel308 Mbu(E284C/S615C)-bismaleimidePEG3 (SEQ ID NO: 10 with mutations E284C/S615C connected by a bismaleimidePEG3 linker, i.e. a helicase in which the opening has been closed).

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one monomer of α-hemolysin-E111N/K147N (α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NO: 8 shows the amino acid sequence of the Hel308 motif.

SEQ ID NO: 9 shows the amino acid sequence of the extended Hel308 motif.

SEQ ID NOs: 10 to 58 show the amino acid sequences of Hel308 helicases in Table 1.

SEQ ID NO: 59 shows the RecD-like motif I.

SEQ ID NOs: 60 to 62 show the extended RecD-like motif I.

SEQ ID NO: 63 shows the RecD motif I.

SEQ ID NO: 64 shows a preferred RecD motif I, namely G-G-P-G-T-G-K-T.

SEQ ID NOs: 65 to 67 show the extended RecD motif I.

SEQ ID NO: 68 shows the RecD-like motif V.

SEQ ID NO: 69 shows the RecD motif V.

SEQ ID NOs: 70 to 77 show the MobF motif III.

SEQ ID NOs: 78 to 84 show the MobQ motif III.

SEQ ID NO: 85 shows the amino acid sequence of TraI Eco.

SEQ ID NO: 86 shows the RecD-like motif I of TraI Eco.

SEQ ID NO: 87 shows the RecD-like motif V of TraI Eco.

SEQ ID NO: 88 shows the MobF motif III of TraI Eco.

SEQ ID NO: 89 shows the XPD motif V.

SEQ ID NO: 90 shows XPD motif VI.

SEQ ID NO: 91 shows the amino acid sequence of XPD Mbu.

SEQ ID NO: 92 shows the XPD motif V of XPD Mbu.

SEQ ID NO: 93 shows XPD motif VI of XPD Mbu.

SEQ ID NO: 94 shows the amino acid sequence of a preferred HhH domain.

SEQ ID NO: 95 shows the amino acid sequence of the ssb from the bacteriophage RB69, which is encoded by the gp32 gene.

SEQ ID NO: 96 shows the amino acid sequence of the ssb from the bacteriophage T7, which is encoded by the gp2.5 gene.

SEQ ID NO: 97 shows the amino acid sequence of the UL42 processivity factor from Herpes virus 1.

SEQ ID NO: 98 shows the amino acid sequence of subunit 1 of PCNA.

SEQ ID NO: 99 shows the amino acid sequence of subunit 2 of PCNA.

SEQ ID NO: 100 shows the amino acid sequence of subunit 3 of PCNA.

SEQ ID NO: 101 shows the amino acid sequence of Phi29 DNA polymerase.

SEQ ID NO: 102 shows the amino acid sequence (from 1 to 319) of the UL42 processivity factor from the Herpes virus 1.

SEQ ID NO: 103 shows the amino acid sequence of the ssb from the bacteriophage RB69, i.e. SEQ ID NO: 95, with its C terminus deleted (gp32RB69CD).

SEQ ID NO: 104 shows the amino acid sequence (from 1 to 210) of the ssb from the bacteriophage T7 (gp2.5T7-R211Del). The full length protein is shown in SEQ ID NO: 96.

SEQ ID NO: 105 shows the amino acid sequence of the $5^{th}$ domain of Hel308 Hla.

SEQ ID NO: 106 shows the amino acid sequence of the $5^{th}$ domain of Hel308 Hvo.

SEQ ID NO: 107 shows the amino acid sequence of the (HhH)2 domain.

SEQ ID NO: 108 shows the amino acid sequence of the (HhH)2-(HhH)2 domain.

SEQ ID NO: 109 shows the amino acid sequence of the peptide linker used to form a helicase in which the opening has been closed.

SEQ ID NOs: 110 to 117 show polynucleotide sequences used in the Examples.

SEQ ID NO: 118 shows the amino acid sequence of the human mitochondrial SSB (HsmtSSB).

SEQ ID NO: 119 shows the amino acid sequence of the p5 protein from Phi29 DNA polymerase.

SEQ ID NO: 120 shows the amino acid sequence of the wild-type SSB from E. coli.

SEQ ID NO: 121 shows the amino acid sequence of the ssb from the bacteriophage T4, which is encoded by the gp32 gene.

SEQ ID NO: 122 shows the amino acid sequence of EcoSSB-CterAla.

SEQ ID NO: 123 shows the amino acid sequence of EcoSSB-CterNGGN.

SEQ ID NO: 124 shows the amino acid sequence of EcoSSB-Q152del.

SEQ ID NO: 125 shows the amino acid sequence of EcoSSB-G117del.

SEQ ID NO: 126 shows the amino acid sequence of TrwC Cba.

SEQ ID NO: 127 shows part of the polynucleotide sequence used in Example 5. Attached to the 3' end of this sequence are four iSpC3 spacers units the last of which is attached to the 5' end of SEQ ID NO: 128.

SEQ ID NO: 128 shows part of the polynucleotide sequence used in Example 5. Attached to the 5' end of this sequence are four iSpC3 spacers units the last of which is attached to the 3' end of SEQ ID NO: 127.

SEQ ID NO: 129 shows the amino acid sequence of Topoisomerase V Mka (*Methanopyrus kandleri*).

SEQ ID NO: 130 shows the amino acid sequence of domains H-L of Topoisomerase V Mka (*Methanopyrus kandleri*).

SEQ ID NOs: 131 to 139 show some of the TraI sequences shown in Table 3.

SEQ ID NO: 140 shows the amino acid sequence of Mutant S (*Escherichia coli*).

SEQ ID NO: 141 shows the amino acid sequence of Sso7d (*Sufolobus solfataricus*).

SEQ ID NO: 142 shows the amino acid sequence of Sso10b1 (*Sulfolobus solfataricus* P2).

SEQ ID NO: 143 shows the amino acid sequence of Sso10b2 (*Sulfolobus solfataricus* P2).

SEQ ID NO: 144 shows the amino acid sequence of Tryptophan repressor (*Escherichia coli*).

SEQ ID NO: 145 shows the amino acid sequence of Lambda repressor (*Enterobacteria phage lambda*).

SEQ ID NO: 146 shows the amino acid sequence of Cren7 (*Histone crenarchaea* Cren7 Sso).

SEQ ID NO: 147 shows the amino acid sequence of human histone (*Homo sapiens*).

SEQ ID NO: 148 shows the amino acid sequence of dsbA (*Enterobacteria phage* T4).

SEQ ID NO: 149 shows the amino acid sequence of Rad51 (*Homo sapiens*).

SEQ ID NO: 150 shows the amino acid sequence of PCNA sliding clamp (*Citromicrobium bathyomarinum* JL354).

SEQ ID NO: 151 shows one of the sequences used in Example 7. This sequence has a carboxyfluorescein attached to a modified thymine located at position 6.

SEQ ID NO: 152 shows one of the sequences used in Example 7. This sequence has a black-hole quencher (BHQ-1) attached to a modified thymine at position 81.

SEQ ID NO: 153 shows one of the sequences used in Example 7.

SEQ ID NO: 154 shows one of the sequences used in Example 9. This sequence is attached at its 5' end by four nitroindoles to the 3' end of SEQ ID NO: 155.

SEQ ID NO: 155 shows one of the sequences used in Example 9. This sequence is attached at its 3' end by four nitroindoles to the 5' end of SEQ ID NO: 154.

SEQ ID NO: 156 shows one of the sequences used in Example 9.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a helicase" includes "helicases", reference to "an opening" includes two or more such openings, reference to "a transmembrane protein pore" includes two or more such pores, and the like.

All publications, patents and patent applications cited herein, whether supra or infra, are hereby incorporated by reference in their entirety.

Modified Helicases with Two or More Parts Connected

The present invention provides a modified helicase that is useful for controlling the movement of a polynucleotide. The modified helicase is based on an unmodified helicase having one or more monomers. In other words, the helicase may be monomeric or oligomeric/multimeric. This is discussed in more detail below. The modified helicase is based on an unmodified helicase comprising a polynucleotide binding domain which comprises in at least one conformational state an opening through which a polynucleotide can unbind from the helicase. In accordance with the invention, the helicase is modified such that two or more parts on the same monomer of the helicase are connected to reduce the size of the opening. The reduced size of the opening does not prevent the helicase from binding to a polynucleotide. For instance, the helicase may bind to a polynucleotide at one of its termini. The reduced size of the opening decreases the ability of the polynucleotide to unbind or disengage from the helicase, particularly from internal nucleotides of the polynucleotide. This is discussed in more detail below and allows the modified helicase to remain bound to the polynucleotide for longer. The modified helicase has the ability to control the movement of a polynucleotide. The modified helicase is artificial or non-natural.

The ability of a helicase to bind to and unbind from a polynucleotide can be determined using any method known in the art. Suitable binding/unbinding assays include, but are not limited to, native polyacrylamide gel electrophoresis (PAGE), fluorescence anisotropy, calorimetry and Surface plasmon resonance (SPR, such as Biacore™). The ability of a helicase to unbind from a polynucleotide can of course be determined by measuring the time for which the helicase can control the movement of a polynucleotide. This may also be determined using any method known in the art. The ability of a helicase to control the movement of a polynucleotide is typically assayed in a nanopore system, such as the ones described below. The ability of a helicase to control the movement of a polynucleotide can be determined as described in the Examples.

A modified helicase of the invention is a useful tool for controlling the movement of a polynucleotide during Strand Sequencing. A problem which occurs in sequencing polynucleotides, particularly those of 500 nucleotides or more, is that the molecular motor which is controlling the movement of the polynucleotide may disengage from the polynucleotide. This allows the polynucleotide to be pulled through the pore rapidly and in an uncontrolled manner in the direction of the applied field. A modified helicase of the invention is less likely to unbind or disengage from the polynucleotide being sequenced. The modified helicase can provide increased read lengths of the polynucleotide as they control the movement of the polynucleotide through a nanopore. The ability to move an entire polynucleotide through a nanopore under the control of a modified helicase of the invention allows characteristics of the polynucleotide, such as its sequence, to be estimated with improved accuracy and speed over known methods. This becomes more important as strand lengths increase and molecular motors are required with improved processivity. A modified helicase of the invention is particularly effective in controlling the movement of target polynucleotides of 500 nucleotides or more, for example 1000 nucleotides, 5000, 10000, 20000, 50000, 100000 or more.

A modified helicase of the invention is also a useful tool for isothermal polymerase chain reaction (PCR). In such methods, the strands of double stranded DNA are typically first separated by a helicase of the invention and coated by single stranded DNA (ssDNA)-binding proteins. In the second step, two sequence specific primers typically hybridise to each border of the DNA template. DNA polymerases may then be used to extend the primers annealed to the templates to produce a double stranded DNA and the two newly synthesized DNA products may then be used as substrates by the helicases of the invention, entering the next round of the reaction. Thus, a simultaneous chain reaction develops, resulting in exponential amplification of the selected target sequence.

The modified helicase has the ability to control the movement of a polynucleotide. The ability of a helicase to control the movement of a polynucleotide can be assayed using any method known in the art. For instance, the helicase may be contacted with a polynucleotide and the position of the polynucleotide may be determined using standard methods. The ability of a modified helicase to control the movement of a polynucleotide is typically assayed in a nanopore system, such as the ones described below and, in particular, as described in the Examples.

A modified helicase of the invention may be isolated, substantially isolated, purified or substantially purified. A helicase is isolated or purified if it is completely free of any other components, such as lipids, polynucleotides, pore monomers or other proteins. A helicase is substantially isolated if it is mixed with carriers or diluents which will not interfere with its intended use. For instance, a helicase is substantially isolated or substantially purified if it is present in a form that comprises less than 10%, less than 5%, less than 2% or less than 1% of other components, such as lipids, polynucleotides, pore monomers or other proteins.

A helicase for use in the invention comprises a polynucleotide binding domain. A polynucleotide binding domain is the part of the helicase that is capable of binding to a polynucleotide. Polynucleotides are defined below. The ability of a domain to bind a polynucleotide can be determined using any method known in the art. The polynucleotide binding domains of known helicases have typically been identified in the art. The domain (with or without bound polynucleotide) may be identified using protein modelling, x-ray diffraction measurement of the protein in a crystalline state (Rupp B (2009). Biomolecular Crystallography: Principles, Practice and Application to Structural Biology. New York: Garland Science.), nuclear magnetic resonance (NMR) spectroscopy of the protein in solution (Mark Rance; Cavanagh, John; Wayne J. Fairbrother; Arthur W. Hunt III; Skelton, N Nicholas J. (2007). Protein NMR spectroscopy: principles and practice (2nd ed.). Boston: Academic Press.) or cryo-electron microscopy of the protein in a frozen-hydrated state (van Heel M, Gowen B, Matadeen R, Orlova E V, Finn R, Pape T, Cohen D, Stark H, Schmidt R, Schatz M, Patwardhan A (2000). "Single-particle electron cryo-microscopy: towards atomic resolution.". Q Rev Biophys. 33: 307-69. Structural information of proteins determined by above mentioned methods are publicly available from the protein bank (PDB) database.

Protein modelling exploits the fact that protein structures are more conserved than protein sequences amongst homologues. Hence, producing atomic resolution models of proteins is dependent upon the identification of one or more protein structures that are likely to resemble the structure of the query sequence. In order to assess whether a suitable protein structure exists to use as a "template" to build a protein model, a search is performed on the protein data bank (PDB) database. A protein structure is considered a suitable template if it shares a reasonable level of sequence identity with the query sequence. If such a template exists, then the template sequence is "aligned" with the query sequence, i.e. residues in the query sequence are mapped onto the template residues. The sequence alignment and template structure are then used to produce a structural model of the query sequence. Hence, the quality of a protein model is dependent upon the quality of the sequence alignment and the template structure.

Proteins, such as helicases, are dynamic structures which are in constant motion. The conformational space that a protein can explore has been described by an energy landscape, in which different conformations are populated based on their energies, and rates of interconversion are dependent on the energy barriers between states (Vinson, *Science*, 2009: 324(5924): 197). Helicases can therefore exist in several conformation states whether in isolation or controlling the movement of a polynucleotide. In at least one conformational state, the polynucleotide binding domain of an unmodified helicase for use in the invention comprises an opening through which a polynucleotide can unbind from the helicase. The opening may be present in all conformational states of the helicase, but does not have to be. For instance, in all conformational states, the polynucleotide binding domain may comprise an opening through which a polynucleotide can unbind from the helicase. Alternatively, in one or more conformational states of the helicase, the polynucleotide binding domain may comprise an opening through which a polynucleotide cannot unbind from the helicase because the opening is too small. In one or more conformational states of the helicase, the polynucleotide binding domain may not comprise an opening through which a polynucleotide can unbind from the helicase.

The polynucleotide binding domain preferably comprises in at least one conformational state an opening through which one or more internal nucleotides of the polynucleotide can unbind from the helicase. An internal nucleotide is a nucleotide which is not a terminal nucleotide in the polynucleotide. For example, it is not a 3' terminal nucleotide or a 5' terminal nucleotide. All nucleotides in a circular polynucleotide are internal nucleotides. Reducing or preventing the unbinding from one or more internal nucleotides in accordance with the invention is advantageous because it results in modified helicases that are capable of binding to one terminus of a polynucleotide, controlling the movement of most, if not all of, the polynucleotide and then unbinding at the other terminus. Such helicases are particularly helpful for Strand Sequencing.

The ability of one or more internal nucleotide to unbind from the helicase may be determined by carrying out a comparative assay. For instance, the ability of a helicase to unbind from a control polynucleotide A is compared with its ability to unbind from the same polynucleotide but with a blocking group attached at the terminal nucleotides (polynucleotide B). The blocking group prevents any unbinding at the terminal nucleotide of strand B, and thus allows only internal unbinding of the helicase. Alternatively, the ability of a helicase to unbind from a circular polynucleotide may be assayed. Unbinding may be assayed as described above.

The opening may be a groove, pocket or recess in the polynucleotide binding domain.

The presence of an opening through which a polynucleotide can unbind from the helicase can be determined using any method known in the art. The presence of an opening can be determined by measuring the ability of a helicase to unbind from a polynucleotide, and in particular from internal nucleotides of the polynucleotide, as discussed in more detail above. Openings in the polynucleotide domain can be identified using protein modelling, x-ray diffraction, NMR spectroscopy or cryo-electron microscopy as discussed above.

In accordance with the invention, the helicase is modified by connecting two or more parts on the same monomer of the helicase. If the helicase is oligomeric or multimeric, the two or more parts cannot be on different monomers. Any number of parts, such as 3, 4, 5 or more parts, may be connected. Preferred methods of connecting the two or more parts are discussed in more detail below.

The two or more parts can be located anywhere on the monomer as long as they reduce the size of the opening when connected in accordance with the invention. The two or more parts may be in the polynucleotide domain or the opening, but do not have to be. For instance, one, both or all of the two or more parts may be outside the polynucleotide binding domain, such as on different domain of the helicase. The maximum distance between the two or more parts is the circumference of the helicase.

The two or more parts are preferably spatially proximate. The two or more parts are preferably less that 50 Angstroms (Å) apart, such as less than 40 Å apart, less than 30 Å apart, less than 25 Å apart, less than 20 Å apart, less than 10 Å apart or less than 10 Å apart.

At least one of the two or more parts preferably forms part of the opening, is adjacent to the opening or is near the opening. It is straightforward to identify parts of the opening, such as amino acids within the opening, as described above. Parts are adjacent to the opening if they are next to, but do not form part of the opening. For instance, an amino acid which is located next to an amino acid that forms part of the opening, but which itself does not form part of the opening is adjacent to the opening. In the context of the invention, "next to" may mean next to in the amino acid sequence of the helicase or next two in the three-dimensional structure of the helicase. A part is typically near to the opening if it is less than 20 Å from an amino acid that forms part of the opening, such as less than 15 Å, less than 10 Å, less than 5 Å or less than 2 Å apart from an amino acid that forms part of the opening. A part is typically near to the opening if it is within 1, 2, 3, 4 or 5 amino acids of an amino acid that forms part of the opening in the amino acid sequence of the helicase. Such amino acids may be identified as discussed above.

The two or more parts may be on opposite sides of the opening. The two or more parts may be on the same side of the opening. In this embodiment, the two or more parts of the helicase may be connected to form a loop, lid, constriction or flap that reduces the size of the opening.

The two or more parts are preferably on the surface of the monomer, i.e. on the surface of the helicase. It is straightforward to connect two or more parts on the surface as described in more detail below. Surface parts may be determined using protein modelling, x-ray diffraction, NMR spectroscopy or cryo-electron microscopy as discussed above.

The modified helicase retains its ability to control the movement of a polynucleotide. This ability of the helicase is typically provided by its three dimensional structure that is typically provided by its β-strands and α-helices. The α-helices and β-strands are typically connected by loop regions. In order to avoid affecting the ability of the helicase to control the movement of a polynucleotide, the two or more parts are preferably loop regions of the monomer. The loop regions of specific helicases can be identified using methods known in the art, such as protein modelling, x-ray diffraction, NMR spectroscopy or cryo-electron microscopy as discussed above.

For Hel308 helicases (SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58), β-strands can only be found in the two RecA-like engine domains (domains 1 and 2). These domains are responsible for coupling the hydrolysis of the fuel nucleotide (normally ATP) with movement. The important domains for ratcheting along a polynucleotide are domains 3 and 4, but above all domain 4. Interestingly, both of domains 3 and 4 comprise only α-helices. There is an important α-helix in domain 4 called the ratchet helix. As a result, in the Hel308 embodiments of the invention, the two or more parts are preferably not in any of the α-helixes.

The size of the opening may be reduced to any degree as long as it reduces the unbinding of the polynucleotides from the helicase. This may be determined as discussed above. Ways in which the size of the opening are reduced are discussed in more detail below.

The two or more parts are preferably connected to close the opening. If the opening is closed, the polynucleotide cannot unbind from the helicase through the opening. The helicase is more preferably modified such that it does not comprise the opening in any conformational state. If the opening is not present in any conformational state of the helicase, the polynucleotide cannot unbind from the helicase through the opening. The helicase is most preferably modified such that it is capable of forming a covalently-closed structure around the polynucleotide. Once the covalently-closed structure is bound to a polynucleotide, for instance at one end of the polynucleotide, it is capable of controlling the movement of the polynucleotide without unbinding until it reaches the other end.

Connection

The two or more parts may be connected in any way. The connection can be transient, for example non-covalent. Even transient connection will reduce the size of the opening and reduce unbinding of the polynucleotide from the helicase through the opening.

The two or more parts are preferably connected by affinity molecules. Suitable affinity molecules are known in the art. The affinity molecules are preferably (a) complementary polynucleotides (International Application No. PCT/GB 10/000132 (published as WO 2010/086602), (b) an antibody or a fragment thereof and the complementary epitope (Biochemistry 6th Ed, W.H. Freeman and co (2007) pp 953-954), (c) peptide zippers (O'Shea et al., Science 254 (5031): 539-544), (d) capable of interacting by β-sheet augmentation (Remaut and Waksman Trends Biochem. Sci. (2006) 31 436-444), (e) capable of hydrogen bonding, pi-stacking or forming a salt bridge, (f) rotaxanes (Xiang Ma and He Tian Chem. Soc. Rev., 2010, 39, 70-80), (g) an aptamer and the complementary protein (James, W. in Encyclopedia of Analytical Chemistry, R. A. Meyers (Ed.) pp. 4848-4871 John Wiley & Sons Ltd, Chichester, 2000) or (h) half-chelators (Hammerstein et al. J Biol Chem. 2011 Apr. 22; 286(16): 14324-14334). For (e), hydrogen bonding occurs between a proton bound to an electronegative atom and another electronegative atom. Pi-stacking requires two aromatic rings that can stack together where the planes of the rings are parallel. Salt bridges are between groups that can delocalize their electrons over several atoms, e.g. between aspartate and arginine.

The two or more parts may be transiently connected by a hexa-his tag or Ni-NTA. The two or more parts may also be modified such that they transiently connect to each other.

The two or more parts are preferably permanently connected. In the context of the invention, a connection is permanent if is not broken while the helicase is used or cannot be broken without intervention on the part of the user, such as using reduction to open —S—S— bonds.

The two or more parts are preferably covalently-attached. The two or more parts may be covalently attached using any method known in the art.

The two or more parts may be covalently attached via their naturally occurring amino acids, such as cysteines, threonines, serines, aspartates, asparagines, glutamates and glutamines. Naturally occurring amino acids may be modified to facilitate attachment. For instance, the naturally occurring amino acids may be modified by acylation, phosphorylation, glycosylation or farnesylation. Other suitable modifications are known in the art. Modifications to naturally occurring amino acids may be post-translation modifications. The two or more parts may be attached via amino acids that have been introduced into their sequences. Such amino acids are preferably introduced by substitution. The introduced amino acid may be cysteine or a non-natural amino acid that facilitates attachment. Suitable non-natural amino acids include, but are not limited to, 4-azido-L-phenylalanine (Faz), any one of the amino acids numbered 1-71 included in FIG. 1 of Liu C. C. and Schultz P. G., Annu. Rev. Biochem., 2010, 79, 413-444 or any one of the amino acids listed below. The introduced amino acids may be modified as discussed above.

In a preferred embodiment, the two or more parts are connected using linkers. Linker molecules are discussed in more detail below. One suitable method of connection is cysteine linkage. This is discussed in more detail below. The two or more parts are preferably connected using one or more, such as two or three, linkers. The one or more linkers may be designed to reduce the size of, or close, the opening as discussed above. If one or more linkers are being used to close the opening as discussed above, at least a part of the one or more linkers is preferably oriented such that it is not parallel to the polynucleotide when it is bound by the helicase. More preferably, all of the linkers are oriented in this manner. If one or more linkers are being used to close the opening as discussed above, at least a part of the one or more linkers preferably crosses the opening in an orientation that is not parallel to the polynucleotide when it bound by the helicase. More preferably, all of the linkers cross the opening in this manner. In these embodiments, at least a part of the one or more linkers may be perpendicular to the polynucleotide. Such orientations effectively close the opening such that the polynucleotide cannot unbind from the helicase through the opening.

Each linker may have two or more functional ends, such as two, three or four functional ends. Suitable configurations of ends in linkers are well known in the art.

One or more ends of the one or more linkers are preferably covalently attached to the helicase. If one end is covalently attached, the one or more linkers may transiently connect the two or more parts as discussed above. If both or all ends are covalently attached, the one or more linkers permanently connect the two or more parts.

At least one of the two or more parts is preferably modified to facilitate the attachment of the one or more linkers. Any modification may be made. The linkers may be attached to one or more reactive cysteine residues, reactive lysine residues or non-natural amino acids in the two or more parts. The non-natural amino acid may be any of those discussed above. The non-natural amino acid is preferably 4-azido-L-phenylalanine (Faz). At least one amino acid in the two or more parts is preferably substituted with cysteine or a non-natural amino acid, such as Faz.

The one or more linkers are preferably amino acid sequences and/or chemical crosslinkers.

Suitable amino acid linkers, such as peptide linkers, are known in the art. The length, flexibility and hydrophilicity of the amino acid or peptide linker are typically designed such that it reduces the size of the opening, but does not to disturb the functions of the helicase. Preferred flexible peptide linkers are stretches of 2 to 20, such as 4, 6, 8, 10 or 16, serine and/or glycine amino acids. More preferred flexible linkers include $(SG)_1$, $(SG)_2$, $(SG)_3$, $(SG)_4$, $(SG)_5$, $(SG)_8$, $(SG)_{10}$, $(SG)_{15}$ or $(SG)_{20}$ wherein S is serine and G is glycine. Preferred rigid linkers are stretches of 2 to 30, such as 4, 6, 8, 16 or 24, proline amino acids. More preferred rigid linkers include $(P)_{12}$ wherein P is proline. The amino acid sequence of a linker preferably comprises a polynucleotide binding moiety. Such moieties and the advantages associated with their use are discussed below.

Suitable chemical crosslinkers are well-known in the art. Suitable chemical crosslinkers include, but are not limited to, those including the following functional groups: maleimide, active esters, succinimide, azide, alkyne (such as dibenzocyclooctynol (DIBO or DBCO), difluoro cycloalkynes and linear alkynes), phosphine (such as those used in traceless and non-traceless Staudinger ligations), haloacetyl (such as iodoacetamide), phosgene type reagents, sulfonyl chloride reagents, isothiocyanates, acyl halides, hydrazines, disulphides, vinyl sulfones, aziridines and photoreactive reagents (such as aryl azides, diaziridines).

Reactions between amino acids and functional groups may be spontaneous, such as cysteine/maleimide, or may require external reagents, such as Cu(I) for linking azide and linear alkynes.

Linkers can comprise any molecule that stretches across the distance required. Linkers can vary in length from one carbon (phosgene-type linkers) to many Angstroms. Examples of linear molecules, include but are not limited to, are polyethyleneglycols (PEGs), polypeptides, polysaccharides, deoxyribonucleic acid (DNA), peptide nucleic acid (PNA), threose nucleic acid (TNA), glycerol nucleic acid (GNA), saturated and unsaturated hydrocarbons, polyamides. These linkers may be inert or reactive, in particular they may be chemically cleavable at a defined position, or may be themselves modified with a fluorophore or ligand. The linker is preferably resistant to dithiothreitol (DTT).

Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octananoate, di-maleimide PEG 1k, di-maleimide PEG 3.4k, di-maleimide PEG 5k, di-maleimide PEG 10k, bis(maleimido)ethane (BMOE), bis-maleimidohexane (BMH), 1A-bis-maleimidobutane (BMB), 1,4 bis-maleimidyl-2,3-dihydroxybutane (BMDB), BM[PEO]2 (1,8-bis-maleimidodiethyleneglycol), BM[PEO]3 (1,11-bis-maleimidotriethylene glycol), tris[2-maleimidoethyl]amine (TMEA), DTME dithiobismaleimidoethane, bis-maleimide PEGS, bis-maleimide PEG11, DBCO-maleimide, DBCO-PEG4-maleimide, DBCO-PEG4-NH2, DBCO-PEG4-NHS, DBCO-NHS, DBCO-PEG-DBCO 2.8 kDa, DBCO-PEG-DBCO 4.0 kDa, DBCO-15 atoms-DBCO, DBCO-26 atoms-DBCO, DBCO-35 atoms-DBCO, DBCO-PEG4-S—S-PEG3-biotin, DBCO-S-S-PEG3-biotin, DBCO-S-S-PEG11-biotin, (succinimidyl 3-(2-pyridyldithio)propionate (SPDP) and maleimide-PEG(2 kDa)-maleimide (ALPHA,OMEGA-BIS-MALEIMIDO POLY(ETHYLENE GLYCOL)). The most preferred crosslinker is maleimide-propyl-SRDFWRS-(1,2-diaminoethane)-propyl-maleimide as used in the Examples.

The one or more linkers may be cleavable. This is discussed in more detail below.

The two or more parts may be connected using two different linkers that are specific for each other. One of the linkers is attached to one part and the other is attached to another part. The linkers should react to form a modified helicase of the invention. The two or more parts may be connected using the hybridization linkers described in International Application No. PCT/GB10/000132 (published as WO 2010/086602). In particular, the two or more parts may be connected using two or more linkers each comprising a hybridizable region and a group capable of forming a covalent bond. The hybridizable regions in the linkers hybridize and link the two or more parts. The linked parts are then coupled via the formation of covalent bonds between the groups. Any of the specific linkers disclosed in International Application No. PCT/GB10/000132 (published as WO 2010/086602) may be used in accordance with the invention.

The two or more parts may be modified and then attached using a chemical crosslinker that is specific for the two modifications. Any of the crosslinkers discussed above may be used.

The linkers may be labeled. Suitable labels include, but are not limited to, fluorescent molecules (such as Cy3 or AlexaFluor®555), radioisotopes $^{125}$I, $^{35}$S, enzymes, antibodies, antigens, polynucleotides and ligands such as biotin. Such labels allow the amount of linker to be quantified. The label could also be a cleavable purification tag, such as biotin, or a specific sequence to show up in an identification method, such as a peptide that is not present in the protein itself, but that is released by trypsin digestion.

A preferred method of connecting the two or more parts is via cysteine linkage. This can be mediated by a bi-functional chemical crosslinker or by an amino acid linker with a terminal presented cysteine residue. Linkage can occur via natural cysteines in the helicase. Alternatively, cysteines can be introduced into the two or more parts of the helicase. If the two or more parts are connected via cysteine linkage, the one or more cysteines have preferably been introduced to the two or more parts by substitution.

The length, reactivity, specificity, rigidity and solubility of any bi-functional linker may be designed to ensure that the size of the opening is reduced sufficiently and the function of the helicase is retained. Suitable linkers include bismaleimide crosslinkers, such as 1,4-bis(maleimido)butane (BMB) or bis(maleimido)hexane. One draw back of bi-functional linkers is the requirement of the helicase to contain no further surface accessible cysteine residues if attachment at specific sites is preferred, as binding of the bi-functional linker to surface accessible cysteine residues may be difficult to control and may affect substrate binding or activity. If the helicase does contain several accessible cysteine residues, modification of the helicase may be required to remove them while ensuring the modifications do not affect the folding or activity of the helicase. This is discussed in International Application No. PCT/GB10/000133 (published as WO 2010/086603). The reactivity of cysteine residues may be enhanced by modification of the adjacent residues, for example on a peptide linker. For instance, the basic groups of flanking arginine, histidine or lysine residues will change the pKa of the cysteines thiol group to that of the more reactive S$^-$ group. The reactivity of cysteine residues may be protected by thiol protective groups such as 5,5'-dithiobis-(2-nitrobenzoic acid) (dTNB). These may be reacted with one or more cysteine residues of the helicase before a linker is attached. Selective deprotection of surface accessible cysteines may be possible using reducing reagents immobilized on beads (for example immobilized tris(2-carboxyethyl) phosphine, TCEP). Cysteine linkage of the two or more parts is discussed in more detail below.

Another preferred method of attaching the two or more parts is via 4-azido-L-phenylalanine (Faz) linkage. This can be mediated by a bi-functional chemical linker or by a polypeptide linker with a terminal presented Faz residue. The one or more Faz residues have preferably been introduced to the helicase by substitution. Faz linkage of two or more helicases is discussed in more detail below.

Helicase

Any helicase formed of one or monomers and comprising a polynucleotide binding domain which comprises in at least one conformational state an opening through which a polynucleotide can unbind from the helicase may modified in accordance with the invention. Helicases are often known as translocases and the two terms may be used interchangeably.

Suitable helicases are well-known in the art (M. E. Fairman-Williams et al., Curr. Opin. Struct Biol., 2010, 20 (3), 313-324, T. M. Lohman et al., Nature Reviews Molecular Cell Biology, 2008, 9, 391-401).

The helicase is preferably a member of superfamily 1 or superfamily 2. The helicase is more preferably a member of one of the following families: Pif1-like, Upf1-like, UvrD/Rep, Ski-like, Rad3/XPD, NS3/NPH-II, DEAD, DEAH/RHA, RecG-like, RECQ-like, T1R-like, Swi/Snf-like and Rig-I-like. The first three of those families are in superfamily 1 and the second ten families are in superfamily 2. The helicase is more preferably a member of one of the following subfamilies: RecD, Upf1 (RNA), PcrA, Rep, UvrD, Hel308, Mtr4 (RNA), XPD, NS3 (RNA), Mss116 (RNA), Prp43 (RNA), RecG, RecQ, T1R, RapA and Hef (RNA). The first five of those subfamilies are in superfamily 1 and the second eleven subfamilies are in superfamily 2. Members of the Upf1, Mtr4, NS3, Mss116, Prp43 and Hef subfamilies are RNA helicases. Members of the remaining subfamilies are DNA helicases.

The helicase may be a multimeric or oligomeric helicase. In other words, the helicase may need to form a multimer or an oligomer, such as a dimer, to function. In such embodiments, the two or more parts cannot be on different monomers. The helicase is preferably monomeric. In other words, the helicase preferably does not need to form a multimer or an oligomer, such as a dimer, to function. Hel308, RecD, TraI and XPD helicases are all monomeric helicases. These are discussed in more detail below. Methods for determining whether or not a helicase is oligomeric/multimeric or monomeric are known in the art. For instance, the kinetics of radiolabelled or fluorescently-labelled polynucleotide unwinding using the helicase can be examined. Alternatively, the helicase can be analysed using size exclusion chromatography.

Monomeric helicases may comprise several domains attached together. For instance, TraI helicases and TraI subgroup helicases may contain two RecD helicase domains, a relaxase domain and a C-terminal domain. The domains typically form a monomeric helicase that is capable of functioning without forming oligomers. The two or more parts may be present on the same or different domains of a monomeric helicase. The unmodified helicase suitable for modification in accordance with the invention is preferably capable of binding to the target polynucleotide at an internal nucleotide. Internal nucleotides are defined above.

Generally, a helicase which is capable of binding at an internal nucleotide is also capable of binding at a terminal nucleotide, but the tendency for some helicases to bind at an internal nucleotide will be greater than others. For an unmodified helicase suitable for modification in accordance with the invention, typically at least 10% of its binding to a polynucleotide will be at an internal nucleotide. Typically, at least 20%, at least 30%, at least 40% or at least 50% of its binding will be at an internal nucleotide. Binding at a terminal nucleotide may involve binding to both a terminal nucleotide and adjacent nucleotides at the same time. For the purposes of the invention, this is not binding to the target polynucleotide at an internal nucleotide. In other words, the helicase for modification using the invention is not only capable of binding to a terminal nucleotide in combination with one or more adjacent internal nucleotides. The helicase may be capable of binding to an internal nucleotide without concurrent binding to a terminal nucleotide.

A helicase which is capable of binding at an internal nucleotide may bind to more than one internal nucleotide. Typically, the helicase binds to at least 2 internal nucleotides, for example at least 3, at least 4, at least 5, at least 10 or at least 15 internal nucleotides. Typically the helicase binds to at least 2 adjacent internal nucleotides, for example at least 3, at least 4, at least 5, at least 10 or at least 15 adjacent internal nucleotides. The at least 2 internal nucleotides may be adjacent or non-adjacent.

If modification in accordance with the invention closes the opening such that unbinding from internal nucleotides is prevented, it is preferred that the unmodified helicase is capable of at least some binding to a terminal nucleotide. This will allow the modified helicase to bind to a polynucleotide at one terminus and control the movement of the polynucleotide along its entire length without unbinding.

The helicase will eventually unbind from the polynucleotide at the opposite terminus from which it became bound.

The ability of a helicase to bind to a polynucleotide at an internal nucleotide may be determined by carrying out a comparative assay. The ability of a helicase to bind to a control polynucleotide A is compared to the ability to bind to the same polynucleotide but with a blocking group attached at the terminal nucleotide (polynucleotide B). The blocking group prevents any binding at the terminal nucleotide of strand B, and thus allows only internal binding of a helicase. Alternatively, the ability of a helicase to bind to an internal nucleotide may also be assayed using circular polynucleotides.

Examples of helicases which are capable of binding at an internal nucleotide include, but are not limited to, Hel308 Tga, Hel308 Mhu and Hel308 Csy. Hence, the helicase preferably comprises (a) the sequence of Hel308 Tga (i.e. SEQ ID NO: 33) or a variant thereof or (b) the sequence of Hel308 Csy (i.e. SEQ ID NO: 22) or a variant thereof or (c) the sequence of Hel308 Mhu (i.e. SEQ ID NO: 52) or a variant thereof. Variants of these sequences are discussed in more detail below. Variants preferably comprise one or more substituted cysteine residues and/or one or more substituted Faz residues to facilitate attachment as discussed above.

The helicase is preferably a Hel308 helicase. Any Hel308 helicase may be used in accordance with the invention. Hel308 helicases are also known as ski2-like helicases and the two terms can be used interchangeably. Suitable Hel308 helicases are disclosed in Table 4 of U.S. Patent Application Nos. 61/549,998 and 61/599,244 and International Application No. PCT/GB2012/052579 (published as WO 2013/057495).

The Hel308 helicase typically comprises the amino acid motif Q-X1-X2-G-R-A-G-R (hereinafter called the Hel308 motif; SEQ ID NO: 8). The Hel308 motif is typically part of the helicase motif VI (Tuteja and Tuteja, Eur. J. Biochem. 271, 1849-1863 (2004)). X1 may be C, M or L. X1 is preferably C. X2 may be any amino acid residue. X2 is typically a hydrophobic or neutral residue. X2 may be A, F, M, C, V, L, I, S, T, P or R. X2 is preferably A, F, M, C, V, L, I, S, T or P. X2 is more preferably A, M or L. X2 is most preferably A or M.

The Hel308 helicase preferably comprises the motif Q-X1-X2-G-R-A-G-R-P (hereinafter called the extended Hel308 motif; SEQ ID NO: 9) wherein X1 and X2 are as described above.

The most preferred Hel308 helicases, Hel308 motifs and extended Hel308 motifs are shown in the Table 1 below.

TABLE 1

Preferred Hel308 helicases and their motifs

| SEQ ID NO: | Helicase | Names | % Identity Hel308 Pfu | % Identity Hel308 Mbu | Hel308 motif | Extended Hel308 motif |
|---|---|---|---|---|---|---|
| 10 | Hel308 Mbu | *Methanococcoides burtonii* | 37% | — | QMAGRAGR (SEQ ID NO: 11) | QMAGRAGRP (SEQ ID NO: 12) |
| 13 | Hel308 Pfu | *Pyrococcus furiosus* DSM 3638 | — | 37% | QMLGRAGR (SEQ ID NO: 14) | QMLGRAGRP (SEQ ID NO: 15) |
| 16 | Hel308 Hvo | *Haloferax volcanii* | 34% | 41% | QMMGRAGR (SEQ ID NO: 17) | QMMGRAGRP (SEQ ID NO: 18) |

TABLE 1-continued

Preferred Hel308 helicases and their motifs

| SEQ ID NO: | Helicase | Names | % Identity Hel308 Pfu | % Identity Hel308 Mbu | Hel308 motif | Extended Hel308 motif |
|---|---|---|---|---|---|---|
| 19 | Hel308 Hla | *Halorubrum lacusprofundi* | 35% | 42% | QMCGRAGR (SEQ ID NO: 20) | QMCGRAGRP (SEQ ID NO: 21) |
| 22 | Hel308 Csy | *Cenarchaeum symbiosum* | 34% | 34% | QLCGRAGR (SEQ ID NO: 23) | QLCGRAGRP (SEQ ID NO: 24) |
| 25 | Hel308 Sso | *Sulfolobus solfataricus* | 35% | 33% | QMSGRAGR (SEQ ID NO: 26) | QMSGRAGRP (SEQ ID NO: 27) |
| 28 | Hel308 Mfr | *Methanogenium frigidum* | 37% | 44% | QMAGRAGR (SEQ ID NO: 11) | QMAGRAGRP (SEQ ID NO: 12) |
| 29 | Hel308 Mok | *Methanothermococcus okinawensis* | 37% | 34% | QCIGRAGR (SEQ ID NO: 30) | QCIGRAGRP (SEQ ID NO: 31) |
| 32 | Hel308 Mig | *Methanotorris igneus* Kol 5 | 40% | 35% | QCIGRAGR (SEQ ID NO: 30) | QCIGRAGRP (SEQ ID NO: 31) |
| 33 | Hel308 Tga | *Thermococcus gammatolerans* EJ3 | 60% | 38% | QMMGRAGR (SEQ ID NO: 17) | QMMGRAGRP (SEQ ID NO: 18) |
| 34 | Hel308 Tba | *Thermococcus barophilus* MP | 57% | 35% | QMIGRAGR (SEQ ID NO: 35) | QMIGRAGRP (SEQ ID NO: 36) |
| 37 | Hel308 Tsi | *Thermococcus sibiricus* MM 739 | 56% | 35% | QMMGRAGR (SEQ ID NO: 17) | QMMGRAGRP (SEQ ID NO: 18) |
| 38 | Hel308 Mba | *Methanosarcina barkeri* str. *Fusaro* | 39% | 60% | QMAGRAGR (SEQ ID NO: 11) | QMAGRAGRP (SEQ ID NO: 12) |
| 39 | Hel308 Mac | *Methanosarcina acetivorans* | 38% | 60% | QMAGRAGR (SEQ ID NO: 11) | QMAGRAGRP (SEQ ID NO: 12) |
| 40 | Hel308 Mmah | *Methanohalophilus mahii* DSM 5219 | 38% | 60% | QMAGRAGR (SEQ ID NO: 11) | QMAGRAGRP (SEQ ID NO: 12) |
| 41 | Hel308 Mmaz | *Methanosarcina mazei* | 38% | 60% | QMAGRAGR (SEQ ID NO: 11) | QMAGRAGRP (SEQ ID NO: 12) |
| 42 | Hel308 Mth | *Methanosaeta thermophila* PT | 39% | 46% | QMAGRAGR (SEQ ID NO: 11) | QMAGRAGRP (SEQ ID NO: 12) |
| 43 | Hel308 Mzh | *Methanosalsum zhilinae* DSM 4017 | 39% | 57% | QMAGRAGR (SEQ ID NO: 11) | QMAGRAGRP (SEQ ID NO: 12) |
| 44 | Hel308 Mev | *Methanohalobium evestigatum* Z-7303 | 38% | 61% | QMAGRAGR (SEQ ID NO: 11) | QMAGRAGRP (SEQ ID NO: 12) |
| 45 | Hel308 Mma | *Methanococcus maripaludis* | 36% | 32% | QCIGRAGR (SEQ ID NO: 30) | QCIGRAGRP (SEQ ID NO: 31) |
| 46 | Hel308 Nma | *Natrialba magadii* | 37% | 43% | QMMGRAGR (SEQ ID NO: 17) | QMMGRAGRP (SEQ ID NO: 18) |

TABLE 1-continued

Preferred Hel308 helicases and their motifs

| SEQ ID NO: | Helicase | Names | % Identity Hel308 Pfu | % Identity Hel308 Mbu | Hel308 motif | Extended Hel308 motif |
|---|---|---|---|---|---|---|
| 47 | Hel308 Mbo | *Methanoregula boonei* 6A8 | 38% | 45% | QMAGRAGR (SEQ ID NO: 11) | QMAGRAGRP (SEQ ID NO: 12) |
| 48 | Hel308 Fac | *Ferroplasma acidarmanus* | 34% | 32% | QMIGRAGR (SEQ ID NO: 35) | QMIGRAGRP (SEQ ID NO: 36) |
| 49 | Hel308 Mfe | *Methanocaldococcus fervens* AG86 | 40% | 35% | QCIGRAGR (SEQ ID NO: 30) | QCIGRAGRP (SEQ ID NO: 31) |
| 50 | Hel308 Mja | *Methanocaldococcus jannaschii* | 24% | 22% | QCIGRAGR (SEQ ID NO: 30) | QCIGRAGRP (SEQ ID NO: 31) |
| 51 | Hel308 Min | *Methanocaldococcus infernus* | 41% | 33% | QCIGRAGR (SEQ ID NO: 30) | QCIGRAGRP (SEQ ID NO: 31) |
| 52 | Hel308 Mhu | *Methanospirillum hungatei* JF-1 | 36% | 40% | QMAGRAGR (SEQ ID NO: 11) | QMAGRAGRP (SEQ ID NO: 12) |
| 53 | Hel308 Afu | *Archaeoglobus fulgidus* DSM 4304 | 40% | 40% | QMAGRAGR (SEQ ID NO: 11) | QMAGRAGRP (SEQ ID NO: 12) |
| 54 | Hel308 Htu | *Haloterrigena turkmenica* | 35% | 43% | QMAGRAGR (SEQ ID NO: 11) | QMMGRAGRP (SEQ ID NO: 12) |
| 55 | Hel308 Hpa | *Haladaptatus paucihalophilus* DX253 | 38% | 45% | QMFGRAGR (SEQ ID NO: 56) | QMFGRAGRP (SEQ ID NO: 57) |
| 58 | Hel308 Hsp ski2-like helicase | *Halobacterium* sp. NRC-1 | 36.8% | 42.0% | QMFGRAGR (SEQ ID NO:56) | QMFGRAGRP (SEQ ID NO: 57) |

The most preferred Hel308 motif is shown in SEQ ID NO: 17. The most preferred extended Hel308 motif is shown in SEQ ID NO: 18.

The Hel308 helicase preferably comprises the sequence of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58 or a variant thereof.

In Hel308 helicases, the polynucleotide domain and opening can be found between domain 2 (one of the ATPase domains) and domain 4 (the ratchet domain) and domain 2 and domain 5 (the molecular brake). The two or more parts connected in accordance with the invention are preferably (a) any amino acid in domain 2 and any amino acid in domain 4 or (b) any amino acid in domain 2 and any amino acid in domain 5. The amino acid residues which define domains 2, 4 and 5 in various Hel308 helicases are listed in Table 2 below.

TABLE 2

Amino acid residues which correspond to domains 2, 4 and 5 in various Hel 308 helicases.

| SEQ ID NO: | Hel308 Homologue | Domain 2 Start | Domain 2 End | Domain 4 Start | Domain 4 End | Domain 5 Start | Domain 5 End |
|---|---|---|---|---|---|---|---|
| 10 | Mbu | W200 | E409 | Y506 | G669 | S670 | Q760 |
| 13 | Pfu | W198 | F398 | Y490 | G640 | I641 | S720 |
| 16 | Hvo | W201 | W418 | Y509 | G725 | V726 | E827 |
| 19 | Hla | W201 | W418 | Y513 | G725 | V726 | R824 |
| 22 | Csy | W205 | G414 | Y504 | G644 | I645 | K705 |
| 25 | Sso | W204 | L420 | Y506 | G651 | I652 | S717 |
| 28 | Mfr | W193 | E397 | Y488 | G630 | I631 | I684 |
| 29 | Mok | W198 | G415 | Y551 | G706 | A707 | I775 |
| 32 | Mig | W200 | E408 | Y495 | G632 | A633 | I699 |
| 33 | Tga | W198 | R399 | Y491 | G639 | V640 | R720 |
| 34 | Tba | W219 | F420 | Y512 | G660 | V661 | K755 |
| 37 | Tsi | W221 | L422 | Y514 | G662 | V663 | K744 |
| 38 | Mba | W200 | E409 | Y498 | G643 | A644 | Y729 |
| 39 | Mac | W200 | E409 | Y499 | G644 | A645 | F730 |

TABLE 2-continued

Amino acid residues which correspond to domains 2, 4 and 5 in various Hel 308 helicases.

| SEQ ID NO: | Hel308 Homologue | Domain 2 | | Domain 4 | | Domain 5 | |
|---|---|---|---|---|---|---|---|
| | | Start | End | Start | End | Start | End |
| 40 | Mmah | W196 | G405 | Y531 | G678 | A679 | N747 |
| 41 | Mmaz | W200 | E409 | Y499 | G644 | A645 | Y730 |
| 42 | Mth | W203 | M404 | Y491 | G629 | A630 | A693 |
| 43 | Mzh | W200 | N409 | Y505 | G651 | I652 | T739 |
| 44 | Mev | W200 | D409 | Y499 | G643 | V644 | F733 |
| 45 | Mma | W196 | G405 | Y531 | G678 | A679 | N747 |
| 46 | Nma | W201 | W413 | Y541 | G688 | V689 | F799 |
| 47 | Mbo | W197 | E402 | Y493 | G637 | I638 | G723 |
| 48 | Fac | F197 | T390 | Y480 | G613 | V614 | R681 |
| 49 | Mfe | W199 | Q408 | Y494 | G629 | A630 | F696 |
| 50 | Mja | W197 | Q406 | Y492 | G627 | A628 | F694 |
| 51 | Min | W189 | Q390 | Y476 | G604 | A605 | I670 |
| 52 | Mhu | W198 | D402 | Y493 | G637 | V638 | C799 |
| 53 | Afu | W201 | F399 | Y487 | G626 | V627 | E696 |
| 54 | Htu | W201 | W413 | Y533 | G680 | V681 | F791 |
| 55 | Hpa | W201 | W412 | Y502 | G657 | V658 | E752 |
| 58 | Hsp (ski2-like helicase) | W210 | Y421 | Y512 | G687 | V688 | S783 |

The Hel308 helicase preferably comprises the sequence of Hel308 Mbu (i.e. SEQ ID NO: 10) or a variant thereof. In Hel308 Mbu, the polynucleotide domain and opening can be found between domain 2 (one of the ATPase domains) and domain 4 (the ratchet domain) and domain 2 and domain 5 (the molecular brake). The two or more parts of Hel308 Mbu connected are preferably (a) any amino acid in domain 2 and any amino acid in domain 4 or (b) any amino acid in domain 2 and any amino acid in domain 5. The amino acid residues which define domains 2, 4 and 5 for Hel308 Mbu are listed in Table 2 above. The two or more parts of Hel308 Mbu connected are preferably amino acids 284 and 615 in SEQ ID NO: 10. These amino acids are preferably substituted with cysteine (i.e. E284C and S615C) such that they can be connected by cysteine linkage.

The invention also provides a mutant Hel308 Mbu protein which comprises a variant of SEQ ID NO: 10 in which E284 and S615 are modified. E284 and S615 are preferably substituted. E284 and S615 are more preferably substituted with cysteine (i.e. E284C and S615C). The variant may differ from SEQ ID NO: 10 at positions other than E284 and S615 as long as E284 and S615 are modified. The variant will preferably be at least 30% homologous to SEQ ID NO: 10 based on amino acid identity as discussed in more detail below. E284 and S615 are not connected. The mutant Hel308 Mbu protein of the invention may be used to form a modified helicase of the invention in which E284 and S615 are connected.

The Hel308 helicase more preferably comprises (a) the sequence of Hel308 Tga (i.e. SEQ ID NO: 33) or a variant thereof, (b) the sequence of Hel308 Csy (i.e. SEQ ID NO: 22) or a variant thereof or (c) the sequence of Hel308 Mhu (i.e. SEQ ID NO: 52) or a variant thereof.

A variant of a Hel308 helicase is an enzyme that has an amino acid sequence which varies from that of the wild-type helicase and which retains polynucleotide binding activity. In particular, a variant of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58 is an enzyme that has an amino acid sequence which varies from that of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58 and which retains polynucleotide binding activity. Polynucleotide binding activity can be determined using methods known in the art. Suitable methods include, but are not limited to, fluorescence anisotropy, tryptophan fluorescence and electrophoretic mobility shift assay (EMSA). For instance, the ability of a variant to bind a single stranded polynucleotide can be determined as described in the Examples.

The variant retains helicase activity. This can be measured in various ways. For instance, the ability of the variant to translocate along a polynucleotide can be measured using electrophysiology, a fluorescence assay or ATP hydrolysis.

The variant may include modifications that facilitate handling of the polynucleotide encoding the helicase and/or facilitate its activity at high salt concentrations and/or room temperature. Variants typically differ from the wild-type helicase in regions outside of the Hel308 motif or extended Hel308 motif discussed above. However, variants may include modifications within these motif(s).

Over the entire length of the amino acid sequence of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58, a variant will preferably be at least 30% homologous to that sequence based on amino acid identity. More preferably, the variant polypeptide may be at least 40%, at least 45%, at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58 over the entire sequence. There may be at least 70%, for example at least 80%, at least 85%, at least 90% or at least 95%, amino acid identity over a stretch of 150 or more, for example 200, 300, 400, 500, 600, 700, 800, 900 or 1000 or more, contiguous amino acids ("hard homology"). Homology is determined as described below. The variant may differ from the wild-type sequence in any of the ways discussed below with reference to SEQ ID NOs: 2 and 4.

A variant of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58 preferably comprises the Hel308 motif or extended Hel308 motif of the wild-type sequence as shown in Table 1 above. However, a variant may comprise the Hel308 motif or extended Hel308 motif from a different wild-type sequence. For instance, a variant of SEQ ID NO: 10 may comprise the Hel308 motif or extended Hel308 motif from SEQ ID NO: 13 (i.e. SEQ ID NO: 14 or 15). Variants of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58 may also include modifications within the Hel308 motif or extended Hel308 motif of the relevant wild-type sequence. Suitable modifications at X1 and X2 are discussed above when defining the two motifs. A variant of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58 preferably comprises one or more substituted cysteine residues and/or one or more substituted Faz residues to facilitate attachment as discussed above.

A variant of SEQ ID NO: 10 may lack the first 19 amino acids of SEQ ID NO: 10 and/or lack the last 33 amino acids of SEQ ID NO: 10. A variant of SEQ ID NO: 10 preferably comprises a sequence which is at least 70%, at least 75%, at least 80%, at least 85%, at least 90% or more preferably at least 95%, at least 97% or at least 99% homologous based on amino acid identity with amino acids 20 to 211 or 20 to 727 of SEQ ID NO: 10.

SEQ ID NO: 10 (Hel308 Mbu) contains five natural cysteine residues. However, all of these residues are located within or around the DNA binding grove of the enzyme. Once a DNA strand is bound within the enzyme, these natural cysteine residues become less accessible for external modifications. This allows specific cysteine mutants of SEQ ID NO: 10 to be designed and attached to the moiety using cysteine linkage as discussed above. Preferred variants of SEQ ID NO: 10 have one or more of the following substitutions: A29C, Q221C, Q442C, T569C, A577C, A700C and S708C. The introduction of a cysteine residue at one or more of these positions facilitates cysteine linkage as discussed above. Other preferred variants of SEQ ID NO: 10 have one or more of the following substitutions: M2Faz, R10Faz, F15Faz, A29Faz, R185Faz, A268Faz, E284Faz, Y387Faz, F400Faz, Y455Faz, E464Faz, E573Faz, A577Faz, E649Faz, A700Faz, Y720Faz, Q442Faz and S708Faz. The introduction of a Faz residue at one or more of these positions facilitates Faz linkage as discussed above.

The helicase is preferably a RecD helicase. Any RecD helicase may be used in accordance with the invention. The structures of RecD helicases are known in the art (FEBS J. 2008 April; 275(8):1835-51. Epub 2008 Mar. 9. ATPase activity of RecD is essential for growth of the Antarctic Pseudomonas syringae Lz4W at low temperature. Satapathy A K, Pavankumar T L, Bhattacharjya S, Sankaranarayanan R. Ray M K; EMS Microbiol Rev. 2009 May; 33(3):657-87. The diversity of conjugative relaxases and its application in plasmid classification. Garcillán-Barcia M P, Francia M V, de la Cruz F; Biol Chem. 2011 Apr. 8; 286(14):12670-82. Epub 2011 Feb. 2. Functional characterization of the multidomain F plasmid TraI relaxase-helicase. Cheng Y, McNamara D E, Miley M J, Nash R P, Redinbo M R).

The RecD helicase typically comprises the amino acid motif X1-X2-X3-G-X4-X5-X6-X7 (hereinafter called the RecD-like motif I; SEQ ID NO: 59), wherein X1 is G, S or A, X2 is any amino acid, X3 is P, A, S or G, X4 is T, A, V, S or C, X5 is G or A, X6 is K or R and X7 is T or S. X1 is preferably G. X2 is preferably G, I, Y or A. X2 is more preferably G. X3 is preferably P or A. X4 is preferably T, A, V or C. X4 is preferably T, V or C. X5 is preferably G. X6 is preferably K. X7 is preferably T or S. The RecD helicase preferably comprises Q-(X8)$_{16-18}$-X1-X2-X3-G-X4-X5-X6-X7 (hereinafter called the extended RecD-like motif I; SEQ NOs: 60, 61 and 62), wherein X1 to X7 are as defined above and X8 is any amino acid. There are preferably 16 X8 residues (i.e. (X8)$_{16}$) in the extended RecD-like motif I (SEQ ID NO: 60). Suitable sequences for (X8)$_{16}$ can be identified in SEQ 14, 17, 20, 23, 26, 29, 32, 35, 38, 41, 44, 47 and 50 of U.S. Patent Application No. 61/581,332 and SEQ ID NOs: 18, 21, 24, 25, 28, 30, 32, 35, 37, 39, 41, 42 and 44 of International Application No. PCT/GB2012/053274 (published as WO 2012/098562).

The RecD helicase preferably comprises the amino acid motif G-G-P-G-Xa-G-K-Xb (hereinafter called the RecD motif I; SEQ ID NO: 63) wherein Xa is T, V or C and Xb is T or S. Xa is preferably T. Xb is preferably I. The Rec-D helicase preferably comprises the sequence G-G-P-G-T-G-K-T (SEQ ID NO: 64). The RecD helicase more preferably comprises the amino acid motif Q-(X8)$_{16-18}$-G-G-P-G-Xa-G-K-Xb (hereinafter called the extended Red) motif I; SEQ ID NO: 65, 66 and 67), wherein Xa and Xb are as defined above and X8 is any amino acid. There are preferably 16 X8 residues (i.e. (X8)$_{16}$) in the extended RecD motif I (SEQ ID NO: 65). Suitable sequences for (X8)$_{16}$ can be identified in SEQ ID NOs: 14, 17, 20, 23, 26, 29, 32, 35, 38, 41, 44, 47 and 50 of U.S. Patent Application No. 61/581,332 and SEQ ID NOs: 18, 21, 24, 25, 28, 30, 32, 35, 37, 39, 41, 42 and 44 of International Application No. PCT/GB2012/053274 (published as WO 2012/098562).

The RecD helicase typically comprises the amino acid motif X1-X2-X3-X4-X5-(X6)$_3$-Q-X7 (hereinafter called the RecD-like motif V; SEQ ID NO: 68), wherein X1 is Y, W or F, X2 is A, T, S, M, C or V, X3 is an amino acid, X4 is T, N or S, X5 is A, T, G, S, V or I, X6 is any amino acid and X7 is G or S. X1 is preferably Y. X2 is preferably A, M, C or V. X2 is more preferably A. X3 is preferably I, M or L. X3 is more preferably I or L. X4 is preferably T or S. X4 is more preferably T. X5 is preferably A, V or I. X5 is more preferably V or I. X5 is most preferably V. (X6)$_3$ is preferably H—K—S, H-M-A, H-G-A or H—R—S. (X6)$_3$ is more preferably H—K—S. X7 is preferably G. The RecD helicase preferably comprises the amino acid motif Xa-Xb-Xc-Xd-Xe-H-K-S-Q-G (hereinafter called the RecD motif V; SEQ ID NO: 69), wherein Xa is Y, W or F, Xb is A, M, C or V, Xc is I, M or L, Xd is T or S and Xe is V or I. Xa is preferably Y. Xb is preferably A. Xd is preferably T. Xd is preferably V. Preferred RecD motifs I are shown in Table 5 of U.S. Patent Application No. 61/581,332. Preferred RecD-like motifs I are shown in Table 7 of U.S. Patent Application No. 61/581,332 and International Application No. PCT/GB2012/053274 (published as WO 2012/098562). Preferred RecD-like motifs V are shown in Tables 5 and 7 of U.S. Patent Application No. 61/581,332 and International Application No. PCT/GB2012/053274 (published as WO 2012/098562).

The RecD helicase is preferably one of the helicases shown in Table 4 or 5 of U.S. Patent Application No. 61/581,332 and International Application No. PCT/GB2012/053274 (published as WO 2012/098562) or a variant thereof. Variants are described in U.S. Patent Application No. 61/581,332 and International Application No. PCT/GB2012/053274 (published as WO 2012/098562).

The RecD helicase is preferably a TraI helicase or a TraI subgroup helicase. TraI helicases and TraI subgroup helicases may contain two RecD helicase domains, a relaxase domain and a C-terminal domain. The TraI subgroup helicase is preferably a TrwC helicase. The TraI helicase or TraI subgroup helicase is preferably one of the helicases shown in Table 6 of U.S. Patent Application No. 61/581,332 and International Application No. PCT/GB2012/053274 (published as WO 2012/098562) or a variant thereof. Variants are described in U.S. Patent Application No. 61/581,332 and International Application No. PCT/GB2012/053274 (published as WO 2012/098562).

The TraI helicase or a TraI subgroup helicase typically comprises a RecD-like motif I as defined above (SD) ID NO: 59) and/or a RecD-like motif V as defined above (SEQ ID NO: 68).

The TraI helicase or a TraI subgroup helicase preferably comprises both a RecD-like motif I (SEQ ID NO: 59) and a RecD-like motif V (SEQ ID NO: 68). The TraI helicase or a TraI subgroup helicase typically further comprises one of the following two motifs:

The amino acid motif H-(X1)$_2$-X2-R-(X3)$_{5-12}$-H-X4-H (hereinafter called the MobF motif III; SEQ ID NOs: 70 to 77), wherein X1 and X2 are any amino acid and X2 and X4 are independently selected from any amino acid except D, K and R. (X1)$_2$ is of course X1a-X1b. X1a and X1b can be the same of different amino acid. X1a is preferably D or E. X1b is preferably T or D. (X1)$_2$ is preferably DT or ED. (X1)$_2$ is most preferably DT. The 5 to 12 amino acids in (X3)$_{5-12}$ can be the same or different. X2 and X4 are independently selected from P, A, V, L, I, M, C, Y, W, H, Q, N, S and T. X2 and X4 are preferably not charged. X2 and X4 are preferably not H. X2 is more preferably N, S or A. X2 is most preferably N. X4 is most preferably F or T. (X3)$_{5-12}$ is preferably 6 or 10 residues in length. Suitable embodiments of (X3)$_{5-12}$ can be derived from SEQ ID NOs: 58, 62, 66 and 70 shown in Table 7 of U.S. Patent Application No. 61/581,332 and SEQ ID NOs: 61, 65, 69, 73, 74, 82, 86, 90, 94, 98, 102, 110, 112, 113, 114, 117, 121, 124, 125, 129, 133, 136, 140, 144, 147, 151, 152, 156, 160, 164 and 168 of International Application No. PCT/GB2012/053274 (published as WO 2012/098562).

The amino acid motif G-X1-X2-X3-X4-X5-X6-X7-H-(X8)$_{6-12}$-H-X9 (hereinafter called the MobQ motif III; SEQ ID NOs: 78 to 84), wherein X1, X2, X3, X5, X6, X7 and X9 are independently selected from any amino acid except D, F, K and R, X4 is D or E and X8 is any amino acid. X1, X2, X3, X6, X7 and X9 are independently selected from G, P, A, V, L, I, M, C, F, Y, W, H, Q, N, S and T. X1, X2, X3, X5, X6, X7 and X9 are preferably not charged. X1, X2, X3, X5, X7 and X9 are preferably not H. The 6 to 12 amino acids in (X8)$_{6-12}$ can be the same or different. Preferred MobF motifs III are shown in Table 7 of U.S. Patent Application No. 61/581,332 and International Application No. PCT/GB2012/053274 (published as WO 2012/098562).

The TraI helicase or TraI subgroup helicase is more preferably one of the helicases shown in Table 6 or 7 of U.S. Patent Application No. 61/581,332 and International Application No. PCT/GB2012/053274 (published as WO 2012/098562) or a variant thereof. The TraI helicase most preferably comprises the sequence shown in SEQ ID NO: 85 or a variant thereof. SEQ ID NO: 85 is TraI Eco (NCBI Reference Sequence: NP_061483.1; Genbank AAQ98619.1; SEQ ID NO: 85). TraI Eco comprises the following motifs: RecD-like motif I (GYAGVGKT; SEQ ID NO: 86), RecD-like motif V (YAITAHGAQG; SEQ ID NO: 87) and Mob F motif III (HDTSRDQEPQLHTH; SEQ ID NO: 88).

The TraI helicase or TraI subgroup helicase more preferably comprises the sequence of one of the helicases shown in Table 3 below, i.e. one of SEQ ID NOs: 85, 126, 134 and 138, or a variant thereof.

(b) amino acids 657 and 339 in SEQ ID NO: 126; (c) amino acids 691 and 350 in SEQ ID NO: 126; or (d) amino acids 690 and 350 in SEQ ID NO: 126. These amino acids are preferably substituted with cysteine such that they can be connected by cysteine linkage.

The invention also provides a mutant TrwC Cba protein which comprises a variant of SEQ ID NO: 126 in which amino acids 691 and 346; 657 and 339; 691 and 350; or 690 and 350 are modified. The amino acids are preferably substituted. The amino acids are more preferably substituted with cysteine. The variant may differ from SEQ ID NO: 126 at positions other than 691 and 346; 657 and 339; 691 and 350; or 690 and 350 as long as the relevant amino acids are modified. The variant will preferably be at least 10% homologous to SEQ ID NO: 126 based on amino acid identity as discussed in more detail below. Amino acid 691 and 346; 657 and 339; 691 and 350; or 690 and 350 are not connected. The mutant TrwC Cba protein of the invention may be used to form a modified helicase of the invention in which the modified amino acids are connected.

A variant of a RecD helicase, TraI helicase or TraI subgroup helicase is an enzyme that has an amino acid sequence which varies from that of the wild-type helicase and which retains polynucleotide binding activity. This can be measured as described above. In particular, a variant of SEQ ID NO: 85, 126, 134 or 138 is an enzyme that has an amino acid sequence which varies from that of SEQ ID NO: 85, 126, 134 or 138 and which retains polynucleotide binding activity. The variant retains helicase activity. The variant must work in at least one of the two modes discussed below. Preferably, the variant works in both modes. The variant may include modifications that facilitate handling of the polynucleotide encoding the helicase and/or facilitate its activity at high salt concentrations and/or room temperature. Variants typically differ from the wild-type helicase in

TABLE 3

More preferred TraI helicase and TraI subgroup helicases

| SEQ ID NO | Name | Strain | NCBI ref | % Identity to TraI Eco | RecD-like motif I (SEQ ID NO:) | RecD-like motif V (SEQ ID NO:) | Mob F motif III (SEQ ID NO:) |
|---|---|---|---|---|---|---|---|
| 85 | TraI Eco | *Escherichia coli* | NCBI Reference Sequence: NP_061483.1 Genbank AAQ98619.1 | — | GYAGVGKT (86) | YAITAHGAQG (87) | HDTSRDQEPQLHTH (88) |
| 126 | TrwC Cba | *Citromicrobium bathyomarinum* JL354 | NCBI Reference Sequence: ZP_06861556.1 | 15% | GIAGAGKS (131) | YALNVHMAQG (132) | HDTNRNQEPNLHFH (133) |
| 134 | TrwC Hne | *Halothiobacillus neapolitanus* c2 | NCBI Reference Sequence: YP_003262832.1 | 11.5% | GAAGAGKT (135) | YCITIHRSQG (136) | HEDARTVDDIADPQLHTH (137) |
| 138 | TrwC Eli | *Erythrobacter litoralis* HTCC2594 | NCBI Reference Sequence: YP_457045.1 | 16% | GIAGAGKS (131) | YALNAHMAQG (139) | HDTNRNQEPNLHFH (133) |

The two or more parts of TrwC Cba connected are preferably (a) amino acids 691 and 346 in SEQ ID NO: 126;

regions outside of the motifs discussed above. However, variants may include modifications within these motif(s).

Over the entire length of the amino acid sequence of any one of SEQ ID NO: 85, 126, 134 and 138, a variant will preferably be at least 10% homologous to that sequence based on amino acid identity. More preferably, the variant polypeptide may be at least 20%, at least 25%, at least 30%, at least 40%, at least 45%, at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of any one of SEQ ID NOs: 85, 126, 134 and 138 over the entire sequence. There may be at least 70%, for example at least 80%, at least 85%, at least 90% or at least 95%, amino acid identity over a stretch of 150 or more, for example 200, 300, 400, 500, 600, 700, 800, 900 or 1000 or more, contiguous amino acids ("hard homology"). Homology is determined as described below. The variant may differ from the wild-type sequence in any of the ways discussed above with reference to SEQ ID NOs: 2 and 4.

A variant of any one of SEQ ID NOs: 85, 126, 134 and 138 preferably comprises the RecD-like motif I and/or RecD-like motif V of the wild-type sequence. However, a variant of SEQ ID NO: 85, 126, 134 or 138 may comprise the RecD-like motif I and/or extended RecD-like motif V from a different wild-type sequence. For instance, a variant may comprise any one of the preferred motifs shown in Tables 5 and 7 of U.S. Patent Application No. 61/581,332 and International Application No. PCT/GB2012/053274 (published as WO 2012/098562). Variants of SEQ ID NOs: 85, 126, 134 and 138 may also include modifications within the RecD-like motifs I and V of the wild-type sequence. A variant of SEQ ID NO: 85, 126, 134 or 138 preferably comprises one or more substituted cysteine residues and/or one or more substituted Faz residues to facilitate attachment as discussed above.

The helicase is preferably an XPD helicase. Any XPD helicase may be used in accordance with the invention. XPD helicases are also known as Rad3 helicases and the two terms can be used interchangeably.

The structures of XPD helicases are known in the art (Cell. 2008 May 30; 133(5):801-12. Structure of the DNA repair helicase XPD. Liu H, Rudolf Johnson K A, McMahon S A, Oke M, Carter L, McRobbie A M, Brown S E, Naismith J H, White M F). The XPD helicase typically comprises the amino add motif X1-X2-X3-G-X4-X5-X6-E-G (hereinafter called XPD motif V; SEQ ID NO: 89). X1, X2, X5 and X6 are independently selected from any amino acid except D, E, K and R, X1. X2, X5 and X6 are independently selected from G, P, A, V, L, I, M, C, F, Y, W, H, Q, N, S and T. X1, X2, X5 and X6 are preferably not charged. X1, X2, X5 and X6 are preferably not H, X1 is more preferably V, L, I, S or Y. X5 is more preferably V, L, I, N or F. X6 is more preferably S or A. X3 and X4 may be any amino acid residue. X4 is preferably K, R or T.

The XPD helicase typically comprises the amino acid motif Q-Xa-Xb-G-R-Xc-Xd-R-(Xe)$_3$-Xf-(Xg)$_7$-D-Xh-R (hereinafter called XPD motif VI; SEQ ID NO: 90). Xa, Xe and Xg may be any amino acid residue. Xb, Xc and Xd are independently selected from any amino acid except D, E, K and R. Xb, Xc and Xd are typically independently selected from G, P, A, V, L, I, M, C, F, Y, W, H, Q, N, S and T, Xb, Xc and Xd are preferably not charged. Xb, Xc and Xd are preferably not H. Xb is more preferably V, A, L, I or M. Xc is more preferably V, A, L, I, M or C. Xd is more preferably I, H, L, F, M or V. Xf may be D or E. (Xg)$_7$ is X$_{g1}$, X$_{g2}$, X$_{g3}$, X$_{g4}$, X$_{g5}$, X$_{g6}$ and X$_{g7}$. X$_{g2}$ is preferably G, A, S or C. X$_{g5}$ is preferably F, V, L, I, M, A, W or Y. X$_{g6}$ is preferably L, F, Y, M, I or V. X$_{g7}$ is preferably A, C, V, L, I, M or S.

The XPD helicase preferably comprises XPD motifs V and VI. The most preferred XPD motifs V and VI are shown in Table 5 of U.S. Patent Application No. 61/581,340 and International Application No. PCT/GB2012/053273 (published as WO 2012/098561).

The XPD helicase preferably further comprises an iron sulphide (FeS) core between two Walker A and B motifs (motifs I and II). An FeS core typically comprises an iron atom coordinated between the sulphide groups of cysteine residues. The FeS core is typically tetrahedral.

The XPD helicase is preferably one of the helicases shown in Table 4 or 5 of U.S. Patent Application No. 61/581,340 and International Application No. PCT/GB2012/053273 (published as WO 2012/098561) or a variant thereof. The XPD helicase most preferably comprises the sequence shown in SEQ ID NO: 91 or a variant thereof. SEQ ID NO: 91 is XPD Mbu (Methanococcoides burtonii; YP_566221.1; GI: 91773529). XPD Mbu comprises YLWGTLSEG (Motif V; SEQ ID NO: 92) and QAMGRV-VRSPTDYGARILLDGR (Motif VI; SEQ ID NO: 93).

A variant of a XPD helicase is an enzyme that has an amino acid sequence which varies from that of the wild-type helicase and which retains polynucleotide binding activity. This can be measured as described above. In particular, a variant of SEQ ID NO: 91 is an enzyme that has an amino acid sequence which varies from that of SEQ ID NO: 91 and which retains polynucleotide binding activity. The variant retains helicase activity. The variant must work in at least one of the two modes discussed below. Preferably, the variant works in both modes. The variant may include modifications that facilitate handling of the polynucleotide encoding the helicase and/or facilitate its activity at high salt concentrations and/or room temperature. Variants typically differ from the wild-type helicase in regions outside of XPD motifs V and VI discussed above. However, variants may include modifications within one or both of these motifs.

Over the entire length of the amino acid sequence of SEQ ID NO: 91, such as SEQ ID NO: 10, a variant will preferably be at least 10%, preferably 30% homologous to that sequence based on amino acid identity. More preferably, the variant polypeptide may be at least 40%, at least 45%, at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 91 over the entire sequence. There may be at least 70%, for example at least 80%, at least 85%, at least 90% or at least 95%, amino acid identity over a stretch of 150 or more, for example 200, 300, 400, 500, 600, 700, 800, 900 or 1000 or more, contiguous amino acids ("hard homology"). Homology is determined as described below. The variant may differ from the wild-type sequence in any of the ways discussed above with reference to SEQ ID NOs: 2 and 4.

A variant of SEQ ID NO: 91 preferably comprises the XPD motif V and/or the XPD motif VI of the wild-type sequence. A variant of SEQ ID NO: 91 more preferably comprises both XPD motifs V and VI of SEQ ID NO: 91. However, a variant of SEQ ID NO: 91 may comprise XPD motifs V and/or VI from a different wild-type sequence. For instance, a variant of SEQ ID NO: 91 may comprise any one of the preferred motifs shown in Table 5 of U.S. Patent Application No. 61/581,340 and International Application No. PCT/GB2012/053273 (published as WO 2012/098561). Variants of SEQ ID NO: 91 may also include modifications within XPD motif V and/or XPD motif VI of the wild-type sequence. Suitable modifications to these motifs are discussed above when defining the two motifs. A variant of SEQ ID NO: 91 preferably comprises one or more substituted cysteine residues and/or one or more substituted Faz residues to facilitate attachment as discussed above.

Modified Hel308 Helicases

The present invention also provides a modified Hel308 helicase that is useful for controlling the movement of a polynucleotide. In accordance with the invention, the helicase is modified by the introduction of one or more cysteine residues and/or one or more non-natural amino acids at one or more of the positions which correspond to D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724 in Hel308 Mbu (SEQ ID NO: 10), wherein the helicase retains its ability to control the movement of a polynucleotide. The one or more cysteine residues and/or one or more non-natural amino acids are preferably introduced by substitution.

These modifications do not prevent the helicase from binding to a polynucleotide. For instance, the helicase may bind to a polynucleotide via internal nucleotides or at one of its termini. These modifications decrease the ability of the polynucleotide to unbind or disengage from the helicase, particularly from internal nucleotides of the polynucleotide. In other words, the one or more modifications increase the processivity of the Hel308 helicase by preventing dissociation from the polynucleotide strand. The thermal stability of the enzyme is also increased by the one or more modifications giving it an improved structural stability that is beneficial in Strand Sequencing. The modified Hel308 helicases of the invention have all of the advantages and uses discussed above.

The modified Hel308 helicase has the ability to control the movement of a polynucleotide. This can be measured as discussed above. The modified Hel308 helicase is artificial or non-natural.

A modified Hel308 helicase of the invention may be isolated, substantially isolated, purified or substantially purified as discussed above.

The Hel308 helicase preferably comprises a variant of one of the helicases shown in Table 1 above which comprises one or more cysteine residues and/or one or more non-natural amino acids at one or more of the positions which correspond to D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724 in Hel308 Mbu (SEQ ID NO: 10). The Hel308 helicase preferably comprises a variant of one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 which comprises one or more cysteine residues and/or one or more non-natural amino acids at one or more of the positions which correspond to D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724 in Hel308 Mbu (SEQ ID NO: 10).

The Hel308 helicase preferably comprises a variant of one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 which comprises one or more cysteine residues and/or one or more non-natural amino acids at one or more of the positions which correspond to D274, E284, E285, E287, S288, T289, G290, E291, N316, K319, S615, K717 or Y720 in Hel308 Mbu (SEQ ID NO: 10).

Table 4a and 4b below show the positions in other Hel308 helicases which correspond to D274, E284, E285, S288, S615, K717, Y720, E287, T289, G290, E291, N316 and K319 in Hel308 Mbu (SEQ ID NO: 10). For instance, in Hel308 Hvo (SEQ ID NO:16), E283 corresponds to D274 in Hel308 Mbu, E293 corresponds to E284 in Hel308 Mbu, I294 corresponds to E285 in Hel308 Mbu, V297 corresponds to S288 in Hel308 Mbu, D671 corresponds to S615 in Hel308 Mbu, K775 corresponds to K717 in Hel308 Mbu and E778 corresponds to Y720 in Hel308 Mbu. The lack of a corresponding position in another Hel308 helicase is marked as a "-".

TABLE 4a

Positions which correspond to D274, E284, E285, S288, S615, K717 and Y720 in Hel308 Mbu (SEQ ID NO: 10).

| SEQ ID NO: | Hel308 homologue | A | B | C | D | E | F | G |
|---|---|---|---|---|---|---|---|---|
| 10 | Mbu | D274 | E284 | E285 | S288 | S615 | K717 | Y720 |
| 13 | Pfu | L265 | E275 | L276 | S279 | P585 | K690 | E693 |
| 16 | Hvo | E283 | E293 | I294 | V297 | D671 | K775 | E778 |
| 19 | Hla | E283 | E293 | I294 | G297 | D668 | R775 | E778 |
| 22 | Csy | D280 | K290 | I291 | S294 | P589 | T694 | N697 |
| 25 | Sso | L281 | K291 | Q292 | D295 | D596 | K702 | Q705 |
| 28 | Mfr | H264 | E272 | K273 | A276 | G576 | K678 | E681 |
| 29 | Mok | S279 | L289 | S290 | D293 | P649 | K753 | R756 |
| 32 | Mig | Y276 | L286 | S287 | D290 | P579 | K679 | K682 |
| 33 | Tga | L266 | S276 | L277 | Q280 | P583 | K689 | D692 |
| 34 | Tba | L287 | E297 | L298 | S301 | S604 | K710 | E713 |
| 37 | Tsi | L289 | Q299 | L300 | G303 | N606 | G712 | E715 |
| 38 | Mba | E274 | D284 | E285 | E288 | S589 | K691 | D694 |
| 39 | Mac | E274 | D284 | E285 | E288 | P590 | K692 | E695 |
| 40 | Mmah | H272 | L282 | S283 | D286 | P621 | K725 | K728 |
| 41 | Mmaz | E274 | D284 | E285 | E288 | P590 | K692 | E698 |
| 42 | Mth | A269 | L279 | A280 | L283 | H575 | K677 | E680 |
| 43 | Mzh | H274 | Q284 | E285 | E288 | P596 | K699 | Q702 |
| 44 | Mev | G274 | E284 | E285 | E288 | T590 | K691 | Y694 |
| 45 | Mma | H272 | L282 | S283 | D286 | P621 | K725 | K728 |
| 46 | Nma | G277 | T287 | E288 | E291 | D634 | K737 | E740 |
| 47 | Mbo | A270 | E277 | R278 | E281 | S583 | G685 | E688 |
| 48 | Fac | Q264 | F267 | E268 | E271 | P559 | K663 | K666 |
| 49 | Mfe | R275 | L285 | S286 | E289 | P576 | K676 | K679 |
| 50 | Mja | I273 | L283 | S284 | E287 | P574 | K674 | K677 |
| 51 | Min | R257 | L267 | S268 | D271 | P554 | K651 | K654 |
| 52 | Mhu | S269 | Q277 | E278 | R281 | S583 | G685 | R688 |
| 53 | Afu | K268 | K277 | A278 | E281 | D575 | R677 | E680 |
| 54 | Htu | D277 | D287 | D288 | D291 | D626 | K729 | E732 |
| 55 | Hpa | D276 | D286 | Q287 | D290 | D595 | K707 | E710 |
| 58 | Hsp (ski2-like helicase) | E286 | E296 | I297 | V300 | D633 | A737 | E740 |

TABLE 4b

Positions which correspond to E287, T289, G290, E291, N316 and K319 in Hel308 Mbu (SEQ ID NO: 10).

| SEQ ID NO: | Hel308 homologue | H | I | J | K | L | M |
|---|---|---|---|---|---|---|---|
| 10 | Mbu | E287 | T289 | G290 | E291 | N316 | K319 |
| 13 | Pfu | D278 | L280 | E281 | E282 | D307 | V310 |
| 16 | Hvo | D296 | S298 | D299 | T300 | E324 | T327 |
| 19 | Hla | S296 | S298 | D299 | T300 | E324 | A327 |
| 22 | Csy | S293 | G295 | G296 | E297 | D322 | S325 |
| 25 | Sso | D294 | I296 | E297 | E298 | A325 | D328 |
| 28 | Mfr | E275 | A277 | A278 | E279 | M304 | T307 |
| 29 | Mok | L292 | N294 | P295 | T296 | E320 | K323 |
| 32 | Mig | L289 | P291 | P292 | T293 | E317 | K320 |
| 33 | Tga | S279 | L281 | L282 | D283 | V308 | T311 |
| 34 | Tba | E300 | L302 | E303 | S304 | A329 | T332 |
| 37 | Tsi | D302 | L304 | D305 | T306 | T331 | S334 |
| 38 | Mba | L287 | N289 | S290 | E291 | P316 | E319 |
| 39 | Mac | L287 | N289 | S290 | E291 | P316 | E319 |

TABLE 4b-continued

Positions which correspond to E287, T289, G290, E291, N316 and K319 in Hel308 Mbu (SEQ ID NO: 10).

| SEQ ID NO: | Hel308 homologue | H | I | J | K | L | M |
|---|---|---|---|---|---|---|---|
| 40 | Mmah | L285 | R287 | P288 | V289 | K313 | K316 |
| 41 | Mmaz | I287 | N289 | S290 | E291 | P316 | E319 |
| 42 | Mth | R282 | S284 | G285 | E286 | E311 | R314 |
| 43 | Mzh | G287 | A289 | G290 | E291 | E316 | R319 |
| 44 | Mev | L287 | T289 | S290 | D291 | A316 | K319 |
| 45 | Mma | L285 | R287 | P288 | V289 | K313 | K316 |
| 46 | Nma | R290 | D292 | S293 | D294 | T319 | S322 |
| 47 | Mbo | L280 | G282 | T283 | P284 | K309 | S312 |
| 48 | Fac | L270 | I272 | P273 | P274 | D299 | T302 |
| 49 | Mfe | L288 | P290 | P291 | T292 | Q316 | K319 |
| 50 | Mja | L286 | P288 | P289 | T290 | Q314 | K317 |
| 51 | Min | F270 | P272 | P273 | T274 | E298 | K301 |
| 52 | Mhu | R280 | L282 | R283 | D284 | Q309 | T312 |
| 53 | Afu | L280 | E282 | N283 | E284 | G309 | R312 |
| 54 | Htu | R290 | D292 | S293 | D294 | T319 | S322 |
| 55 | Hpa | R289 | V291 | S292 | D293 | D318 | S321 |
| 58 | Hsp (ski2-like helicase) | G299 | S301 | D302 | T303 | E327 | E330 |

The Hel308 helicase more preferably comprises a variant of one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 which comprises one or more cysteine residues and/or one or more non-natural amino acids at one or more of the positions which correspond to D274, E284, E285, S288, S615, K717 and Y720 in Hel308 Mbu (SEQ ID NO: 10). The relevant positions are shown in columns A to G in Table 4a above.

The helicase may comprise a cysteine residue at one, two, three, four, five, six or seven of the positions which correspond to D274, E284, E285, S288, S615, K717 and Y720 in Hel308 Mbu (SEQ ID NO: 10). Any combination of these positions may be substituted with cysteine. For instance, for each row of Table 4a above, the helicase of the invention may comprise a cysteine at any of the following combinations of the positions labelled A to G in that row: {A}, {B}, {C}, {D}, {G}, {E}, {F}, {A and B}, {A and C}, {A and D}, {A and G}, {A and E}, {A and F}, {B and C}, {B and D}, {B and G}, {B and E}, {B and F}, {C and D}, {C and G}, {C and E}, {C and F}, {D and G}, {D and E}, {D and F}, {G and E}, {G and F}, {E and F}, {A, B and C}, {A, B and D}, {A, B and G}, {A, B and E}, {A, B and F}, {A, C and D}, {A, C and G}, {A, C and E}, {A, C and F}, {A, D and G}, {A, D and E}, {A, D and F}, {A, G and E}, {A, G and F}, {A, E and F}, {B, C and D}, {B, C and G}, {B, C and E}, {B, C and F}, {B, D and G}, {B, D and E}, {B, D and F}, {B, G and E}, {B, G and F}, {B, E and F}, {C, D and G}, {C, D and E}, {C, D and F}, {C, G and E}, {C, G and F}, {C, E and F}, {D, G and E}, {D, G and F}, {D, E and F}, {G, E and F}, {A, B, C and D}, {A, B, C and G}, {A, B, C and E}, {A, B, C and F}, {A, B, D and G}, {A, B, D and E}, {A, B, D and F}, {A, B, G and E}, {A, B, G and F}, {A, B, E and F}, {A, C, D and G}, {A, C, D and E}, {A, C, D and F}, {A, C, G and E}, {A, C, G and F}, {A, C, E and F}, {A, D, G and E}, {A, D, G and F}, {A, D, E and F}, {A, G, E and F}, {B, C, D and G}, {B, C, D and E}, {B, C, D and F}, {B, C, G and E}, {B, C, G and F}, {B, C, E and F}, {B, D, G and E}, {B, D, G and F}, {B, D, E and F}, {B, G, E and F}, {C, D, G and E}, {C, D, G and F}, {C, D, E and F}, {C, G, E and F}, {D, G, E and F}, {A, B, C, D and G}, {A, B, C, D and E}, {A, B, C, G and E}, {A, B, C, G and F}, {A, B, C, E and F}, {A, B, D, G and E}, {A, B, D, G and F}, {A, B, D, E and F}, {A, B, G, E and F}, {A, C, D, G and E}, {A, C, D, G and F}, {A, C, D, E and F}, {A, C, G, E and F}, {A, D, G, E and F}, {B, C, D, G and E}, {B, C, D, G and F}, {B, C, D, E and F}, {B, C, G, E and F}, {C, D, G, E and F}, {A, B, C, D, G and E}, {A, B, C, D, G and F}, {A, B, C, D, E and F}, {A, B, C, G, E and F}, {A, B, D, G, E and F}, {A, C, D, G, E and F}, {B, C, D, G, E and F}, or {A, B, C, D, G, E and F}.

The helicase may comprises a non-natural amino acid, such as Faz, at one, two, three, four, five, six or seven of the positions which correspond to D274, E284, E285, S288, S615, K717 and Y720 in Hel308 Mbu (SEQ ID NO: 10). Any combination of these positions may be substituted with a non-natural amino acid, such as Faz. For instance, for each row of Table 4a above, the helicase of the invention may comprise a non-natural amino acid, such as Faz, at any of the combinations of the positions labelled A to G above.

The helicase may comprise a combination of one or more cysteines and one or more non-natural amino acids, such as Faz, at two or more of the positions which correspond to D274, E284, E285, S288, S615, K717 and Y720 in Hel308 Mbu (SEQ ID NO: 10). Any combination of one or more cysteine residues and one or more non-natural amino acids, such as Faz, may be present at the relevant positions. For instance, for each row of Table 4a and 4b above, the helicase of the invention may comprise one or more cysteines and one or more non-natural amino acids, such as Faz, at any of the combinations of the positions labelled A to G above.

The Hel308 helicase more preferably comprises a variant of one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 which comprises one or more cysteine residues and/or one or more non-natural amino acids at one or more of the positions which correspond to D274, E284, E285, S288 and S615 in Hel308 Mbu (SEQ ID NO: 10). The relevant positions are shown in columns A to E in Table 4a above.

The helicase may comprise a cysteine residue at one, two, three, four or five, six or seven of the positions which correspond to D274, E284, E285, S288, S615, K717 and Y720 in Hel308 Mbu (SEQ ID NO: 10). Any combination of these positions may be substituted with cysteine. For instance, for each row of Table 4a above, the helicase of the invention may comprise a cysteine at any of the following combinations of the positions labelled A to E in that row: {A}, {B}, {C}, {D}, {E}, {A and B}, {A and C}, {A and D}, {A and E}, {B and C}, {B and D}, {B and E}, {C and D}, {C and E}, {D and E}, {A, B and C}, {A, B and D}, {A, B and E}, {A, C and D}, {A, C and E}, {A, D and E}, {B, C and D}, {B, C and E}, {B, D and E}, {C, D and E}, {A, B, C and D}, {A, B, C and E}, {A, B, D and E}, {A, C, D and E}, {B, C, D and E} or {A, B, C, D and E}.

The helicase may comprises a non-natural amino acid, such as Faz, at one, two, three, four or five of the positions which correspond to D274, E284, E285, S288, S615, K717 and Y720 in Hel308 Mbu (SEQ ID NO: 10). Any combination of these positions may be substituted with a non-natural amino acid, such as Faz. For instance, for each row of Table 4a above, the helicase of the invention may comprise a non-natural amino acid, such as Faz, at any of the combinations of the positions labelled A to E above.

The helicase may comprise a combination of one or more cysteines and one or more non-natural amino acids, such as Faz, at two or more of the positions which correspond to D274, E284, E285, S288 and S615 in Hel308 Mbu (SEQ ID NO: 10). Any combination of one or more cysteine residues and one or more non-natural amino acids, such as Faz, may be present at the relevant positions. For instance, for each row of Table 4a above, the helicase of the invention may comprise one or more cysteines and one or more non-natural amino acids, such as Faz, at any of the combinations of the positions labelled A to E above.

The Hel308 helicase preferably comprises a variant of the sequence of Hel308 Mbu (i.e. SEQ ID NO: 10) which comprises one or more cysteine residues and/or one or more non-natural amino acids at D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724. The variant preferably comprises D272C, N273C, D274C, G281C, E284C, E285C, E287C, S288C, T289C, G290C, E291C, D293C, T294C, N300C, R303C, K304C, N314C, S315C, N316C, H317C, R318C, K319C, L320C, E322C, R326C, N328C, S615C, K717C, Y720C, N721C or S724C. The variant preferably comprises D272Faz, N273Faz, D274Faz, G281Faz, E284Faz, E285Faz, E287Faz, S288Faz, T289Faz, G290Faz, E291Faz, D293Faz, T294Faz, N300Faz, R303Faz, K304Faz, N314Faz, S315Faz, N316Faz, H317 Faz, R318Faz, K319Faz, L320Faz, E322Faz, R326Faz, N328Faz, S615Faz, K717Faz, Y720Faz, N721Faz or S724Faz.

The Hel308 helicase preferably comprises a variant of the sequence of Hel308 Mbu (i.e. SEQ ID NO: 10) which comprises one or more cysteine residues and/or one or more non-natural amino acids at D274, E284, E285, S288, S615, K717 and Y720. The helicase of the invention may comprise one or more cysteines, one or more non-natural amino acids, such as Faz, or a combination thereof at any of the combinations of the positions labelled A to G above.

The Hel308 helicase preferably comprises a variant of the sequence of Hel308 Mbu (i.e. SEQ ID NO: 10) which comprises one or more cysteine residues and/or one or more non-natural amino acids at one or more of D274, E284, E285, S288 and S615. For instance, for Hel308 Mbu (SEQ ID NO: 10), the helicase of the invention may comprise a cysteine or a non-natural amino acid, such as Faz, at any of the following combinations of positions: {D274}, {E284}, {E285}, {S288}, {S615}, {D274 and E284}, {D274 and E285}, {D274 and S288}, {D274 and S615}, {E284 and E285}, {E284 and S288}, {E284 and S615}, {E285 and S288}, {E285 and S615}, {S288 and S615}, {D274, E284 and E285}, {D274, E284 and S288}, {D274, E284 and S615}, {D274, E285 and S288}, {D274, E285 and S615}, {D274, S288 and S615}, {E284, E285 and S288}, {E284, E285 and S615}, {E284, S288 and S615}, {E285, S288 and S615}, {D274, E284, E285 and S288}, {D274, E284, E285 and S615}, {D274, E284, S288 and S615}, {D274, E285, S288 and S615}, {E284, E285, S288 and S615} or {D274, E284, E285, S288 and S615}.

The helicase preferably comprises a variant of SEQ ID NO: 10 which comprises (a) E284C and S615C, (b), E284Faz and S615Faz, (c) E284C and S615Faz or (d) E284Faz and S615C.

The helicase more preferably comprises the sequence shown in SEQ ID NO: 10 with E284C and S615C.

Preferred non-natural amino acids for use in the invention include, but are not limited to 4-Azido-L-phenylalanine (Faz), 4-Acetyl-L-phenylalanine, 3-Acetyl-L-phenylalanine, 4-Acetoacetyl-L-phenylalanine, O-Allyl-L-tyrosine, 3-(Phenylselanyl)-L-alanine, O-2-Propyn-1-yl-L-tyrosine, 4-(Dihydroxyboryl)-L-phenylalanine, 4-[(Ethylsulfanyl) carbonyl]-L-phenylalanine, (2S)-2-amino-3-{4-[(propan-2-ylsulfanyl)carbonyl]phenyl}propanoic acid, (2S)-2-amino-3-{4-[(2-amino-3-sulfanylpropanoyl)amino] phenyl}propanoic acid, O-Methyl-L-tyrosine, 4-Amino-L-phenylalanine, 4-Cyano-L-phenylalanine, 3-Cyano-L-phenylalanine, 4-Fluoro-L-phenylalanine, 4-Iodo-L-phenylalanine, 4-Bromo-L-phenylalanine, O-(Trifluoromethyl)tyrosine, 4-Nitro-L-phenylalanine, 3-Hydroxy-L-tyrosine, 3-Amino-L-tyrosine, 3-Iodo-L-tyrosine, 4-Isopropyl-L-phenylalanine, 3-(2-Naphthyl)-L-alanine, 4-Phenyl-L-phenylalanine, (2S)-2-amino-3-(naphthalen-2-ylamino)propanoic acid, 6-(Methylsulfanyl) norleucine, 6-Oxo-L-lysine, D-tyrosine, (2R)-2-Hydroxy-3-(4-hydroxyphenyl)propanoic acid, (2R)-2-Ammoniooctanoate3-(2,2'-Bipyridin-5-yl)-D-alanine, 2-amino-3-(8-hydroxy-3-quinolyl)propanoic acid, 4-Benzoyl-L-phenylalanine, S-(2-Nitrobenzyl)cysteine, (2R)-2-amino-3-[(2-nitrobenzyl)sulfanyl]propanoic acid, (2S)-2-amino-3-[(2-nitrobenzyl)oxy]propanoic acid, O-(4,5-Dimethoxy-2-nitrobenzyl)-L-serine, (2S)-2-amino-6-({[(2-nitrobenzyl)oxy]carbonyl}amino)hexanoic acid, O-(2-Nitrobenzyl)-L-tyrosine, 2-Nitrophenylalanine, 4-[(E)-Phenyldiazenyl]-L-phenylalanine, 4-[3-(Trifluoromethyl)-3H-diaziren-3-yl]-D-phenylalanine, 2-amino-3-[[5-(dimethylamino)-1-naphthyl]sulfonylamino]propanoic acid, (2S)-2-amino-4-(7-hydroxy-2-oxo-2H-chromen-4-yl)butanoic acid, (2S)-3-[(6-acetylnaphthalen-2-yl)amino]-2-aminopropanoic acid, 4-(Carboxymethyl)phenylalanine, 3-Nitro-L-tyrosine, O-Sulfo-L-tyrosine, (2R)-6-Acetamido-2-ammoniohexanoate, 1-Methylhistidine, 2-Aminononanoic acid, 2-Aminodecanoic acid, L-Homocysteine, 5-Sulfanylnorvaline, 6-Sulfanyl-L-norleucine, 5-(Methylsulfanyl)-L-norvaline, $N^6$-{[(2R,3R)-3-Methyl-3,4-dihydro-2H-pyrrol-2-yl]carbonyl}-L-lysine, $N^6$-[(Benzyloxy)carbonyl]lysine, (2S)-2-amino-6-[(cyclopentylcarbonyl)amino] hexanoic acid, $N^6$-[(Cyclopentyloxy)carbonyl]-L-lysine, (2S)-2-amino-6-{[(2R)-tetrahydrofuran-2-ylcarbonyl] amino}hexanoic acid, (2S)-2-amino-8-[(2R,3S)-3-ethynyltetrahydrofuran-2-yl]-8-oxooctanoic acid, $N^6$-(tert-Butoxycarbonyl)-L-lysine, (2S)-2-Hydroxy-6-({[(2-methyl-2-propanyl)oxy]carbonyl}amino)hexanoic acid, $N^6$-[(Allyloxy)carbonyl]lysine, (2S)-2-amino-6-({[(2-azidobenzyl)oxy]carbonyl}amino)hexanoic acid, $N^6$-L-Prolyl-L-lysine, (2S)-2-amino-6-{[(prop-2-yn-1-yloxy) carbonyl]amino}hexanoic acid and $N^6$-[(2-Azidoethoxy) carbonyl]-L-lysine.

The most preferred non-natural amino acid is 4-azido-L-phenylalanine (Faz).

As discussed above, variant of a Hel308 helicase is an enzyme that has an amino acid sequence which varies from that of the wild-type helicase and which retains polynucleotide binding activity. In the Hel308 helicases of the invention, a variant of one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 may comprise additional modifications as long as it comprises one or more cysteine residues and/or one or more non-natural amino acids at one or more of the positions which correspond to D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724 in Hel308 Mbu (SEQ ID NO: 10). Suitable modifications and variants are discussed above with reference to the embodiments with two or more parts connected.

A variant may comprise the mutations in domain 5 disclosed in Woodman et al. (J. Mol. Biol. (2007) 374, 1139-1144). These mutations correspond to R685A, R687A and R689A in SEQ ID NO: 10.

Connecting Two or More Parts of the Hel308 Helicases of the Invention

The Hel308 helicases modified in the invention comprise a polynucleotide binding domain. Polynucleotide binding domains are defined above. The polynucleotide binding domain of an unmodified Hel308 helicase for use in the invention comprises an opening through which a polynucleotide can unbind from the helicase.

In a preferred embodiment, the Hel308 helicase is further modified such that two or more parts of the helicase are connected to reduce the size of an opening in the polynucleotide binding domain through which a polynucleotide can unbind from the helicase. The two or more parts may be connected in any of the ways discussed above.

No Connection

In another embodiment, the Hel308 helicase is not modified such that two or more parts of the helicase are connected to reduce the size of an opening in the polynucleotide binding domain through which a polynucleotide can unbind from the helicase. Preferably, none of the one or more cysteines or one or more non-natural amino acids is connected to another amino acid in the helicase. Preferably, no two amino acids in the helicase are connected together via their natural or non-natural R groups.

Construct

The invention also provides a construct comprising a helicase of the invention and an additional polynucleotide binding moiety, wherein the helicase is attached to the polynucleotide binding moiety and the construct has the ability to control the movement of a polynucleotide. The helicase is attached to the additional polynucleotide binding moiety. The construct is artificial or non-natural.

A construct of the invention is a useful tool for controlling the movement of a polynucleotide during Strand Sequencing. A construct of the invention is even less likely than a modified helicase of the invention to disengage from the polynucleotide being sequenced. The construct can provide even greater read lengths of the polynucleotide as it controls the translocation of the polynucleotide through a nanopore.

A targeted construct that binds to a specific polynucleotide sequence can also be designed. As discussed in more detail below, the polynucleotide binding moiety may bind to a specific polynucleotide sequence and thereby target the helicase portion of the construct to the specific sequence.

The construct has the ability to control the movement of a polynucleotide. This can be determined as discussed above.

A construct of the invention may be isolated, substantially isolated, purified or substantially purified. A construct is isolated or purified if it is completely free of any other components, such as lipids, polynucleotides or pore monomers. A construct is substantially isolated if it is mixed with carriers or diluents which will not interfere with its intended use. For instance, a construct is substantially isolated or substantially purified if it is present in a form that comprises less than 10%, less than 5%, less than 2% or less than 1% of other components, such as lipids, polynucleotides or pore monomers.

The helicase is preferably covalently attached to the additional polynucleotide binding moiety. The helicase may be attached to the moiety at more than one, such as two or three, points.

The helicase can be covalently attached to the moiety using any method known in the art. Suitable methods are discussed above with reference to connecting the two or more parts.

The helicase and moiety may be produced separately and then attached together. The two components may be attached in any configuration. For instance, they may be attached via their terminal (i.e. amino or carboxy terminal) amino acids. Suitable configurations include, but are not limited to, the amino terminus of the moiety being attached to the carboxy terminus of the helicase and vice versa. Alternatively, the two components may be attached via amino acids within their sequences. For instance, the moiety may be attached to one or more amino acids in a loop region of the helicase. In a preferred embodiment, terminal amino acids of the moiety are attached to one or more amino acids in the loop region of a helicase.

In a preferred embodiment, the helicase is chemically attached to the moiety, for instance via one or more linker molecules as discussed above. In another preferred embodiment, the helicase is genetically fused to the moiety. A helicase is genetically fused to a moiety if the whole construct is expressed from a single polynucleotide sequence. The coding sequences of the helicase and moiety may be combined in any way to form a single polynucleotide sequence encoding the construct. Genetic fusion of a pore to a nucleic acid binding protein is discussed in International Application No. PCT/GB09/001679 (published as WO 2010/004265).

The helicase and moiety may be genetically fused in any configuration. The helicase and moiety may be fused via their terminal amino acids. For instance, the amino terminus of the moiety may be fused to the carboxy terminus of the helicase and vice versa. The amino acid sequence of the moiety is preferably added in frame into the amino acid sequence of the helicase. In other words, the moiety is preferably inserted within the sequence of the helicase. In such embodiments, the helicase and moiety are typically attached at two points, i.e. via the amino and carboxy terminal amino acids of the moiety. If the moiety is inserted within the sequence of the helicase, it is preferred that the amino and carboxy terminal amino acids of the moiety are in close proximity and are each attached to adjacent amino acids in the sequence of the helicase or variant thereof. In a preferred embodiment, the moiety is inserted into a loop region of the helicase.

The construct retains the ability of the helicase to control the movement of a polynucleotide. This ability of the helicase is typically provided by its three dimensional structure that is typically provided by its β-strands and α-helices. The α-helices and β-strands are typically connected by loop regions. In order to avoid affecting the ability of the helicase to control the movement of a polynucleotide, the moiety is preferably genetically fused to either end of the helicase or inserted into a surface-exposed loop region of the helicase. The loop regions of specific helicases can be identified using methods known in the art. In the Hel308 embodiments of the invention, the moiety is preferably not genetically fused to any of the α-helixes.

The helicase may be attached directly to the moiety. The helicase is preferably attached to the moiety using one or more, such as two or three, linkers as discussed above. The one or more linkers may be designed to constrain the mobility of the moiety. The helicase and/or the moiety may be modified to facilitate attachment of the one or more linker as discussed above.

Cleavable linkers can be used as an aid to separation of constructs from non-attached components and can be used to further control the synthesis reaction. For example, a heterobifunctional linker may react with the helicase, but not the moiety. If the free end of the linker can be used to bind the helicase protein to a surface, the unreacted helicases from the first reaction can be removed from the mixture. Subsequently, the linker can be cleaved to expose a group that reacts with the moiety. In addition, by following this sequence of linkage reactions, conditions may be optimised first for the reaction to the helicase, then for the reaction to the moiety after cleavage of the linker. The second reaction would also be much more directed towards the correct site of reaction with the moiety because the linker would be confined to the region to which it is already attached.

The helicase may be covalently attached to the bifunctional crosslinker before the helicase/crosslinker complex is covalently attached to the moiety. Alternatively, the moiety may be covalently attached to the bifunctional crosslinker before the bifunctional crosslinker/moiety complex is attached to the helicase. The helicase and moiety may be covalently attached to the chemical crosslinker at the same time.

Preferred methods of attaching the helicase to the moiety are cysteine linkage and Faz linkage as described above. In a preferred embodiment, a reactive cysteine is presented on a peptide linker that is genetically attached to the moiety. This means that additional modifications will not necessarily be needed to remove other accessible cysteine residues from the moiety.

Cross-linkage of helicases or moieties to themselves may be prevented by keeping the concentration of linker in a vast excess of the helicase and/or moiety. Alternatively, a "lock and key" arrangement may be used in which two linkers are used. Only one end of each linker may react together to form a longer linker and the other ends of the linker each react with a different part of the construct (i.e. helicase or moiety). This is discussed in more detail below.

The site of attachment is selected such that, when the construct is contacted with a polynucleotide, both the helicase and the moiety can bind to the polynucleotide and control its movement.

Attachment can be facilitated using the polynucleotide binding activities of the helicase and the moiety. For instance, complementary polynucleotides can be used to bring the helicase and moiety together as they hybridize. The helicase can be bound to one polynucleotide and the moiety can be bound to the complementary polynucleotide. The two polynucleotides can then be allowed to hybridise to each other. This will bring the helicase into close contact with the moiety, making the linking reaction more efficient. This is especially helpful for attaching two or more helicases in the correct orientation for controlling movement of a target polynucleotide. An example of complementary polynucleotides that may be used are shown below.

Region of Overlap

For helicase-Phi29 constructs the DNA below could be used.

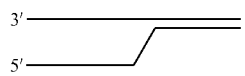

Tags can be added to the construct to make purification of the construct easier. These tags can then be chemically or enzymatically cleaved off, if their removal is necessary. Fluorophores or chromophores can also be included, and these could also be cleavable.

A simple way to purify the construct is to include a different purification tag on each protein (i.e. the helicase and the moiety), such as a hexa-His-tag and a Strep-Tag®. If the two proteins are different from one another, this method is particularly useful. The use of two tags enables only the species with both tags to be purified easily.

If the two proteins do not have two different tags, other methods may be used. For instance, proteins with free surface cysteines or proteins with linkers attached that have not reacted to form a construct could be removed, for instance using an iodoacetamide resin for maleimide linkers.

Constructs of the invention can also be purified from unreacted proteins on the basis of a different DNA processivity property. In particular, a construct of the invention can be purified from unreacted proteins on the basis of an increased affinity for a polynucleotide, a reduced likelihood of disengaging from a polynucleotide once bound and/or an increased read length of a polynucleotide as it controls the translocation of the polynucleotide through a nanopore A targeted construct that binds to a specific polynucleotide sequence can also be designed. As discussed in more detail below, the polynucleotide binding moiety may bind to a specific polynucleotide sequence and thereby target the helicase portion of the construct to the specific sequence.

Polynucleotide Binding Moiety

The constructs of the invention comprise a polynucleotide binding moiety. A polynucleotide binding moiety is a polypeptide that is capable of binding to a polynucleotide. The moiety is preferably capable of specific binding to a defined polynucleotide sequence. In other words, the moiety preferably binds to a specific polynucleotide sequence, but displays at least 10 fold less binding to different sequences or more preferably at least 100 fold less binding to different sequences or most preferably at least 1000 fold less binding to different sequences. The different sequence may be a random sequence. In some embodiments, the moiety binds to a specific polynucleotide sequence, but binding to different sequences cannot be measured. Moieties that bind to specific sequences can be used to design constructs that are targeted to such sequences.

The moiety typically interacts with and modifies at least one property of a polynucleotide. The moiety may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the target polynucleotide can be oxidized or methylated. One or more nucleotides in the target polynucleotide may be damaged. For instance, the polynucleotide may comprise a pyrimidine dimer. Such dimers are typically associated with damage by ultraviolet light and are the primary cause of skin melanomas. One or more nucleotides in the target polynucleotide may be modified, for instance with a label or a tag. Suitable labels are described above. The target polynucleotide may comprise one or more spacers.

A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), guanosine monophosphate (GMP), thymidine monophosphate (TMP), uridine monophosphate (UMP), cytidine monophosphate (CMP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP) and deoxycytidine monophosphate (dCMP). The nucleotides are preferably selected from AMP, TMP, GMP, CMP, UMP, dAMP, dTMP, dGMP, dCMP and dUMP.

A nucleotide may be abasic (i.e. lack a nucleobase). A nucleotide may also lack a nucleobase and a sugar (i.e. is a C3 spacer).

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be single stranded or double stranded. At least a portion of the polynucleotide is preferably double stranded.

The polynucleotide can be a nucleic acid, such as deoxyribonucleic acid (DNA) or ribonucleic acid (RNA). The target polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains.

It is preferred that the tertiary structure of the moiety is known. Knowledge of the three dimensional structure of the moiety allows modifications to be made to the moiety to facilitate its function in the construct of the invention.

The moiety may be any size and have any structure. For instance, the moiety may be an oligomer, such as a dimer or trimer. The moiety is preferably a small, globular polypeptide formed from one monomer. Such moieties are easy to handle and are less likely to interfere with the ability of the helicase to control the movement of the polynucleotide, particularly if fused to or inserted into the sequence of the helicase.

The amino and carboxy terminii of the moiety are preferably in close proximity. The amino and carboxy terminii of the moiety are more preferably presented on same face of the moiety. Such embodiments facilitate insertion of the moiety into the sequence of the helicase. For instance, if the amino and carboxy terminii of the moiety are in close proximity, each can be attached by genetic fusion to adjacent amino acids in the sequence of the helicase.

It is also preferred that the location and function of the active site of the moiety is known. This prevents modifications being made to the active site that abolish the activity of the moiety. It also allows the moiety to be attached to the helicase so that the moiety binds to the polynucleotide and controls its movement. Knowledge of the way in which a moiety may bind to and orient polynucleotides also allows an effective construct to be designed.

The constructs of the invention are useful in Strand Sequencing. The moiety preferably binds the polynucleotide in a buffer background which is compatible with Strand Sequencing and the discrimination of the nucleotides. The moiety preferably has at least residual activity in a salt concentration well above the normal physiological level, such as from 100 mM to 2M. The moiety is more preferably modified to increase its activity at high salt concentrations. The moiety may also be modified to improve its processivity, stability and shelf life.

Suitable modifications can be determined from the characterisation of polynucleotide binding moieties from extremphiles such as halophilic, moderately halophilic bacteria, thermophilic and moderately thermophilic organisms, as well as directed evolution approaches to altering the salt tolerance, stability and temperature dependence of mesophilic or thermophilic exonucleases.

The polynucleotide binding moiety preferably comprises one or more domains independently selected from helix-hairpin-helix (HhH) domains, eukaryotic single-stranded binding proteins (SSBs), bacterial SSBs, archaeal SSBs, viral SSBs, double-stranded binding proteins, sliding clamps, processivity factors, DNA binding loops, replication initiation proteins, telomere binding proteins, repressors, zinc fingers and proliferating cell nuclear antigens (PCNAs).

The helix-hairpin-helix (HhH) domains are polypeptide motifs that bind DNA in a sequence non-specific manner. They have been shown to confer salt stability and processivity when fused to polymerases, as well as increasing their thermal stability. Suitable domains include domain H (residues 696-751) and domain HI (residues 696-802) from Topoisomerase V from *Methanopyrus kandleri* (SEQ ID NO: 129). As discussed below, the polynucleotide binding moiety may be domains H-L of SEQ ID NO: 129 as shown in SEQ ID NO: 130. Topoisomerase V from *Methanopyrus kandleri* is an example of a double-stranded binding protein as discussed below.

The HhH domain preferably comprises the sequence shown in SEQ ID NO: 94 or 107 or 108 or a variant thereof. This domain increases the processivity and the salt tolerance of a helicase when used in a construct of the invention. A variant of SEQ ID NO: 94 or 107 or 108 is a protein that has an amino acid sequence which varies from that of SEQ ID NO: 94 or 107 or 108 and which retains polynucleotide binding activity. This can be measured as described above. A variant typically has at least 50% homology to SEQ ID NO: 94 or 107 or 108 based on amino acid identity over its entire sequence (or any of the % homologies discussed above in relation to helicases) and retains polynucleotide binding activity. A variant may differ from SEQ ID NO: 94 or 107 or 108 in any of the ways discussed above in relation to helicases or below in relation to pores. A variant preferably comprises one or more substituted cysteine residues and/or one or more substituted Faz residues to facilitate attachment to the helicase as discussed above.

SSBs bind single stranded DNA with high affinity in a sequence non-specific manner. They exist in all domains of life in a variety of forms and bind DNA either as monomers or multimers. Using amino acid sequence alignment and logorithms (such as Hidden Markov models) SSBs can be classified according to their sequence homology. The Pfam family, PF00436, includes proteins that all show sequence similarity to known SSBs. This group of SSBs can then be further classified according to the Structural Classification of Proteins (SCOP). SSBs fall into the following lineage: Class; All beta proteins, Fold; OB-fold, Superfamily: Nucleic acid-binding proteins, Family; Single strand DNA-binding domain, SSB. Within this family SSBs can be classified according to subfamilies, with several type species often characterised within each subfamily.

The SSB may be from a eukaryote, such as from humans, mice, rats, fungi, protozoa or plants, from a prokaryote, such as bacteria and archaea, or from a virus.

Eukariotic SSBs are known as replication protein A (RPAs). In most cases, they are hetero-trimers formed of different size units. Some of the larger units (e.g. RPA70 of *Saccharomyces cerevisiae*) are stable and bind ssDNA in monomeric form.

Bacterial SSBs bind DNA as stable homo-tetramers (e.g. *E. coli, Mycobacterium smegmatis* and *Helicobacter pylori*) or homo-dimers (e.g. *Deinococcus radiodurans* and *Thermotoga maritima*). The SSBs from archaeal genomes are considered to be related with eukaryotic RPAs. Few of them, such as the SSB encoded by the crenarchaeote *Sulfolobus solfataricus*, are homo-tetramers. The SSBs from most other species are closer related to the replication proteins from eukaryotes and are referred to as RPAs. In some of these species they have been shown to be monomeric (*Methanococcus jannaschii* and *Methanothermobacter thermoautotrophicum*). Still, other species of Archaea, including *Archaeoglobus fulgidus* and *Methanococcoides burtonii*, appear to each contain two open reading frames with sequence similarity to RPAs. There is no evidence at protein level and no published data regarding their DNA binding capabilities or oligomeric state. However, the presence of two oligonucleotide/oligosaccharide (OB) folds in each of these genes (three OB folds in the case of one of the *M. burtonii* ORFs) suggests that they also bind single stranded DNA.

Viral SSBs bind DNA as monomers. This, as well as their relatively small size renders them amenable to genetic fusion to other proteins, for instance via a flexible peptide linker. Alternatively, the SSBs can be expressed separately and attached to other proteins by chemical methods (e.g. cysteines, unnatural amino-acids). This is discussed in more detail below.

The SSB is preferably either (i) an SSB comprising a carboxy-terminal (C-terminal) region which does not have a net negative charge or (ii) a modified SSB comprising one or more modifications in its C-terminal region which decreases the net negative charge of the C-terminal region. Such SSBs do not block the transmembrane pore and therefore allow characterization of the target polynucleotide.

Examples of SSBs comprising a C-terminal region which does not have a net negative charge include, but are not limited to, the human mitochondrial SSB (HsmtSSB; SEQ ID NO: 118, the human replication protein A 70 kDa subunit, the human replication protein A 14 kDa subunit, the telomere end binding protein alpha subunit from *Oxytricha nova*, the core domain of telomere end binding protein beta subunit from *Oxytricha nova*, the protection of telomeres protein 1 (Pot1) from *Schizosaccharomyces pombe*, the human Pot1, the OB-fold domains of BRCA2 from mouse or rat, the p5 protein from phi29 (SEQ ID NO: 119) or a variant of any of those proteins. A variant is a protein that has an amino acid sequence which varies from that of the wild-type protein and which retains single stranded polynucleotide binding activity. Polynucleotide binding activity can be determined using methods known in the art (and as described above). For instance, the ability of a variant to bind a single stranded polynucleotide can be determined as described in the Examples.

A variant of SEQ ID NO 118 or 119 typically has at least 50% homology to SEQ ID NO: 118 or 119 based on amino acid identity over its entire sequence (or any of the % homologies discussed above in relation to helicases) and retains single stranded polynucleotide binding activity. A variant may differ from SEQ ID NO: 118 or 119 in any of the ways discussed above in relation to helicases. In particular, a variant may have one or more conservative substitutions as shown in Tables 8 and 9.

Examples of SSBs which require one or more modifications in their C-terminal region to decrease the net negative charge include, but are not limited to, the SSB of *E. coli* (EcoSSB; SEQ ID NO: 120, the SSB of *Mycobacterium tuberculosis*, the SSB of *Deinococcus radiodurans*, the SSB of *Thermus thermophiles*, the SSB from *Sulfolobus solfataricus*, the human replication protein A 32 kDa subunit (RPA32) fragment, the CDC13 SSB from *Saccharomyces cerevisiae*, the Primosomal replication protein N (PriB) from *E. coli*, the PriB from *Arabidopsis thaliana*, the hypothetical protein At4g28440, the SSB from T4 (gp32; SEQ ID NO: 121), the SSB from RB69 (gp32; SEQ ID NO: 95), the SSB from T7 (gp2.5; SEQ ID NO: 96) or a variant of any of these proteins. Hence, the SSB used in the method of the invention may be derived from any of these proteins.

In addition to the one or more modifications in the C-terminal region, the SSB used in the method may include additional modifications which are outside the C-terminal region or do not decrease the net negative charge of the C-terminal region. In other words, the SSB used in the method of the invention is derived from a variant of a wild-type protein. A variant is a protein that has an amino acid sequence which varies from that of the wild-type protein and which retains single stranded polynucleotide binding activity. Polynucleotide binding activity can be determined as discussed above.

The SSB used in the invention may be derived from a variant of SEQ ID NO: 95, 96, 120 or 121. In other words, a variant of SEQ ID NO: 95, 96, 120 or 121 may be used as the starting point for the SSB used in the invention, but the SSB actually used further includes one or more modifications in its C-terminal region which decreases the net negative charge of the C-terminal region. A variant of SEQ ID NO: 95, 96, 120 or 121 typically has at least 50% homology to SEQ ID NO: 95, 96, 120 or 121 based on amino acid identity over its entire sequence (or any of the % homologies discussed above in relation to helicases) and retains single stranded polynucleotide binding activity. A variant may differ from SEQ ID NO: 95, 96, 120 or 121 in any of the ways discussed above in relation to helicases. In particular, a variant may have one or more conservative substitutions as shown in Tables 8 and 9.

It is straightforward to identify the C-terminal region of the SSB in accordance with normal protein N to C nomenclature. The C-terminal region of the SSB is preferably about the last third of the SSB at the C-terminal end, such as the last third of the SSB at the C-terminal end. The C-terminal region of the SSB is more preferably about the last quarter, fifth or eighth of the SSB at the C-terminal end, such as the last quarter, fifth or eighth of the SSB at the C-terminal end. The last third, quarter, fifth or eighth of the SSB may be measured in terms of numbers of amino acids or in terms of actual length of the primary structure of the SSB protein. The length of the various amino acids in the N to C direction are known in the art.

The C-terminal region is preferably from about the last 10 to about the last 60 amino acids of the C-terminal end of the SSB. The C-terminal region is more preferably about the last 15, about the last 20, about the last 25, about the last 30, about the last 35, about the last 40, about the last 45, about the last 50 or about the last 55 amino acids of the C-terminal end of the SSB.

The C-terminal region typically comprises a glycine and/or proline rich region. This proline/glycine rich region gives the C-terminal region flexibility and can be used to identify the C-terminal region.

Suitable modifications for decreasing the net negative charge are disclosed in U.S. Provisional Application No. 61/673,457 (filed 19 Jul. 2012), U.S. Provisional Application No. 61/774,688 (filed 8 Mar. 2013) and the International application being filed concurrently with this application (Oxford Nanopore Ref: ONT IP 035). The SSB may be any of the SSBs disclosed in the US Provisional Applications and International application.

The modified SSB most preferably comprises a sequence selected from those shown in SEQ ID NOs: 103, 104, 122 to 125.

Double-stranded binding proteins bind double stranded DNA with high affinity. Suitable double-stranded binding proteins include, but are not limited to Mutator S (MutS; NCBI Reference Sequence: NP_417213.1; SEQ ID NO: 140), Sso7d (*Sufolobus solfataricus* P2; NCBI Reference Sequence: NP_343889.1; SEQ ID NO: 141; Nucleic Acids Research, 2004, Vol 32, No. 3, 1197-1207), Sso10b1 (NCBI Reference Sequence: NP_342446.1; SEQ ID NO: 142), Sso10b2 (NCBI Reference Sequence: NP_342448.1; SEQ ID NO: 143), Tryptophan repressor (Trp repressor; NCBI Reference Sequence: NP_291006.1; SEQ ID NO: 144), Lambda repressor (NCBI Reference Sequence: NP_040628.1; SEQ ID NO: 145), Cren7 (NCBI Reference Sequence: NP_342459.1; SEQ ID NO: 146), major histone classes H1/H5, H2A, H2B, H3 and H4 (NCBI Reference Sequence: NP_066403.2, SEQ ID NO: 147), dsbA (NCBI Reference Sequence: NP_049858.1; SEQ ID NO: 148), Rad51 (NCBI Reference Sequence: NP_002866.2; SEQ ID NO: 149), sliding clamps and Topoisomerase V Mka (SEQ ID NO: 129) or a variant of any of these proteins. A variant of SEQ ID NO: 129, 140, 141, 142, 143, 144, 145, 146, 147, 148 or 149 typically has at least 50% homology to SEQ ID NO: 129, 140, 141, 142, 143, 144, 145, 146, 147, 148 or 149 based on amino acid identity over its entire sequence (or any of the % homologies discussed above in relation to helicases) and retains single stranded polynucleotide binding activity. A variant may differ from SEQ ID NO: 129, 140, 141, 142, 143, 144, 145, 146, 147, 148 or 149 in any of the ways discussed above in relation to helicases. In particular, a variant may have one or more conservative substitutions as shown in Tables 8 and 9. Most polymerases achieve processivity by interacting with sliding clamps. In general, these are multimeric proteins (homo-dimers or homo-trimers) that encircle dsDNA. These sliding clamps require accessory proteins (clamp loaders) to assemble them around the DNA helix in an ATP-dependent process. They also do not contact DNA directly, acting as a topological tether. As sliding clamps interact with their cognate polymerases in a specific manner via a polymerase domain, this fragment could be fused to the helicase in order to incite recruitment of helicases onto the sliding clamp. This interaction could be further stabilized by the generation of a covalent bond (introduction of cysteines or unnatural amino-acids).

Related to DNA sliding clamps, processivity factors are viral proteins that anchor their cognate polymerases to DNA, leading to a dramatic increase in the length of the fragments generated. They can be monomeric (as is the case for UL42 from Herpes simplex virus 1) or multimeric (UL44 from Cytomegalovirus is a dimer), they do not form closed rings around the DNA strand and they contact DNA directly. UL42 has been shown to increase processivity without reducing the rate of its corresponding polymerase, suggesting that it interacts with DNA in a different mode to SSBs. The UL42 preferably comprises the sequence shown in SEQ ID NO: 97 or SEQ ID NO: 102 or a variant thereof. A variant of SEQ ID NO: 97 or 102 is a protein that has an amino acid sequence which varies from that of SEQ ID NO: 97 or 102 and which retains polynucleotide binding activity. This can be measured as described above. A variant typically has at least 50% homology to SEQ ID NO: 97 or 102 based on amino acid identity over its entire sequence (or any of the % homologies discussed above in relation to helicases) and retains polynucleotide binding activity. A variant may differ from SEQ ID NO: 97 or SEQ ID NO: 102 in any of the ways discussed above in relation to helicases or below in relation to pores. A variant preferably comprises one or more substituted cysteine residues and/or one or more substituted Faz residues to facilitate attachment to the helicase as discussed above.

Attaching UL42 to a helicase could be done via genetic fusion or chemical attachment (cysteines, unnatural amino-acids). As the polymerase polypeptide that binds UL42 is visible in the crystal structure, these 35 amino acids (residues 1200-1235) could be fused onto the C-terminus of the helicase and the natural affinity between this polypeptide and the processivity factor used to form a complex. The interaction could be stabilized by introducing a covalent interaction (cysteines or unnatural amino-acids). One option is to utilize a natural UL42 cysteine (C300) that is located close to the polypeptide interaction site and introduce a point mutation into the polymerase polypeptide (e.g. L1234C).

A reported method of increasing polymerase processivity is by exploiting the interaction between *E. coli* thioredoxin (Trx) and the thioredoxin binding domain (TBD) of bacteriophage T7 DNA polymerase (residues 258-333). The binding of Trx to TBD causes the polypeptide to change conformation to one that binds DNA. TBD is believed to clamp down onto a DNA strand and limit the polymerase off-rate, thus increasing processivity. Chimeric polymerases have been made by transferring TBD onto a non-processive polymerase, resulting in 1000 fold increase in polymerised fragment length. There were no attempts to attach TBD to any other class of proteins, but a covalent link between TBD and Trx was engineered and can be used to stabilise the interaction.

Some helicases use accessory proteins in-vivo to achieve processivity (e.g. cisA from phage Φx174 and geneII protein from phage M13 for *E. coli* Rep helicase). Some of these proteins have been shown to interact with more than one helicase (e.g. MutL acts on both UvrD and Rep, though not to the same extent). These proteins have intrinsic DNA binding capabilities, some of them recognizing a specific DNA sequence. The ability of some of these accessory proteins to covalently attach themselves to a specific DNA sequence could also be used to create a set starting point for the helicase activity.

The proteins that protect the ends of chromosomes bind to telomeric ssDNA sequences in a highly specific manner. This ability could either be exploited as is or by using point mutations to abolish the sequence specificity.

Small DNA binding motifs (such as helix-turn-helix) recognize specific DNA sequences. In the case of the bacteriophage 434 repressor, a 62 residue fragment was engineered and shown to retain DNA binding abilities and specificity.

An abundant motif in eukaryotic proteins, zinc fingers consist of around 30 amino-acids that bind DNA in a specific manner. Typically each zinc finger recognizes only three DNA bases, but multiple fingers can be linked to obtain recognition of a longer sequence.

Proliferating cell nuclear antigens (PCNAs) form a very tight clamp (doughnut) which slides up and down the dsDNA or ssDNA. The PCNA from *crenarchaeota* is unique in being a hetero-trimer so it is possible to functionalise one subunit and retain activity. Its subunits are shown in SEQ ID NOs: 98, 99 and 100. The PCNA is preferably a trimer comprising the sequences shown in SEQ ID NOs: 98, 99 and 100 or variants thereof. PCNA sliding clamp (NCBI Reference Sequence: ZP_06863050.1; SEQ ID NO: 150) forms a dimer. The PCNA is preferably a dimer comprising SEQ ID NO: 150 or a variant thereof. A variant is a protein that has an amino acid sequence which varies from that of SEQ ID NO: 98, 99, 100 or 150 and which retains polynucleotide binding activity. This can be measured as described above. A variant is typically a trimer comprising sequences that have at least 50% homology to SEQ ID NOs: 98, 99 and 100 or a dimer comprising sequences that have at least 50% homology to SEQ ID NO: 150 based on amino acid identity over each entire sequence (or any of the % homologies discussed above in relation to helicases) and which retains polynucleotide binding activity. A variant may comprise sequences which differ from SEQ ID NO: 98, 99, 100 or 150 in any of the ways discussed above in relation to helicases or below in relation to pores. A variant preferably comprises one or more substituted cysteine residues and/or one or more substituted Faz residues to facilitate attachment to the helicase as discussed above. In a preferred embodiment, subunits 1 and 2 of the PCNA from *crenarchaeota* (i.e. SEQ ID NOs: 98 and 99 or variants thereof) are attached, such as genetically fused, and the resulting protein is attached to a helicase to form a construct of the invention. During use of the construct, subunit 3 (i.e. SEQ ID NO: 100 or a variant thereof) may be added to complete the PCNA clamp (or doughnut) once the construct has bound the polynucleotide. In a preferred embodiment, one monomer of the PCNA sliding clamp (i.e. SEQ ID NO: 150 or a variant thereof) is attached, such as genetically fused, to a helicase to form a construct of the invention. During use of the construct, the second monomer (i.e. SEQ ID NO: 150 or a variant thereof) may be added to complete the PCNA clamp (or doughnut) once the construct has bound the polynucleotide.

The polynucleotide binding motif may be selected from any of those shown in Table 5 below.

TABLE 5

Suitable polynucleotide binding motifs

| No. | Name | Class | Organism | Structure | Sequence | Functional form | MW (Da) | Notes |
| --- | --- | --- | --- | --- | --- | --- | --- | --- |
| 1 | SSBEco | ssb | *Escherichia coli* | 1QVC, 1EYG | P0AGE0 | homo-tetramer | 18975 | |
| 2 | SSBBhe | ssb | *Bartonella henselae* | 3LGJ, 3PGZ | Q6G302 | homo-tetramer | 16737 | structure only |
| 3 | SSBCbu | ssb | *Coxiella burnetii* | 3TQY | Q83EP4 | homo-tetramer | 17437 | structure only |
| 4 | SSBTma | ssb | *Thermathoga maritima* | 1Z9F | Q9WZ73 | homo-dimer | 16298 | small, thermostable, salt independent DNA binding |
| 5 | SSBHpy | ssb | *Helicobacter pylori* | 2VW9 | O25841 | homo-tetramer | 20143 | |
| 6 | SSBDra | ssb | *Deinococcus radiodurans* | 1SE8 | Q9RY51 | homo-dimer | 32722 | |
| 7 | SSBTaq | ssb | *Thermus aquaticus* | 2FXQ | Q9KHO6 | homo-dimer | 30026 | |
| 8 | SSBMsm | ssb | *Mycobacterium smegmatis* | 3A5U, 1X3E | Q9AFI5 | homo-tetramer | 17401 | tetramer more stable than E.coli, binding less salt dependent |
| 9 | SSBSso | ssb/RPA | *Sulfolobus solfataricus* | 1O71 | Q97W73 | homo-tetramer | 16138 | similarities with RPA |
| 10 | SSBMHsmt | ssb | *Homo sapiens* | 3ULL | Q04837 | homo-tetramer | 17260 | |
| 11 | SSBMle | ssb | *Mycobacterium leprae* | 3AFP | P46390 | homo-tetramer | 17701 | |
| 12 | gp32T4 | ssb | Bacteriohage T4 | 1GPC | P03695 | monomer | 33506 | Homo-dimer in the absence of DNA, monomer when binding DNA. |
| 13 | gp32RB69 | ssb | Bacteriophage RB69 | 2A1K | Q7Y265 | monomer | 33118 | |
| 14 | gp2.5T7 | ssb | Bacteriophage T7 | 1JE5 | P03696 | monomer | 25694 | |
| 15 | UL42 | processivity factor | Herpes virus 1 | 1DML | P10226 | monomer | 51159 | binds ssDNA dsDNA, structure shows link with polymerase |
| 16 | UL44 | processivity factor | Herpes virus 5 (cytomegalovirus) | 1YYP | P16790 | homo-dimer | 46233 | forms C shaped clamp on DNA |
| 17 | pf8 | processivity factor | KSHV | 3I2M | Q77ZG5 | homo-dimer | 42378 | |

TABLE 5-continued

Suitable polynucleotide binding motifs

| No. | Name | Class | Organism | Structure | Sequence | Functional form | MW (Da) | Notes |
|---|---|---|---|---|---|---|---|---|
| 18 | RPAMja | RPA | Methanococcus jannaschii | 3DM3 | Q58559 | monomer | 73842 | contains 4 OB folds. Structure of fragment |
| 19 | RPAMma | RPA | Methanococcus maripaludis | 3E0E, 2K5V | Q6LYF9 | monomer | 71388 | Core domain structure |
| 20 | RPAMth | RPA | Methanothermobacter thermoautotrophicus | | | monomer | 120000 | Shown to interact directly with Hel308. Sequence from paper. |
| 21 | RPA70Sce | RPA | Saccharomyces cerevisiae | 1YNX | P22336 | hetero-trimer | 70348 | unit has two OB folds and binds DNA |
| 22 | RPAMbu1 | RPA | Methanococcoides burtonii | | Q12V72 | ? | 41227 | three OB folds identified |
| 23 | RPAMbu2 | RPA | Methanococcoides burtonii | | Q12W96 | ? | 47082 | two OB folds identified |
| 24 | RPA70Hsa | RPA | Homo sapiens | 1JMC | P27694 | hetero-trimer | 68138 | |
| 25 | RPA14Hsa | RPA | Homo sapiens | 3KDF | P35244 | hetero-trimer | 13569 | in complex with RPA32 |
| 26 | gp45T4 | sliding clamp | Bacteriophage T4 | 1CZD | P04525 | homo-trimer | 24858 | ring shape threads DNA |
| 27 | BetaEco | sliding clamp | E.coli | 3BEP | P0A988 | homo-dimer | 40587 | ring shape threads DNA, may bind ssDNA in poket |
| 28 | PCNASce | sliding clamp | Saccharomyces cerevisiae | 1PLQ, 3K4X | P15873 | homo-dimer | 28916 | ring shape threads DNA |
| 29 | PCNATko | sliding clamp | Thermococcus kodakaraensis | 3LX1 | Q5JF32 | homo-dimer | 28239 | |
| 30 | PCNAHvo | sliding clamp | Haloferax volcanii | 3IFV | D0VWY8 | homo-dimer | 26672 | |
| 31 | PCNAPfu | sliding clamp | Pyrococcus furiosus | 1GE8 | O73947 | homo-dimer | 28005 | |
| 32 | PCNAMbu | sliding clamp | Methanococcoides burtonii | | Q12U18 | homo-dimer | 27121 | Inferred from homology |
| 33 | BetaMtu | sliding clamp | Mycobacterium tuberculosis | 3P16 | Q50790 | homo-dimer | 42113 | |
| 34 | BetaTma | sliding clamp | Thermotoga maritima | 1VPK | Q9WYA0 | homo-dimer | 40948 | |
| 35 | BetaSpy | sliding clamp | Streptococcus pyrogenes | 2AVT | Q9EVR1 | homo-dimer | 41867 | |
| 36 | gp45RB69 | sliding clamp | Bacteriophage RB69 | 1B77 | O80164 | homo-trimer | 25111 | Structure shows interaction with polypeptide fom polymerase |
| 37 | p55Hsa | DNA binding protein | Homo sapiens (mitochondrial) | 2G4C, 3IKL, 3IKM | Q9UHN | monomer | 54911 | interacts with specific polymerase domain |
| 38 | p55Dme | DNA binding protein | Drosophylla melanogaster | | Q9VJV8 | monomer | 41027 | associates with polymerase Gamma conferring salt tolerance, processivity and increased activity |
| 39 | p55Xla | DNA binding protein | Xenopus laevis | | Q9W6G7 | monomer | 52283 | |
| 40 | RepDSau | replication initiation protein | Staphylococcus aureus | | P08115 | homo-dimer | 37874 | increases processivity of PcrA, covalently and specifically links DNA |
| 41 | G2P | replication initiation protein | Enterobacteria phage 1 | | P69546 | monomer | 46168 | increases processivity of Rep, covalently and specifically links DNA |
| 42 | MutLEco | mismatch repair protein | Escherichia coli | 1BKN, 1B62, 1B63 | P23367 | homo-dimer | 67924 | increases processivity of UvrD (and Rep) |

TABLE 5-continued

Suitable polynucleotide binding motifs

| No. | Name | Class | Organism | Structure | Sequence | Functional form | MW (Da) | Notes |
|---|---|---|---|---|---|---|---|---|
| 43 | KuMtu | DNA repair protein | *Mycobacterium tuberculosis* | | O05866 | homo-dimer | 30904 | increases processivity of UvrD1. Structure available for human Ku |
| 44 | OnTEBP | telomere binding protein | *Oxytricha* nova-Alpha | 1OTC | P29549 | hetero-dimer | 56082 | Specific biding to 3' end T4G4T4G4. Alpha subunit may be enough |
| | | | *Oxytricha* nova-Beta | | P16458 | | 41446 | |
| 45 | EcrTEBP | telomere binding protein | *Euplotes crassus* | | Q06183 | monomer | 53360 | Homolog to OnTEBP with no Beta subunit in genome |
| 46 | TteTEBP | telomere binding protein | *Tetrachymena termophila* Alpha | | Q23FB9 | hetero-dimer | 53073 | Homolog to OnTEBP-Alpha |
| | | | *Tetrachymena termophila* Beta | | Q23FH0 | | 54757 | May be homolog to OnTEBP Beta |
| 47 | pot1Spo | telomere binding proteins | *Schizosaccharomyces pombe* | | O13988 | monomer | 64111 | related to TEBP |
| 48 | Cdc13pSce | telomere binding proteins | *Saccharomyces cerevisiae* | | C7GSV7 | monomer | 104936 | specific binding to telomeric DNA |
| 49 | C1 | repressor | Bacteriophage 434 | | P16117 | homo-dimer | 10426 | binds DNA specifically as homo-dimer |
| 50 | LexA | repressor | *Escherichia coli* | 1LEB | P0A7C2 | homo-dimer | 22358 | binds DNA specifically as homo-dimer |

The polynucleotide binding moiety is preferably derived from a polynucleotide binding enzyme. A polynucleotide binding enzyme is a polypeptide that is capable of binding to a polynucleotide and interacting with and modifying at least one property of the polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide binding moiety does not need to display enzymatic activity as long as it is capable of binding the polynucleotide and controlling its movement. For instance, the moiety may be derived from an enzyme that has been modified to remove its enzymatic activity or may be used under conditions which prevent it from acting as an enzyme.

The polynucleotide binding moiety is preferably derived from a nucleolytic enzyme. The enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are exonucleases, polymerases, helicases and topoisomerases, such as gyrases. Suitable exonucleases include, but are not limited to, exonuclease I from *E. coli*, exonuclease III enzyme from *E. coli*, RecJ from *T. thermophilus* and bacteriophage lambda exonuclease and variants thereof.

The polymerase is preferably a member of any of the Moiety Classification (EC) groups 2.7.7.6, 2.7.7.7, 2.7.7.19, 2.7.7.48 and 2.7.7.49. The polymerase is preferably a DNA-dependent DNA polymerase, an RNA-dependent DNA polymerase, a DNA-dependent RNA polymerase or an RNA-dependent RNA polymerase. The polynucleotide binding moiety is preferably derived from Phi29 DNA polymerase (SEQ ID NO: 101). The moiety may comprise the sequence shown in SEQ ID NO: 101 or a variant thereof. A variant of SEQ ID NO: 101 is an enzyme that has an amino acid sequence which varies from that of SEQ ID NO: 101 and which retains polynucleotide binding activity. This can be measured as described above. The variant may include modifications that facilitate binding of the polynucleotide and/or facilitate its activity at high salt concentrations and/or room temperature.

Over the entire length of the amino acid sequence of SEQ ID NO: 101, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 101 over the entire sequence. There may be at least 80%, for example at least 85%, 90% or 95%, amino acid identity over a stretch of 200 or more, for example 230, 250, 270 or 280 or more, contiguous amino acids ("hard homology"). Homology is determined as described below. The variant may differ from the wild-type sequence in any of the ways discussed below with reference to SEQ ID NOs: 2 and 4.

The helicase may be any of those discussed above. Helicase dimers and multimers are discussed in detail below. The polynucleotide binding moiety may be a polynucleotide binding domain derived from a helicase. For instance, the polynucleotide binding moiety preferably comprises the sequence shown in SEQ ID NOs: 105 or 106 or a variant thereof. A variant of SEQ ID NOs: 105 or 106 is a protein that has an amino acid sequence which varies from that of SEQ ID NOs: 105 or 106 and which retains polynucleotide binding activity. This can be measured as described above. The variant may include modifications that facilitate binding of the polynucleotide and/or facilitate its activity at high salt concentrations and/or room temperature.

Over the entire length of the amino acid sequence of SEQ ID NOs: 105 or 106, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NOs: 105 or 106 over the entire sequence. There may be at least 80%, for example at least 85%, 90% or 95%, amino acid identity over a stretch of 40 or more, for example 50, 60, 70 or 80 or more, contiguous amino acids ("hard homology"). Homology is determined as described below. The variant may differ from the wild-type sequence in any of the ways discussed below with reference to SEQ ID NOs: 2 and 4.

The topoisomerase is preferably a member of any of the Moiety Classification (EC) groups 5.99.1.2 and 5.99.1.3.

The polynucleotide binding moiety may be any of the enzymes discussed above.

The moiety may be labelled with a revealing label. The label may be any of those described above.

The moiety may be isolated from any moiety-producing organism, such as E. coli, T. thermophilus or bacteriophage, or made synthetically or by recombinant means. For example, the moiety may be synthesized by in vitro translation and transcription as described below. The moiety may be produced in large scale following purification as described below.

Helicase Oligomers

As will be clear from the discussion above, the polynucleotide binding moiety is preferably derived from a helicase. For instance, it may be a polynucleotide domain from a helicase. The moiety more preferably comprises one or more helicases. The helicases may be any of those discussed above, including the helicases of the invention. In such embodiments, the constructs of the invention of course comprise two or more helicases attached together where at least one of the helicases is modified in accordance with the invention. The constructs may comprise two, three, four, five or more helicases. In other words, the constructs of the invention may comprise a helicase dimer, a helicase trimer, a helicase tetramer, a helicase pentamer and the like.

The two or more helicases can be attached together in any orientation. Identical or similar helicases may be attached via the same amino acid position or spatially proximate amino acid positions in each helicase. This is termed the "head-to-head" formation. Alternatively, identical or similar helicases may be attached via positions on opposite or different sides of each helicase. This is termed the "head-to-tail" formation. Helicase trimers comprising three identical or similar helicases may comprise both the head-to-head and head-to-tail formations.

The two or more helicases may be different from one another (i.e. the construct is a hetero-dimer, -trimer, -tetramer or -pentamer etc.). For instance, the constructs of the invention may comprise: (a) one or more Hel308 helicases and one or more XPD helicases; (b) one or more Hel308 helicases and one or more RecD helicases; (c) one or more Hel308 helicases and one or more TraI helicases; (d) one or more XPD helicases and one or more RecD helicases; (e) one or more XPD helicases and one or more TraI helicases; or (f) one or more RecD helicases and one or more TraI helicases. The construct may comprise two different variants of the same helicase. For instance, the construct may comprise two variants of one of the helicases discussed above with one or more cysteine residues or Faz residues introduced at different positions in each variant. In this instance, the helicases can be in a head-to-tail formation. In a preferred embodiment, a variant of SEQ ID NO: 10 comprising Q442C may be attached via cysteine linkage to a variant of SEQ ID NO: 10 comprising Q557C. Cys mutants of Hel308Mbu can also be made into hetero-dimers if necessary. In this approach, two different Cys mutant pairs such as Hel308Mbu-Q442C and Hel308Mbu-Q577C can be linked in head-to-tail fashion. Hetero-dimers can be formed in two possible ways. The first involves the use of a homo-bifunctional linker as discussed above. One of the helicase variants can be modified with a large excess of linker in such a way that one linker is attached to one molecule of the protein. This linker modified variant can then be purified away from unmodified proteins, possible homo-dimers and unreacted linkers to react with the other helicase variant. The resulting dimer can then be purified away from other species.

The second involves the use of hetero-bifunctional linkers. For example, one of the helicase variants can be modified with a first PEG linker containing maleimide or iodoacetamide functional group at one end and a cyclooctyne functional group (DIBO) at the other end. An example of this is shown below:

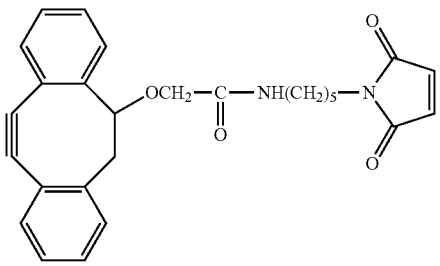

The second helicase variant can be modified with a second PEG linker containing maleimide or iodoacetamide functional group at one end and an azide functional group at the other end. An example is show below:

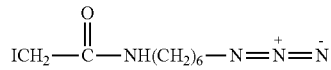

The two helicase variants with two different linkers can then be purified and clicked together (using copper free click chemistry) to make a dimer. Copper free click chemistry has been used in these applications because of its desirable properties. For example, it is fast, clean and not poisonous towards proteins. However, other suitable bio-orthogonal chemistries include, but are not limited to, Staudinger chemistry, hydrazine or hydrazide/aldehyde or ketone reagents (HyNic+4FB chemistry, including all Solulink™ reagents), Diels-Alder reagent pairs and boronic acid/salicyhydroxamate reagents.

These two ways of linking two different variants of the same helicase are also valid for any of the constructs discussed above in which the helicase and the moiety are different from one another, such as dimers of two different helicases and a helicase-polymerase dimer.

Similar methodology may also be used for linking different Faz variants. One Faz variant (such as SEQ ID NO: 10 comprising Q442Faz) can be modified with a large excess of linker in such a way that one linker is attached to one molecule of the protein. This linker modified Faz variant can then be purified away from unmodified proteins, possible homo-dimers and unreacted linkers to react with the second Faz variant (such as SEQ ID NO: 10 comprising Q577Faz). The resulting dimer can then be purified away from other species.

Hetero-dimers can also be made by linking cysteine variants and Faz variants of the same helicase or different helicases. For example, any of the above cysteine variants (such as SEQ ID NO: 10 comprising Q442C) can be used to make dimers with any of the above Faz variants (such SEQ ID NO: 10 comprising Q577Faz). Hetero-bifunctional PEG linkers with maleimide or iodoacetamide functionalities at one end and DBCO functionality at the other end can be used in this combination of mutants. An example of such a linker is shown below (DBCO-PEG4-maleimide):

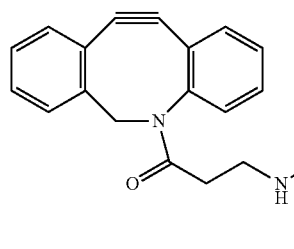

The length of the linker can be varied by changing the number of PEG units between the two functional groups.

Helicase hetero-trimers can comprise three different types of helicases selected from Hel308 helicases, XPD helicases, RecD helicases, TraI helicases and variants thereof. The same is true for oligomers comprising more than three helicases. The two or more helicases within a construct may be different variants of the same helicase, such as different variants of SEQ ID NO: 10, 22, 33 or 52. The different variants may be modified at different positions to facilitate attachment via the different positions. The hetero-trimers may therefore be in a head-to-tail and head-to-head formation.

The two or more helicases in the constructs of the invention may be the same as one another (i.e. the construct is a homo-dimer, -trimer, -tetramer or -pentamer etc.) Homo-oligomers can comprise two or more Hel308 helicases, two or more XPD helicases, two or more RecD helicases, two or more TraI helicases or two or more of any of the variants discussed above. In such embodiments, the helicases are preferably attached using the same position in each helicase. The helicases are therefore attached head-to-head. The helicases may be linked using a cysteine residue or a Faz residue that has been substituted into the helicases at the same position. Cysteine residues in identical helicase variants can be linked using a homo-bifunctional linker containing thiol reactive groups such as maleimide or iodoacetamide. These functional groups can be at the end of a polyethyleneglycol (PEG) chain as in the following example:

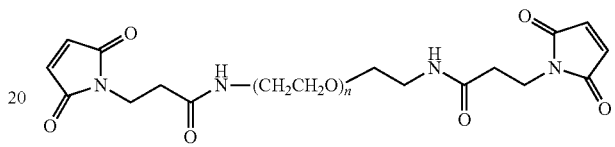

The length of the linker can be varied to suit the required applications. For example, n can be 2, 3, 4, 8, 11, 12, 16 or more. PEG linkers are suitable because they have favourable properties such as water solubility. Other non PEG linkers can also be used in cysteine linkage.

By using similar approaches, identical Faz variants can also be made into homo-dimers. Homo-bifunctional linkers with DIBO functional groups can be used to link two molecules of the same Faz variant to make homo-dimers using $Cu^{2+}$ free click chemistry. An example of a linker is given below:

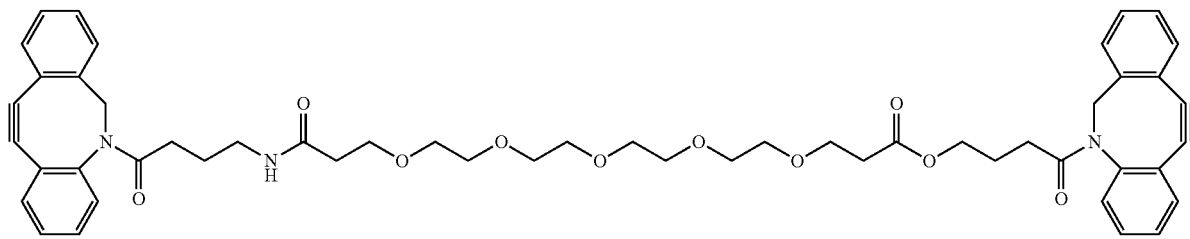 [SMILES: O=C(CCOCCOCCOCCOCCOCCC(=O)OCCCC(=O)N1Cc2ccccc2C#Cc2ccccc21)NCCCC(=O)N1Cc2ccccc2C#Cc2ccccc21]

The length of the PEG linker can vary to include 2, 4, 8, 12, 16 or more PEG units. Such linkers can also be made to incorporate a florescent tag to ease quantifications. Such fluorescence tags can also be incorporated into Maleimide linkers.

The invention also provides a construct comprising a helicase of the invention and an amino acid sequence comprising SEQ ID NO: 130 (H-L domains from Topoisomerase V from *Methanopyrus kandleri*; SEQ ID NO: 129) or a variant thereof having at least 80% homology to SEQ ID NO: 130 based on amino acid identity over the entire sequence of SEQ ID NO: 130, wherein the helicase is attached to the amino acid sequence and the construct has the ability to control the movement of a polynucleotide. The helicase may be attached to the amino acid sequence in any of the ways discussed above.

Preferred constructs of the invention are shown in the Table 6 below. Each row shows a preferred construct in which the helicase in the left-hand column is attached to additional polynucleotide binding moiety in the right-hand column in accordance with the invention. If the polynucleotide binding moiety in the right-hand column is a helicase, it may also be a helicase of the invention.

| Helicase of the invention | Additional polynucleotide binding moiety |
|---|---|
| Hel308 helicase of the invention as defined above (preferably SEQ ID NO: 10, 22, 33 or 52 or a variant thereof as defined above) | Polymerase (preferably SEQ ID NO: 101 or a variant thereof as defined above) |
| TraI helicase of the invention as defined above (preferably SEQ ID NO: 85, 126, 134 and 138 or a variant thereof as defined above) | Polymerase (preferably SEQ ID NO: 101 or a variant thereof as defined above) |
| Hel308 helicase of the invention as defined above (preferably SEQ ID NO: 10, 22, 33 or 52 or a variant thereof as defined above) | Hel308 helicase as defined above (preferably SEQ ID NO: 10, 22, 33 or 52 or a variant thereof as defined above) |
| TraI helicase of the invention as defined above (preferably SEQ ID NO: 85, 126, 134 and 138 or a variant thereof as defined above) | TraI helicase as defined above (preferably SEQ ID NO: 85, 126, 134 and 138 or a variant thereof as defined above) |
| Hel308 helicase of the invention as defined above (preferably SEQ ID NO: 10, 22, 33 or 52 or a variant thereof as defined above) | TraI helicase as defined above (preferably SEQ ID NO: 85, 126, 134 and 138 or a variant thereof as defined above) |
| TraI helicase of the invention as defined above (preferably SEQ ID NO: 85, 126, 134 and 138 or a variant thereof as defined above) | Hel308 helicase as defined above (preferably SEQ ID NO: 10, 22, 33 or 52 or a variant thereof as defined above) |

Polynucleotide Sequences

Any of the proteins described herein may be expressed using methods known in the art. Polynucleotide sequences may be isolated and replicated using standard methods in the art. Chromosomal DNA may be extracted from a helicase producing organism, such as *Methanococcoides burtonii*, and/or a SSB producing organism, such as *E. coli*. The gene encoding the sequence of interest may be amplified using PCR involving specific primers. The amplified sequences may then be incorporated into a recombinant replicable vector such as a cloning vector. The vector may be used to replicate the polynucleotide in a compatible host cell. Thus polynucleotide sequences may be made by introducing a polynucleotide encoding the sequence of interest into a replicable vector, introducing the vector into a compatible host cell, and growing the host cell under conditions which bring about replication of the vector. The vector may be recovered from the host cell. Suitable host cells for cloning of polynucleotides are known in the art and described in more detail below.

The polynucleotide sequence may be cloned into a suitable expression vector. In an expression vector, the polynucleotide sequence is typically operably linked to a control sequence which is capable of providing for the expression of the coding sequence by the host cell. Such expression vectors can be used to express a construct.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide may be introduced into the vector.

The expression vector may then be introduced into a suitable host cell. Thus, a construct can be produced by inserting a polynucleotide sequence encoding a construct into an expression vector, introducing the vector into a compatible bacterial host cell, and growing the host cell under conditions which bring about expression of the polynucleotide sequence.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example an ampicillin resistance gene. Promoters and other expression regulation signals may be selected to be compatible with the host cell for which the expression vector is designed. A T7, trc, lac, ara or $\lambda_L$ promoter is typically used.

The host cell typically expresses the construct at a high level. Host cells transformed with a polynucleotide sequence will be chosen to be compatible with the expression vector used to transform the cell. The host cell is typically bacterial and preferably *E. coli*. Any cell with a λ DE3 lysogen, for example C41 (DE3), BL21 (DE3), JM109 (DE3), B834 (DE3), TUNER, Origami and Origami B, can express a vector comprising the T7 promoter.

Methods of the Invention

The invention provides a method of controlling the movement of a target polynucleotide. The method comprises contacting the target polynucleotide with a helicase of the invention or a construct of the invention and thereby controlling the movement of the polynucleotide. The method is preferably carried out with a potential applied across the pore. As discussed in more detail below, the applied potential typically results in the formation of a complex between the pore and the helicase or construct. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5.

The invention also provides a method of characterising a target polynucleotide. The method comprises (a) contacting the target polynucleotide with a transmembrane pore and a helicase of the invention or a construct of the invention such that the helicase or construct controls the movement of the target polynucleotide through the pore. The method also comprises (b) taking one or more measurements as the polynucleotide moves with respect to the pore wherein the measurements are indicative of one or more characteristics of the target polynucleotide and thereby characterising the target polynucleotide.

Steps (a) and (b) are preferably carried out with a potential applied across the pore as discussed above. In some instances, the current passing through the pore as the polynucleotide moves with respect to the pore is used to determine the sequence of the target polynucleotide. This is Strand Sequencing.

The method of the invention is for characterising a target polynucleotide. A polynucleotide is defined above.

The whole or only part of the target polynucleotide may be characterised using this method. The target polynucleotide can be any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs in length or 100000 or more nucleotide pairs in length.

The target polynucleotide is present in any suitable sample. The invention is typically carried out on a sample that is known to contain or suspected to contain the target polynucleotide. Alternatively, the invention may be carried out on a sample to confirm the identity of one or more target polynucleotides whose presence in the sample is known or expected.

The sample may be a biological sample. The invention may be carried out in vitro on a sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well in the membrane along which or into which hydrated ions may flow.

Any transmembrane pore may be used in the invention. The pore may be biological or artificial. Suitable pores include, but are not limited to, protein pores, polynucleotide pores and solid state pores.

Any membrane may be used in accordance with the invention. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic molecules may be synthetic or naturally occurring. Non-naturally occurring amphiphiles and amphiphiles which form a monolayer are known in the art and include, for example, 7 s (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer.

The amphiphilic layer may be a monolayer or a bilayer. The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and $SiO$, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647).

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below. The method of the invention is typically carried out in vitro.

The polynucleotide may be coupled to the membrane. This may be done using any known method. If the membrane is an amphiphilic layer, such as a lipid bilayer (as discussed in detail above), the polynucleotide is preferably coupled to the membrane via a polypeptide present in the membrane or a hydrophobic anchor present in the membrane. The hydrophobic anchor is preferably a lipid, fatty acid, sterol, carbon nanotube or amino acid.

The polynucleotide may be coupled directly to the membrane. The polynucleotide is preferably coupled to the membrane via a linker. Preferred linkers include, but are not limited to, polymers, such as polynucleotides, polyethylene glycols (PEGs) and polypeptides. If a polynucleotide is coupled directly to the membrane, then some data will be lost as the characterising run cannot continue to the end of the polynucleotide due to the distance between the membrane and the helicase. If a linker is used, then the polynucleotide can be processed to completion. If a linker is used, the linker may be attached to the polynucleotide at any position. The linker is typically attached to the polynucleotide at the tail polymer.

The coupling may be stable or transient. For certain applications, the transient nature of the coupling is preferred. If a stable coupling molecule were attached directly to either the 5' or 3' end of a polynucleotide, then some data will be lost as the characterising run cannot continue to the end of the polynucleotide due to the distance between the bilayer and the helicase's active site. If the coupling is transient, then when the coupled end randomly becomes free of the bilayer, then the polynucleotide can be processed to completion. Chemical groups that form stable or transient links with the membrane are discussed in more detail below. The polynucleotide may be transiently coupled to an amphiphilic layer, such as a lipid bilayer using cholesterol or a fatty acyl chain. Any fatty acyl chain having a length of from 6 to 30 carbon atoms, such as hexadecanoic acid, may be used.

In preferred embodiments, the polynucleotide is coupled to an amphiphilic layer. Coupling of polynucleotides to synthetic lipid bilayers has been carried out previously with various different tethering strategies. These are summarised in Table 7 below.

TABLE 7

| Attachment group | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |

TABLE 7-continued

| Attachment group | Type of coupling | Reference |
|---|---|---|
| Biotin | Stable | Nikolov, V., R. Lipowsky, et al. (2007). "Behavior of giant vesicles with anchored DNA molecules." *Biophys J* 92(12): 4356-68 |
| Cholesterol | Transient | Pfeiffer, I. and F. Hook (2004). "Bivalent cholesterol-based coupling of oligonucletides to lipid membrane assemblies." *J Am Chem Soc* 126(33): 10224-5 |
| Lipid | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Polynucleotides may be functionalized using a modified phosphoramidite in the synthesis reaction, which is easily compatible for the addition of reactive groups, such as thiol, cholesterol, lipid and biotin groups. These different attachment chemistries give a suite of attachment options for polynucleotides. Each different modification group tethers the polynucleotide in a slightly different way and coupling is not always permanent so giving different dwell times for the polynucleotide to the bilayer. The advantages of transient coupling are discussed above.

Coupling of polynucleotides can also be achieved by a number of other means provided that a reactive group can be added to the polynucleotide. The addition of reactive groups to either end of DNA has been reported previously. A thiol group can be added to the 5' of ssDNA using polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82).

Alternatively, the reactive group could be considered to be the addition of a short piece of DNA complementary to one already coupled to the bilayer, so that attachment can be achieved via hybridisation. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." *Proc Natl Acad Sci USA* 89(20): 9823-5). Alternatively either ssDNA or dsDNA could be ligated to native dsDNA and then the two strands separated by thermal or chemical denaturation. To native dsDNA, it is possible to add either a piece of ssDNA to one or both of the ends of the duplex, or dsDNA to one or both ends. Then, when the duplex is melted, each single strand will have either a 5' or 3' modification if ssDNA was used for ligation or a modification at the 5' end, the 3' end or both if dsDNA was used for ligation. If the polynucleotide is a synthetic strand, the coupling chemistry can be incorporated during the chemical synthesis of the polynucleotide. For instance, the polynucleotide can be synthesized using a primer with a reactive group attached to it.

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. By using an antisense primer that has a reactive group, such as a cholesterol, thiol, biotin or lipid, each copy of the amplified target DNA will contain a reactive group for coupling.

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a lipid bilayer, to the other. The transmembrane protein pore allows a polynucleotide, such as DNA or RNA, to be moved through the pore.

The transmembrane protein pore may be a monomer or an oligomer. The pore is preferably made up of several repeating subunits, such as 6, 7, 8 or 9 subunits. The pore is preferably a hexameric, heptameric, octameric or nonameric pore.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et at (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et at (1990) J Mol Biol 215:403-10. Software for performing BLAST analyses is publicly available through the National Center for Biotechnology Information (http://www.ncbi.nlm.nih.gov/).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 2 has the mutation L88N in addition to all the mutations of MS-(B1)8 and is called MS-(B2)8. The pore used in the invention is preferably MS-(B2)8. The further preferred variant comprises the mutations G75S/G77S/L88N/Q126R. The variant of SEQ ID NO: 2 has the mutations G75S/G77S/L88N/Q126R in addition to all the mutations of MS-(B1)8 and is called MS-(B2C)8. The pore used in the invention is preferably MS-(B2)8 or MS-(B2C)8.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 8 below. Where amino acids have similar polarity, this can also be determined by reference to the hydropathy scale for amino acid side chains in Table 9.

TABLE 8

Chemical properties of amino acids

| Ala | aliphatic, hydrophobic, neutral | Met | hydrophobic, neutral |
|---|---|---|---|
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

TABLE 9

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7):497-505).

The monomer derived from Msp may be labelled with a revealing label. The revealing label may be any suitable label which allows the pore to be detected. Suitable labels are described above.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with NaBH$_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

The transmembrane protein pore is also preferably derived from α-hemolysin (α-HL). The wild type α-HL pore is formed of seven identical monomers or subunits (i.e. it is heptameric). The sequence of one monomer or subunit of α-hemolysin-NN is shown in SEQ ID NO: 4. The transmembrane protein pore preferably comprises seven monomers each comprising the sequence shown in SEQ ID NO: 4 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 4 form part of a constriction of the barrel or channel of α-HL.

In such embodiments, a pore comprising seven proteins or monomers each comprising the sequence shown in SEQ ID NO: 4 or a variant thereof are preferably used in the method of the invention. The seven proteins may be the same (homo-heptamer) or different (hetero-heptamer).

A variant of SEQ ID NO: 4 is a protein that has an amino acid sequence which varies from that of SEQ ID NO: 4 and which retains its pore forming ability. The ability of a variant to form a pore can be assayed using any method known in the art. For instance, the variant may be inserted into an amphiphilic layer, such as a lipid bilayer, along with other appropriate subunits and its ability to oligomerise to form a pore may be determined. Methods are known in the art for inserting subunits into amphiphilic layers, such as lipid bilayers. Suitable methods are discussed above.

The variant may include modifications that facilitate covalent attachment to or interaction with the helicase or construct. The variant preferably comprises one or more reactive cysteine residues that facilitate attachment to the helicase or construct. For instance, the variant may include a cysteine at one or more of positions 8, 9, 17, 18, 19, 44, 45, 50, 51, 237, 239 and 287 and/or on the amino or carboxy terminus of SEQ ID NO: 4. Preferred variants comprise a substitution of the residue at position 8, 9, 17, 237, 239 and 287 of SEQ ID NO: 4 with cysteine (A8C, T9C, N17C, K237C, S239C or E287C). The variant is preferably any one of the variants described in International Application No. PCT/GB09/001690 (published as WO 2010/004273), PCT/GB09/001679 (published as WO 2010/004265) or PCT/GB10/000133 (published as WO 2010/086603).

The variant may also include modifications that facilitate any interaction with nucleotides.

The variant may be a naturally occurring variant which is expressed naturally by an organism, for instance by a Staphylococcus bacterium. Alternatively, the variant may be expressed in vitro or recombinantly by a bacterium such as Escherichia coli. Variants also include non-naturally occurring variants produced by recombinant technology. Over the entire length of the amino acid sequence of SEQ ID NO: 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 may additionally be deleted from the polypeptides described above. Up to 1, 2, 3, 4, 5, 10, 20 or 30 residues may be deleted, or more.

Variants may be fragments of SEQ ID NO: 4. Such fragments retain pore-forming activity. Fragments may be at least 50, 100, 200 or 250 amino acids in length. A fragment preferably comprises the pore-forming domain of SEQ ID NO: 4. Fragments typically include residues 119, 121, 135, 113 and 139 of SEQ ID NO: 4.

One or more amino acids may be alternatively or additionally added to the polypeptides described above. An extension may be provided at the amino terminus or carboxy terminus of the amino acid sequence of SEQ ID NO: 4 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 4 is a subunit that has an amino acid sequence which varies from that of SEQ ID NO: 4 and which retains its ability to form a pore. A variant typically contains the regions of SEQ ID NO: 4 that are responsible for pore formation. The pore forming ability of α-HL, which contains a β-barrel, is provided by β-strands in each subunit. A variant of SEQ ID NO: 4 typically comprises the regions in SEQ ID NO: 4 that form β-strands. The amino acids of SEQ ID NO: 4 that form β-strands are discussed above. One or more modifications can be made to the regions of SEQ ID NO: 4 that form β-strands as long as the resulting variant retains its ability to form a pore. Specific modifications that can be made to the β-strand regions of SEQ ID NO: 4 are discussed above.

A variant of SEQ ID NO: 4 preferably includes one or more modifications, such as substitutions, additions or deletions, within its α-helices and/or loop regions. Amino acids that form α-helices and loops are discussed above.

The variant may be modified to assist its identification or purification as discussed above.

Pores derived from α-HL can be made as discussed above with reference to pores derived from Msp.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The transmembrane protein pore may be chemically modified by the attachment of any molecule. For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

The reactivity of cysteine residues may be enhanced by modification of the adjacent residues. For instance, the basic groups of flanking arginine, histidine or lysine residues will change the pKa of the cysteines thiol group to that of the more reactive S$^-$ group. The reactivity of cysteine residues may be protected by thiol protective groups such as dTNB. These may be reacted with one or more cysteine residues of the pore before a linker is attached.

The molecule (with which the pore is chemically modified) may be attached directly to the pore or attached via a linker as disclosed in International Application Nos. PCT/GB09/001690 (published as WO 2010/004273), PCT/GB09/001679 (published as WO 2010/004265) or PCT/GB10/000133 (published as WO 2010/086603).

The helicase or construct may be covalently attached to the pore. The helicase or construct is preferably not covalently attached to the pore. The application of a voltage to the pore and helicase or construct typically results in the formation of a sensor that is capable of sequencing target polynucleotides. This is discussed in more detail below.

Any of the proteins described herein, i.e. the helicases, the transmembrane protein pores or constructs, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the helicase, pore or construct. An example of this would be to react a gel-shift reagent to a cysteine engineered on the outside of the pore. This has been demonstrated as a method for separating hemolysin hetero-oligomers (Chem Biol. 1997 July; 4(7):497-505).

The helicase, pore or construct may be labelled with a revealing label. The revealing label may be any suitable label which allows the pore to be detected. Suitable labels include, but are not limited to fluorescent molecules, radioisotopes, e.g. $^{125}$I, $^{35}$S, enzymes, antibodies, antigens, polynucleotides and ligands such as biotin.

Proteins may be made synthetically or by recombinant means. For example, the helicase, pore or construct may be synthesized by in vitro translation and transcription (IVTT). The amino acid sequence of the helicase, pore or construct may be modified to include non-naturally occurring amino acids or to increase the stability of the protein. When a protein is produced by synthetic means, such amino acids may be introduced during production. The helicase, pore or construct may also be altered following either synthetic or recombinant production.

The helicase, pore or construct may also be produced using D-amino acids. For instance, the pore or construct may comprise a mixture of L-amino acids and D-amino acids. This is conventional in the art for producing such proteins or peptides.

The helicase, pore or construct may also contain other non-specific modifications as long as they do not interfere with pore formation or helicase or construct function. A number of non-specific side chain modifications are known in the art and may be made to the side chains of the protein(s). Such modifications include, for example, reductive alkylation of amino acids by reaction with an aldehyde followed by reduction with NaBH$_4$, amidation with methylacetimidate or acylation with acetic anhydride.

The helicase, pore and construct can be produced using standard methods known in the art. Polynucleotide sequences encoding a helicase, pore or construct may be derived and replicated using standard methods in the art. Polynucleotide sequences encoding a helicase, pore or construct may be expressed in a bacterial host cell using standard techniques in the art. The helicase, pore and/or construct may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

The helicase, pore and/or construct may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

The method of the invention involves measuring one or more characteristics of the target polynucleotide. The method may involve measuring two, three, four or five or more characteristics of the target polynucleotide. The one or more characteristics are preferably selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified. Any combination of (i) to (v) may be measured in accordance with the invention.

For (i), the length of the polynucleotide may be measured for example by determining the number of interactions between the target polynucleotide and the pore or the duration of interaction between the target polynucleotide and the pore.

For (ii), the identity of the polynucleotide may be measured in a number of ways. The identity of the polynucleotide may be measured in conjunction with measurement of the sequence of the target polynucleotide or without measurement of the sequence of the target polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the target polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the target polynucleotide is modified by methylation, by oxidation, by damage, with one or more proteins or with one or more labels, tags or spacers. Specific modifications will result in specific interactions with the pore which can be measured using the methods described below. For instance, methylcytosine may be distinguished from cytosine on the basis of the current flowing through the pore during its interaction with each nucleotide.

A variety of different types of measurements may be made. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

In a preferred embodiment, the method comprises:

(a) contacting the target polynucleotide with a transmembrane pore and a helicase of the invention or a construct of the invention such that the target polynucleotide moves through the pore and the helicase or construct controls the movement of the target polynucleotide through the pore; and (b) measuring the current passing through the pore as the polynucleotide moves with respect to the pore wherein the current is indicative of one or more characteristics of the target polynucleotide and thereby characterising the target polynucleotide.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08/000562 (WO 2008/102120).

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. Hel308, XPD, RecD and TraI helicases surprisingly work under high salt concentrations. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

The method may be carried out in the presence of free nucleotides or free nucleotide analogues and/or an enzyme cofactor that facilitates the action of the helicase or construct. The method may also be carried out in the absence of free nucleotides or free nucleotide analogues and in the absence of an enzyme cofactor. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the helicase or construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

The target polynucleotide may be contacted with the helicase or construct and the pore in any order. In is preferred that, when the target polynucleotide is contacted with the helicase or construct and the pore, the target polynucleotide firstly forms a complex with the helicase or construct. When the voltage is applied across the pore, the target polynucleotide/helicase or construct complex then forms a complex with the pore and controls the movement of the polynucleotide through the pore.

As discussed above, helicases may work in two modes with respect to the pore. The helicases of the invention or the constructs of the invention can also work in two modes. First, the method is preferably carried out using the helicase or construct such that it moves the target sequence through the pore with the field resulting from the applied voltage. In this mode the 3' end of the DNA is first captured in the pore (for a 3'-5' helicase), and the helicase or construct moves the DNA into the pore such that the target sequence is passed through the pore with the field until it finally translocates through to the trans side of the bilayer (See FIG. 8). Alternatively, the method is preferably carried out such that the helicase or construct moves the target sequence through the pore against the field resulting from the applied voltage. In this mode the 5' end of the DNA is first captured in the pore (for a 3'-5' helicase), and the helicase or construct moves the DNA through the pore such that the target sequence is pulled out of the pore against the applied field until finally ejected back to the cis side of the bilayer (see FIG. 7).

Other Methods

The invention also provides a method of forming a sensor for characterising a target polynucleotide. The method comprises forming a complex between a pore and a helicase of the invention or a construct of the invention. The complex may be formed by contacting the pore and the helicase or construct in the presence of the target polynucleotide and then applying a potential across the pore. The applied potential may be a chemical potential or a voltage potential as described above. Alternatively, the complex may be formed by covalently attaching the pore to the helicase or construct. Methods for covalent attachment are known in the art and disclosed, for example, in International Application Nos. PCT/GB09/001679 (published as WO 2010/004265) and PCT/GB10/000133 (published as WO 2010/086603). The complex is a sensor for characterising the target polynucleotide. The method preferably comprises forming a complex between a pore derived from Msp and a helicase of the invention or a construct of the invention. Any of the embodiments discussed above with reference to the methods of the invention equally apply to this method. The invention also provides a sensor produced using the method of the invention.

Kits

The present invention also provides a kit for characterising a target polynucleotide. The kit comprises (a) a pore and (b) a helicase of the invention or a construct of the invention. Any of the embodiments discussed above with reference to the method of the invention equally apply to the kits.

The kit may further comprise the components of a membrane, such as the phospholipids needed to form an amphiphilic layer, such as a lipid bilayer.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

Apparatus

The invention also provides an apparatus for characterising a target polynucleotide. The apparatus comprises a plurality of pores and a plurality of helicases of the invention or a plurality of constructs of the invention. The apparatus preferably further comprises instructions for carrying out the method of the invention. The apparatus may be any conventional apparatus for polynucleotide analysis, such as an array or a chip. Any of the embodiments discussed above with reference to the methods of the invention are equally applicable to the apparatus of the invention.

The apparatus is preferably set up to carry out the method of the invention.

The apparatus preferably comprises:

a sensor device that is capable of supporting the plurality of pores and being operable to perform polynucleotide characterisation using the pores and constructs; and at least one reservoir for holding material for performing the characterisation.

The apparatus preferably comprises:

a sensor device that is capable of supporting the plurality of pores and being operable to perform polynucleotide characterisation using the pores and helicases or constructs; and at least one reservoir for holding material for performing the characterisation.

The apparatus preferably comprises:

a sensor device that is capable of supporting the membrane and plurality of pores and being operable to perform polynucleotide characterising using the pores and helicases or constructs;

at least one reservoir for holding material for performing the characterising;

a fluidics system configured to controllably supply material from the at least one reservoir to the sensor device; and one or more containers for receiving respective samples, the fluidics system being configured to supply the samples selectively from one or more containers to the sensor device. The apparatus may be any of those described in International Application No. No. PCT/GB08/004127 (published as WO 2009/077734), PCT/GB10/000789 (published as WO 2010/122293), International Application No. PCT/GB10/002206 (not yet published) or International Application No. PCT/US99/25679 (published as WO 00/28312).

Methods of Producing Helicases of the Invention

The invention also provides methods of producing a helicase of the invention. In one embodiment, the method comprises providing a helicase formed from one or more monomers and comprising a polynucleotide binding domain which comprises an opening through which a polynucleotide can unbind from the helicase. Any of the helicases discussed above can be used in the methods.

The method also comprises modifying the helicase such that two or more parts on the same monomer of the helicase are connected to reduce the size of the opening. The site of and method of connection are selected as discussed above.

In another embodiment, the method comprises providing a Hel308 helicase. Any of the Hel308 helicases described above may be used.

The method further comprises introducing one or more cysteine residues and/or one or more non-natural amino acids at one or more of the positions which correspond to D272, N273, D274, G281, E284, E285, E287, S288, T289, G290, E291, D293, T294, N300, R303, K304, N314, S315, N316, H317, R318, K319, L320, E322, R326, N328 and S615 in Hel308 Mbu (SEQ ID NO: 10).

The method preferably further comprises (c) heating the modified helicase, for instance by heating at 50° C. for 10 minutes, (d) exposing the modified helicase to UV light, for instance by exposing the modified helicase to high intensity UV light at 254 nm for about 10 to about 15 minutes or (e) exposing the modified helicase to ferrocyanide and ferricyanide, such as potassium ferrocyanide and potassium ferricyanide. Any combination of steps (c), (d) and (e) may be performed, such as (c), (d), (e), (c) and (d), (d) and (e), (c) and (e) or (c), (d) and (e).

The method preferably further comprises determining whether or not the helicase is capable of controlling the movement of a polynucleotide. Assays for doing this are described above. If the movement of a polynucleotide can be controlled, the helicase has been modified correctly and a helicase of the invention has been produced. If the movement of a polynucleotide cannot be controlled, a helicase of the invention has not been produced.

Methods of Producing Constructs of the Invention

The invention also provides a method of producing a construct of the invention. The method comprises attaching, preferably covalently attaching a helicase of the invention to an additional polynucleotide binding moiety. Any of the helicases and moieties discussed above can be used in the methods. The site of and method of covalent attachment are selected as discussed above.

The method preferably further comprises determining whether or not the construct is capable of controlling the movement of a polynucleotide. Assays for doing this are described above. If the movement of a polynucleotide can be controlled, the helicase and moiety have been attached correctly and a construct of the invention has been produced. If the movement of a polynucleotide cannot be controlled, a construct of the invention has not been produced.

The following Example illustrates the invention.

Example 1

This Example describes the method of synthesising the Hel308 Mbu (E284C/S615C)-bismaleimidePEG3 (SEQ ID NO: 10 with the mutations E284C/S615C connected by a bismaleimidePEG3 linker). In this case a covalent link between cysteines at positions 284 and 615 in the primary sequence of Hel308 Mbu (SEQ ID NO: 10) was made by reacting these positions with a bismaleimidePEG3 linker (approximately 3.7 nm in length).

In detail, 6 µl of 1 M DTT was added to 600 µL of Hel308 Mbu(E284C/S615C) (SEQ ID NO: 10 with the mutations E284C/S615C, stored in 50 mM Tris-HCl pH 8.0, 421 mM NaCl, 10% Glycerol, 10 mM DTT) and the mixture was incubated at room temperature on a 10" wheel rotating at 20 rpm for 30 minutes. This mixture was buffer exchanged through Pierce 2 mL Zeba desalting columns, 7k MWCO into 100 mM potassium phosphate, 500 mM NaCl, 5 mM EDTA, 0.1% Tween-20 pH 8.0 to give 550 µL of sample. To this was added, 5.5 µL of bismaleimidePEG3 (QuantaBiodesign, Product Ref=10215) and the mixture incubated at room temperature on a 10" wheel rotating at 20 rpm for 120 minutes. To stop the reaction, 5.5 µL of 1 M DTT was added to quench any remaining maleimides. Analysis of the reaction was by 7.5% polyacrylamide gel or by reverse phase HPLC (chromatographed on a Jupiter C5 300A 5 µm 150× 4.6 mm column, using a gradient of acetonitrile in 0.1% TFA). FIG. 1 shows a coomassie stained 7.5% Tris-HCl gel (loaded with Laemmli loading buffer) of the Hel308 Mbu (E284C/S615C)-bismaleimidePEG3 (SEQ ID NO: 10 with the mutations E284C/S615C connected by a bismaleimide-PEG3 linker) reaction mixture. Lane X shows an appropriate protein ladder (the mass unit markers are shown on the left of the gel). Lanes a-c contain 2 µL, 5 µL or 10 µL of approximately 2.5 µM Hel308 Mbu(E284C/S615C) monomer (SEQ ID NO: 10 with mutations E284C/S615C). Lanes d-f contain 2 µL, 5 µL or 10 µL of approximately 2.5 µM Hel308 Mbu(E284C/S615C)-bismaleimidePEG3 (SEQ ID NO: 10 with the mutations E284C/S615C connected by a bismaleimidePEG3 linker), it was clear from the gel that the reaction to attach the bismaleimidePEG3 linker went to nearly 100% yield. The Hel308 Mbu(E284C/S615C)-bismaleimidePEG3 (SEQ ID NO: 10 with the mutations E284C/S615C connected by a bismaleimidePEG3 linker) was then buffer exchanged to 50 mM Tris, 500 mM NaCl, 2 mM DTT, 10% glycerol pH 8.0.

Example 2

This example describes the method of synthesising the Hel308 Mbu (E284C/S615C)-mal-pep-mal (SEQ ID NO: 10 with the mutations E284C/S615C connected by a bismaleimide peptide linker (maleimide-propyl-SRDFWRS-(1,2-diaminoethane)-propyl-maleimide, SEQ ID NO: 109 corresponds to the peptide sequence SRDFWRS)). In this case a covalent link between cysteines at positions 284 and 615 in the primary sequence of Hel308 Mbu (SEQ ID NO: 10) was made by reacting these positions with a bismaleimide peptide linker (maleimide-propyl-SRDFWRS-(1,2-diaminoethane)-propyl-maleimide, SEQ ID NO: 109 corresponds to the peptide sequence SRDFWRS).

Figure 2:
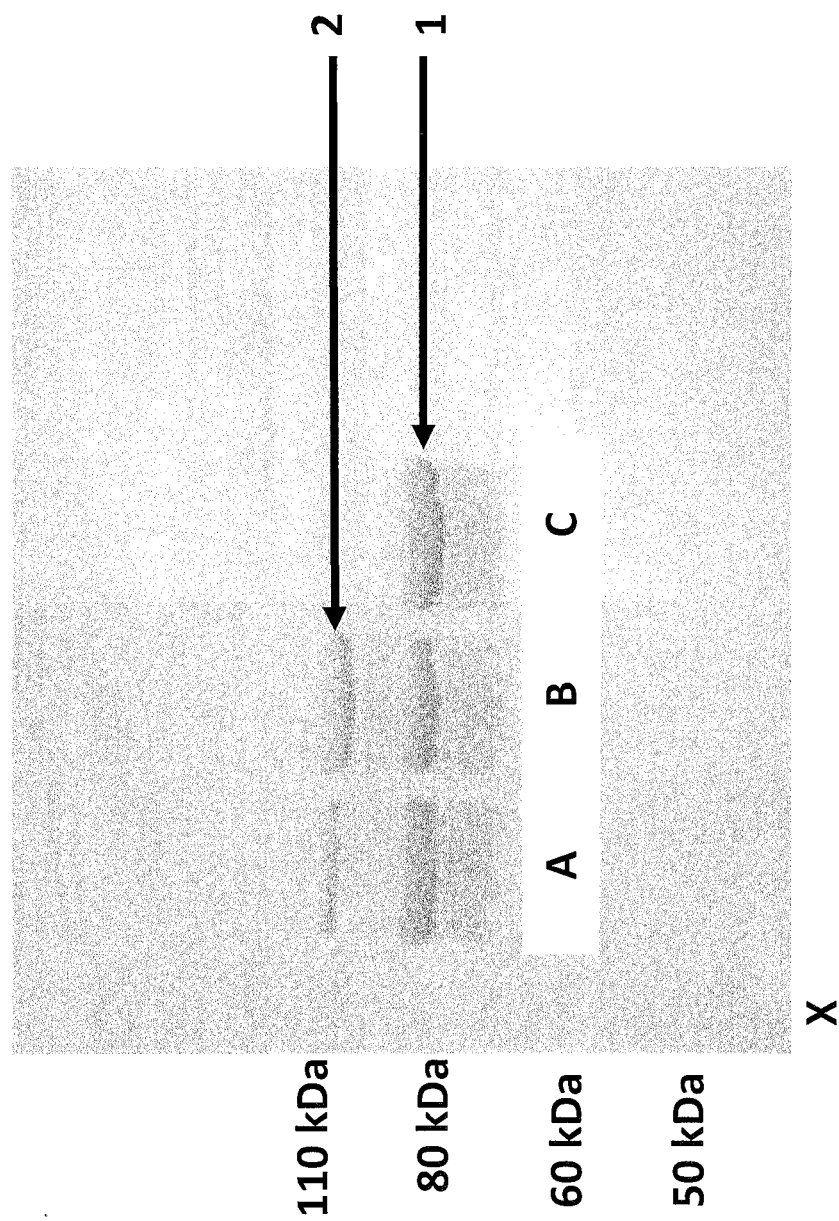
FIG. 2 shows a coomassie stained 7.5% Tris-HCl gel of the Hel308 Mbu (E284C/S615C)-mal-pep-mal (SEQ ID NO: 10 with the mutations E284C/S615C connected by a bismaleimide peptide linker (maleimide-propyl-SRDFWRS (SEQ ID NO: 109)-(1,2-diaminoethane)-propyl-maleimide)) reaction mixture. Lane X shows an appropriate protein ladder (the mass unit markers are shown on the left of the gel). Lane A contains 5 µL of approximately 10 µM Hel308 Mbu(E284C/S615C)-bismaleimidePEG3 (SEQ ID NO: 10 with the mutations E284C/S615C connected by a bismaleimidePEG3 linker) as a reference. The upper band (labelled 2) corresponds to Hel308 Mbu(E284C/S615C)-bismaleimidePEG3 and the lower band (labelled 1) to Hel308 Mbu (E284C/S615C) (SEQ ID NO: 10 with the mutations E284C/S615C). Lane B contains 5 µL of approximately 10 µM Hel308 Mbu (E284C/S615C)-mal-pep-mal (SEQ ID NO: 10 with the mutations E284C/S615C connected by a bismaleimide peptide linker (maleimide-propyl-SRDF-WRS-(1,2-diaminoethane)-propyl-maleimide), it was clear from the gel that the reaction to attach the mal-pep-mal linker did not go to completion as a band for the Hel308 Mbu (E284C/S615C)-mal-pep-mal (SEQ ID NO: 10 with the mutations E284C/S615C connected by a bismaleimide peptide linker (maleimide-propyl-SRDFWRS-(1,2-diaminoethane)-propyl-maleimide) (upper band) and the Hel308 Mbu (E284C/S615C) (SEQ ID NO: 10 with the mutations E284C/S615C) (lower band) are observed. Lane C contains Hel308 Mbu (E284C/S615C) (SEQ ID NO: 10 with the mutations E284C/S615C).

In detail, 2 μl of 1 M DTT was added to 200 μL of Hel308 Mbu(E284C/S615C) (SEQ ID NO: 10 with the mutations E284C/S615C, stored in 50 mM Tris-HCl pH 8.0, 421 mM NaCl, 10% Glycerol, 10 mM DTT) and the mixture was incubated at room temperature on a 10" wheel rotating at 20 rpm for 30 minutes. This mixture was buffer exchanged through Pierce 2 mL Zeba desalting columns, 7k MWCO into 100 mM potassium phosphate, 500 mM NaCl, 5 mM EDTA, 0.1% Tween-20 pH 8.0 to give 540 μL of sample. To an aliquot of 100 ul, 0.5 ul of 10 mM maleimide-propyl-SRDFWRS-(1,2-diaminoethane)-propyl-maleimide (PPRL, Product Ref=16450) was added and the mixture incubated at room temperature on a 10" wheel rotating at 20 rpm for 120 minutes. To stop the reaction, 1 ul of 1 M DTT was added to quench any remaining maleimides. Analysis of the reaction is by 7.5% polyacrylamide gel or by reverse phase HPLC (chromatographed on a Jupiter C5 300A 5 μm 150× 4.6 mm column, using a gradient of acetonitrile in 0.1% TFA). FIG. 2 shows a coomassie stained 7.5% Tris-HCl gel of the Hel308 Mbu (E284C/S615C)-mal-pep-mal (SEQ ID NO: 10 with the mutations E284C/S615C connected by a bismaleimide peptide linker (maleimide-propyl-SRDFWRS-(1,2-diaminoethane)-propyl-maleimide) reaction mixture. Lane X shows an appropriate protein ladder (the mass unit markers are shown on the left of the gel). Lane A contains 5 μL of approximately 10 μM Hel308 Mbu(E284C/S615C)-bismaleimidePEG3 (SEQ ID NO: 10 with the mutations E284C/S615C connected by a bismaleimidePEG3 linker) as a reference. The upper band corresponds to Hel308 Mbu(E284C/S615C)-bismaleimidePEG3 and the lower band to Hel308 Mbu (E284C/S615C) (SEQ ID NO: 10 with the mutations E284C/S615C). Lane B contains 5 μL of approximately 10 μM Hel308 Mbu (E284C/S615C)-mal-pep-mal (SEQ ID NO: 10 with the mutations E284C/S615C connected by a bismaleimide peptide linker (maleimide-propyl-SRDFWRS-(1,2-diaminoethane)-propyl-maleimide), it was clear from the gel that the reaction to attach the mal-pep-mal linker did not go to completion as a band for the Hel308 Mbu (E284C/S615C)-mal-pep-mal (SEQ ID NO: 10 with the mutations E284C/S615C connected by a bismaleimide peptide linker (maleimide-propyl-SRDFWRS-(1,2-diaminoethane)-propyl-maleimide) (upper band) and the Hel308 Mbu (E284C/S615C) (SEQ ID NO: 10 with the mutations E284C/S615C) (lower band) are observed. Lane C contains Hel308 Mbu (E284C/S615C) (SEQ ID NO: 10 with the mutations E284C/S615C).

The Hel308 Mbu (E284C/S615C)-mal-pep-mal (SEQ ID NO: 10 with the mutations E284C/S615C connected by a bismaleimide peptide linker (maleimide-propyl-SRDFWRS-(1,2-diaminoethane)-propyl-maleimide, SEQ ID NO: 109 corresponds to the peptide sequence SRDFWRS)) was then buffer exchanged to 50 mM Tris, 500 mM NaCl, 2 mM DTT, 10% glycerol pH 8.0.

Example 3

This example compares the enzyme processivity of two Hel308 Mbu helicases in which the opening has been closed (Hel308 Mbu(E284C/S615C)-bismaleimidePEG11 (SEQ ID NO: 10 with mutations E284C/S615C connected by a bismaleimidePEG11) and Hel308 Mbu(E284C/S615C)-bismaleimidePEG3) (SEQ ID NO: 10 with the mutations E284C/S615C connected by a bismaleimidePEG3 linker) to that of the Hel308 Mbu monomer (SEQ ID NO: 10) using a fluorescence based assay.

Materials and Methods

SEQ ID NOs: 110 to 114. SEQ ID NO: 112 has a carboxyfluorescein at the 5' end and a black-hole quencher at the 3' end.

Figure 3:
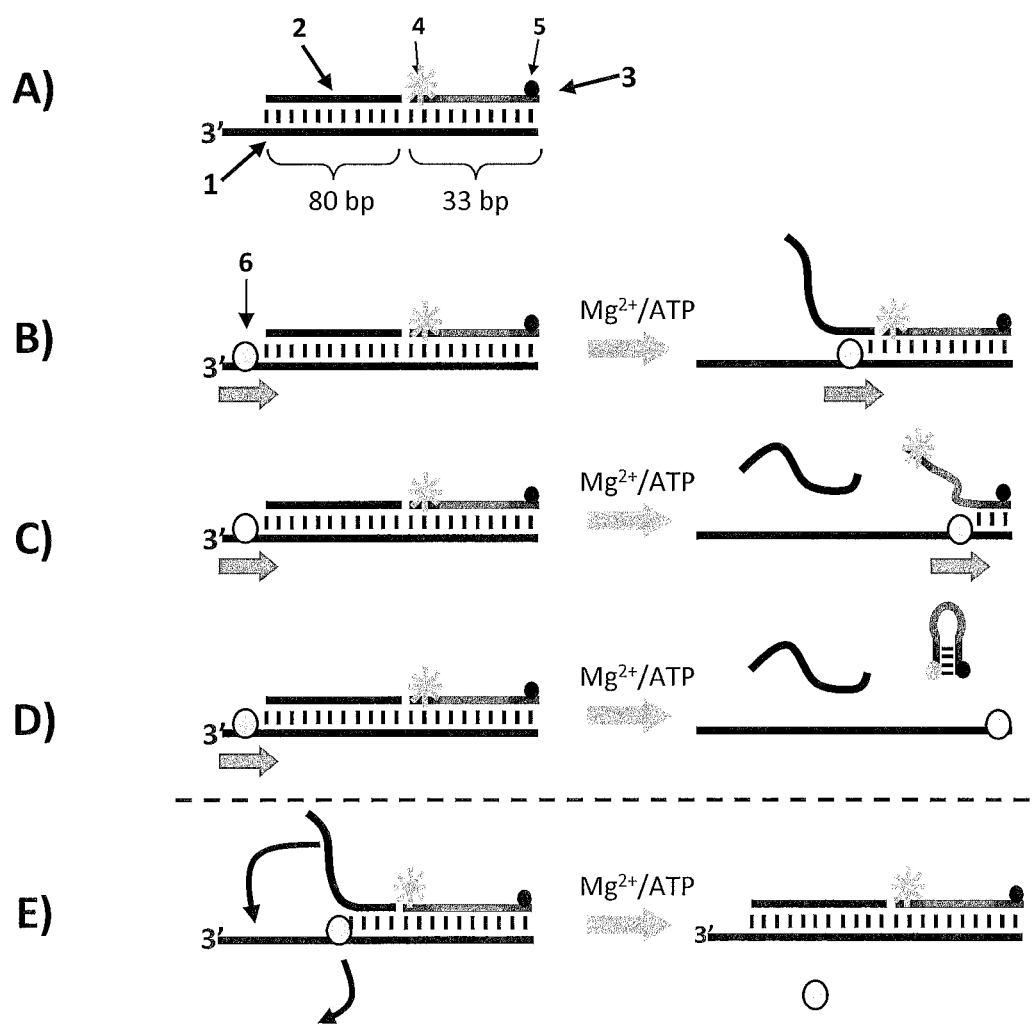
FIG. 3 shows a fluorescence assay used to compare the enzyme processivity of two Hel308 Mbu helicases in which the opening has been closed (Hel308 Mbu(E284C/S615C)-bismaleimidePEG11 (SEQ ID NO: 10 with mutations E284C/S615C connected by a bismaleimidePEG11 linker) and Hel308 Mbu(E284C/S615C)-bismaleimidePEG3 (SEQ ID NO: 10 with mutations E284C/S615C connected by a bismaleimidePEG3 linker)) to that of the Hel308 Mbu monomer (SEQ ID NO: 10). A custom fluorescent substrate was used to assay the ability of the helicase to displace hybridised dsDNA. The fluorescent substrate (50 nM final) has a 3' ssDNA overhang, and 80 and 33 base-pair sections of hybridised dsDNA (section A, SEQ ID NO: 110, labelled 1). The major bottom "template" strand is hybridised to an 80 nt "blocker" strand (SEQ ID NO: 111, labelled 2), adjacent to its 3' overhang, and a 33 nt fluorescent probe (labelled 3), labelled at its 5' and 3' ends with carboxyfluorescein (FAM, labelled 4) and black-hole quencher (BHQ-1, labelled 5) bases (SEQ ID NO: 112), respectively. When hybridised, the FAM is distant from the BHQ-1 and the substrate is essentially fluorescent. In the presence of ATP (1 mM) and MgCl$_2$ (10 mM), the helicase (labelled 6, 10 nM) binds to the substrate's 3' overhang (SEQ ID NO: 110), moves along the lower strand, and begins to displace the 80 nt blocker strand (SEQ ID NO: 111), as shown in section B. If processive, the helicase displaces the fluorescent probe too (section C, SEQ ID NO: 112, labelled with a carboxyfluorescein (FAM) at its 5' end a black-hole quencher (BHQ-1) at its 3' end). The fluorescent probe is designed in such a way that its 5' and 3' ends are self-complementary and thus form a kinetically-stable hairpin once displaced, preventing the probe from re-annealing to the template strand (section D). Upon formation of the hairpin product, the FAM is brought into the vicinity of the BHQ-1 and its fluorescence is quenched. A processive enzyme, capable of displacing the 80 mer "blocker" (SEQ ID NO: 111) and fluorescent (SEQ ID NO: 112, labelled with a carboxyfluorescein (FAM) at its 5' end a black-hole quencher (BHQ-1) at its 3' end) strands will therefore lead to a decrease in fluorescence over time. However, if the enzyme has a processivity of less than 80 nt it would be unable to displace the fluorescent strand (SEQ ID NO: 112, labelled with a carboxyfluorescein (FAM) at its 5' end a black-hole quencher (BHQ-1) at its 3' end) and, therefore, the "blocker" strand (SEQ ID NO: 111) would reanneal to the major bottom strand (section E).

A custom fluorescent substrate was used to assay the ability of the helicase to displace hybridised dsDNA (FIG. 3). The fluorescent substrate (50 nM final) has a 3' ssDNA overhang, and 80 and 33 base-pair sections of hybridised dsDNA (FIG. 3 section A, SEQ ID NO: 110). The major lower "template" strand is hybridised to an 80 nt "blocker" strand (SEQ ID NO: 111), adjacent to its 3' overhang, and a 33 nt fluorescent probe, labelled at its 5' and 3' ends with carboxyfluorescein (FAM) and black-hole quencher (BHQ-1) bases, respectively (SEQ ID NO: 112). When hybridised, the FAM is distant from the BHQ-1 and the substrate is essentially fluorescent. In the presence of ATP (1 mM) and $MgCl_2$ (10 mM), the helicase (10 nM) binds to the substrate's 3' overhang (SEQ ID NO: 110), moves along the lower strand, and begins to displace the 80 nt blocker strand (SEQ ID NO: 111), as shown in FIG. 3 section B. If processive, the helicase displaces the fluorescent probe (SEQ ID NO: 112, labelled with a carboxyfluorescein (FAM) at its 5' end a black-hole quencher (BHQ-1) at its 3' end) too (FIG. 3 section C). The fluorescent probe is designed in such a way that its 5' and 3' ends are self-complementary and thus form a kinetically-stable hairpin once displaced, preventing the probe from re-annealing to the template strand (FIG. 3 section D). Upon formation of the hairpin product, the FAM is brought into the vicinity of the BHQ-1 and its fluorescence is quenched. A processive enzyme, capable of displacing the 80 mer "blocker" (SEQ ID NO: 111) and fluorescent (SEQ ID NO: 112, labelled with a carboxyfluorescein (FAM) at its 5' end a black-hole quencher (BHQ-1) at its 3' end) strands will therefore lead to a decrease in fluorescence over time. However, if the enzyme has a processivity of less than 80 nt it would be unable to displace the fluorescent strand (SEQ ID NO: 112, labelled with a carboxyfluorescein (FAM) at its 5' end a black-hole quencher (BHQ-1) at its 3' end) and, therefore, the "blocker" strand (SEQ ID NO: 111) would reanneal to the major bottom strand (FIG. 3 section E, SEQ ID NO: 110).

Figure 4:
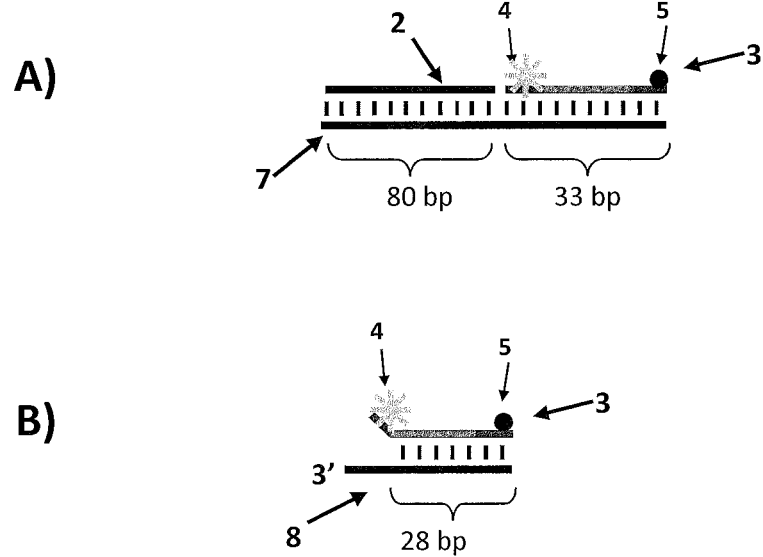
FIG. 4 shows additional custom fluorescent substrates which were also used for control purposes. The substrate used as a negative control was identical to that of the one described in FIG. 3 but lacking the 3' overhang (section A, (SEQ ID NO's: 111 (labelled 2 in figure), 112 (Strand labeled 3 in figure, labelled with a carboxyfluorescein (FAM, labelled 4 in figure) at its 5' end a black-hole quencher (BHQ-1, labelled 5 in figure) at its 3' end) and 113 labelled 7 in figure)). A similar substrate to that described in FIG. 3 but lacking the 80 base pair section (SEQ ID NO's: 112 (strand labelled 3 in figure, labelled with a carboxy-fluorescein (FAM labelled 4 in figure) at its 5' end a black-hole quencher (BHQ-1, labelled 5 in figure) at its 3' end) and 114 labelled 8 in figure), was used as a positive control for active, but not necessarily processive, helicases (section B).

Additional custom fluorescent substrates were also used for control purposes. The substrate used as a negative control was identical to that of the one described in FIG. 3 but lacking the 3' overhang (FIG. 4 section A, (SEQ ID NOs: 111, 112 (labelled with a carboxyfluorescein (FAM) at its 5' end a black-hole quencher (BHQ-1) at its 3' end) and 113)). A similar substrate to that described in FIG. 3 but lacking the 80 base pair section, used as a positive control for active, but not necessarily processive, helicases (FIG. 4 section B, (SEQ ID NO's: 112 (labelled with a carboxyfluorescein (FAM) at its 5' end a black-hole quencher (BHQ-1) at its 3' end) and 114)).

Figure 5:
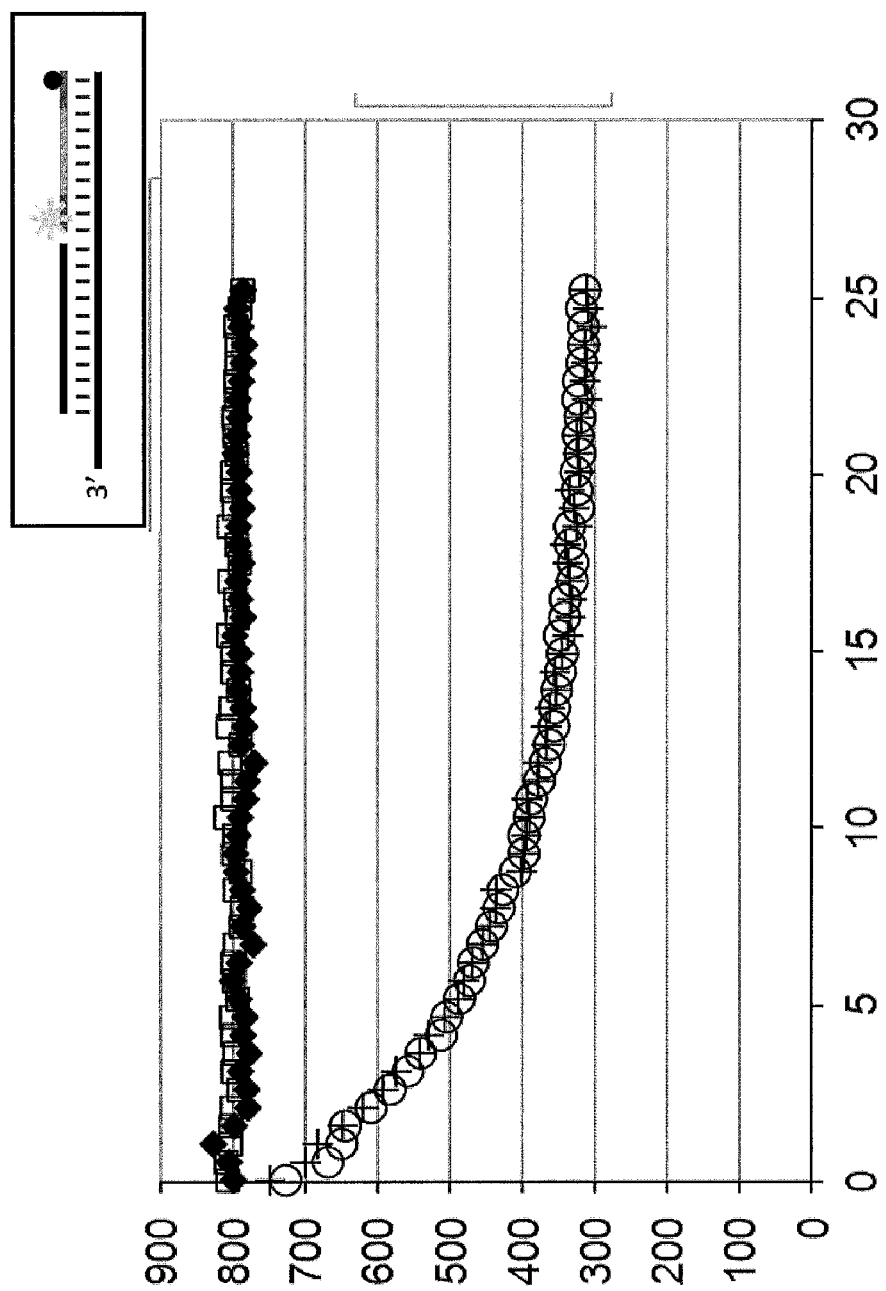
FIG. 5 shows a graph (y-axis label=Normalised fluorescence (arbitrary values), x-axis label=time (min)) of the time-dependent fluorescence changes upon testing Hel308 Mbu, Hel308 Mbu(E284C/S615C)-bismaleimidePEG11 (SEQ ID NO: 10 with mutations E284C/S615C connected by a bismaleimidePEG11 linker) and Hel308 Mbu(E284C/S615C)-bismaleimidePEG3 (SEQ ID NO: 10 with mutations E284C/S615C connected by a bismaleimidePEG3 linker) against the processivity substrate shown in FIG. 3 in buffered solution (400 mM NaCl, 10 mM Hepes pH 8.0, 1 mM ATP, 10 mM MgCl$_2$, 50 nM fluorescent substrate DNA (SEQ ID NOs: 110, 111 and 112 (labelled with a carboxyfluorescein (FAM) at its 5' end a black-hole quencher (BHQ-1) at its 3' end). The data points marked with a black diamond correspond to a buffer blank, the white square data points correspond to Hel308 Mbu monomer (SEQ ID NO: 10), the black cross data points correspond to Hel308 Mbu(E284C/S615C)-bismaleimidePEG11 (SEQ ID NO: 10 with mutations E284C/S615C connected by a bismaleimidePEG11 linker) and the white circle data points correspond to Hel308 Mbu(E284C/S615C)-bismaleimidePEG3 (SEQ ID NO: 10 with mutations E284C/S615C connected by a bismaleimidePEG3 linker). The decrease in fluorescence exhibited by Hel308 Mbu(E284C/S615C)-bismaleimide-PEG11 (SEQ ID NO: 10 with mutations E284C/S615C connected by a bismaleimidePEG11 linker) and Hel308 Mbu(E284C/S615C)-bismaleimidePEG3 (SEQ ID NO: 10 with mutations E284C/S615C connected by a bismaleimidePEG3 linker), denote the increased processivity of these complexes as compared to Hel308 Mbu monomer (SEQ ID NO: 10).
Figure 6:
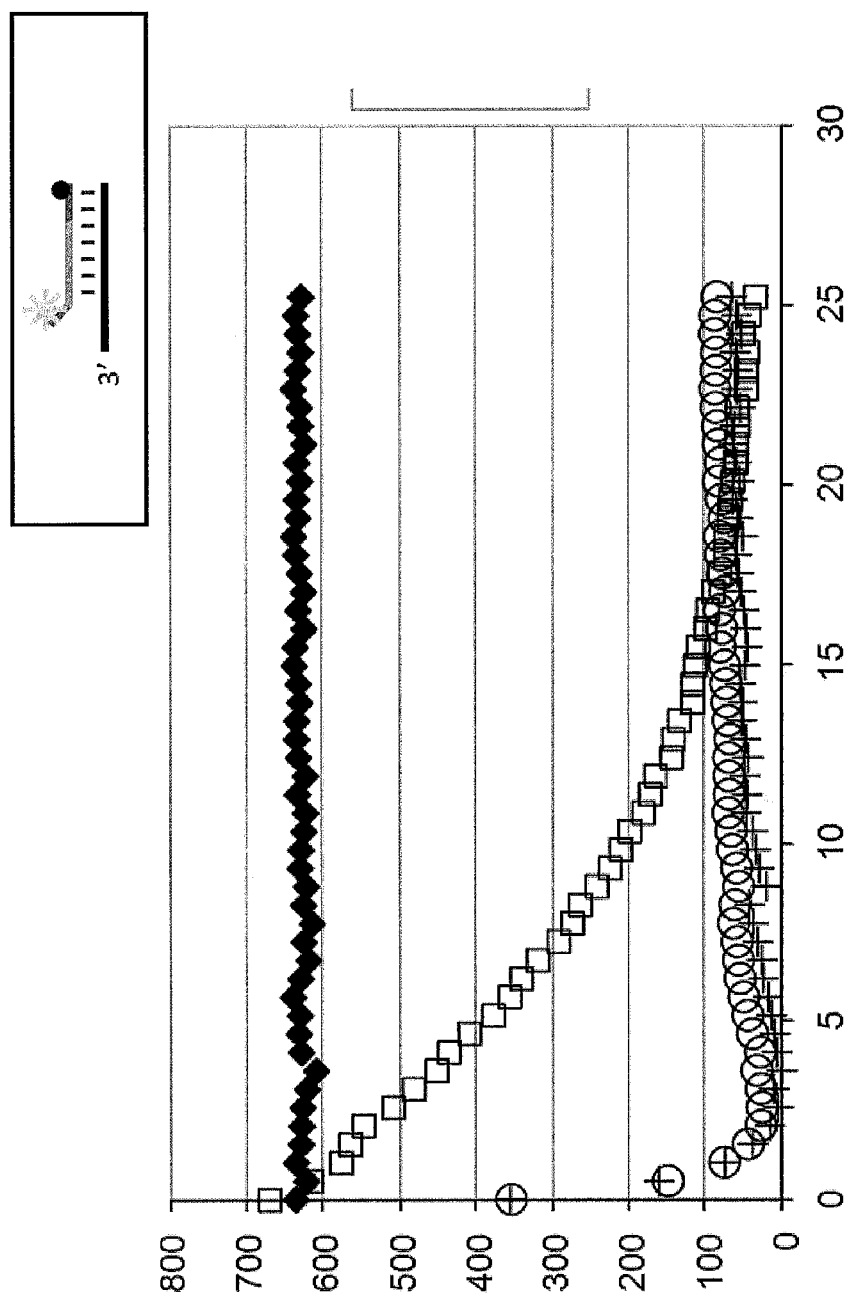
FIG. 6 shows a graph (y-axis label=Normalised fluorescence (arbitrary values), x-axis label=time (min)) of the time-dependent fluorescence changes upon testing Hel308 Mbu (SEQ ID NO: 10), Hel308 Mbu(E284C/S615C)-bis-maleimidePEG11 (SEQ ID NO: 10 with mutations E284C/S615C connected by a bismaleimidePEG11 linker) and Hel308 Mbu(E284C/S615C)-bismaleimidePEG3 (SEQ ID NO: 10 with mutations E284C/S615C connected by a bis-maleimidePEG3 linker) against the positive control processivity substrate (shown in FIG. 4 section B, SEQ ID NOs: 112 (labelled with a carboxyfluorescein (FAM) at its 5' end a black-hole quencher (BHQ-1) at its 3' end) and 60) in buffered solution (400 mM NaCl, 10 mM Hepes pH 8.0, 1 mM ATP, 10 mM MgCl$_2$, 50 nM fluorescent substrate DNA (SEQ ID NOs: 112 (labelled with a carboxyfluorescein (FAM) at its 5' end a black-hole quencher (BHQ-1) at its 3' end) and 114)). The data points marked with a black diamond correspond to a buffer blank, the white square data points correspond to Hel308 Mbu monomer (SEQ ID NO: 10), the black cross data points correspond to Hel308 Mbu(E284C/S615C)-bismaleimidePEG11 (SEQ ID NO: 10 with mutations E284C/S615C connected by a bismaleim- idePEG11 linker) and the white circle data points correspond to Hel308 Mbu(E284C/S615C)-bismaleimidePEG3 (SEQ ID NO: 10 with mutations E284C/S615C connected by a bismaleimidePEG3 linker). This positive control demonstrated that all complexes were indeed active, as denoted by a fluorescence decrease for all samples.

FIG. 5 shows a graph of the time-dependent fluorescence changes upon testing Hel308 Mbu monomer (SEQ ID NO: 10), Hel308 Mbu(E284C/S615C)-bismaleimidePEG11 (SEQ ID NO: 10 with mutations E284C/S615C connected by a bismaleimidePEG11 linker) and Hel308 Mbu(E284C/S615C)-bismaleimidePEG3 (SEQ ID NO: 10 with mutations E284C/S615C connected by a bismaleimidePEG3 linker) against the processivity substrate shown in FIG. 3 in buffered solution (400 mM NaCl, 10 mM Hepes pH 8.0, 1 mM ATP, 10 mM $MgCl_2$, 50 nM fluorescent substrate DNA (SEQ ID NOs: 110, 111 and 112 (labelled with a carboxyfluorescein (FAM) at its 5' end a black-hole quencher (BHQ-1) at its 3' end))). The decrease in fluorescence exhibited by Hel308 Mbu(E284C/S615C)-bismaleimidePEG11 (SEQ ID NO: 10 with mutations E284C/S615C connected by a bismaleimidePEG11 linker) and Hel308 Mbu(E284C/S615C)-bismaleimidePEG3 (SEQ ID NO: 10 with mutations E284C/S615C connected by a bismaleimidePEG3 linker), denote the increased processivity of these complexes as compared to Hel308 Mbu monomer (SEQ ID NO: 10). FIG. 6 shows positive controls demonstrating that all helicases were indeed active, as denoted by a fluorescence decrease for all samples.

Example 4

Figure 7:
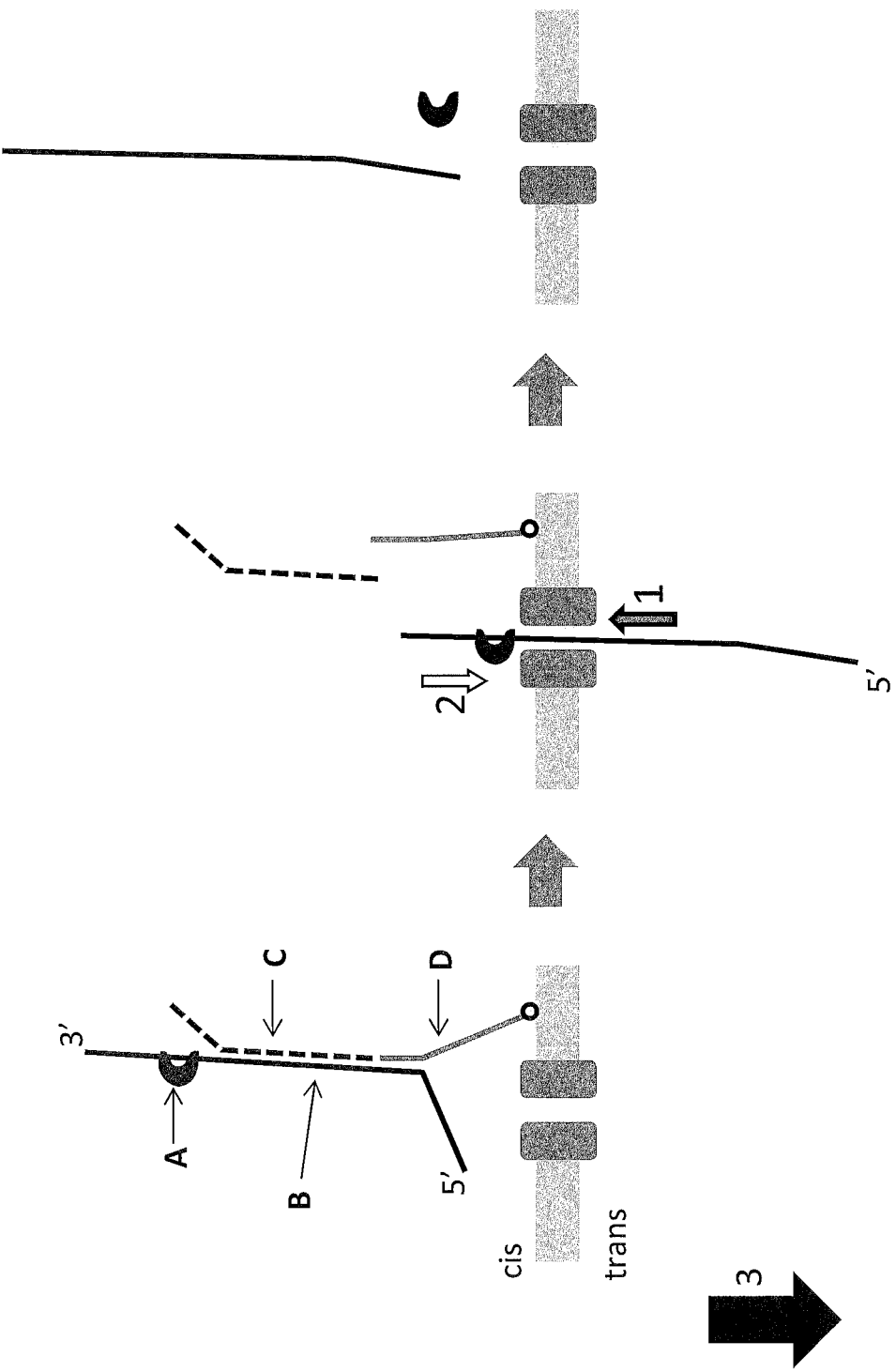
FIG. 7 shows a schematic of enzyme controlled translocation of a polynucleotide through a nanopore in a membrane, where the enzyme controls the movement of the polynucleotide against the force of the applied field. The schematic shows the example of a 3' to 5' enzyme (labelled A), where the capture of a polynucleotide in the pore by the 5' end leads to the enzyme controlling the movement of the polynucleotide (the polynucleotide sequences used in example 4 are SEQ ID NO: 115 (labelled B in FIG. 7), SEQ ID NO:116 (labelled C in FIG. 7) and SEQ ID NO: 117 (labelled D in FIG. 7)) against the force of the applied field. During DNA capture the hybridised strands are unzipped. Arrow 1 denotes the direction of DNA movement through the nanopore, the white arrow 2 denotes the direction of enzyme movement along the DNA and arrow 3 denotes the direction of the applied field. As long as the enzyme does not dissociate from the DNA the enzyme will pull the DNA out of the pore until it is finally ejected on the cis side of the membrane.
Figure 8:
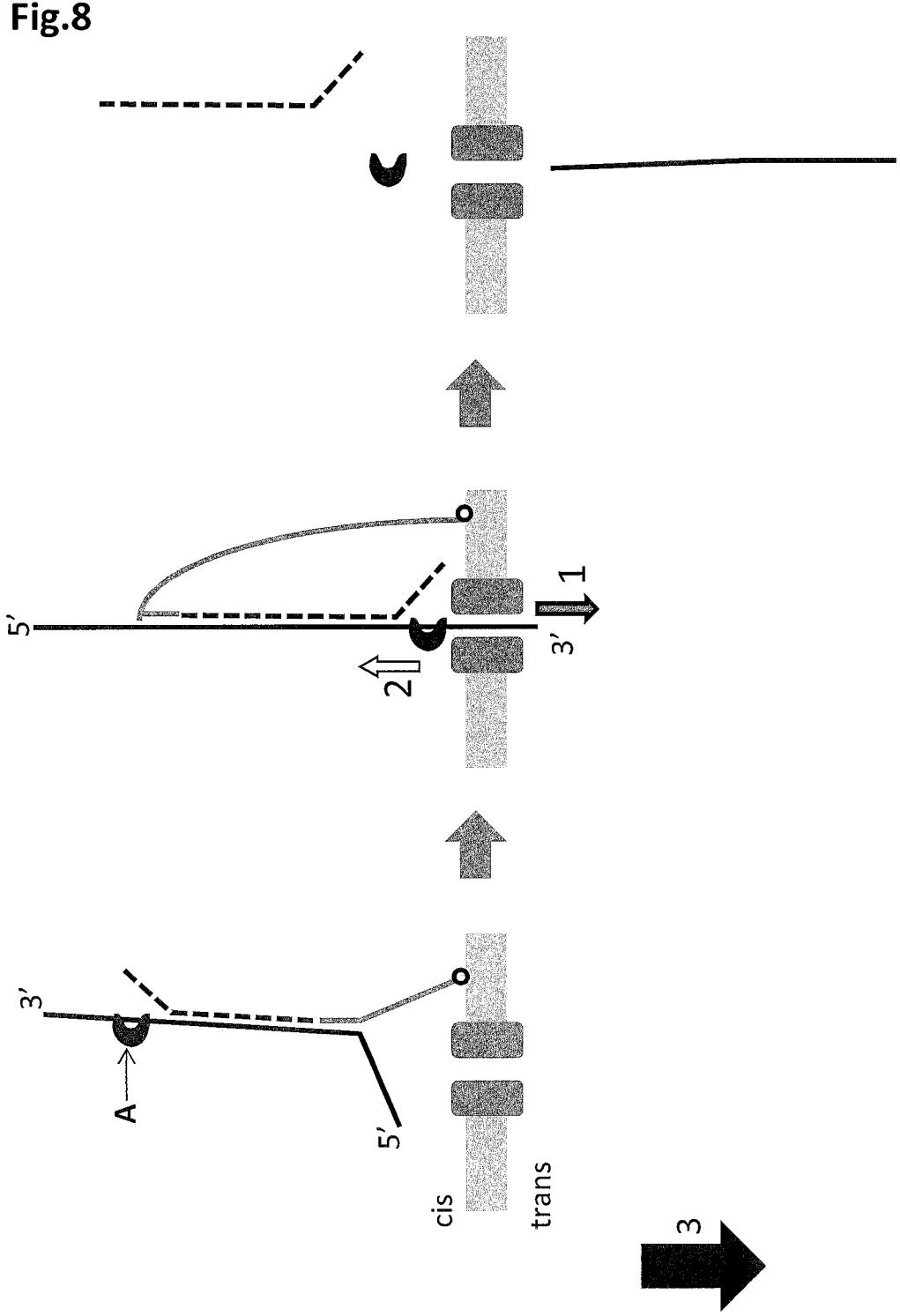
FIG. 8 shows a schematic of enzyme controlled translocation of a polynucleotide through a nanopore in a membrane, where the enzyme controls the movement of the polynucleotide in the same direction as the force of the applied field. The schematic shows the example of a 3' to 5' enzyme (labelled A), where the capture of a polynucleotide in the pore by the 3' end leads to the enzyme controlling the movement of the polynucleotide with the force of the applied field. Arrow 1 denotes the direction of the DNA movement through the nanopore, the white arrow 2 denotes the direction of enzyme movement along DNA and arrow 3 denotes the direction of the applied field. As long as the enzyme does not dissociate from the DNA the enzyme will feed the DNA through the pore until it is finally ejected on the trans side of the membrane.

This example compares the ability of a Hel308 Mbu monomer (SEQ ID NO: 10), to control the movement of intact DNA strands (900 mer) through a nanopore, to that of the Hel308 Mbu(E284C/S615C)-bismaleimidePEG3 (SEQ ID NO. 10 with the following mutations E284C/S615C connected by a bismaleimidePEG3 linker). The general method for controlled DNA translocation against the field is shown in FIG. 7 and with the field in FIG. 8.

Materials and Methods

Figure 9:
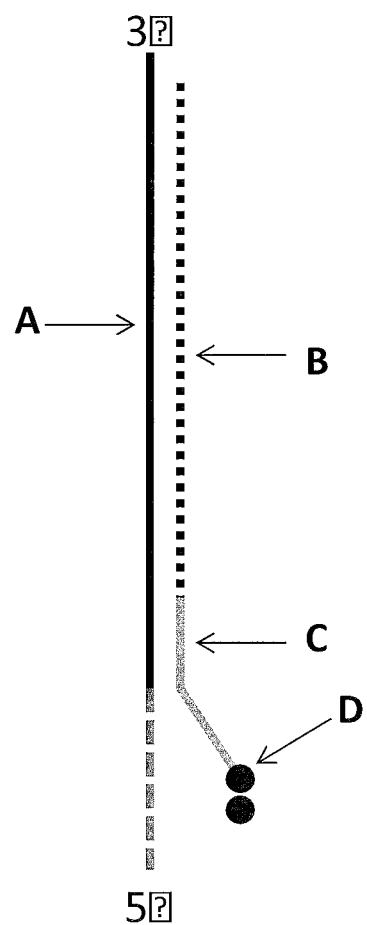
FIG. 9 shows the DNA substrate design used in Example 4. The 900mer sense strand (SEQ ID NO: 115) is labelled A, the anti-sense strand which is minus the 4 base-pair leader (SEQ ID NO: 116) is labelled B and the primer (SEQ ID NO: 117) is labelled C. The primer has a 3' cholesterol tag which is labelled D.

The DNA was formed by ligating a 50-polyT 5' leader to a ~900 base fragment of PhiX dsDNA. The leader also contains a complementary section to which SEQ ID NO: 117 (which at the 3' end of the sequence has six iSp18 spacers attached to two thymine residues and a 3' cholesterol TEG) was hybridized to allow the DNA to be tethered to the bilayer. Finally the 3' end of the PhiX dsDNA was digested with AatII digestion enzyme to yield a 4nt 3'-overhang of ACGT (see FIG. 9 for diagram of the DNA substrate design).

Buffered Solution Used for Hel308 Mbu:
400 mM NaCl, 100 mM Hepes, 10 mM potassium ferrocyanide, 10 mM potassium ferricyanide pH8.0, 1 mM ATP, 1 mM MgCl$_2$, Buffered Solution Used for Hel308 Mbu(E284C/S615C)-bismaleimidePEG3:
400 mM NaCl, 100 mM Hepes, 10 mM potassium ferrocyanide, 10 mM potassium ferricyanide pH8.0, 2 mM ATP, 2 mM MgCl$_2$, Nanopore:
E. coli MS(B1-G75S/G77S/L88N/Q126R)8 MspA (SEQ ID NO: 2 with the mutations G75S/G77S/L88N/Q126R)

Enzymes:
Hel308 Mbu (SEQ ID NO: 10) added at 200 nM final and Hel308 Mbu(E284C/S615C)-bismaleimidePEG3 (SEQ ID NO: 10 with the following mutations E284C/S615C connected by a bismaleimide3PEG linker) added at 10 nM final.

Electrical measurements were acquired from single MspA nanopores inserted in 1,2-diphytanoyl-glycero-3-phosphocholine lipid (Avanti Polar Lipids) bilayers. Bilayers were formed across ~100 um diameter apertures in 20 um thick PTFE films (in custom Delrin chambers) via the Montal-Mueller technique, separating two 1 mL buffered solutions. All experiments were carried out in the stated buffered solution. Single-channel currents were measured on Axopatch 200B amplifiers (Molecular Devices) equipped with 1440A digitizers. Platinum electrodes are connected to the buffered solutions so that the cis compartment (to which both nanopore and enzyme/DNA are added) is connected to the ground of the Axopatch headstage, and the trans compartment is connected to the active electrode of the headstage.

After achieving a single pore in the bilayer, DNA complex (SEQ ID NOs: 115, 116 and 117 (which at the 3' end of the sequence has six iSp18 spacers attached to two thymine residues and a 3' cholesterol TEG)), DNA=0.1 nM for the Hel308 Mbu monomer (SEQ ID NO: 10) and 0.05 nM for the Hel308 Mbu(E284C/S615C)-bismaleimidePEG3 (SEQ ID NO: 10 with mutations E284C/S615C connected by a bismaleimidePEG3 linker), MgCl$_2$ (2 mM) and ATP (2 mM) were added to the cis compartment of the electrophysiology chamber. A control experiment was run at +140 mV. The helicase Hel308 Mbu monomer (SEQ ID NO: 10, 200 nM) or the Hel308 Mbu(E284C/S615C)-bismaleimidePEG3 (SEQ ID NO: 10 with mutations E284C/S615C connected by a bismaleimidePEG3 linker, 10 nM) was then added to the cis compartment. Experiments were carried out at a constant potential of +140 mV.

Results and Discussion

Figure 10:
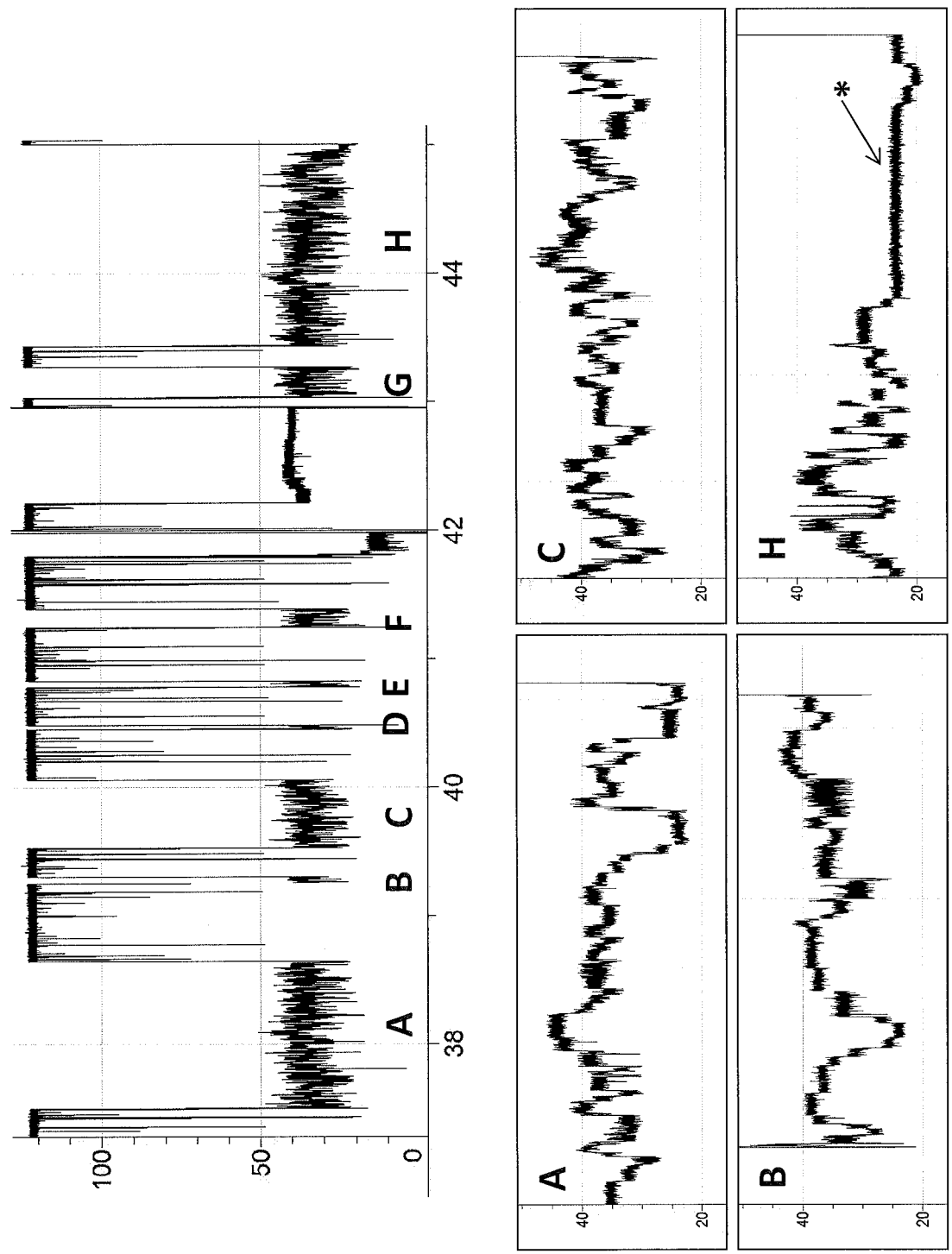
FIG. 10 shows example current traces observed when a helicase controls the translocation of DNA (+140 mV, 400 mM NaCl, 100 mM Hepes pH 8.0, 10 mM potassium ferrocyanide, 10 mM potassium ferricyanide, 0.1 nM 900mer DNA (SEQ ID NO: 115, 116 and 117 (which at the 3' end of the sequence has six iSp18 spacers attached to two thymine residues and a 3' cholesterol TEG)), 1 mM ATP, 1 mM MgCl$_2$) through an MspA nanopore (MS(B1-G75S/G77S/L88N/Q126R)8 MspA (SEQ ID NO: 2 with mutations G75S/G77S/L88N/Q126R) using Hel308 Mbu monomer (200 nM, SEQ ID NO: 10). The top electrical trace (y-axis label=current (pA), x-axis label=time (min)) shows the open pore current (~120 pA) dropping to a DNA level (20-50 pA) when DNA is captured under the force of the applied potential (+140 mV). DNA with enzyme attached results in a long block that shows stepwise changes in current as the enzyme moves the DNA through the pore. The upper trace shows a sequence of 8 separate helicase-controlled DNA movements marked A-H. All of the helicase-controlled DNA movements in this section of trace are being moved through the nanopore against the field by the enzyme (DNA captured 5' down) (see FIG. 7 for details). Below are enlargements of the last section of 4 of the helicase-controlled DNA movements as the DNA exits the nanopore. Of the 8 helicase-controlled DNA movements in this section, only 1 (H) ends in the characteristic long polyT level that indicates that the enzyme has reached the end of the DNA and moved the 50T 5'-leader of the DNA substrate through the pore (labelled with a *). In the full run with Hel308Mbu (SEQ ID NO: 10) it was found that ~30% of the helicase-controlled DNA movements end at the polyT (n=19 helicase-controlled DNA movements in this experiment).

The addition of helicase monomer-DNA substrate to MspA nanopores (as shown in FIG. 7) produces characteristic current blocks as shown in FIG. 10. The helicase Hel308 Mbu monomer (SEQ ID NO: 10) is able to move DNA through a nanopore in a controlled fashion, producing stepwise changes in current as the DNA moves through the nanopore. Example current traces observed when a helicase controls the translocation of DNA (+140 mV, 400 mM NaCl, 100 mM Hepes pH 8.0, 10 mM potassium ferrocyanide, 10 mM potassium ferricyanide, 0.1 nM 900mer DNA (SEQ ID NOs: 115, 116 and 117 (which at the 3' end of the sequence has six iSp18 spacers attached to two thymine residues and a 3' cholesterol TEG)), 1 mM ATP, 1 mM MgCl$_2$) through an MspA nanopore (MS(B1-G75S/G77S/L88N/Q126R)8 MspA (SEQ ID NO: 2 with mutations G75S/G77S/L88N/ Q126R) using Hel308 Mbu (200 nM, SEQ ID NO: 10) are shown in FIG. 10. The top electrical trace shows the open pore current (~120 pA) dropping to a DNA level (20-50 pA) when DNA is captured under the force of the applied potential (+140 mV). DNA with an enzyme attached results in a long block that shows stepwise changes in current as the enzyme moves the DNA through the pore. The upper trace shows a sequence of 8 separate helicase-controlled DNA movements marked A-H (see FIG. 10). All the helicase-controlled DNA movements in this section of trace are being moved through the nanopore against the field by the enzyme (DNA captured 5' down) (see FIG. 7 for details). Below are enlargements of the last section of 4 of the helicase-controlled DNA movements as the DNA exits the nanopore. Of the 8 helicase-controlled DNA movements in this section, only 1 (H) ends in the characteristic long polyT level that indicates that the enzyme has reached the end of the DNA and moved the 50T 5'-leader of the DNA substrate through the pore. In the full run with Hel308 Mbu monomer (SEQ ID NO: 10) it was found that ~30% of the helicase-controlled DNA movements end at the polyT (n=19 helicase-controlled DNA movements in this experiment).

Figure 11:
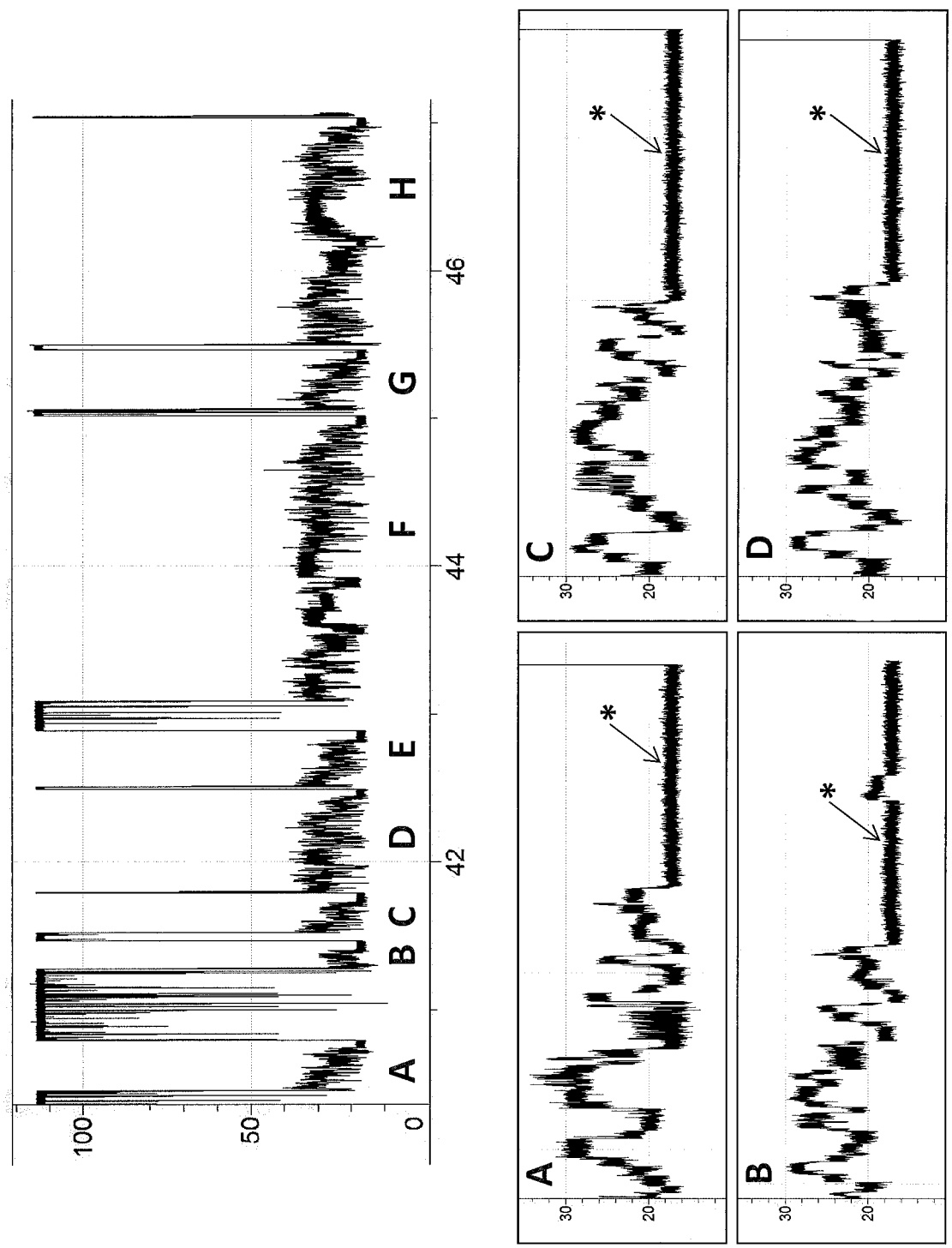
FIG. 11 shows example current traces observed when a helicase controls the translocation of DNA (+140 mV, 400 mM NaCl, 100 mM Hepes pH 8.0, 10 mM potassium ferrocyanide, 10 mM potassium ferricyanide, 0.05 nM 900mer DNA (SEQ ID NO: 115, 116 and 117 (which at the 3' end of the sequence has six iSp18 spacers attached to two thymine residues and a 3' cholesterol TEG)), 2 mM ATP, 2 mM $MgCl_2$) through an MspA nanopore (MS(B1-G75S/G77S/L88N/Q126R)8 MspA (SEQ ID NO: 2 with mutations G75S/G77S/L88N/Q126R) using the Hel308 Mbu(E284C/S615C)-bismaleimidePEG3 (10 nM, SEQ ID NO: 10 with mutations E284C/S615C connected by a bismaleimidePEG3 linker). The top electrical trace (y-axis label=current (pA), x-axis label=time (min)) shows the open pore current (~115 pA) dropping to a DNA level (15-40 pA) when DNA is captured under the force of the applied potential (+140 mV). DNA with enzyme attached results in a long block that shows stepwise changes in current as the enzyme moves the DNA through the pore. The upper trace shows a sequence of 8 separate helicase-controlled DNA movements marked A-H. All the helicase-controlled DNA movements in this section of trace are being moved through the nanopore against the field by the enzyme (DNA captured 5'down) (see FIG. 7 for details). Below are enlargements of the last section of 4 of the helicase-controlled DNA movements as the DNA exits the nanopore. Of the 8 helicase-controlled DNA movements in this section, every one ends in the characteristic long polyT level that indicates that the enzyme has reached the end of the DNA and moved the 50T 5'-leader of the DNA substrate through the pore (labelled with a *). In the full run with Hel308 Mbu (E284C/S615C)-bismaleimidePEG3 (SEQ ID NO: 10 with mutations E284C/S615C connected by a bismaleimidePEG3 linker) it was found that ~85% of the helicase-controlled DNA movements against the field (5' down) end at the polyT (n=27 helicase-controlled DNA movements in this experiment).

The Hel308 Mbu(E284C/S615C)-bismaleimidePEG3 (10 nM, SEQ ID NO: 10 with mutations E284C/S615C connected by a bismaleimidePEG3 linker) is able to move DNA through a nanopore in a controlled fashion against the field, producing stepwise changes in current as the DNA moves through the nanopore. Example current traces observed when a helicase controls the translocation of DNA (+140 mV, 400 mM NaCl, 100 mM Hepes pH 8.0, 10 mM potassium ferrocyanide, 10 mM potassium ferricyanide, 0.05 nM 900mer DNA (SEQ ID NO: 115, 116 and 117 (which at the 3' end of the sequence has six iSp18 spacers attached to two thymine residues and a 3' cholesterol TEG)), 2 mM ATP, 2 mM MgCl$_2$) through an MspA nanopore (MS(B1-G75S/G77S/L88N/Q126R)8 MspA (SEQ ID NO: 2 with mutations G75S/G77S/L88N/Q126R) using the Hel308 Mbu(E284C/S615C)-bismaleimidePEG3 (10 nM, SEQ ID NO: 10 with mutations E284C/S615C connected by a bis-maleimidePEG3 linker) are shown in FIG. 11. The top electrical trace shows the open pore current (~115 pA) dropping to a DNA level (15-40 pA) when DNA is captured under the force of the applied potential (+140 mV). DNA with enzyme attached results in a long block that shows stepwise changes in current as the enzyme moves the DNA through the pore. The upper trace shows a sequence of 8 separate helicase-controlled DNA movements marked A-H (see FIG. 11). All the helicase-controlled DNA movements in this section of trace are being moved through the nanopore against the field by the enzyme (DNA captured 5' down) (see FIG. 7 for details). Below are enlargements of the last section of 4 of the helicase-controlled DNA movements as the DNA exits the nanopore. Of the 8 helicase-controlled DNA movements in this section, every one ends in the characteristic long polyT level that indicates that the enzyme has reached the end of the DNA and moved the 50T 5'-leader of the DNA substrate through the pore. In the full run with Hel308 Mbu(E284C/S615C)-bismaleimidePEG3 (SEQ ID NO: 10 with mutations E284C/S615C connected by a bismaleimidePEG3 linker) it was found that ~85% of the helicase-controlled DNA movements against the field (5' down) end at the polyT (n=27 helicase-controlled DNA movements in this experiment), thus demonstrating substantially improved processivity relative to the unmodified Hel308 Mbu This experiment required only 10 nM enzyme in order to observe helicase-controlled DNA movement, however, Hel308 Mbu monomer (SEQ ID NO: 10) experiments used 200 nM enzyme. Therefore, much lower enzyme concentrations of the helicases in which the opening has been closed can be used while still achieving long read lengths.

Figure 12:
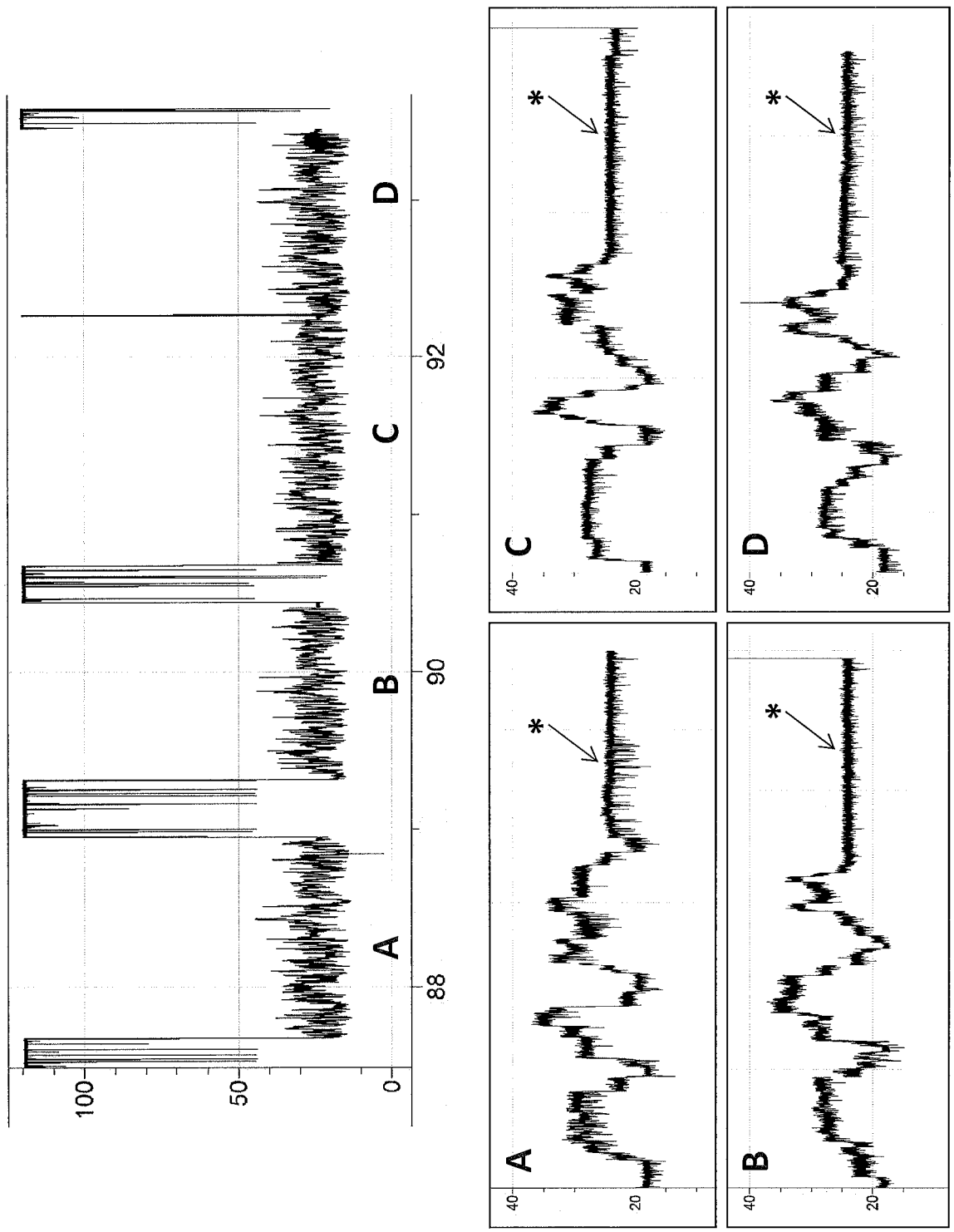
FIG. 12 shows example current traces observed when a helicase controls the translocation of DNA (+140 mV, 400 mM NaCl, 100 mM Hepes pH 8.0, 10 mM potassium ferrocyanide, 10 mM potassium ferricyanide, 0.05 nM 900mer DNA (SEQ ID NO: 115, 116 and 117 (which at the 3' end of the sequence has six iSp18 spacers attached to two thymine residues and a 3' cholesterol TEG)), 2 mM ATP, 2 mM $MgCl_2$) through an MspA nanopore (MS(B1-G75S/G77S/L88N/Q126R)8 MspA (SEQ ID NO: 2 with mutations G75S/G77S/L88N/Q126R) using the Hel308 Mbu(E284C/S615C)-bismaleimidePEG3 (10 nM, SEQ ID NO: 10 with mutations E284C/S615C connected by a bismaleimidePEG3 linker). The top electrical trace (y-axis label=current (pA), x-axis label=time (min)) shows the open pore current (~120 pA) dropping to a DNA level (15-40 pA) when DNA is captured under the force of the applied potential (+140 mV). DNA with enzyme attached results in a long block that shows stepwise changes in current as the enzyme moves the DNA through the pore. The upper trace shows a sequence of 4 separate helicase-controlled DNA movements marked A-D. All the helicase-controlled DNA movements in this section of trace are being moved through the nanopore with the field by the enzyme (DNA captured 3' down) (see FIG. 8 for details). Below are enlargements of the last section of the helicase-controlled DNA movements as the DNA exits the nanopore. 3' down DNA shows a characteristically different signature to 5' down DNA, with a different current to sequence relationship, and different variance. Of the 4 helicase-controlled DNA movements in this section, every one ends in the characteristic long polyT level that indicates that the enzyme has reached the end of the DNA and moved the 50T 5'-leader of the DNA substrate through the pore (labelled with a *). In the full run with Hel308 Mbu(E284C/S615C)-bismaleimidePEG3 (SEQ ID NO: 10 with mutations E284C/S615C connected by a bismaleimidePEG3 linker) it was found that ~87% of the helicase-controlled DNA movements with the field (3' down) end at the polyT (n=15 helicase-controlled DNA movements in this experiment).

Hel308 Mbu(E284C/S615C)-bismaleimidePEG3 (SEQ ID NO: 10 with mutations E284C/S615C connected by a bismaleimidePEG3 linker) shows enhanced ability to move DNA through a nanopore with the force of the applied field (see FIG. 8 for details), producing stepwise changes in current as the DNA moves through the nanopore. Example current traces observed when a helicase controls the translocation of DNA (+140 mV, 400 mM NaCl, 100 mM Hepes pH 8.0, 10 mM potassium ferrocyanide, 10 mM potassium ferricyanide, 0.05 nM 900mer DNA (SEQ ID NO: 115, 116 and 117 (which at the 3' end of the sequence has six iSp18 spacers attached to two thymine residues and a 3' cholesterol TEG)), 2 mM ATP, 2 mM MgCl$_2$) through an MspA nanopore (MS(B1-G75S/G77S/L88N/Q126R)8 MspA(SEQ ID NO: 2 with mutations G75S/G77S/L88N/Q126R) using the Hel308 Mbu(E284C/S615C)-bismaleimidePEG3 (10 nM, SEQ ID NO: 10 with mutations E284C/S615C connected by a bismaleimidePEG3 linker) are shown in FIG. 12. The top electrical trace shows the open pore current (~120 pA) dropping to a DNA level (15-40 pA) when DNA is captured under the force of the applied potential (+140 mV). DNA with enzyme attached results in a long block that shows stepwise changes in current as the enzyme moves the DNA through the pore. The upper trace shows a sequence of 4 separate helicase-controlled DNA movements marked A-D (see FIG. 12). All the helicase-controlled DNA movements in this section of trace are being moved through the nanopore with the field by the enzyme (DNA captured 3' down) (see FIG. 8 for details). Below are enlargements of the last section of the helicase-controlled DNA movements as the DNA exits the nanopore. 3' down DNA shows a characteristically different signature to 5' down DNA, with a different current to sequence relationship, and different variance. Of the 4 helicase-controlled DNA movements in this section, every one ends in the characteristic long polyT level that indicates that the enzyme has reached the end of the DNA and moved the 50T 5'-leader of the DNA substrate through the pore. In the full run with Hel308 Mbu(E284C/S615C)-bismaleimidePEG3 (SEQ ID NO: 10 with mutations E284C/S615C connected by a bismaleimidePEG3 linker) it was found that ~87% of helicase-controlled DNA movements with the field (3' down) end at the polyT (n=15 helicase-controlled DNA movements in this experiment). In comparison, 3' down helicase-controlled DNA movements are rarely observed when using Hel308 Mbu monomer (SEQ ID NO: 10), and when they are the movements are short with typically less than 50 states observed, indicating a high level of enzyme dissociation in this orientation. The long 3' down helicase-controlled DNA movements, with Hel308 Mbu (E284C/S615C)-bismaleimidePEG3 (SEQ ID NO: 10 with mutations E284C/S615C connected by a bismaleimidePEG3 linker), show a surprising improvement in processivity in the 3' down mode.

Example 5

This example shows that the Hel308 Mbu (E284C/S615C)-mal-pep-mal (SEQ ID NO: 10 with the mutations E284C/S615C connected by a bismaleimide peptide linker (maleimide-propyl-SRDFWRS (SEQ ID NO: 109)-(1,2-di-aminoethane)-propyl-maleimide)) has the ability to control the movement of intact DNA strands (SEQ ID NO: 127 attached at its 3' end to four iSpC3 spacers, the last of which is attached to the 5' end of SEQ ID NO: 128) through a nanopore. The general method for controlled DNA translocation against the field is shown in FIG. 7 and with the field in FIG. 8.

Materials and Methods

Prior to setting up the experiment, the DNA (0.5 nM, (SEQ ID NO: 127 attached at its 3' end to four iSpC3 spacers, the last of which is attached to the 5' end of SEQ ID NO: 128) and Hel308 Mbu (E284C/S615C)-mal-pep-mal (SEQ ID NO: 10 with the mutations E284C/S615C connected by a bismaleimide peptide linker (maleimide-propyl-SRDFWRS (SEQ ID NO: 109)-(1,2-diaminoethane)-propyl-maleimide)) were pre-incubated together for 1 hour.

Electrical measurements were acquired from single MspA nanopores (MS(B1-G75S/G77S/L88N/Q126R)8 MspA (SEQ ID NO: 2 with mutations G75S/G77S/L88N/Q126R) inserted in block co-polymer in buffer (625 mM KCl, 100 mM Hepes, 75 mM Potassium Ferrocyanide (II), 25 mM Potassium ferricyanide (III), pH 8). MgCl$_2$ (10 mM) and ATP (1 mM) were mixed together with buffer (625 mM KCl, 100 mM Hepes, 75 mM Potassium Ferrocyanide (II), 25 mM Potassium ferricyanide (III), pH 8) and then added to the DNA (SEQ ID NO: 127 attached at its 3' end to four iSpC3 spacers, the last of which is attached to the 5' end of SEQ ID NO: 128), Hel308 Mbu (E284C/S615C)-mal-pep-mal (SEQ ID NO: 10 with the mutations E284C/S615C connected by a bismaleimide peptide linker (maleimide-propyl-SRDFWRS (SEQ ID NO: 109)-(1,2-diaminoethane)-propyl-maleimide)) pre-mix. After achieving a single pore in the bilayer, the pre-mix was added to the single nanopore experimental system. Experiments were carried out at a constant potential of +120 mV and helicase-controlled DNA movement was monitored.

Results and Discussion

Figure 13:
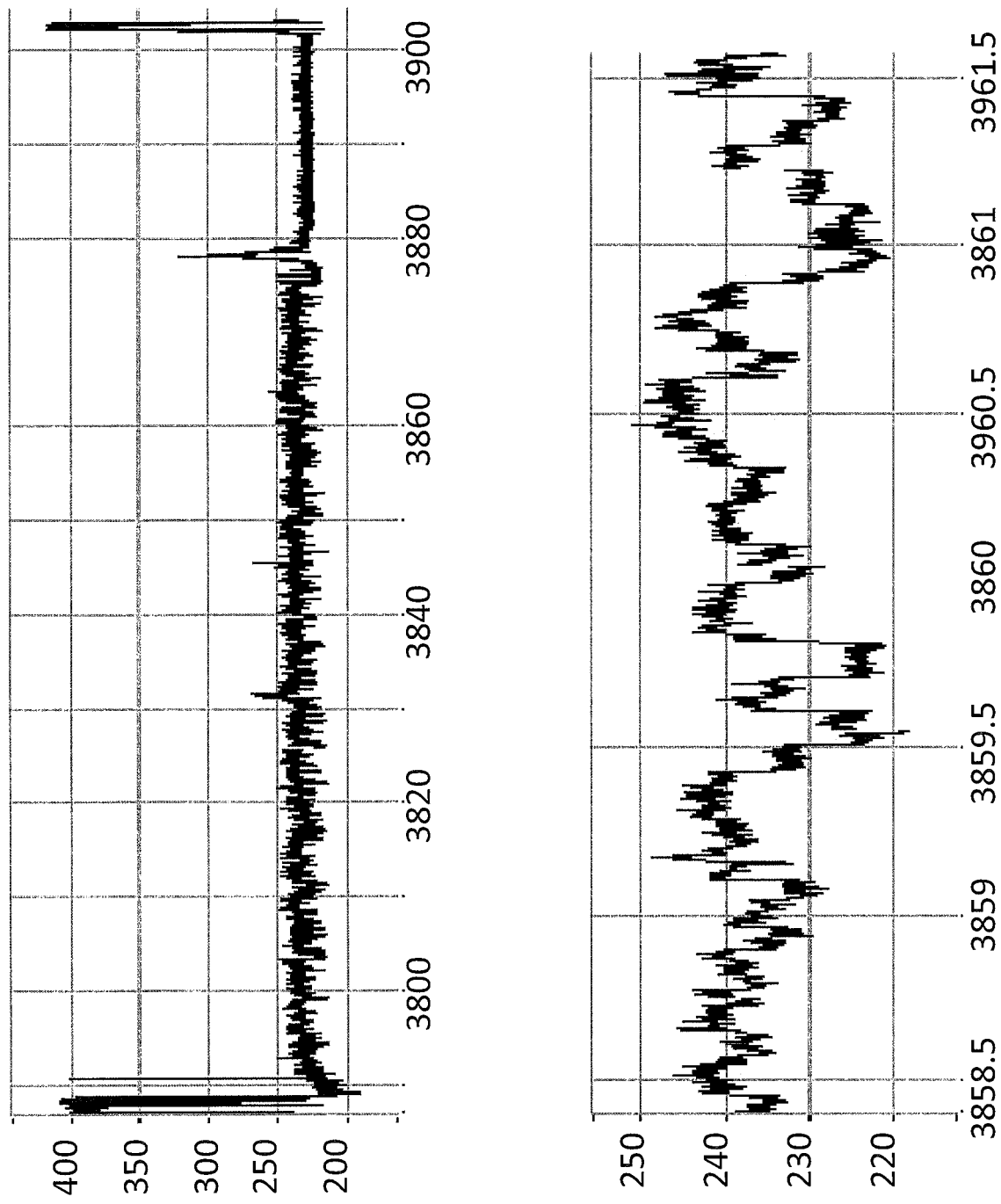
FIG. 13 shows example current traces (y-axis=current (pA), x-axis=time (s) for upper and lower traces) observed when a helicase controls the translocation of DNA (+120 mV, (625 mM KCl, 100 mM Hepes, 75 mM Potassium Ferrocyanide (II), 25 mM Potassium ferricyanide (III), pH 8, 0.5 nM DNA (SEQ ID NO: 127 attached at its 3' end to four iSpC3 spacers, the last of which is attached to the 5' end of SEQ ID NO: 128), 1 mM ATP, 10 mM $MgCl_2$) through an MspA nanopore (MS(B1-G75S/G77S/L88N/Q126R)8 MspA (SEQ ID NO: 2 with mutations G75S/G77S/L88N/Q126R) using the Hel308 Mbu (E284C/S615C)-mal-pep-mal (SEQ ID NO: 10 with the mutations E284C/S615C connected by a bismaleimide peptide linker (maleimide-propyl-SRDFWRS (SEQ ID NO: 109)-(1,2-diaminoethane)-propyl-maleimide)). The top electrical trace shows the open pore current (~400 pA) dropping to a DNA level (250-220 pA) when DNA is captured under the force of the applied potential (+120 mV). DNA with enzyme attached results in a long block that shows stepwise changes in current as the enzyme moves the DNA through the pore. The lower trace is a zoomed in region of the upper trace.

Helicase controlled DNA movement was observed for the closed complex Hel308 Mbu (E284C/S615C)-mal-pep-mal (SEQ ID NO: 10 with the mutations E284C/S615C connected by a bismaleimide peptide linker (maleimide-propyl-SRDFWRS (SEQ ID NO: 109)-(1,2-diaminoethane)-propyl-maleimide)). An example of a helicase-controlled DNA movement is shown in FIG. 13.

Example 6

This example describes the method of synthesising the TrwC Cba-N691C/Q346C-PEG11 (SEQ ID NO: 126 with the mutations N691C/Q346C connected by a PEG11 linker). In this case a covalent link between cysteines at positions 346 and 691 in the primary sequence of TrwC Cba (SEQ ID NO: 126) was made by reacting these positions with a PEG11 linker.

Materials and Methods

Figure 14:
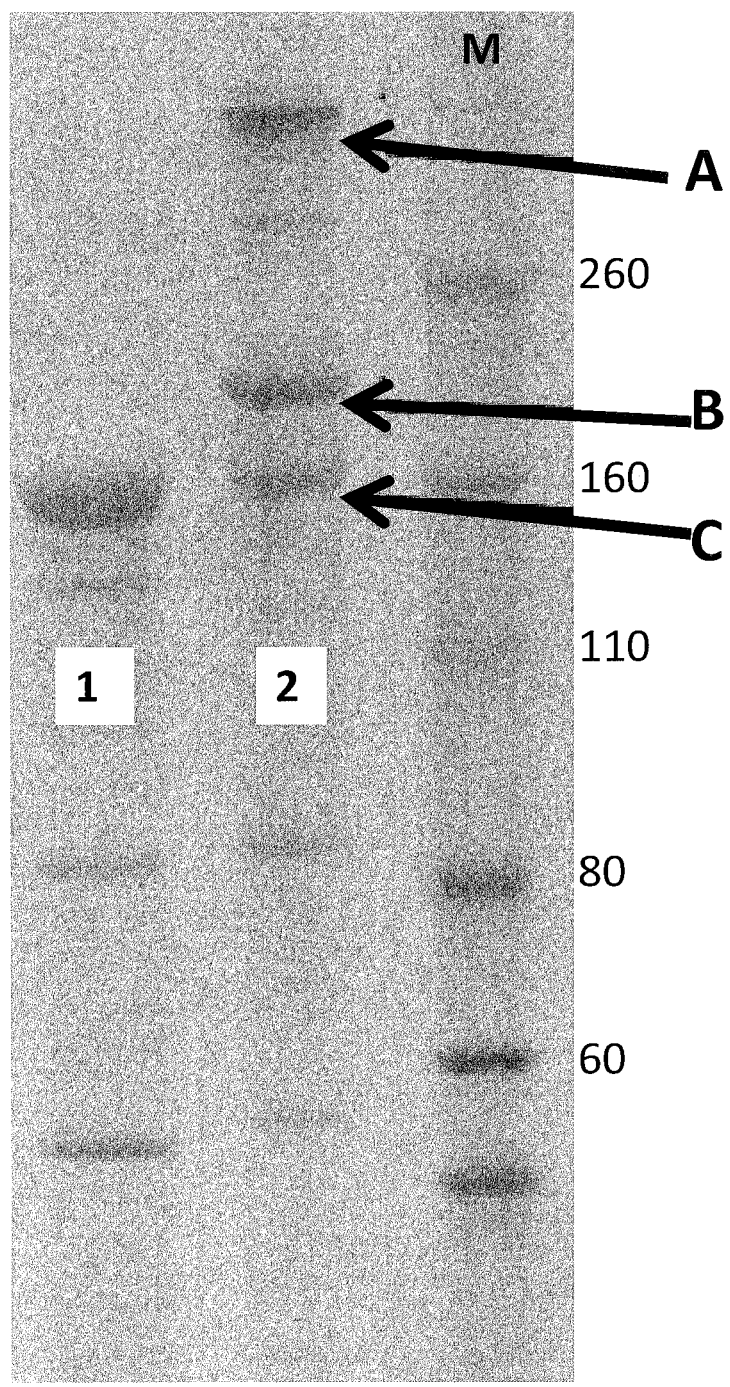
FIG. 14 shows a coomassie stained 7.5% Tris-HCl gel of the TrwC Cba-N691C/Q346C-mal-PEG11-mal (SEQ ID NO: 126 with the mutations N691C/Q346C connected by a bismaleimide polyethylene glycol linker) reaction mixture. The lane on the right of the gel (labelled M) shows an appropriate protein ladder (the mass unit markers are shown on the right of the gel). Lane 1 contains 5 µL of approximately 10 µM TrwC Cba-D657C/R339C alone (SEQ ID NO: 126 with mutation D657C/R339C) as a reference. Lane 2 contains 5 µL of approximately 10 µM TrwC Cba-N691C/Q346C-bismaleimidePEG11 (SEQ ID NO: 126 with the mutations N691C/Q346C connected by a bismaleimide PEG11 linker). As indicated in lane 2, the upper band corresponds to the dimeric enzyme species (labelled A), the middle band corresponds to the closed complex (labelled B) TraI-Cba-N691C/Q346C-bidmaleimidePEG11 (SEQ ID NO: 126 with the mutations N691C/Q346C connected by a bismaleimide PEG11 linker). It was clear from the gel that the reaction to attach the mal-PEG11-mal linker did not go to completion as a band for unmodified starting material (labelled C) TrwC Cba-N691C/Q346C (SEQ ID NO: 126 with the mutations N691C/Q346C) was observed.

In detail, DTT (2 µl, 1 M) was added to TrwC Cba-N691C/Q346C (200 SEQ ID NO: 126 with the mutations N691C/Q346C, stored in 50 mM Hepes, 10% glycerol, 10 mM DTT, 692 mM NaCl pH7.5) and the mixture was incubated at room temperature on a 10" wheel rotating at 20 rpm for 30 minutes. This mixture was buffer exchanged through Pierce 2 mL Zeba desalting columns, 7k MWCO into 100 mM potassium phosphate, 500 mM NaCl, 5 mM EDTA, 0.1% Tween-20 pH 8.0 and diluted in the same buffer to give 10 µL aliquots of sample. Maleimide-PEG11-maleimide (50 uM final concentration, Quanta Biodesign, product #10397) was added to one of the aliquots and the mixture incubated at room temperature on a 10" wheel rotating at 20 rpm for 120 minutes. To stop the reaction, DTT (1 ul of 1 M) was added to quench any remaining maleimides. Analysis of the reaction is by 7.5% polyacrylamide gel. FIG. 14 shows a coomassie stained 7.5% Tris-HCl gel of the TrwC Cba-N691C/Q346C-mal-PEG11-mal (SEQ ID NO: 126 with the mutations N691C/Q346C connected by a bismaleimide polyethylene glycol linker) reaction mixture. The lane on the right of the gel (labelled M) shows an appropriate protein ladder (the mass unit markers are shown on the right of the gel). Lane 1 contains 5 µL of approximately 10 µM TrwC Cba-D657C/R339C alone (SEQ ID NO: 126 with mutation D657C/R339C) as a reference. Lane 2 contains 5 µL of approximately 10 µM TrwC Cba-N691C/Q346C-bismaleimdiePEG11 (SEQ ID NO: 126 with the mutations N691C/Q346C connected by a bismaleimide PEG11 linker). As indicated in lane 2, the upper band corresponds to the dimeric enzyme species (labelled A), the middle band corresponds to the closed complex (labelled B) TraI-Cba-N691C/Q346C-bismaleimidePEG11 (SEQ ID NO: 126 with the mutations N691C/Q346C connected by a bismaleimide PEG11 linker). It was clear from the gel that the reaction to attach the mal-PEG11-mal linker did not go to completion as a band for unmodified starting material (labelled C) TrwC Cba-N691C/Q346C (SEQ ID NO: 126 with the mutations N691C/Q346C) was observed.

The TrwC Cba-N691C/Q346C-PEG11 (SEQ ID NO: 126 with the mutations N691C/Q346C connected by a PEG11 linker) was then buffer exchanged to 50 mM Tris, 500 mM NaCl, 2 mM DTT, pH 8.0.

Using an analogous procedure to that described in this example, it was possible to make the following closed complexes listed in Table 10 below.

TABLE 10

| Entry No. | Closed complex | Sequence |
|---|---|---|
| 1 | TrwC Cba-N691C/Q346C-mal-pep-mal | SEQ ID NO: 126 with the mutations N691C/Q346C connected by a bismaleimide peptide linker (maleimide-propyl-SRDFWRS (SEQ ID NO: 109)-(1,2-diaminoethane)-propyl-maleimide) |
| 2 | TrwC Cba-N691C/Q346C-bismaleimidePEG3 | SEQ ID NO: 126 with the mutations N691C/Q346C connected by a bismaleimide PEG3 linker |
| 3 | TrwC Cba-D657C/R339C-mal-pep-mal | SEQ ID NO: 126 with the mutations D657C/R339C connected by a bismaleimide peptide linker (maleimide-propyl-SRDFWRS (SEQ ID NO: 109)-(1,2-diaminoethane)-propyl-maleimide) |
| 4 | TrwC Cba-D657C/R339C-bismaleimidePEG3 | SEQ ID NO: 126 with the mutations D657C/R339C connected by a bismaleimide PEG3 linker |
| 5 | TrwC Cba-D657C/R339C-bismaleimidePEG11 | SEQ ID NO: 126 with the mutations D657C/R339C connected by a bismaleimide PEG11 linker |
| 6 | TrwC Cba-N691C/S350C-mal-pep-mal | SEQ ID NO: 126 with the mutations N691C/S350C connected by a bismaleimide peptide linker (maleimide-propyl-SRDFWRS (SEQ ID NO: 109)-(1,2-diaminoethane)-propyl-maleimide) |
| 7 | TrwC Cba-N691C/S350C-bismaleimidePEG3 | SEQ ID NO: 126 with the mutations N691C/S350C connected by a bismaleimide PEG3 linker |
| 8 | TrwC Cba-N691C/S350C-bismaleimidePEG11 | SEQ ID NO: 126 with the mutations N691C/S350C connected by a bismaleimide PEG11 linker |
| 9 | TrwC Cba-V690C/S350C-mal-pep-mal | SEQ ID NO: 126 with the mutations V690C/S350C connected by a bismaleimide peptide linker (maleimide-propyl-SRDFWRS (SEQ ID NO: 109)-(1,2-diaminoethane)-propyl-maleimide) |
| 10 | TrwC Cba-V690C/S350C-bismaleimidePEG3 | SEQ ID NO: 126 with the mutations V690C/S350C connected by a bismaleimide PEG3 linker |
| 11 | TrwC Cba-V690C/S350C-bismaleimidePEG11 | SEQ ID NO: 126 with the mutations V690C/S350C connected by a bismaleimide PEG11 linker |

Example 7

This Example illustrates that when a number of helicases were investigated (Hel308 Mbu (SEQ ID NO: 10), Hel308 Mbu-E284C (SEQ ID NO: 10 with the mutation E284C), Hel308 Mbu-E284C/C301A (SEQ ID NO: 10 with the mutations E284C/C301A), Hel308 Mbu-E285C (SEQ ID NO: 10 with the mutation E285C), Hel308 Mbu-S288C (SEQ ID NO: 10 with the mutation S288C), and Hel308 Mbu-D274C (SEQ ID NO: 10 with the mutation D274C) for their rate of turnover of dsDNA molecules (min$^{-1}$enzyme$^{-1}$) using a fluorescent assay, the mutant helicases (Hel308 Mbu-E284C (SEQ ID NO: 10 with the mutation E284C), Hel308 Mbu-E284C/C301A (SEQ ID NO: 10 with the mutations E284C/C301A), Hel308 Mbu-E285C (SEQ ID NO: 10 with the mutation E285C), Hel308 Mbu-S288C (SEQ ID NO: 10 with the mutation S288C), and Hel308 Mbu-D274C (SEQ ID NO: 10 with the mutation D274C)) tested had increased rate of turnover of dsDNA molecules (min$^{-1}$enzyme$^{-1}$) in comparison to Hel308 Mbu (SEQ ID NO: 10).

Materials and Methods

Figure 15:
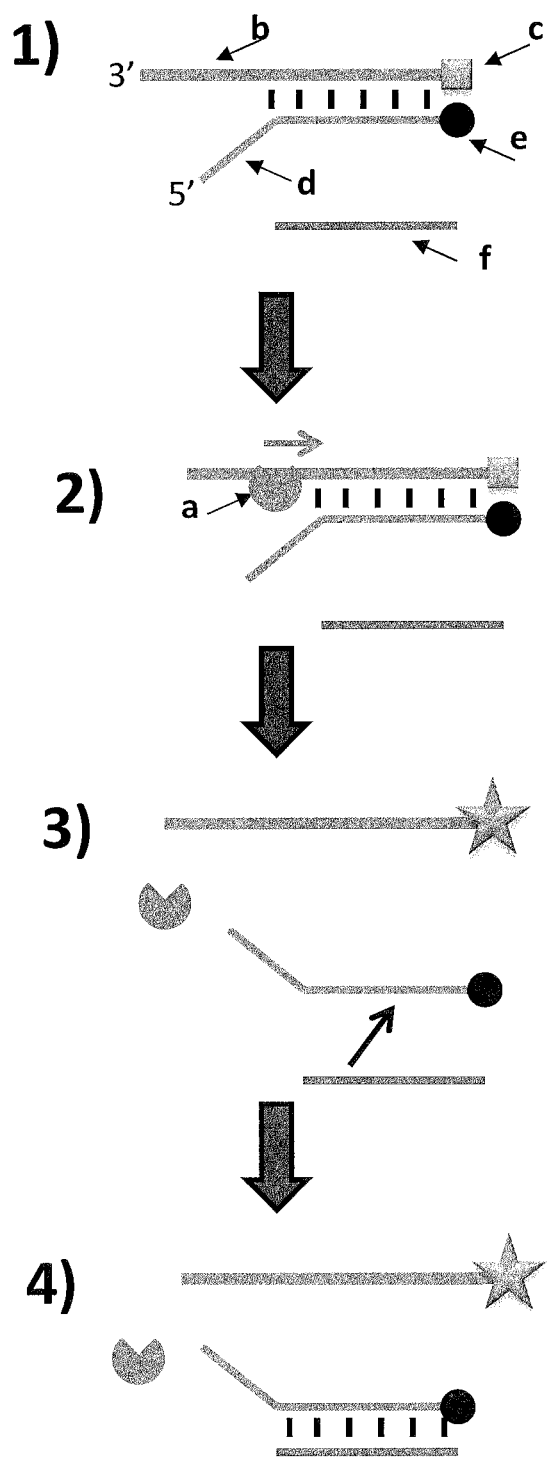
FIG. 15 shows a fluorescence assay for testing the rate of turnover of dsDNA molecules ($min^{-1}$ $enzyme^{-1}$). A custom fluorescent substrate was used to assay the ability of the helicase (a) to displace hybridised dsDNA. 1) The fluorescent substrate strand (50 nM final, SEQ ID NO: 151 and 152) has both a 3' and 5' ssDNA overhang. The upper strand (b) has a carboxyfluorescein base (c) near the 5' end (the carboxyfluorescein is attached to a modified thymine at position 6 in SEQ ID NO: 151), and the hybridised complement (d) has a black-hole quencher (BHQ-1) base (e) near the 3' end (the black-hole quencher is attached to a modified thymine at position 81 in SEQ ID NO: 152). When hybridised, the fluorescence from the fluorescein is quenched by the local BHQ-1, and the substrate is essentially non-fluorescent. 1 μM of a capture strand (f, SEQ ID NO: 153) that is part-complementary to the lower strand of the fluorescent substrate is included in the assay. 2) In the presence of ATP (1 mM) and MgCl$_2$ (10 mM), helicase (10 nM) added to the substrate binds to the 3' tail of the fluorescent substrate, moves along the upper strand, and displaces the complementary strand (d) as shown. 3) Once the complementary strand with BHQ-1 is fully displaced the fluorescein on the major strand fluoresces. 4) Displaced lower strand (d) preferentially anneals to an excess of capture strand (f) to prevent re-annealing of initial substrate and loss of fluorescence.

A custom fluorescent substrate was used to assay the ability of a number of Hel308 Mbu helicases (Hel308 Mbu-E284C (SEQ ID NO: 10 with the mutation E284C), Hel308 Mbu-E284C/C301A (SEQ ID NO: 10 with the mutations E284C/C301A), Hel308 Mbu-E285C (SEQ ID NO: 10 with the mutation E285C), Hel308 Mbu-S288C (SEQ ID NO: 10 with the mutation S288C), and Hel308 Mbu-D274C (SEQ ID NO: 10 with the mutation D274C)) to displace hybridised dsDNA. As shown in 1) of FIG. 15, the fluorescent substrate strand (50 nM final) has both a 3' and 5' ssDNA overhang, and a 44 base section of hybridised dsDNA. The upper strand, containing the 3' ssDNA overhang, has a carboxyfluorescein base (the carboxyfluorescein (labelled c in FIG. 15) is attached to a thymine at position 6 in SEQ ID NO: 151) at the 5' end, and the hybrised complement has a black-hole quencher (BHQ-1, labelled e in FIG. 15) base (the black-hole quencher is attached to a thymine at position 81 in SEQ ID NO: 152) at the 3' end. When the two strands are hybridised the fluorescence from the fluorescein is quenched by the local BHQ-1, and the substrate is essentially non-fluorescent. 1 µM of a capture strand (SEQ ID NO: 153) that is part-complementary to the lower strand of the fluorescent substrate is included in the assay. As shown in 2), in the presence of ATP (1 mM) and $MgCl_2$ (10 mM), appropriate helicase (10 nM) added to the substrate binds to the 3' tail of the fluorescent substrate, moves along the upper strand, and displaces the complementary strand. As shown in 3), once the complementary strand with BHQ-1 is fully displaced the fluorescein on the major strand fluoresces. As shown in 4) the displaced strand preferentially anneals to an excess of capture strand to prevent re-annealing of initial substrate and loss of fluorescence.

Results and Discussion

Figure 16:
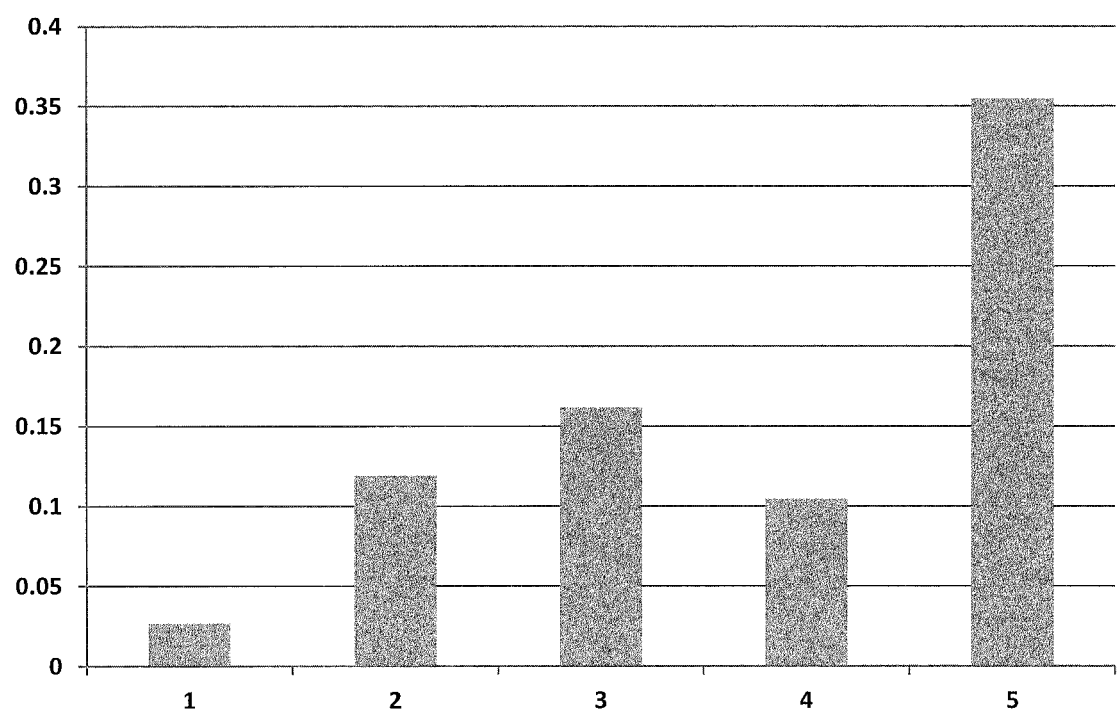
FIG. 16 shows dsDNA turnover (enzyme$^{-1}$ min$^{-1}$) in buffer (400 mM KCl, 100 mM Hepes pH 8.0, 1 mM ATP, 10 mM MgCl$_2$, 50 nM fluorescent substrate DNA (SEQ ID NOs: 151 and 152), 1 μM capture DNA (SEQ ID NO: 153)) for a number of helicases (Hel308 Mbu (labelled 1, SEQ ID NO: 10), Hel308 Mbu-E284C (labelled 2, SEQ ID NO: 10 with the mutation E284C), Hel308 Mbu-E284C/C301A (labelled 3, SEQ ID NO: 10 with the mutations E284C/C301A), Hel308 Mbu-E285C (labelled 4, SEQ ID NO: 10 with the mutation E285C) and Hel308 Mbu-S288C (labelled 5, SEQ ID NO: 10 with the mutation S288C)). Hel308 Mbu-E284C (SEQ ID NO: 10 with the mutation E284C), Hel308 Mbu-E284C/C301A (SEQ ID NO: 10 with the mutations E284C/C301A), Hel308 Mbu-E285C (SEQ ID NO: 10 with the mutation E285C) and Hel308 Mbu-S288C (SEQ ID NO: 10 with the mutation S288C) showed increased rate of turnover of dsDNA molecules (min$^{-1}$enzyme$^{-1}$) when compared to Hel308 Mbu (SEQ ID NO: 10).
Figure 17:
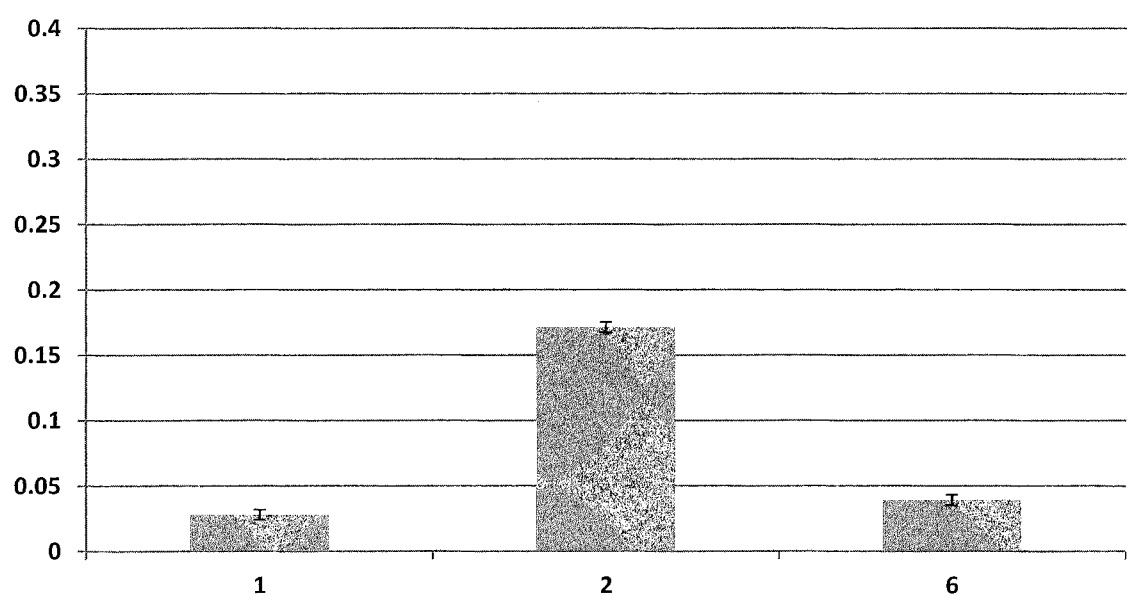
FIG. 17 shows dsDNA turnover (enzyme$^{-1}$min$^{-1}$) in buffer (400 mM KCl, 100 mM Hepes pH 8.0, 1 mM ATP, 10 mM MgCl$_2$, 50 nM fluorescent substrate DNA (SEQ ID NOs: 151 and 152), 1 μM capture DNA (SEQ ID NO: 153)) for a number of helicases (Hel308 Mbu (labelled 1, SEQ ID NO: 10), Hel308 Mbu-E284C (labelled 2, SEQ ID NO: 10 with the mutation E284C) and Hel308 Mbu-D274C (labelled 6, SEQ ID NO: 10 with the mutation D274C)). Hel308 Mbu-E284C (SEQ ID NO: 10 with the mutation E284C) and Hel308 Mbu-D274C (SEQ ID NO: 10 with the mutations D274C) showed increased rate of turnover of dsDNA molecules (min$^{-1}$enzyme$^{-1}$) when compared to Hel308 Mbu (SEQ ID NO: 10).

The graphs in FIGS. 16 and 17 show the dsDNA turnover (enzyme$^{-1}$min$^{-1}$) in buffer (400 mM KCl, 100 mM Hepes pH 8.0, 1 mM ATP, 10 mM $MgCl_2$, 50 nM fluorescent substrate DNA (SEQ ID NOs: 151 and 152), 1 µM capture DNA (SEQ ID NO: 153)) for a number of helicases (Hel308 Mbu (labelled 1 in FIGS. 16 and 17, SEQ ID NO: 10), Hel308 Mbu-E284C (labelled 2 in FIGS. 16 and 17, SEQ ID NO: 10 with the mutation E284C), Hel308 Mbu-E284C/C301A (labelled 3 in FIG. 16, SEQ ID NO: 10 with the mutations E284C/C301A), Hel308 Mbu-E285C (labelled 4 in FIG. 16, SEQ ID NO: 10 with the mutation E285C), Hel308 Mbu-S288C (labelled 5 in FIG. 16, SEQ ID NO: 10 with the mutation S288C) and Hel308 Mbu-D274C (labelled 6 in FIG. 17, SEQ ID NO: 10 with the mutation D274C)). At the salt concentration investigated (400 mM KCl) the following helicases Hel308 Mbu-E284C (FIGS. 16 and 17 labelled 2, SEQ ID NO: 10 with the mutation E284C), Hel308 Mbu-E284C/C301A (FIG. 16 labelled 3, SEQ ID NO: 10 with the mutations E284C/C301A), Hel308 Mbu-E285C (FIG. 16 labelled 4, SEQ ID NO: 10 with the mutation E285C), Hel308 Mbu-S288C (FIG. 16 labelled 5, SEQ ID NO: 10 with the mutation S288C) and Hel308 Mbu-D274C (FIG. 17 labelled 6, SEQ ID NO: 10 with the mutation D274C) exhibited a higher rate of dsDNA turnover than the control Hel308 Mbu (FIGS. 16 and 17 labelled 1, SEQ ID NO: 10) (see FIGS. 16 and 17). This indicates that these enzymes show increased rate of turnover of dsDNA molecules (min$^{-1}$enzyme$^{-1}$) when compared to the Hel 308 Mbu control (SEQ ID NO: 10) under the conditions investigated.

Example 8

This example describes two procedures for the light treatment of Hel308 Mbu-E284Faz (SEQ ID NO: 10 with the mutation E284Faz) and Hel308 Mbu-S288Faz (SEQ ID NO: 10 with the mutation S288Faz).

Procedure 1—Exposure to UV Light

Hel308 Mbu-E284Faz (SEQ ID NO: 10 with the mutation E284Faz) or Hel308 Mbu-S288Faz (SEQ ID NO: 10 with the mutation E288Faz) in storage buffer (50 mM Tris pH8.0 at 4° C., NaCl (360-390 mM) and 5% Glycerol) was pipetted into PCR tubes (Fisher 0.2 mL thin wall tubes). The sample was placed on ice and exposed to high intensity UV light at 254 nm (Spectroline Longlife Filter lamp (254 nm and 365 nm) from above, at a distance of 4.5 cm. The Hel308 Mbu-E284Faz (SEQ ID NO: 10 with the mutation E284Faz) sample was exposed for 15 mins and the Hel308 Mbu-S288Faz (SEQ ID NO: 10 with the mutation E288Faz) sample was exposed for 10 mins. The samples were then both centrifuged for 5 mins at 16 000 g to remove any precipitated protein. The soluble fraction was carefully removed from the insoluble pellet by pipette.

Procedure 2—Exposure to White Light (LED Source)

Hel308 Mbu-S288Faz (SEQ ID NO: 10 with the mutation E288Faz) in storage buffer (50 mM Tris pH8.0 at 4° C., NaCl (370 mM) and 5% Glycerol) was pipetted into Microcentrifuge tube (Eppendorf, 1.5 mL, Protein Lo Bind). The sample was placed on ice (with the cap open) and exposed to LED light source (Schott A20960.1) on full power from above, at a distance of 3 cm. The Hel308 Mbu-S288Faz (SEQ ID NO: 10 with the mutation E288Faz) sample was exposed for 3 hours.

Procedure 3—Exposure to White Light (LED Source) and Heating

Hel308 Mbu-S288Faz (SEQ ID NO: 10 with the mutation E288Faz) in storage buffer (50 mM Tris pH8.0 at 4° C., NaCl (370 mM) and 5% Glycerol) was pipetted into Microcentrifuge tube (Eppendorf, 1.5 mL, Protein Lo Bind). The sample was placed on ice (with the cap open) and exposed to LED light source (Schott A20960.1) on full power from above, at a distance of 1 cm. The Hel308 Mbu-S288Faz (SEQ ID NO: 10 with the mutation E288Faz) sample was exposed for 1 hour. The sample was transferred in a PCR tube (Fisher 0.2 mL thin wall tube) and heated at 50° C. for 10 min before ramping to 4° C., then centrifuged for 5 mins at 16 000 g to remove any precipitated protein. The soluble fraction was carefully removed from the insoluble pellet by pipette.

Example 9

Figure 18:
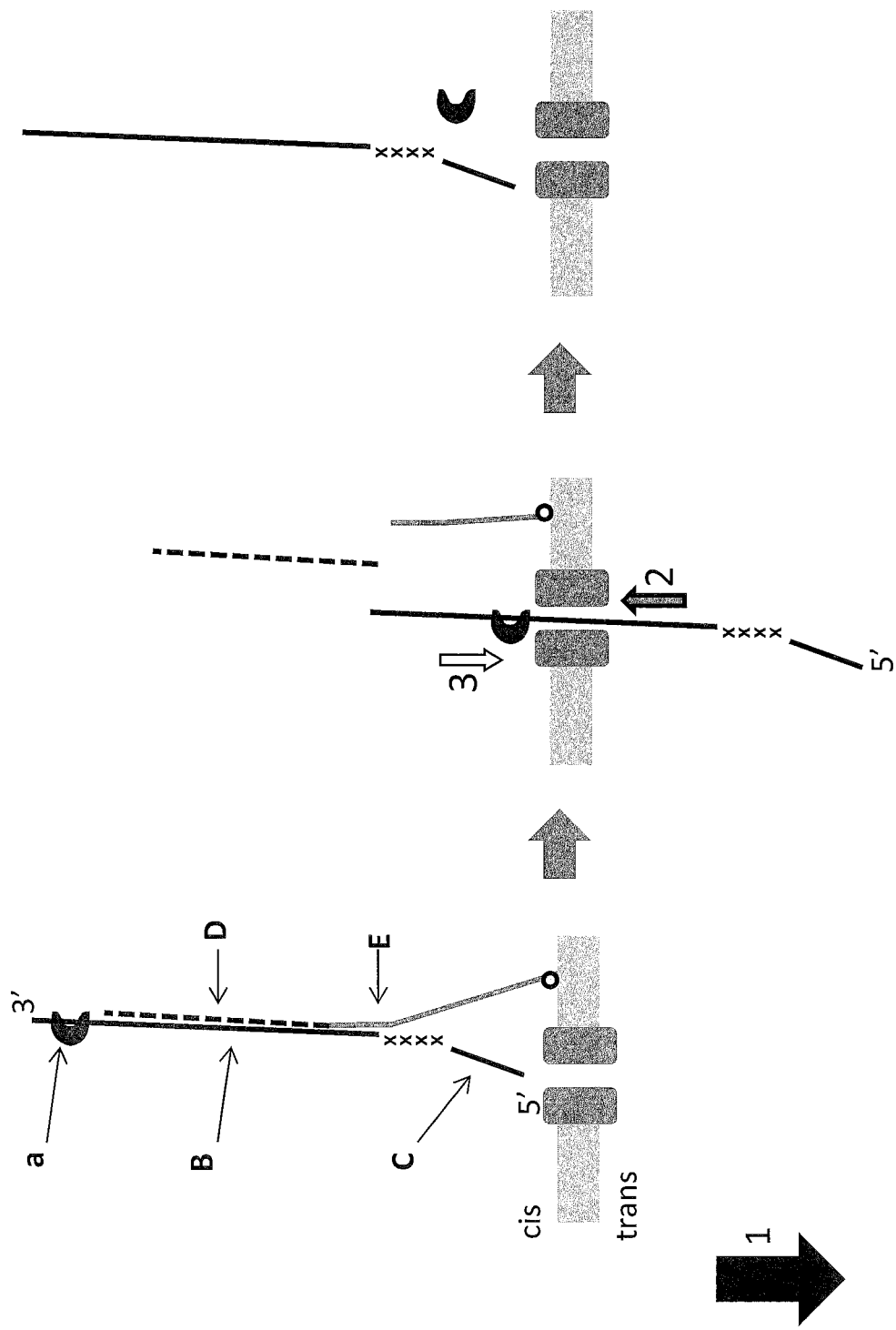
FIG. 18 shows a schematic of enzyme controlled translocation of a polynucleotide through a nanopore in a membrane, where the enzyme controls the movement of the polynucleotide against the force of the applied field. The schematic shows the example of a 3' to 5' enzyme (labelled A), where the capture of a polynucleotide (the polynucleotide sequences used in Example 9 are SEQ ID NO: 154 (labelled B in FIG. 18), SEQ ID NO: 155 (labelled C in FIG. 18) and SEQ ID NO: 156 (labelled D in FIG. 18) and SEQ ID NO: 117 (labelled E in FIG. 18)) in the pore by the 5' end leads to the enzyme controlling the movement of the polynucleotide against the force of the applied field (the direction of the applied field is indicated by arrow 1). During DNA capture the hybridised strands are unzipped. Arrow 2 denotes the direction of DNA movement through the nanopore and the arrow 3 denotes the direction of enzyme movement along the DNA. As long as the enzyme does not dissociate from the DNA the enzyme will pull the DNA out of the pore until it is finally ejected on the cis side of the membrane.
Figure 19:
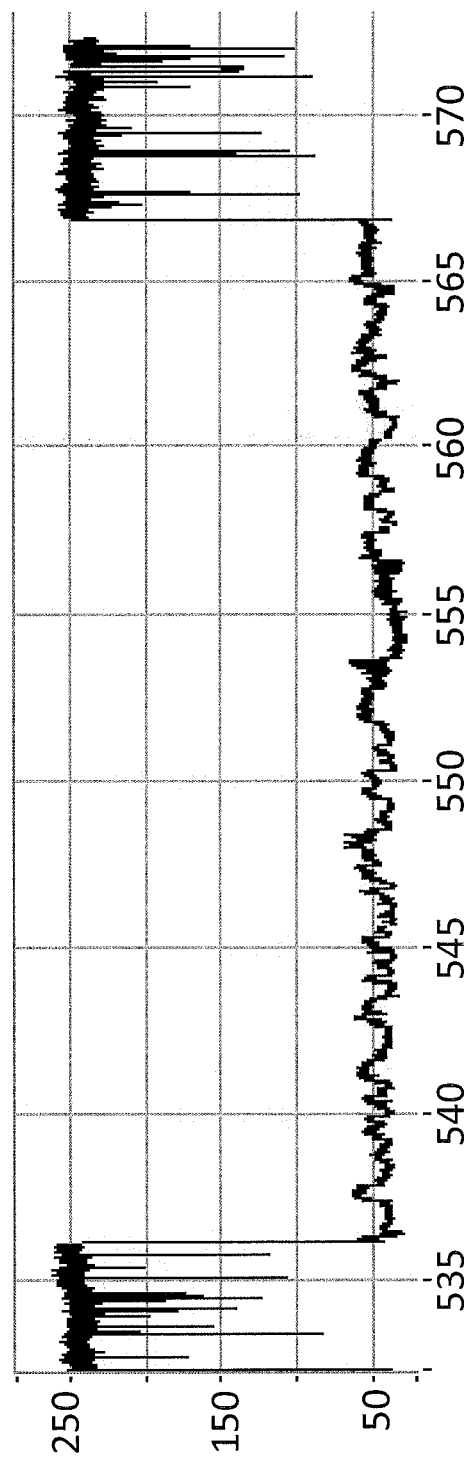
FIG. 19 shows an example current trace (y-axis=current (pA), x-axis=time (s)) observed when Hel308 Mbu (SEQ ID NO: 10) controls the translocation of DNA (+120 mV, (960 mM KCl, 25 mM potassium phosphate, 3 mM potassium ferrocyanide, 1 mM potassium ferricyanide pH 8.0, 10 mM MgCl$_2$ and 1 mM ATP) 0.2 nM DNA ((SEQ ID NO: 154 attached at its 5' end to four nitroindoles the last of which is attached to the 3' end of SEQ ID NO: 155), SEQ ID NO: 156 and SEQ ID NO: 117) through an MspA nanopore (MS(B1-G75S/G77S/L88N/Q126R)8 MspA (SEQ ID NO: 2 with mutations G75S/G77S/L88N/Q126R). The electrical trace shows the open pore current (~250 pA) dropping to a DNA level (~50 pA) when DNA is captured under the force of the applied potential (+120 mV). DNA with enzyme attached results in a long block that shows stepwise changes in current as the enzyme moves the DNA through the pore.
Figure 20:
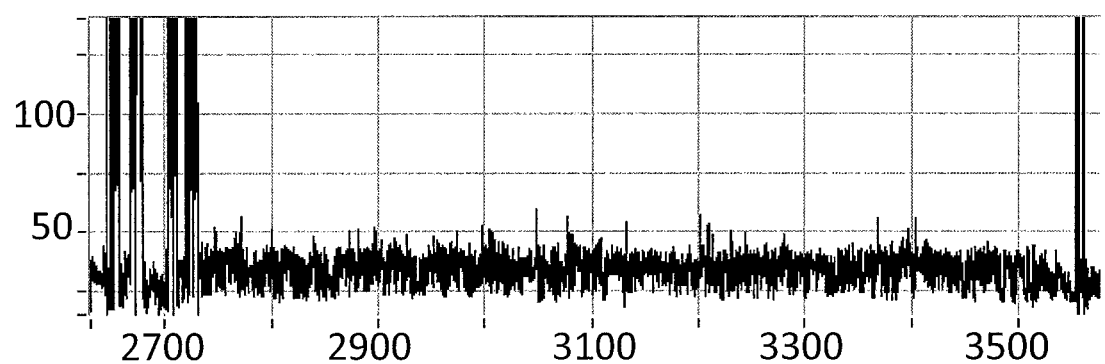
FIG. 20 shows example current traces (y-axis=current (pA), x-axis=time (s) for both traces) observed when Hel308 Mbu-E284C (SEQ ID NO: 10 with the mutation E284C) controls the translocation of DNA (+120 mV, (960 mM KCl, 25 mM potassium phosphate, 3 mM potassium ferrocyanide, 1 mM potassium ferricyanide pH 8.0, 10 mM MgCl$_2$ and 1 mM ATP) 0.2 nM DNA ((SEQ ID NO: 154 attached at its 5' end to four nitroindoles the last of which is attached to the 3' end of SEQ ID NO: 155), SEQ ID NO: 156 and SEQ ID NO: 117) through an MspA nanopore (MS(B1-G75S/G77S/L88N/Q126R)8 MspA (SEQ ID NO: 2 with mutations G75S/G77S/L88N/Q126R). The upper electrical trace shows the DNA level (~35 pA) when DNA is captured under the force of the applied potential (+120 mV). DNA with enzyme attached results in a long block that shows stepwise changes in current as the enzyme moves the DNA through the pore. The lower trace shows a zoomed in view of the helicase controlled DNA movement shown in the upper trace.
Figure 20:
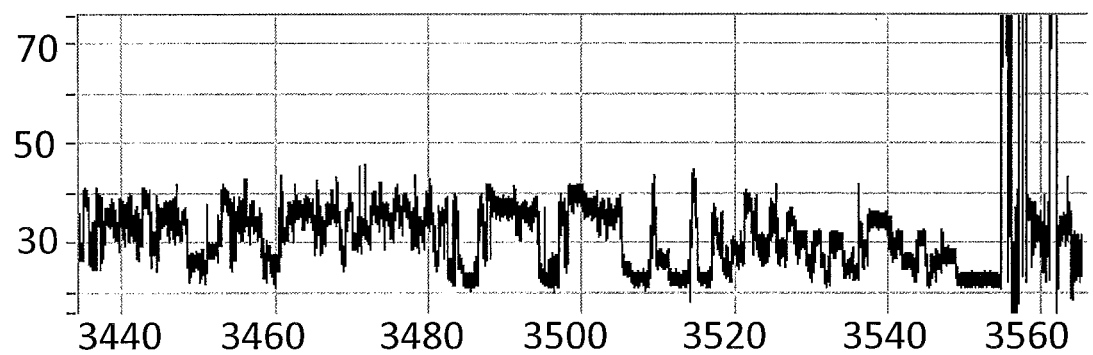
Figure 21:
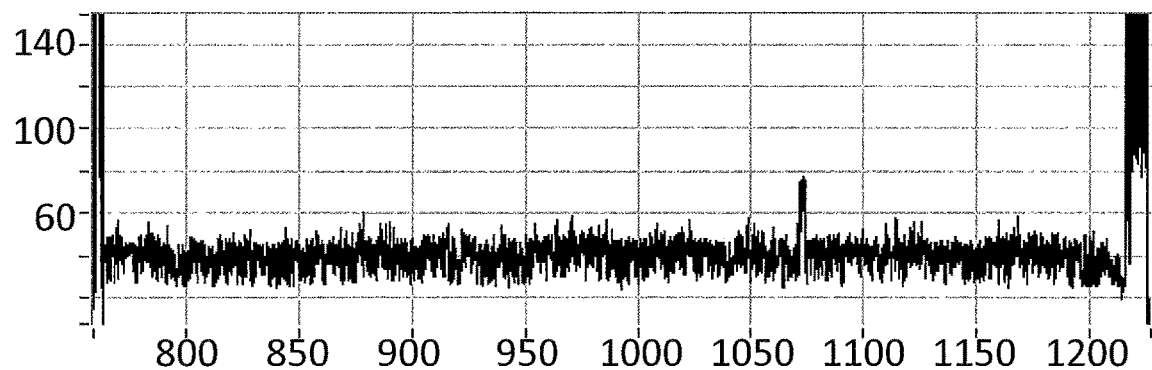
FIG. 21 shows example current traces (y-axis=current (pA), x-axis=time (s) for both traces) observed when Hel308 Mbu-S288C (SEQ ID NO: 10 with the mutation S288C) controls the translocation of DNA (+120 mV, (960 mM KCl, 25 mM potassium phosphate, 3 mM potassium ferrocyanide, 1 mM potassium ferricyanide pH 8.0, 10 mM MgCl$_2$ and 1 mM ATP) 0.2 nM DNA ((SEQ ID NO: 154 attached at its 5' end to four nitroindoles the last of which is attached to the 3' end of SEQ ID NO: 155), SEQ ID NO: 156 and SEQ ID NO: 117) through an MspA nanopore (MS(B1-G75S/G77S/L88N/Q126R)8 MspA (SEQ ID NO: 2 with mutations G75S/G77S/L88N/Q126R). The upper electrical trace shows the DNA level (~40 pA) when DNA is captured under the force of the applied potential (+120 mV). DNA with enzyme attached results in a long block that shows stepwise changes in current as the enzyme moves the DNA through the pore. The lower trace shows a zoomed in view of the helicase controlled DNA movement shown in the upper trace.
Figure 21:
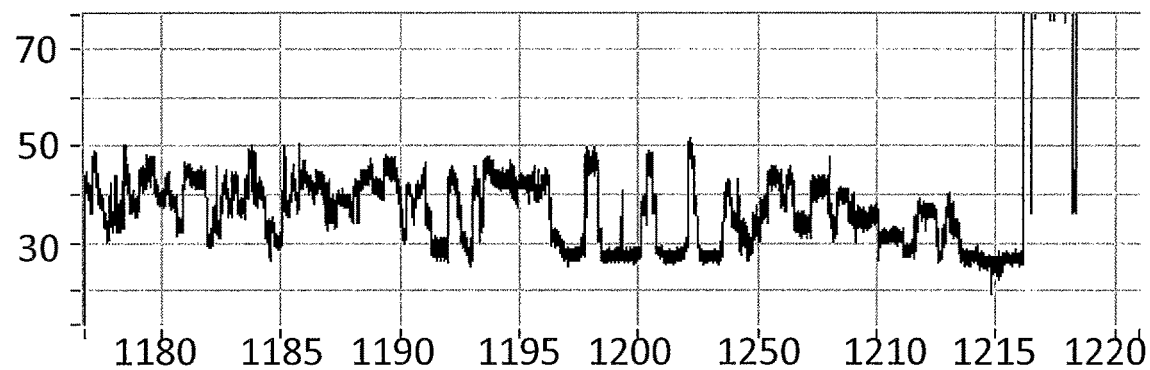
Figure 22:
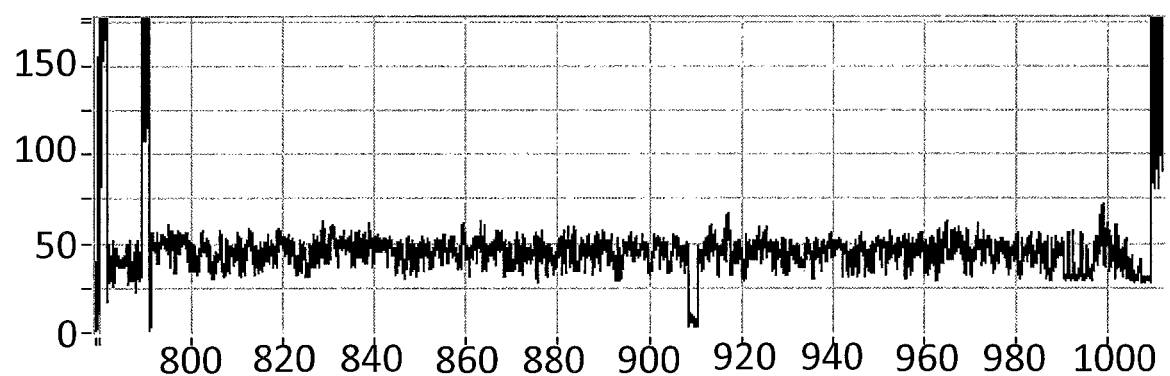
FIG. 22 shows example current traces (y-axis=current (pA), x-axis=time (s) for both traces) observed when Hel308 Mbu-E284Faz (SEQ ID NO: 10 with the mutation E284Faz) controls the translocation of DNA (+120 mV, (960 mM KCl, 25 mM potassium phosphate, 3 mM potassium ferrocyanide, 1 mM potassium ferricyanide pH 8.0, 10 mM MgCl$_2$ and 1 mM ATP) 0.2 nM DNA ((SEQ ID NO: 154 attached at its 5' end to four nitroindoles the last of which is attached to the 3' end of SEQ ID NO: 155), SEQ ID NO: 156 and SEQ ID NO: 117) through an MspA nanopore (MS(B1-G75S/G77S/L88N/Q126R)8 MspA (SEQ ID NO: 2 with mutations G75S/G77S/L88N/Q126R). The upper electrical trace shows the DNA level (~50 pA) when DNA is captured under the force of the applied potential (+120 mV). DNA with enzyme attached results in a long block that shows stepwise changes in current as the enzyme moves the DNA through the pore. The lower trace shows a zoomed in view of the helicase controlled DNA movement shown in the upper trace.
Figure 22:
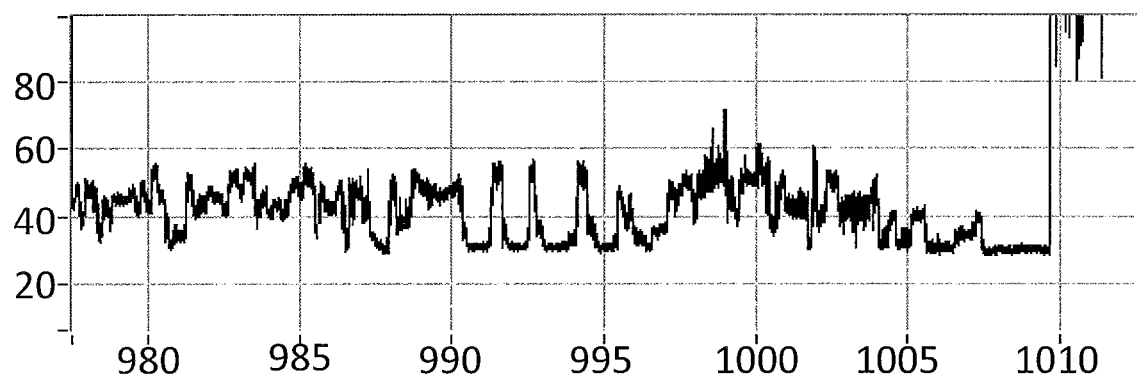
Figure 23:
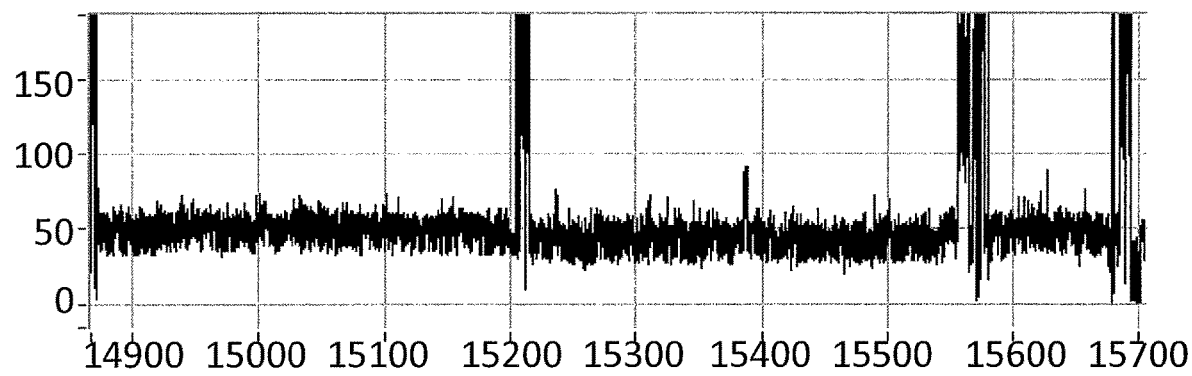
FIG. 23 shows example current traces (y-axis=current (pA), x-axis=time (s) for both traces) observed when heat treated Hel308 Mbu-E284Faz (SEQ ID NO: 10 with the mutation E284Faz, the enzyme was heated in 50 mM Tris pH 8.0, 375 mM NaCl, 5% Glycerol buffer from 4° C. to 50° C. for 10 mins and then cooled to 4° C. in a BioRad PCR block) controls the translocation of DNA (+120 mV, (960 mM KCl, 25 mM potassium phosphate, 3 mM potassium ferrocyanide, 1 mM potassium ferricyanide pH 8.0, 10 mM $MgCl_2$ and 1 mM ATP) 0.2 nM DNA ((SEQ ID NO: 154 attached at its 5' end to four nitroindoles the last of which is attached to the 3' end of SEQ ID NO: 155), SEQ ID NO: 156 and SEQ ID NO: 117) through an MspA nanopore (MS(B1-G75S/G77S/L88N/Q126R)8 MspA (SEQ ID NO: 2 with mutations G75S/G77S/L88N/Q126R). The upper electrical trace shows the DNA level (~50 pA) for a number of helicase controlled DNA movements (each movement is numbered 1-3) when DNA is captured under the force of the applied potential (+120 mV). DNA with enzyme attached results in a long block that shows stepwise changes in current as the enzyme moves the DNA through the pore. The lower trace shows a zoomed in view of the helicase controlled DNA movement labelled 1 in the upper trace.
Figure 23:
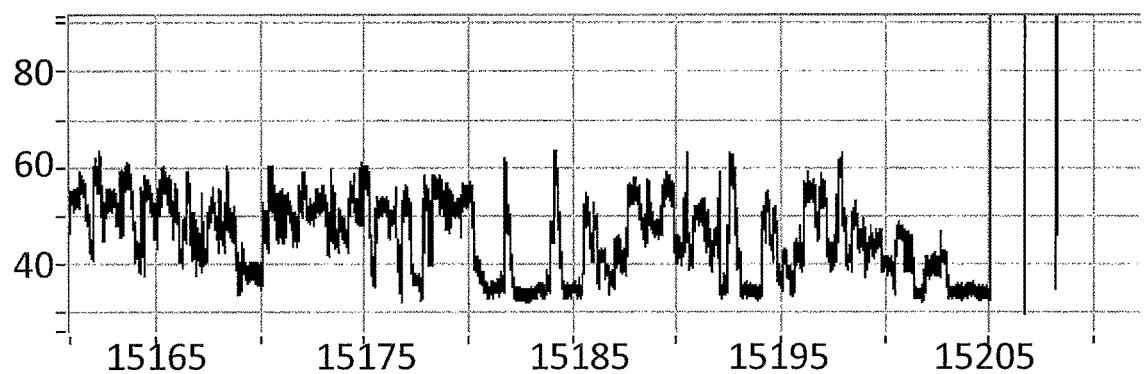

This example compares the ability of Hel308 Mbu (SEQ ID NO: 10), to control the movement of intact DNA strands (3.6 kb) through a nanopore, to that of a number of Hel308 Mbu mutants (Hel308 Mbu-E284C (SEQ ID NO: 10 with the mutation E284C), Hel308 Mbu-S288C (SEQ ID NO: 10 with the mutation S288C), Hel308 Mbu-E284Faz (SEQ ID NO: 10 with the mutation E284Faz) and heat treated Hel308 Mbu-E284Faz (SEQ ID NO: 10 with the mutation E284Faz, the enzyme was heated in 50 mM Tris pH 8.0, 375 mM NaCl, 5% Glycerol buffer from 4° C. to 50° C. for 10 mins and then cooled to 4° C. in a BioRad PCR block)). The general method for controlled DNA translocation against the field is shown in FIG. 18.

Materials and Methods

Prior to setting up the experiment, the DNA (0.2 nM, (SEQ ID NO: 154 attached at its 5' end to four nitroindoles (labelled as x's in FIG. 18), the last of which is attached to the 3' end of SEQ ID NO: 155), SEQ ID NO: 156 and SEQ ID NO: 117) and appropriate helicase (Hel 308 Mbu (100 nM, SEQ ID NO: 10), Hel308 Mbu-E284C (100 nM, SEQ ID NO: 10 with the mutation E284C), Hel308 Mbu-S288C (100 nM, SEQ ID NO: 10 with the mutation S288C), Hel308 Mbu-E284Faz (100 nM, SEQ ID NO: 10 with the mutation E284Faz) and heat treated Hel308 Mbu-E284Faz (500 nM, SEQ ID NO: 10 with the mutation E284Faz, the enzyme was heated in 50 mM Tris pH 8.0, 375 mM NaCl, 5% Glycerol buffer from 4° C. to 50° C. for 10 mins and then cooled to 4° C. in a BioRad PCR block)) were dissolved in buffer (960 mM KCl, 25 mM potassium phosphate, 3 mM potassium ferrocyanide, 1 mM potassium ferricyanide pH 8.0, 10 mM $MgCl_2$ and 1 mM ATP).

Electrical measurements were acquired from single MspA nanopores (MS(B1-G75S/G77S/L88N/Q126R)8 MspA (SEQ ID NO: 2 with mutations G75S/G77S/L88N/Q126R) inserted in block co-polymer in buffer (960 mM KCl, 25 mM potassium phosphate, 3 mM potassium ferrocyanide, 1 mM potassium ferricyanide pH 8.0). After achieving a single pore in the block co-polymer, buffer (3 mL of 960 mM KCl, 25 mM potassium phosphate, 3 mM potassium ferrocyanide, 1 mM potassium ferricyanide pH 8.0) was then flowed through the system. Finally, the pre-mix (described above) was added to the single nanopore experimental system. Experiments were carried out at a constant potential of +120 mV and helicase-controlled DNA movement was monitored.

Results and Discussion

Helicase controlled DNA movement was observed for all of the enzymes tested—Hel 308 Mbu (SEQ ID NO: 10), Hel308 Mbu-E284C (SEQ ID NO: 10 with the mutation E284C), Hel308 Mbu-S288C (SEQ ID NO: 10 with the mutation S288C), Hel308 Mbu-E284Faz (SEQ ID NO: 10 with the mutation E284Faz) and heat treated Hel308 Mbu-E284Faz (SEQ ID NO: 10 with the mutation E284Faz, the enzyme was heated in 50 mM Tris pH 8.0, 375 mM NaCl, 5% Glycerol buffer from 4° C. to 50° C. for 10 mins and then cooled to 4° C. in a BioRad PCR block). Example current traces showing helicase controlled DNA movement are shown in FIGS. 19-23. However, the mutant Hel308 Mbu helicases (Hel308 Mbu-E284C (SEQ ID NO: 10 with the mutation E284C), Hel308 Mbu-S288C (SEQ ID NO: 10 with the mutation S288C), Hel308 Mbu-E284Faz (SEQ ID NO: 10 with the mutation E284Faz) and heat treated Hel308 Mbu-E284Faz (SEQ ID NO: 10 with the mutation E284Faz, the enzyme was heated in 50 mM Tris pH 8.0, 375 mM NaCl, 5% Glycerol buffer from 4° C. to 50° C. for 10 mins and then cooled to 4° C. in a BioRad PCR block)) showed increased processivity in comparison to Hel308 Mbu (SEQ ID NO: 10) see Table 11. Of the helicase controlled DNA movements observed in the experiments, the % of movements which processed the DNA all the way to the end of the strand (to the polyT region) were significantly higher for the mutant helicases (Hel308 Mbu-E284C (SEQ ID NO: 10 with the mutation E284C), Hel308 Mbu-S288C (SEQ ID NO: 10 with the mutation S288C), Hel308 Mbu-E284Faz (SEQ ID NO: 10 with the mutation E284Faz) and heat treated Hel308 Mbu-E284Faz (SEQ ID NO: 10 with the mutation E284Faz, the enzyme was heated in 50 mM Tris pH 8.0, 375 mM NaCl, 5% Glycerol buffer from 4° C. to 50° C. for 10 mins and then cooled to 4° C. in a BioRad PCR block)) when compared to Hel308 Mbu (SEQ ID NO: 10).

TABLE 11

| Helicase | % of Helicase Controlled DNA movement that reached the polyT region of the DNA strand (SEQ ID NO: 154 attached at its 5' end to four nitroindoles the last of which is attached to the 3' end of SEQ ID NO: 155) |
|---|---|
| Hel308 Mbu (SEQ ID NO: 10) | 2 |
| Hel308 Mbu-E284C (SEQ ID NO: 10 with the mutation E284C) | 32 |
| Hel308 Mbu-E288C (SEQ ID NO: 10 with the mutation E288C) | 49 |
| Hel308 Mbu-E284Faz (SEQ ID NO: 10 with the mutation E284Faz) | 28 |
| Heat treated Hel308 Mbu-E284Faz (SEQ ID NO: 10 with the mutation E284Faz, the enzyme was heated in 50 mM Tris pH 8.0, 375 mM NaCl, 5% Glycerol buffer from 4° C. to 50° C. for 10 mins and then cooled to 4° C. in a BioRad PCR block) | 71 |

The invention claimed is:

1. A complex comprising (i) a monomeric helicase that comprises a polynucleotide binding domain and two RecA-like domains, and (ii) a target polynucleotide bound to the polynucleotide binding domain, wherein two amino acid residues that are located in different structural domains on the surface of the helicase surrounding the polynucleotide binding domain are artificially covalently connected via a linkage between the two amino acid residues, such that the helicase has a covalently-closed structure and the distance between the two amino acids is less than 50 Angstroms (Å), wherein the bound target polynucleotide is encircled by the covalently-closed structure.

2. The complex according to claim 1, wherein at least one amino acid of the two amino acid residues is substituted with cysteine, a non-natural amino acid or 4-azido-L-phenylalanine (Faz).

3. The complex according to claim 1, wherein the two amino acid residues are on one or more loop regions connecting α-helices and β-strands of the helicase and/or are spatially located proximal to the polynucleotide binding domain.

4. The complex according to claim 1, wherein the helicase is (a) a Hel308 helicase, a RecD helicase, a TraI helicase, a TraI subgroup helicase, an XPD helicase or a variant thereof; or (b) one of the helicases as set forth in SEQ ID NO: 10, 13, 16, 19, 22, 25, 28, 29, 32-34, 37-55, 58, 85, 126, 134, 138 or a variant thereof.

5. The complex according to claim 1, wherein the helicase further comprises a second set of two amino acid residues in different structural domains of the helicase surrounding the polynucleotide binding domain that are artificially covalently connected via a linkage between the two amino acid residues of the second set.

6. The complex according to claim 1, wherein the linkage between the two amino acid residues comprises an amino acid sequence.

7. The complex according to claim 6, wherein the amino acid sequence comprises a polynucleotide binding moiety.

8. The complex according to claim 1, wherein the linkage between the two amino acid residues comprises a polyethyleneglycol (PEG), polysaccharide, or polyamide.

9. The complex according to claim 1, wherein the linkage between the two amino acid residues comprises a deoxyribonucleic acid (DNA) sequence, peptide nucleic acid (PNA), threose nucleic acid (TNA), or glycerol nucleic acid (GNA).

10. The complex according to claim 1, wherein the helicase is a member of a helicase family selected from the group consisting of: Pif1-like helicases, Upf1-like helicases, UvrD/Rep helicases, Ski-like helicases, Rad3/XPD helicases, NS3/NPH-II helicases, DEAD helicases, DEAHi RHA helicases, RecG-like helicases, REcQ-like helicases, T1R-like helicases, Swi/Snf-like helicases, and Rig-I-like helicases.

11. The complex according to claim 1, wherein the helicase is a member of a helicase subfamily selected from the group consisting of: RecD helicases, Upf1 helicases, PcrA helicases, Rep helicases, UvrD helicases, Hel308 helicases, Mtr4 helicases, XPD helicases, NS3 helicases, Mssl 16 helicases, Prp43 helicases, RecG helicases, RecQ helicases, T1R helicases, RapA helicases and Hef helicases.

12. The complex according to claim 1, wherein the helicase has a covalently-closed structure and the distance between the two amino acids is less than 30 Å.

* * * * *